(12) United States Patent
Fulkerson et al.

(10) Patent No.: US 10,258,731 B2
(45) Date of Patent: *Apr. 16, 2019

(54) MANIFOLD DIAPHRAGMS

(71) Applicant: Fresenius Medical Care Holdings, Inc., Waltham, MA (US)

(72) Inventors: Barry Neil Fulkerson, Longmont, CO (US); Alec Huang, Irvine, CA (US); Brian Thomas Kelly, Anaheim Hills, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 220 days.

This patent is subject to a terminal disclaimer.

(21) Appl. No.: 15/055,857

(22) Filed: Feb. 29, 2016

(65) Prior Publication Data

US 2017/0021088 A1 Jan. 26, 2017

Related U.S. Application Data

(60) Continuation of application No. 13/852,918, filed on Mar. 28, 2013, now Pat. No. 9,308,307, which is a (Continued)

(51) Int. Cl.
*A61M 1/16* (2006.01)
*B01D 61/30* (2006.01)
(Continued)

(52) U.S. Cl.
CPC ............ *A61M 1/3656* (2014.02); *A61M 1/16* (2013.01); *A61M 1/166* (2014.02);
(Continued)

(58) Field of Classification Search
CPC ...... B01D 61/24; B01D 61/243; B01D 61/28; B01D 61/30; B01D 61/32; B01D 61/18;
(Continued)

(56) References Cited

U.S. PATENT DOCUMENTS 2,276,843 A 3/1942 Hathaway
2,328,381 A 8/1943 Jaffe
(Continued)

FOREIGN PATENT DOCUMENTS

CN 2183771 Y 11/1994
CN 1146728 4/1997
(Continued)

OTHER PUBLICATIONS

International Search Report for PCT/US2013/068506, dated Apr. 9, 2014.
(Continued)

*Primary Examiner* — Joseph W Drodge
(74) *Attorney, Agent, or Firm* — Novel IP

(57) ABSTRACT

The specification discloses a portable dialysis machine having a detachable controller unit and base unit. The controller unit includes a door having an interior face, a housing with a panel, where the housing and panel define a recessed region configured to receive the interior face of the door, and a manifold receiver fixedly attached to the panel. The manifold includes diaphragms adapted to minimize the dead space between the dialysis machine pins and improve responsivity. The base unit has a planar surface for receiving a container of fluid, a scale integrated with the planar surface and a heater in thermal communication with the container. Embodiments of the disclosed portable dialysis system have improved structural and functional features, including improved modularity, ease of use, and safety features.

15 Claims, 85 Drawing Sheets

Related U.S. Application Data continuation-in-part of application No. 13/023,490, filed on Feb. 8, 2011, now Pat. No. 8,597,505, which is a continuation-in-part of application No. 12/237,914, filed on Sep. 25, 2008, now Pat. No. 8,105,487, which is a continuation-in-part of application No. 12/610,032, filed on Oct. 30, 2009, and a continuation-in-part of application No. 12/324,924, filed on Nov. 28, 2008, now Pat. No. 8,114,288, and a continuation-in-part of application No. 12/249,090, filed on Oct. 10, 2008, and a continuation-in-part of application No. 12/575,449, filed on Oct. 7, 2009, now Pat. No. 8,040,493, and a continuation-in-part of application No. 12/751,930, filed on Mar. 31, 2010, now Pat. No. 9,199,022, and a continuation-in-part of application No. 12/705,054, filed on Feb. 12, 2010, now Pat. No. 8,535,522, and a continuation-in-part of application No. 12/875,888, filed on Sep. 3, 2010, which is a division of application No. 12/238,055, filed on Sep. 25, 2008, said application No. 13/023,490 is a continuation-in-part of application No. 12/210,080, filed on Sep. 12, 2008, and a continuation-in-part of application No. 12/351,969, filed on Jan. 12, 2009, now Pat. No. 8,240,636, and a continuation-in-part of application No. 12/713,447, filed on Feb. 26, 2010, now Pat. No. 8,475,399, and a continuation-in-part of application No. 12/575,450, filed on Oct. 7, 2009, now Pat. No. 8,137,553.

(60) Provisional application No. 60/975,157, filed on Sep. 25, 2007, provisional application No. 61/109,834, filed on Oct. 30, 2008, provisional application No. 60/990,959, filed on Nov. 29, 2007, provisional application No. 61/021,962, filed on Jan. 18, 2008, provisional application No. 60/979,113, filed on Oct. 11, 2007, provisional application No. 61/103,271, filed on Oct. 7, 2008, provisional application No. 61/165,389, filed on Mar. 31, 2009, provisional application No. 61/151,912, filed on Feb. 12, 2009, provisional application No. 60/975,840, filed on Sep. 28, 2007, provisional application No. 60/971,937, filed on Sep. 13, 2007, provisional application No. 61/155,548, filed on Feb. 26, 2009, provisional application No. 61/103,274, filed on Oct. 7, 2008.

(51) Int. Cl.
   *B01D 61/32* (2006.01)
   *A61M 1/36* (2006.01)
   *B01D 61/18* (2006.01)

(52) U.S. Cl.
   CPC ........ *A61M 1/1609* (2014.02); *A61M 1/1645* (2014.02); *A61M 1/1692* (2013.01); *A61M 1/1696* (2013.01); *A61M 1/3626* (2013.01); *A61M 1/3646* (2014.02); *B01D 61/18* (2013.01); *B01D 61/30* (2013.01); *B01D 61/32* (2013.01); *A61M 1/3639* (2013.01); *A61M 2205/126* (2013.01); *A61M 2205/13* (2013.01); *A61M 2205/14* (2013.01); *A61M 2205/15* (2013.01); *A61M 2205/18* (2013.01); *A61M 2205/3317* (2013.01); *A61M 2205/3324* (2013.01); *A61M 2205/3331* (2013.01); *A61M 2205/3334* (2013.01); *A61M 2205/3368* (2013.01); *A61M 2205/3375* (2013.01); *A61M 2205/3393* (2013.01); *A61M 2205/3553* (2013.01); *A61M 2205/3584* (2013.01); *A61M 2205/502* (2013.01); *A61M 2205/505* (2013.01); *A61M 2205/52* (2013.01); *B01D 2313/10* (2013.01); *B01D 2313/105* (2013.01); *B01D 2313/12* (2013.01); *B01D 2313/125* (2013.01); *B01D 2313/243* (2013.01)

(58) Field of Classification Search
   CPC ............. B01D 61/20; B01D 2313/105; B01D 2313/125; B01D 2313/10; B01D 2313/12; B01D 2313/243; B01D 61/22; A61M 1/16; A61M 1/1621; A61M 1/1631; A61M 1/28; A61M 2205/12; A61M 2205/121; A61M 2205/122; A61M 2205/123; A61M 2205/128; A61M 1/1645; A61M 1/166; A61M 1/1696; A61M 1/1692; A61M 1/3656; A61M 1/1609; A61M 1/3639; A61M 2205/126; A61M 2205/3393; A61M 2205/3368; A61M 2205/3553; A61M 2205/13; A61M 2205/14; A61M 2205/15; A61M 1/3626; A61M 1/3646; A61M 2205/3317; A61M 2205/3324; A61M 2205/3334; A61M 2205/3375; A61M 2205/505; A61M 2205/18; A61M 2205/52; A61M 2205/3331; A61M 2205/502; A61M 1/1601; A61M 1/1635; A61M 1/1647; A61M 2205/3584; A61M 2205/3353; F16K 11/02; F16K 11/022; F16K 11/027; F16K 31/126; F16K 31/1262; F16K 31/1264; F16K 31/1266; F16K 31/1268; F16K 31/128
   USPC ...... 210/321.6, 645–647; 604/4.01–6.11, 28, 604/29
   See application file for complete search history.

(56) References Cited

U.S. PATENT DOCUMENTS

| | | |
|---|---|---|
| 2,569,105 A | 9/1951 | James |
| 2,977,791 A | 4/1961 | Dubsky |
| 3,200,591 A | 8/1965 | Ray |
| 3,216,281 A * | 11/1965 | Teichert ................. F16H 39/32 60/438 |
| 3,242,456 A | 3/1966 | Duncan |
| 3,308,798 A | 3/1967 | Snider |
| 3,388,803 A | 6/1968 | Scott |
| 3,420,492 A | 1/1969 | Ray |
| 3,464,448 A * | 9/1969 | Schmitz ................. F15B 18/00 137/625.18 |
| 3,511,469 A | 5/1970 | Bell |
| 3,514,674 A | 5/1970 | Ito |
| 3,597,124 A | 8/1971 | Adams |
| 3,669,878 A | 6/1972 | Marantz |
| 3,669,880 A | 6/1972 | Marantz |
| 3,709,222 A | 1/1973 | De Vries |
| 3,728,654 A | 4/1973 | Tada |
| 3,746,175 A | 7/1973 | Markley |
| 3,752,189 A | 8/1973 | Marr |
| 3,803,913 A | 4/1974 | Tracer |
| 3,814,376 A | 6/1974 | Reinicke |
| 3,841,799 A | 10/1974 | Spinosa |
| 3,850,835 A | 11/1974 | Marantz |
| 3,884,808 A | 5/1975 | Scott |
| 3,894,431 A | 7/1975 | Muston |
| 3,902,490 A | 9/1975 | Jacobsen |
| 3,918,037 A | 11/1975 | Hall |
| 3,946,731 A | 3/1976 | Lichtenstein |
| 3,961,918 A | 6/1976 | Johnson |
| 3,983,361 A | 9/1976 | Wild |
| 3,989,622 A | 11/1976 | Marantz |
| 3,989,625 A | 11/1976 | Mason |
| 3,994,799 A | 11/1976 | Yao |

(56) References Cited

U.S. PATENT DOCUMENTS

| | | |
|---|---|---|
| 4,000,072 A | 12/1976 | Sato |
| 4,047,099 A | 9/1977 | Berger |
| 4,071,444 A | 1/1978 | Ash |
| 4,079,007 A | 3/1978 | Hutchisson |
| 4,083,777 A | 4/1978 | Hutchisson |
| 4,094,775 A | 6/1978 | Mueller |
| 4,099,700 A | 7/1978 | Young |
| 4,113,614 A | 9/1978 | Rollo |
| 4,118,314 A | 10/1978 | Yoshida |
| 4,155,852 A | 5/1979 | Fischel |
| 4,159,748 A | 7/1979 | Staudinger |
| 4,209,392 A | 6/1980 | Wallace |
| 4,212,738 A | 7/1980 | Henne |
| 4,247,393 A | 1/1981 | Wallace |
| 4,253,493 A | 3/1981 | English |
| 4,259,985 A | 4/1981 | Bergmann |
| 4,267,040 A | 5/1981 | Schael |
| 4,269,708 A | 5/1981 | Bonomini |
| 4,326,955 A | 4/1982 | Babb |
| 4,348,283 A | 9/1982 | Ash |
| 4,354,562 A | 10/1982 | Newman |
| 4,368,737 A | 1/1983 | Ash |
| 4,371,385 A | 2/1983 | Johnson |
| 4,381,999 A | 5/1983 | Boucher |
| 4,387,777 A | 6/1983 | Ash |
| 4,390,073 A | 6/1983 | Rosen |
| 4,397,189 A | 8/1983 | Johnson |
| 4,397,519 A | 8/1983 | Cooney |
| 4,402,694 A | 9/1983 | Ash |
| 4,403,765 A | 9/1983 | Fisher |
| 4,403,984 A | 9/1983 | Ash |
| 4,413,988 A | 11/1983 | Handt |
| 4,430,098 A | 2/1984 | Bowman |
| 4,436,620 A | 3/1984 | Bellotti |
| 4,443,333 A | 4/1984 | Mahurkar |
| 4,460,555 A | 7/1984 | Thompson |
| 4,464,172 A | 8/1984 | Lichtenstein |
| 4,466,804 A | 8/1984 | Hino |
| 4,469,593 A | 9/1984 | Ishihara |
| 4,477,342 A | 10/1984 | Allan |
| 4,480,483 A | 11/1984 | McShane |
| 4,498,902 A | 2/1985 | Ash |
| 4,531,799 A | 7/1985 | Gray |
| 4,535,637 A | 8/1985 | Feller |
| 4,559,039 A | 12/1985 | Ash |
| 4,563,170 A | 1/1986 | Aigner |
| 4,581,141 A | 4/1986 | Ash |
| 4,586,576 A | 5/1986 | Inoue |
| 4,596,550 A | 6/1986 | Troutner |
| 4,599,055 A | 7/1986 | Dykstra |
| 4,606,826 A | 8/1986 | Sano |
| 4,630,799 A | 12/1986 | Nolan |
| 4,650,587 A | 3/1987 | Polak |
| 4,661,246 A | 4/1987 | Ash |
| 4,666,598 A | 5/1987 | Heath |
| 4,680,122 A | 7/1987 | Barone |
| 4,683,053 A | 7/1987 | Polaschegg |
| 4,710,164 A | 12/1987 | Levin |
| 4,731,072 A | 3/1988 | Aid |
| 4,740,755 A | 4/1988 | Ogawa |
| 4,750,705 A | 6/1988 | Zippe |
| 4,762,618 A | 8/1988 | Gummesson |
| 4,765,421 A | 8/1988 | Newton |
| 4,765,907 A | 8/1988 | Scott |
| 4,777,953 A | 10/1988 | Ash |
| 4,802,540 A | 2/1989 | Grabovac |
| 4,806,247 A | 2/1989 | Schoendorfer |
| 4,808,089 A | 2/1989 | Buchholtz |
| 4,815,547 A | 3/1989 | Dillon |
| 4,823,597 A | 4/1989 | White |
| 4,826,663 A | 5/1989 | Alberti |
| 4,828,543 A | 5/1989 | Weiss |
| 4,828,693 A | 5/1989 | Lindsay |
| 4,831,884 A | 5/1989 | Drenthen |
| 4,840,542 A | 6/1989 | Abbott |
| 4,854,322 A | 8/1989 | Ash |
| 4,861,242 A | 8/1989 | Finsterwald |
| 4,881,839 A | 11/1989 | Grimm |
| 4,882,937 A | 11/1989 | Leon |
| 4,885,942 A | 12/1989 | Magori |
| 4,894,164 A | 1/1990 | Polaschegg |
| 4,897,189 A | 1/1990 | Greenwood |
| 4,909,713 A | 3/1990 | Finsterwald |
| 4,914,819 A | 4/1990 | Ash |
| 4,931,777 A | 6/1990 | Chiang |
| 4,943,279 A | 7/1990 | Samiotes |
| 4,950,244 A | 8/1990 | Fellingham |
| 4,950,395 A | 8/1990 | Richalley |
| 4,968,422 A | 11/1990 | Runge |
| 4,985,015 A | 1/1991 | Obermann |
| 4,990,258 A | 2/1991 | Bjare |
| 4,994,035 A | 2/1991 | Mokros |
| 4,995,268 A | 2/1991 | Ash |
| 4,997,570 A | 3/1991 | Polaschegg |
| 5,000,274 A | 3/1991 | Bullivant |
| 5,002,054 A | 3/1991 | Ash |
| 5,009,101 A | 4/1991 | Branam |
| 5,011,607 A | 4/1991 | Shinzato |
| 5,032,261 A | 7/1991 | Pyper |
| 5,074,368 A | 12/1991 | Bullivant |
| 5,100,554 A | 3/1992 | Polaschegg |
| 5,114,580 A | 5/1992 | Ahmad |
| 5,138,138 A | 8/1992 | Theilacker |
| 5,147,613 A | 9/1992 | Heilmann |
| 5,152,174 A | 10/1992 | Labudde |
| 5,157,332 A | 10/1992 | Reese |
| 5,161,779 A | 11/1992 | Graner |
| 5,170,789 A | 12/1992 | Narayan |
| 5,188,604 A | 2/1993 | Orth |
| 5,198,335 A | 3/1993 | Sekikawa |
| 5,211,643 A | 5/1993 | Reinhardt |
| 5,215,450 A | 6/1993 | Tamari |
| 5,220,843 A | 6/1993 | Rak |
| 5,228,308 A | 7/1993 | Day |
| 5,230,341 A | 7/1993 | Polaschegg |
| 5,230,614 A | 7/1993 | Zanger |
| 5,258,127 A | 11/1993 | Gsell |
| 5,259,961 A | 11/1993 | Eigendorf |
| 5,277,820 A | 1/1994 | Ash |
| 5,284,470 A | 2/1994 | Beltz |
| 5,284,559 A | 2/1994 | Lim |
| 5,295,505 A | 3/1994 | Polaschegg |
| 5,304,349 A | 4/1994 | Polaschegg |
| 5,308,315 A | 5/1994 | Khuri |
| 5,322,258 A | 6/1994 | Bosch |
| 5,322,519 A | 6/1994 | Ash |
| 5,336,165 A | 8/1994 | Twardowski |
| 5,339,699 A | 8/1994 | Carignan |
| 5,346,472 A | 9/1994 | Keshaviah |
| 5,347,115 A | 9/1994 | Sherman |
| 5,352,364 A | 10/1994 | Kruger |
| 5,360,445 A | 11/1994 | Goldowsky |
| 5,385,005 A | 1/1995 | Ash |
| D355,816 S | 2/1995 | Ash |
| 5,391,143 A | 2/1995 | Kensey |
| 5,405,315 A | 4/1995 | Khuri |
| 5,405,320 A | 4/1995 | Twardowski |
| 5,408,576 A | 4/1995 | Bishop |
| 5,415,532 A | 5/1995 | Loughnane |
| 5,441,636 A | 8/1995 | Chevallet |
| 5,445,630 A | 8/1995 | Richmond |
| 5,460,493 A | 10/1995 | Deniega |
| 5,468,388 A | 11/1995 | Goddard |
| 5,469,737 A | 11/1995 | Smith |
| 5,476,444 A | 12/1995 | Keeling |
| 5,518,015 A | 5/1996 | Berget |
| D370,531 S | 6/1996 | Ash |
| 5,536,412 A | 7/1996 | Ash |
| 5,540,265 A | 7/1996 | Polaschegg |
| 5,545,131 A | 8/1996 | Davankov |
| 5,577,891 A | 11/1996 | Loughnane |
| 5,580,460 A | 12/1996 | Polaschegg |
| 5,591,344 A | 1/1997 | Kenley |
| 5,609,770 A | 3/1997 | Zimmerman |

(56) References Cited

U.S. PATENT DOCUMENTS

| | | |
|---|---|---|
| 5,614,677 A | 3/1997 | Wamsiedler |
| 5,629,871 A | 3/1997 | Love |
| 5,616,305 A | 4/1997 | Mathieu |
| 5,624,551 A | 4/1997 | Baumann |
| 5,624,572 A | 4/1997 | Larson |
| 5,632,897 A | 5/1997 | Mathieu |
| 5,644,285 A | 7/1997 | Maurer |
| 5,647,853 A | 7/1997 | Feldmann |
| 5,650,704 A | 7/1997 | Pratt |
| 5,674,390 A | 10/1997 | Matthews |
| 5,679,245 A | 10/1997 | Manica |
| 5,690,821 A | 11/1997 | Kenley |
| 5,693,008 A | 12/1997 | Brugger |
| 5,695,473 A | 12/1997 | Olsen |
| 5,698,083 A | 12/1997 | Glass |
| 5,711,883 A | 1/1998 | Folden |
| 5,713,850 A | 2/1998 | Heilmann |
| 5,725,773 A | 3/1998 | Polaschegg |
| 5,725,776 A | 3/1998 | Kenley |
| 5,744,027 A | 4/1998 | Connell |
| 5,760,313 A | 6/1998 | Guentner |
| 5,762,782 A | 6/1998 | Kenley |
| 5,765,591 A | 6/1998 | Wasson |
| 5,770,806 A | 6/1998 | Hiismaeki |
| 5,782,796 A | 7/1998 | Din |
| 5,794,669 A | 8/1998 | Polaschegg |
| 5,840,068 A | 11/1998 | Cartledge |
| 5,858,186 A | 1/1999 | Glass |
| 5,876,419 A | 3/1999 | Carpenter |
| 5,902,336 A | 5/1999 | Mishkin |
| 5,906,978 A | 5/1999 | Ash |
| 5,919,369 A | 7/1999 | Ash |
| 5,928,177 A | 7/1999 | Brugger |
| 5,938,938 A | 8/1999 | Bosetto |
| 5,944,684 A | 8/1999 | Roberts |
| 5,945,343 A | 8/1999 | Munkholm |
| 5,947,953 A | 9/1999 | Ash |
| 5,951,870 A | 9/1999 | Utterberg |
| 5,980,481 A | 11/1999 | Gorsuch |
| 5,984,891 A | 11/1999 | Keilman |
| 5,989,423 A | 11/1999 | Kamen |
| 5,989,438 A | 11/1999 | Fumiyama |
| 6,012,342 A | 1/2000 | Blight |
| 6,042,561 A | 3/2000 | Ash |
| 6,044,691 A | 4/2000 | Kenley |
| 6,047,108 A | 4/2000 | Sword |
| 6,062,256 A | 5/2000 | Miller |
| 6,069,343 A | 5/2000 | Kolowich |
| 6,086,753 A | 7/2000 | Ericson |
| 6,116,269 A | 9/2000 | Maxson |
| 6,117,100 A | 9/2000 | Powers |
| 6,117,122 A | 9/2000 | Din |
| 6,118,082 A | 9/2000 | Bissette |
| 6,121,555 A | 9/2000 | Nowosielski |
| 6,156,007 A | 12/2000 | Ash |
| 6,168,578 B1 | 1/2001 | Diamond |
| 6,190,349 B1 | 2/2001 | Ash |
| 6,196,922 B1 | 3/2001 | Hantschk |
| 6,196,992 B1 | 3/2001 | Keilman |
| 6,200,485 B1 | 3/2001 | Kitaevich |
| 6,217,540 B1 | 4/2001 | Yazawa |
| 6,228,047 B1 | 5/2001 | Dadson |
| 6,234,989 B1 | 5/2001 | Brierton |
| 6,240,789 B1 | 6/2001 | Morlan |
| 6,254,567 B1 | 7/2001 | Treu |
| 6,264,611 B1 | 7/2001 | Ishikawa |
| 6,264,680 B1 | 7/2001 | Ash |
| 6,280,406 B1 | 8/2001 | Dolcek |
| 6,284,131 B1 | 9/2001 | Hogard |
| 6,287,516 B1 | 9/2001 | Matson |
| 6,289,749 B1 | 9/2001 | Sanders |
| 6,303,036 B1 | 10/2001 | Collins |
| 6,325,774 B1 | 12/2001 | Bene |
| 6,332,985 B1 | 12/2001 | Sherman |
| 6,341,758 B1 | 1/2002 | Shih |
| 6,348,162 B1 | 2/2002 | Ash |
| 6,354,565 B1 | 3/2002 | Doust |
| 6,406,631 B1 | 6/2002 | Collins |
| 6,409,699 B1 | 6/2002 | Ash |
| 6,416,293 B1 | 7/2002 | Bouchard |
| 6,468,427 B1 | 10/2002 | Frey |
| 6,471,872 B2 | 10/2002 | Kitaevich |
| 6,487,904 B1 | 12/2002 | Myhre |
| 6,491,656 B1 | 12/2002 | Morris |
| 6,491,673 B1 | 12/2002 | Palumbo |
| 6,497,675 B1 | 12/2002 | Davankov |
| 6,517,044 B1 | 2/2003 | Lin |
| 6,517,045 B1 | 2/2003 | Northedge |
| 6,551,513 B2 | 4/2003 | Nikaido |
| 6,554,789 B1 | 4/2003 | Brugger |
| 6,561,997 B1 | 5/2003 | Weitzel |
| 6,565,395 B1 | 5/2003 | Schwarz |
| 6,572,576 B2 | 6/2003 | Brugger |
| 6,572,641 B2 | 6/2003 | Brugger |
| 6,579,253 B1 | 6/2003 | Burbank |
| 6,579,460 B1 | 6/2003 | Willis |
| 6,582,385 B2 | 6/2003 | Burbank |
| 6,589,482 B1 | 7/2003 | Burbank |
| 6,595,943 B1 | 7/2003 | Burbank |
| 6,607,495 B1 | 8/2003 | Skalak |
| 6,610,036 B2 | 8/2003 | Branch |
| 6,623,470 B2 | 9/2003 | Munis |
| 6,627,164 B1 | 9/2003 | Wong |
| 6,632,192 B2 | 10/2003 | Gorsuch |
| 6,638,477 B1 | 10/2003 | Treu |
| 6,638,478 B1 | 10/2003 | Treu |
| 6,649,063 B2 | 11/2003 | Brugger |
| 6,653,841 B1 | 11/2003 | Koerdt |
| 6,673,314 B1 | 1/2004 | Burbank |
| 6,681,624 B2 | 1/2004 | Furuki |
| 6,685,664 B2 | 2/2004 | Levin |
| 6,690,280 B2 | 2/2004 | Citrenbaum |
| 6,695,803 B1 | 2/2004 | Robinson |
| 6,702,561 B2 | 3/2004 | Stillig |
| 6,706,007 B2 | 3/2004 | Gelfand |
| 6,730,266 B2 | 5/2004 | Matson |
| 6,743,193 B2 | 6/2004 | Brugger |
| 6,752,172 B2 | 6/2004 | Lauer |
| 6,758,975 B2 | 7/2004 | Peabody |
| 6,764,460 B2 | 7/2004 | Dolecek |
| 6,773,412 B2 | 8/2004 | OMahony |
| 6,776,912 B2 | 8/2004 | Baurmeister |
| 6,796,955 B2 | 9/2004 | OMahony |
| 6,818,196 B2 | 11/2004 | Wong |
| 6,830,553 B1 | 12/2004 | Burbank |
| 6,836,201 B1 | 12/2004 | Devenyi |
| 6,841,172 B1 | 1/2005 | Ash |
| 6,843,779 B1 | 1/2005 | Andrysiak |
| 6,852,090 B2 | 2/2005 | Burbank |
| 6,872,346 B2 | 3/2005 | Stillig |
| 6,878,283 B2 | 4/2005 | Thompson |
| 6,886,801 B2 | 5/2005 | Hallback et al. |
| 6,890,315 B1 | 5/2005 | Levin |
| 6,899,691 B2 | 5/2005 | Bainbridge |
| 6,923,782 B2 | 8/2005 | OMahony |
| 6,948,697 B2 | 9/2005 | Herbert |
| 6,955,655 B2 | 10/2005 | Burbank |
| 6,958,049 B1 | 10/2005 | Ash |
| 6,960,179 B2 | 11/2005 | Gura |
| 6,960,328 B2 | 11/2005 | Bortun |
| 6,979,309 B2 | 12/2005 | Burbank |
| 7,004,924 B1 | 2/2006 | Brugger |
| 7,007,549 B2 | 3/2006 | Kwon |
| 7,033,498 B2 | 4/2006 | Wong |
| 7,037,428 B1 | 5/2006 | Robinson |
| 7,040,142 B2 | 5/2006 | Burbank |
| 7,059,195 B1 | 6/2006 | Liu |
| 7,087,026 B2 | 8/2006 | Callister |
| 7,087,033 B2 | 8/2006 | Brugger |
| 7,097,148 B2 | 8/2006 | DeWall |
| 7,101,519 B2 | 9/2006 | Wong |
| 7,112,273 B2 | 9/2006 | Weigel |
| 7,115,095 B2 | 10/2006 | Egler |
| 7,135,156 B2 | 11/2006 | Hai |

(56) References Cited

U.S. PATENT DOCUMENTS

| | | |
|---|---|---|
| 7,144,386 B2 | 12/2006 | Korkor |
| 7,146,861 B1 | 12/2006 | Cook |
| 7,147,613 B2 | 12/2006 | Burbank |
| 7,169,303 B2 | 1/2007 | Sullivan |
| 7,175,809 B2 | 2/2007 | Gelfand |
| 7,214,312 B2 | 5/2007 | Brugger |
| 7,226,538 B2 | 6/2007 | Brugger |
| 7,241,272 B2 | 7/2007 | Karoor |
| 7,252,767 B2 | 8/2007 | Bortun |
| 7,267,658 B2 | 9/2007 | Treu |
| 7,270,015 B1 | 9/2007 | Feller |
| 7,273,465 B2 | 9/2007 | Ash |
| 7,276,042 B2 | 10/2007 | Polaschegg |
| 7,300,413 B2 | 11/2007 | Burbank |
| 7,309,323 B2 | 12/2007 | Gura |
| 7,314,208 B1 | 1/2008 | Rightley |
| 7,317,967 B2 | 1/2008 | DiGianfilippo |
| 7,332,096 B2 | 2/2008 | Blickhan |
| 7,337,674 B2 | 3/2008 | Burbank |
| 7,338,460 B2 | 3/2008 | Burbank |
| 7,347,849 B2 | 3/2008 | Brugger |
| 7,351,218 B2 | 4/2008 | Bene |
| 7,387,022 B1 | 6/2008 | Korniyenko |
| 7,494,590 B2 | 2/2009 | Felding |
| 7,531,098 B2 | 5/2009 | Robinson |
| 7,566,432 B2 | 7/2009 | Wong |
| 7,597,677 B2 | 10/2009 | Gura |
| 7,605,710 B2 | 10/2009 | Crnkovich |
| 7,618,531 B2 | 11/2009 | Sugioka |
| 7,628,378 B2 | 12/2009 | Adams |
| 7,645,253 B2 | 1/2010 | Gura |
| 7,648,476 B2 | 1/2010 | Bock |
| 7,696,762 B2 | 4/2010 | Quackenbush |
| 7,713,226 B2 | 5/2010 | Ash |
| 7,736,507 B2 | 6/2010 | Wong |
| 7,755,488 B2 | 7/2010 | Dvorsky |
| 7,766,873 B2 | 8/2010 | Moberg |
| 7,776,210 B2 | 8/2010 | Rosenbaum |
| 7,780,619 B2 | 8/2010 | Brugger |
| 7,794,141 B2 | 9/2010 | Perry |
| 7,861,740 B2 | 1/2011 | Phallen |
| 7,873,489 B2 | 1/2011 | Dolgos |
| 7,874,999 B2 | 1/2011 | Busby |
| 7,886,611 B2 | 2/2011 | OMahony |
| 7,896,829 B2 | 3/2011 | Gura |
| 7,901,376 B2 | 3/2011 | Steck |
| 7,922,898 B2 | 4/2011 | Jonsson |
| 7,922,899 B2 | 4/2011 | Vasta |
| 7,935,074 B2 | 5/2011 | Plahey |
| 7,959,129 B2 | 6/2011 | Matsumoto |
| 7,981,082 B2 | 7/2011 | Wang |
| 7,981,280 B2 | 7/2011 | Carr |
| 7,995,816 B2 | 8/2011 | Roger |
| 7,998,101 B2 | 8/2011 | Ash |
| 8,021,319 B2 | 9/2011 | Delnevo |
| 8,029,454 B2 | 10/2011 | Kelly |
| 8,034,161 B2 | 10/2011 | Gura |
| 8,034,235 B2 | 10/2011 | Rohde |
| 8,062,513 B2 | 11/2011 | Yu |
| 8,066,658 B2 | 11/2011 | Karoor |
| 8,070,707 B2 | 12/2011 | Gelfand |
| 8,075,509 B2 | 12/2011 | Molducci |
| 8,078,333 B2 | 12/2011 | Kienman |
| 8,083,677 B2 | 12/2011 | Rohde |
| 8,105,260 B2 | 1/2012 | Tonelli |
| 8,105,487 B2 | 1/2012 | Fulkerson |
| 8,114,288 B2 | 2/2012 | Robinson |
| 8,118,276 B2 | 2/2012 | Sanders |
| 8,152,751 B2 | 2/2012 | Roger |
| 8,142,383 B2 | 3/2012 | Dannenmaier |
| 8,187,184 B2 | 5/2012 | Muller |
| 8,192,401 B2 | 6/2012 | Morris |
| 8,197,431 B2 | 6/2012 | Bennison |
| 8,206,338 B2 | 6/2012 | Childers |
| 8,210,493 B2 | 7/2012 | Miyagawa |
| 8,221,320 B2 | 7/2012 | Bouton |
| 8,240,636 B2 | 8/2012 | Smith |
| 8,273,049 B2 | 9/2012 | Demers |
| 8,316,725 B2 | 11/2012 | Wade |
| 8,323,492 B2 | 12/2012 | Childers |
| 8,342,478 B1 | 1/2013 | Cordray |
| 8,376,978 B2 | 2/2013 | Roger |
| 8,449,487 B2 | 5/2013 | Hovland |
| 8,491,184 B2 | 7/2013 | Kamen |
| 8,597,505 B2 | 12/2013 | Fulkerson |
| 8,622,365 B2 | 1/2014 | Fukano |
| 8,696,626 B2 | 4/2014 | Kirsch |
| 9,308,307 B2 * | 4/2016 | Fulkerson ........... A61M 1/1692 |
| 9,354,640 B2 | 5/2016 | Byler |
| 9,360,129 B2 | 6/2016 | Smith |
| 9,517,296 B2 | 12/2016 | Fulkerson |
| 2001/0038083 A1 | 11/2001 | Sakurai |
| 2002/0050412 A1 | 5/2002 | Emery |
| 2002/0068364 A1 | 6/2002 | Arai |
| 2002/0085951 A1 | 7/2002 | Gelfand |
| 2002/0112609 A1 | 8/2002 | Wong |
| 2002/0113016 A1 | 8/2002 | Takai |
| 2002/0139419 A1 | 10/2002 | Flinchbaugh |
| 2002/0147423 A1 | 10/2002 | Burbank |
| 2002/0158019 A1 | 10/2002 | Collins |
| 2002/0187069 A1 | 12/2002 | Levin |
| 2002/0193679 A1 | 12/2002 | Malave |
| 2003/0001590 A1 | 1/2003 | Mengle |
| 2003/0012905 A1 | 1/2003 | Zumbrum |
| 2003/0048185 A1 | 3/2003 | Citrenbaum |
| 2003/0056585 A1 | 3/2003 | Furuki |
| 2003/0113931 A1 | 6/2003 | Pan |
| 2003/0113932 A1 | 6/2003 | Sternberg |
| 2003/0128125 A1 | 7/2003 | Burbank |
| 2003/0216677 A1 | 11/2003 | Pan |
| 2003/0220598 A1 | 11/2003 | Busby |
| 2003/0220606 A1 | 11/2003 | Busby |
| 2003/0236482 A1 | 12/2003 | Gorsuch |
| 2004/0018100 A1 | 1/2004 | Takagi |
| 2004/0019312 A1 | 1/2004 | Childers |
| 2004/0021108 A1 | 2/2004 | Hallback |
| 2004/0031756 A1 | 2/2004 | Suzuki |
| 2004/0167465 A1 | 8/2004 | Mihai |
| 2004/0195055 A1 | 10/2004 | Gilles |
| 2005/0010190 A1 | 1/2005 | Yeakley |
| 2005/0070837 A1 | 3/2005 | Ferrarini |
| 2005/0086008 A1 | 4/2005 | DiGianfilippo |
| 2005/0092079 A1 | 5/2005 | Ales |
| 2005/0101901 A1 | 5/2005 | Gura |
| 2005/0131332 A1 | 6/2005 | Kelly |
| 2005/0133439 A1 | 6/2005 | Blickhan |
| 2005/0150309 A1 | 7/2005 | Beard |
| 2005/0209547 A1 | 9/2005 | Burbank |
| 2005/0230292 A1 | 10/2005 | Beden |
| 2005/0240233 A1 | 10/2005 | Lippert |
| 2006/0064053 A1 | 3/2006 | Bollish |
| 2006/0091056 A1 * | 5/2006 | Brugger ............... A61M 1/3627 210/321.88 |
| 2006/0113249 A1 * | 6/2006 | Childers ................ A61M 1/28 210/645 |
| 2006/0117859 A1 | 6/2006 | Liu |
| 2006/0122552 A1 | 6/2006 | OMahony |
| 2006/0195064 A1 | 8/2006 | Plahey |
| 2006/0226057 A1 | 10/2006 | Robinson |
| 2006/0226090 A1 | 10/2006 | Robinson |
| 2006/0241543 A1 | 10/2006 | Gura |
| 2006/0289342 A1 | 12/2006 | Sugioka |
| 2007/0060786 A1 | 3/2007 | Gura |
| 2007/0112297 A1 | 5/2007 | Plahey |
| 2007/0158249 A1 | 7/2007 | Ash |
| 2007/0158268 A1 | 7/2007 | DeComo |
| 2007/0161113 A1 | 7/2007 | Ash |
| 2007/0179425 A1 | 8/2007 | Gura |
| 2007/0213654 A1 | 9/2007 | Lundtveit |
| 2007/0276328 A1 | 11/2007 | Childers |
| 2008/0006570 A1 | 1/2008 | Gura |
| 2008/0021366 A1 | 1/2008 | Gura |
| 2008/0041136 A1 | 2/2008 | Kopelman |
| 2008/0041792 A1 | 2/2008 | Crnkovich |

(56) References Cited

U.S. PATENT DOCUMENTS

| | | |
|---|---|---|
| 2008/0051689 A1 | 2/2008 | Gura |
| 2008/0058696 A1 | 3/2008 | Gura |
| 2008/0065006 A1 | 3/2008 | Roger |
| 2008/0077068 A1* | 3/2008 | Orr .......................... F04B 7/02 604/6.11 |
| 2008/0149563 A1 | 6/2008 | Ash |
| 2008/0195021 A1 | 8/2008 | Roger |
| 2008/0195060 A1 | 8/2008 | Roger |
| 2008/0208103 A1 | 8/2008 | Demers |
| 2008/0217245 A1 | 9/2008 | Rambod |
| 2008/0230450 A1 | 9/2008 | Burbank |
| 2008/0258735 A1 | 10/2008 | Quackenbush |
| 2008/0264498 A1 | 10/2008 | Thompson |
| 2008/0290974 A1 | 11/2008 | Adams |
| 2009/0004053 A1 | 1/2009 | Kenley |
| 2009/0008306 A1 | 1/2009 | Cicchello |
| 2009/0008331 A1* | 1/2009 | Wilt ........................ A61M 1/16 210/647 |
| 2009/0010627 A1 | 1/2009 | Lindsay |
| 2009/0076434 A1 | 3/2009 | Mischelevich |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0083331 A1 | 3/2009 | Oh |
| 2009/0095679 A1 | 4/2009 | Demers |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105627 A1 | 4/2009 | Rohde |
| 2009/0107902 A1 | 4/2009 | Childers |
| 2009/0112155 A1 | 4/2009 | Zhao |
| 2009/0112507 A1 | 4/2009 | Edney |
| 2009/0113335 A1 | 4/2009 | Sandoe |
| 2009/0114037 A1 | 5/2009 | Smith |
| 2009/0120864 A1 | 5/2009 | Fulkerson |
| 2009/0124963 A1 | 5/2009 | Hogard |
| 2009/0127193 A1 | 5/2009 | Updyke |
| 2009/0127793 A1 | 5/2009 | Ferris |
| 2009/0137940 A1* | 5/2009 | Orr ........................ A61M 1/106 604/6.11 |
| 2009/0173682 A1* | 7/2009 | Robinson ................ A61M 1/16 210/232 |
| 2009/0282980 A1 | 11/2009 | Gura |
| 2009/0312694 A1 | 12/2009 | Bedingfield |
| 2010/0022936 A1 | 1/2010 | Gura |
| 2010/0078381 A1 | 4/2010 | Merchant |
| 2010/0078387 A1 | 4/2010 | Wong |
| 2010/0084330 A1 | 4/2010 | Wong |
| 2010/0094193 A1 | 4/2010 | Gura |
| 2010/0100034 A1 | 4/2010 | Wich-Heiter |
| 2010/0101664 A1 | 4/2010 | Yamamoto |
| 2010/0116048 A1 | 5/2010 | Fulkerson |
| 2010/0116740 A1 | 5/2010 | Fulkerson |
| 2010/0129247 A1 | 5/2010 | Lauer |
| 2010/0133153 A1 | 6/2010 | Beden |
| 2010/0140149 A1 | 6/2010 | Fulkerson |
| 2010/0179464 A1 | 7/2010 | Smith |
| 2010/0184198 A1 | 7/2010 | Joseph |
| 2010/0192686 A1 | 8/2010 | Kamen |
| 2010/0209300 A1 | 8/2010 | Dirac |
| 2010/0234786 A1 | 9/2010 | Fulkerson |
| 2010/0252490 A1 | 10/2010 | Fulkerson |
| 2010/0312161 A1 | 12/2010 | Jonsson |
| 2010/0326911 A1 | 12/2010 | Rosenbaum |
| 2010/0326916 A1 | 12/2010 | Wrazel |
| 2010/0331754 A1 | 12/2010 | Fulkerson |
| 2011/0000830 A1 | 1/2011 | Ikeda |
| 2011/0000832 A1 | 1/2011 | Kelly |
| 2011/0009799 A1 | 1/2011 | Mullick |
| 2011/0017665 A1 | 1/2011 | Updyke |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0054378 A1 | 3/2011 | Fulkerson |
| 2011/0071465 A1 | 3/2011 | Wang |
| 2011/0083746 A1 | 4/2011 | Hoang |
| 2011/0087187 A1 | 4/2011 | Beck |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanksi |
| 2011/0107251 A1 | 5/2011 | Guaitoli |
| 2011/0108482 A1 | 5/2011 | Lovell |
| 2011/0125073 A1 | 5/2011 | Rambod |
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0232388 A1 | 9/2011 | Butterfield |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272337 A1 | 11/2011 | Palmer |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2011/0319823 A1 | 12/2011 | Bojan |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |
| 2012/0029937 A1 | 2/2012 | Neftel |
| 2012/0031826 A1 | 2/2012 | Childers |
| 2012/0035534 A1 | 2/2012 | Yu |
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |

(56) References Cited

U.S. PATENT DOCUMENTS

| | | | |
|---|---|---|---|
| 2012/0214117 A1 | 8/2012 | Broker |
| 2012/0259282 A1 | 10/2012 | Alderete |
| 2013/0140652 A1 | 6/2013 | Erdler |
| 2013/0184638 A1 | 7/2013 | Scarpaci |
| 2013/0199998 A1 | 8/2013 | Kelly |
| 2013/0220907 A1 | 8/2013 | Fulkerson |
| 2013/0233395 A1 | 9/2013 | Dinh |
| 2013/0292319 A1 | 11/2013 | Fulkerson |
| 2014/0199193 A1 | 7/2014 | Wilt |

FOREIGN PATENT DOCUMENTS

| | | |
|---|---|---|
| CN | 1235849 A | 11/1999 |
| CN | 1471617 A | 1/2004 |
| CN | 101175514 | 5/2008 |
| CN | 101269247 | 9/2008 |
| CN | 101311589 | 11/2008 |
| CN | 101801432 | 8/2010 |
| CN | 201600175 U | 10/2010 |
| CN | 101977642 | 2/2011 |
| CN | 102596283 A | 7/2012 |
| CN | 102639201 A | 8/2012 |
| CN | 103476486 A | 12/2013 |
| EP | 0121085 | 10/1984 |
| EP | 0808633 | 11/1997 |
| EP | 2237814 | 10/2010 |
| GB | 1579177 | 11/1980 |
| JP | S50126866 A | 10/1975 |
| JP | S56138580 U | 10/1981 |
| JP | S5755010 U | 3/1982 |
| JP | S5913770 U | 1/1984 |
| JP | S59127978 U | 8/1984 |
| JP | S6037674 U | 3/1985 |
| JP | S60108870 | 6/1985 |
| JP | S60108870 U | 7/1985 |
| JP | S63202882 A | 8/1988 |
| JP | S63192912 U | 12/1988 |
| JP | H02114269 U | 9/1990 |
| JP | H0413143 U | 2/1992 |
| JP | 005176991 A | 7/1993 |
| JP | H05172268 A | 9/1993 |
| JP | H06230023 A | 8/1994 |
| JP | H11137673 A | 5/1999 |
| JP | 2002119585 A | 4/2002 |
| JP | 2002139165 A | 5/2002 |
| JP | 2002523772 | 7/2002 |
| JP | 2003502091 | 1/2003 |
| JP | 2004057284 | 2/2004 |
| JP | 3126509 U | 11/2006 |
| JP | 2008055185 A | 3/2008 |
| JP | 2008291911 A | 4/2008 |
| JP | 2008511094 A | 4/2008 |
| JP | 2008531192 | 8/2008 |
| JP | 2008531192 A | 8/2008 |
| JP | 2008531192 A1 | 8/2008 |
| JP | 2009521965 | 6/2009 |
| JP | 2012510826 A | 5/2012 |
| MX | 20103880 | 7/2010 |
| TW | 200824731 A | 6/2008 |
| WO | 1980002806 | 12/1980 |
| WO | 199318380 | 9/1993 |
| WO | 1993018380 A1 | 9/1993 |
| WO | 9420154 A1 | 9/1994 |
| WO | 199428386 | 12/1994 |
| WO | 1996025214 | 8/1996 |
| WO | 1997027490 | 7/1997 |
| WO | 9823353 | 6/1998 |
| WO | 1999030757 A1 | 6/1999 |
| WO | 20015069412 A1 | 7/2001 |
| WO | 2004009158 A2 | 1/2004 |
| WO | 2005065126 A2 | 7/2005 |
| WO | 2005089832 A2 | 9/2005 |
| WO | 200609362 | 9/2006 |
| WO | 2006120415 | 11/2006 |
| WO | 2007028056 | 3/2007 |
| WO | 2007140241 A1 | 12/2007 |
| WO | 2008053259 A1 | 5/2008 |
| WO | 2008129830 A1 | 10/2008 |
| WO | 2009045589 A2 | 4/2009 |
| WO | 2009065598 | 5/2009 |
| WO | 2009073567 | 6/2009 |
| WO | 2009091963 | 7/2009 |
| WO | 2009157877 | 12/2009 |
| WO | 2010042666 | 4/2010 |
| WO | 2010042667 | 4/2010 |
| WO | 2010062698 | 6/2010 |
| WO | 2010062698 A2 | 6/2010 |
| WO | 2010081121 | 7/2010 |
| WO | 2010081121 A1 | 7/2010 |
| WO | 2010114932 | 10/2010 |
| WO | 2012108910 | 8/2012 |
| WO | 2014105267 A1 | 7/2014 |
| WO | 2014105755 | 7/2014 |

OTHER PUBLICATIONS

Notice of Allowance dated Jun. 9, 2015 for U.S. Appl. No. 13/726,450.
Office Action dated Apr. 17, 2015 for U.S. Appl. No. 13/726,457.
Office Action dated Feb. 12, 2015 for U.S. Appl. No. 13/548,711.
Office Action dated Jan. 15, 2015 for U.S. Appl. No. 13/726,450.
Office Action dated Jan. 27, 2015 for U.S. Appl. No. 13/372,202.
Office Action dated Jul. 15, 2014 for U.S. Appl. No. 13/548,711.
Office Action dated Mar. 4, 2015 for U.S. Appl. No. 13/337,227.
Office Action dated Mar. 7, 2014 for U.S. Appl. No. 13/548,711.
Office Action dated Sep. 17, 2015 for U.S. Appl. No. 13/548,711.
Office Action dated Sep. 3, 2015 for U.S. Appl. No. 13/726,457.
Office Action dated Aug. 27, 2015 for U.S. Appl. No. 13/337,227.
Notice of Allowance dated Jul. 27, 2015 for U.S. Appl. No. 12/751,390.
Notice of Allowance dated Dec. 1, 2015 for U.S. Appl. No. 13/852,918.
First Office Action for Canadian Patent Application No. CA2749171, dated Jan. 8, 2016.
First Office Action for PA11004600, dated Aug. 15, 2014.
International Preliminary Report on Patentability for PCT/US13/77234, dated Jun. 30, 2015.
Notice of Allowance dated Nov. 17, 2015 for U.S. Appl. No. 13/372,202.
Office Action dated Jul. 16, 2015 for U.S. Appl. No. 14/077,112.
International Search Report for PCT/US14/60122, dated Jan. 21, 2015.
Notice of Allowance dated Feb. 8, 2016 for U.S. Appl. No. 13/726,457.
Second Office Action for Canadian Application No. CA2706919, dated Oct. 27, 2015.
Office Action for Canadian Patent Application No. CA2739807, dated Oct. 28, 2015.
First Office Action for Canadian Patent Application No. CA2739786, dated Oct. 21, 2015.
Third Office Action for CN2010800039317, dated Sep. 10, 2014.
Notice of Allowance dated Feb. 5, 2016 for U.S. Appl. No. 13/548,711.
Notice of Allowance dated Feb. 1, 2016 for U.S. Appl. No. 13/337,227.
Notice of Allowance dated Dec. 28, 2015 for U.S. Appl. No. 14/077,112.
First Examination Report for New Zealand Patent Application No. 614053, dated Jun. 9, 2014.
First Examination Report for New Zealand Patent Application No. 627386, dated Aug. 4, 2015.
First Examination Report for New Zealand Patent Application No. 627392, dated Aug. 4, 2015.
Patent Examination Report No. 1 for Australian Patent Application No. AU2014262300, dated Sep. 11, 2015.
First Office Action for Japanese Patent Application No. JP2014203093, dated Nov. 10, 2015.
First Examination Report for New Zealand Patent Application No. 627399, dated Nov. 9, 2015.

(56) References Cited

OTHER PUBLICATIONS

First Office Action for Japanese Patent Application No. JP2013553422, dated Sep. 1, 2015.
Office Action dated Mar. 11, 2016 for U.S. Appl. No. 14/040,362.
Notice of Allowance dated Apr. 13, 2016 for U.S. Appl. No. 14/291,448.
Notice of Allowance dated Aug. 3, 2016 for U.S. Appl. No. 14/040,362.
Supplementary European Search Report for EP14773805, dated Sep. 27, 2016.
Examination Report for Mexican Patent Application No. MX/a/2015/004503, dated Aug. 8, 2016.
Office Action dated Jun. 14, 2016 for U.S Appl. No. 14/923,904.
Third Office Action for Canadian Application No. CA2706919, dated Sep. 7, 2016.
Search Report for Eurasian patent application No. 201690595, dated Sep. 13, 2016.
Office Action dated Dec. 16, 2016 for U.S. Appl. No. 14/923,904.
Notice of Allowance dated May 5, 2017 for U.S. Appl. No. 14/923,904.
First Office Action for Chinese Patent Application No. CN2015103917943, dated Dec. 26, 2016.
Examination Report No. 1 for Australian Patent Application No. 2011358554, dated Mar. 2, 2017.
Supplementary European Search Report for EP13869170, completed on Jul. 4, 2016.
First Office Action for CN201380073721.9, dated May 5, 2016.
Second Office Action for CN201380073721.9, dated Mar. 3, 2017.
Examination Report No. 1 for Australian Patent Application No. 2013370583, dated Jul. 6, 2017.
First Office Action for CN201480061648.8, dated Jan. 24, 2017.
Examination Report for Application No. EP20090829649, dated Dec. 22, 2016.
Office Action for CN2015105674626, dated Mar. 1, 2017.
Office Action for CA2928208, dated Apr. 25, 2017.
Office Action dated Aug. 7, 2017 for U.S. Appl. No. 15/139,144; (pp. 1-28).
Office Ation dated Aug. 30, 2017 for U.S. Appl. No. 15/044,194; (pp. 1-13).
Office Action for Japanese Patent Application No. 2016-159787, dated Aug. 1, 2017.
Office ACtion dated Aug. 8, 2017 for U.S. Appl. No. 15/146,509; (pp. 1-33).
Office Action dated Apr. 28, 2017 for U.S. Appl. No. 14/848,012.
Notice of Allowance dated Aug. 11, 2017 for U.S. Appl. No. 14/848,012; (pp. 1-5).
Supplementary European Search Report for EP13868466, completed on Jun. 24, 2016.
First office action for Chinese Application No. CN201380072668.0, dated Dec. 29, 2016.
Further Examination Report for New Zealand Patent Application No. 627392, dated Nov. 16, 2016.
First Examination Report for New Zealand Patent Application No. 725880, dated Nov. 16, 2016.
Extended European Search Report for Application No. EP09819849.2, dated Jul. 21, 2017.
First Office Action for CN201480029452.0, dated Jul. 12, 2016.
Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).
CD Medical, Inc., 'Operator's Manual Drake Willock 480 Ultrafiltration Control Single Patient Delivery System', 1988.
Cobe Laboratories, Inc., 'CentrySystem 3 Dialysis Control Unit Operators Manual', Sep. 1988.
Cobe Renal Care, Inc., "Sorbent Dialysis Primer", Edition 4, Sep. 1993.
Examination Report for PCT/US08/85062, Mexican Patent Office, dated Mar. 11, 2013.
Examination Report for PCT/US09/59906, New Zealand Intellectual Property Office, dated May 15, 2012.
Fresenius AG, 'Acumen Acute Dialysis Machine Operating Instructions', Version 1.0, May 1996.
Fresenius USA, Inc., "Fresenius 2008H Hemodialysis Machine", Part No. 490005, Revision H, 1994-2001.
International Preliminary Report on Patentability for PCT/US2009/059907, dated Apr. 15, 2010, Fresenius Medical Care Holdings, Inc.
International Search Report for PCT/US09/31228, Xcorporeal, Inc., dated Jun. 19, 2009.
International Search Report for PCT/US09/59906, Xcorporeal, Inc., dated May 8, 2012.
International Search Report for PCT/US09/59907, Xcorporeal, Inc., dated Apr. 13, 2010.
International Search Report for PCT/US09/62840, Xcorporeal, Inc. dated Feb. 10, 2012.
International Search Report for PCT/US10/20698, Xcorporeal, Inc., dated Jun. 16, 2010.
International Search Report for PCT/US10/29500, Xcorporeal, Inc., dated Jul. 2, 2010.
International Search Report for PCT/US11/53184, Xcorporeal, Inc., dated Mar. 2, 2012.
International Search Report PCT/US08/85062, dated Mar. 20, 2009, XCorporeal, Inc.
Manns et al., 'The acu-men: A New Device for Continuous Renal Replacement Therapy in Acute Renal Failure', Kidney International, vol. 54 (1998), 268-274.
NxStage Medical, Inc., 'NxStage System One User's Guide', Software Version 4.3, Part 1 through Part 6-20, 2006.
NxStage Medical, Inc., 'NxStage System One User's Guide', Software Version 4.3, Part 6-20 through Part C-17, 2006.
Office Action dated Jul. 1, 2015 for U.S. Appl. No. 13/852,918.
REDY 2000 Operator's Manual (1991) (Sorbent cartridge-based hemodialysis system).
REDY 2000 Service Manual (1989) (Sorbent cartridge-based hemodialysis system).
Renal Solutions, Inc., 'Dialysate Tubing Set and Dialysate Reservoir Bag for the Allient Sorbent Hemodialysis System', Instructions, 2004.
Renal Solutions, Inc., 510(K) for the SORB+ and HISORB+ Cartridges, Mar. 31, 2003.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Sections M.3 and M.4), Renal Solutions, Inc., Dec. 17, 2004.
Renal Solutions, Portions of the Allient Sorbent Hemodialysis System, Home User Manual, 2006, Chapters 1-3.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.
Renal Solutions, Portions of the Allient Sorbent Hemodialysis System, Operator Manual Model 1500, 2008, Chapters 1 to 2.
Renal Solutions, Special 510(k) Device Modification, Allient Sorbent Hemodialysis System, Mar. 15, 2007.

(56) References Cited

OTHER PUBLICATIONS

Reyes et al., 'Acid-Base Derangements During Sorbent Regenerative Hemodialysis in Mechanically Ventilated Patients', Critical Care Medicine, vol. 19, No. 4, 1991, 554-559 (col. 2, lines 17-22).
Seratron Dialysis Control System Operations Manual (cumulative 1980).
Timby et al., Introductory Medical-Surgical Nursing, Lippincott Williams Wilkins, Ninth Edition, Chapter 28, p. 433.
Ward et al., 'Sorbent Dialysis Regenerated Dialysis Delivery Systems', Peritoneal Dialysis Bulletin, Chapter 8, 3(2): S41-S48 (Apr.-Jun. 1983).
Extended European Search Report for Application No. EP10729646. 9, dated Jul. 23, 2015.
International Search Report for PCT/US13/77234, dated Jun. 9, 2014.
European Search Report for Application No. EP20090829649, dated Jan. 22, 2015.
First Office Action for Canadian Application No. CA2706919, dated Jan. 20, 2015.
First office action for Chinese Patent Application No. CN201180069761, dated Jan. 21, 2015.
Office Action dated Oct. 11, 2017 for U.S. Appl. No. 15/141,464; (pp. 1-9).
Office Action for for EP13868466, dated Jul. 20, 2017.
Office Action dated Oct. 30, 2017 for U.S. Appl. No. 15/206,685; (pp. 1-9).
Notice of Allowance dated Jan. 12, 2018 for U.S. Appl. No. 15/044,194; (pp. 1-7).
Office Action dated Jan. 25, 2018 for U.S. Appl. No. 15/146,509; (pp. 1-8).
First Office Action for Japanese Patent Application No. JP2015549820, dated Nov. 14, 2017.
First Examination Report for Australian Patent Applicatin No. 2013368506, dated Oct. 26, 2017.
Second office action for Chinese Application No. CN201380072668. 0, dated Oct. 31, 2017.
Extended European Search Report for EP08857899.2, dated Sep. 7, 2017.
Second Office Action for Chinese Patent Application No. CN2015103917943, dated Nov. 1, 2017.
Notice of Allowance dated Mar. 14, 2018 for U.S. Appl. No. 15/139,144 (pp. 1-12).
Notice of Allowance dated Mar. 19, 2018 for U.S. Appl. No. 15/141,464 (pp. 1-5).
Notice of Allowance dated Mar. 28, 2018 for U.S. Appl. No. 12/610,032 (pp. 1-8).
Notice of Allowance dated Mar. 27, 2018 for U.S. Appl. No. 15/206,685 (pp. 1-5).
Corrected Notice of Allowability dated Apr. 4, 2018 for U.S. Appl. No. 15/139,144 (pp. 1-4).
Office Action dated May 16, 2018 for U.S. Appl. No. 15/666,821 (pp. 1-11).
Office Action for Canadian Patent Application No. CA2826775, dated Jul. 19, 2018.
Extended European Search Report for EP11858396.2, dated Dec. 4, 2017.
Office Action for Korean Patent Application No. 10-2013-7023737, dated Mar. 21, 2018.
Office Action for Japanese Patent Application No. JP2017149845, dated Jul. 24, 2018.
Office Action for Canadian Patent Application No. CA2960103, dated Feb. 14, 2018.
Office Action for CN2015105674626, dated Jul. 1, 2017.
Office Action for Japanese Patent Application No. 2017-121399, dated Jul. 3, 2018.
Office Action dated Sep. 5, 2018 for U.S. Appl. No. 15/341,953 (pp. 1-7).
Office Action dated Sep. 14, 2018 for U.S. Appl. No. 15/147,639 (pp. 1-10).
Notice of Allowance dated Sep. 28, 2018 for U.S. Appl. No. 15/146,509 (pp. 1-5).
Decision of Rejection for Japanese Patent Application No. JP2015549820, dated Oct. 2, 2018.
Examination Report No. 1 for Australian Patent Application No. 2017203445, dated Aug. 29, 2018.
Summons to Oral Proceedings for European Patent Application No. EP09819489.2, dated Oct. 8, 2018.

\* cited by examiner

| | Symbol | Equation | Units | Value | Value | Value | Value | Value | Value | Value | Value |
|---|---|---|---|---|---|---|---|---|---|---|---|
| 4701 Flow rate | Q | | mL/min | 600.0 | 500.0 | 400.0 | 300.0 | 200.0 | 100.0 | 50.0 | 25.0 |
| 4702 Fluid Velocity | V | | mm/s | 416.67 | 347.22 | 277.78 | 208.33 | 138.89 | 69.44 | 34.72 | 17.36 |
| 4703 Probe Separation | d | | mm | 15.0 | 15.0 | 15.0 | 15.0 | 15.0 | 15.0 | 15.0 | 15.0 |
| 4704 Travel Time | t | | sec | 0.0360 | 0.043 | 0.054 | 0.072 | 0.108 | 0.216 | 0.432 | 0.864 |
| 4705 Excitation Frequency | f | | Hz | 27.778 | 23.148 | 18.519 | 13.889 | 9.259 | 4.630 | 2.315 | 1.157 |
| 4706 Receiver Amplitude | $R_p$ | | | 0.00 | 0.00 | 0.00 | 0.00 | 0.00 | 0.00 | 0.00 | 0.00 |
| | | | | 18.00E-3 | 21.60E-3 | 27.00E-3 | 36.00E-3 | 54.00E-3 | 108.00E-3 | 216.00E-3 | 432.00E-3 |

FIG. 47

| | Symbol | Equation | Units | Value | Value | Value | Value | Value | Value | Value | Value | Value |
|---|---|---|---|---|---|---|---|---|---|---|---|---|
| 4901 Flow rate | Q | | mL/min | 600.0 | 500.0 | 400.0 | 300.0 | 200.0 | 100.0 | 50.0 | 25.0 | |
| 4902 Fluid Velocity | V | | mm/s | 416.67 | 347.22 | 277.78 | 208.33 | 138.89 | 69.44 | 34.72 | 17.36 | |
| Probe Separation | d | | mm | 15.0 | 15.0 | 15.0 | 15.0 | 15.0 | 15.0 | 15.0 | 15.0 | |
| 4904 Travel Time | t | | sec | 0.0360 | 0.043 | 0.054 | 0.072 | 0.108 | 0.216 | 0.432 | 0.864 | |
| 4905 Harmonic | | | | 1.000 | | | | | | | | |
| 4906 Excitation Frequency | f | | Hz | 1.157 | 1.157 | 1.157 | 1.157 | 1.157 | 1.157 | 1.157 | 1.157 | |
| 4907 Receiver Amplitude | $R_P$ | | | 0.26 | 0.31 | 0.38 | 0.50 | 0.71 | 1.00 | 0.00 | 0.00 | |
| | | | | 18.00E-3 | 21.60E-3 | 27.00E-3 | 36.00E-3 | 54.00E-3 | 108.00E-3 | 216.00E-3 | 432.00E-3 | |

FIG. 49

| | | Symbol | Equation | Units | Value | Value | Value | Value | Value | Value | Value | Value |
|---|---|---|---|---|---|---|---|---|---|---|---|---|
| 5101 | Flow rate | Q | | mL/min | 600.0 | 500.0 | 400.0 | 300.0 | 200.0 | 100.0 | 50.0 | 25.0 |
| | Flow rate | Q | | mL/sec | 10.00 | 8.333 | 6.667 | 5.000 | 3.333 | 1.667 | 0.833 | 0.417 |
| | Flow rate | Q | | mm³/sec | 10000 | 8333 | 6667 | 5000 | 3333 | 1667 | 833 | 417 |
| 5102 | Channel Height | h | | mm | 3.00 | 3.00 | 3.00 | 3.00 | 3.00 | 3.00 | 3.00 | 3.00 |
| | Channel Height | h | | m | 3.000E-3 | 3.000E-3 | 3.000E-3 | 3.000E-3 | 3.000E-3 | 3.000E-3 | 3.000E-3 | 3.000E-3 |
| 5103 | Channel Width | w | | mm | 8.00 | 8.00 | 8.00 | 8.00 | 8.00 | 8.00 | 8.00 | 8.00 |
| | Channel Width | w | | m | 8.00E-3 | 8.00E-3 | 8.00E-3 | 8.00E-3 | 8.00E-3 | 8.00E-3 | 8.00E-3 | 8.00E-3 |
| 5104 | Channel Length | L | | mm | 50.0 | 50.0 | 50.0 | 50.0 | 50.0 | 50.0 | 50.0 | 50.0 |
| | Channel Length | L | | m | 0.05 | 0.05 | 0.05 | 0.05 | 0.05 | 0.05 | 0.05 | 0.05 |
| 5105 | Channel Area | A | | mm² | 24.00 | 24.00 | 24.00 | 24.00 | 24.00 | 24.00 | 24.00 | 24.00 |
| 5106 | Hydraulic Diameter | $D_h$ | $2hw/(h+w)$ | mm | 4.36 | 4.36 | 4.36 | 4.36 | 4.36 | 4.36 | 4.36 | 4.36 |
| | Hydraulic Diameter | $D_h$ | $2hw/(h+w)$ | m | 4.364E-3 | 4.364E-3 | 4.364E-3 | 4.364E-3 | 4.364E-3 | 4.364E-3 | 4.364E-3 | 4.364E-3 |
| 5107 | Velocity | V | | mm/sec | 416.7 | 347.2 | 277.8 | 208.3 | 138.9 | 69.4 | 34.7 | 17.4 |
| | Velocity | V | | m/sec | 0.417 | 0.347 | 0.278 | 0.208 | 0.139 | 0.069 | 0.035 | 0.017 |
| 5108 | Water | | | | | | | | | | | |
| | Density | ρ | | kg/m³ | 998 | 998 | 998 | 998 | 998 | 998 | 998 | 998 |
| | Dynamic Viscosity | μ | | Kg/(m·s) | 1.000E-3 | 1.000E-3 | 1.000E-3 | 1.000E-3 | 1.000E-3 | 1.000E-3 | 1.000E-3 | 1.000E-3 |
| | Kinematic Viscosity | ν | $\mu/\rho$ | m²/s | 1.002E-6 | 1.002E-6 | 1.002E-6 | 1.002E-6 | 1.002E-6 | 1.002E-6 | 1.002E-6 | 1.002E-6 |
| 5109 | Reynolds Number | $Re_{ch}$ | $VD_h/\nu$ | | 1815 | 1512 | 1210 | 907 | 605 | 302 | 151 | 76 |

*FIG. 51*

|  | Symbol | Equation | Units | Value |
|---|---|---|---|---|
| Excitation Probe | | | | |
| Material: Brass | | | | |
| Density | $\rho$ | | $Kg/m^3$ | 8500 |
| Thermal Conductivity | $\kappa$ | | $W/mK$ | 1.090 |
| Specific Heat | $C_p$ | | $J/KgK$ | 0.380 |
| Size | | | | |
| Diameter | $d$ | | $mm$ | 2.000 |
| Length | $l$ | | $mm$ | 6.000 |
| Volume | $V$ | | $mm^3$ | 18.85 |
| Volume | $V$ | | $m^3$ | 18.85E-9 |
| Mass | $M$ | | $Kg$ | 160.2E-6 |
| Exposed Surface Area | $A_e$ | | $mm^2$ | 6.849 |
| Exposed Surface Area | $A_e$ | | $m^2$ | 6.849E-3 |
| Convection Coefficient | $h$ | | $W/(m^2K)$ | 15.0 |
| Thermal Time Constant | $\tau_t$ | | $sec$ | 593E-6 |

FIG. 52

| % diff. between Pumps A & B | Max. Diff. mL | Swap at | Minutes |
|---|---|---|---|
| 1 % | 2 | 200 mL / 2mL | 100 |
| 2 % | 4 | 200 mL / 4mL | 50 |
| 5 % | 10 | 200 mL / 10mL | 20 |
| 10 % | 20 | 200 mL / 20mL | 10 |

| Contents | Weight of total package |
|---|---|
| Sodium Chloride | 45.5 gm |
| Sodium Bicarbonate | 13.0 gm |
| Dextrose | 27.1 gm |

*FIG. 79*

MANIFOLD DIAPHRAGMS

CROSS REFERENCE

The present application is a continuation application of U.S. patent application Ser. No. 13/852,918, entitled "Manifold Diaphragms" and filed on Mar. 28, 2013, which is a continuation-in-part application of U.S. patent application Ser. No. 13/023,490 (the "'490 Application"), filed on Feb. 8, 2011 and entitled "Portable Dialysis Machine".

The '490 Application is a continuation-in-part of U.S. patent application Ser. No. 12/237,914, filed on Sep. 25, 2008, which relies on U.S. Patent Provisional Application No. 60/975,157 filed on Sep. 25, 2007 for priority.

The '490 Application is a continuation-in-part of U.S. patent application Ser. No. 12/610,032, filed on Oct. 30, 2009, which relies on U.S. Patent Provisional Application No. 61/109,834 filed on Oct. 30, 2008 for priority.

The '490 Application is a continuation-in-part of U.S. patent application Ser. No. 12/324,924, which relies on, for priority, U.S. Provisional Patent Application No. 60/990,959, entitled "System and Method of Changing Fluidic Circuit Between Hemodialysis Protocol and Hemofiltration Protocol", filed on Nov. 29, 2007 and U.S. Provisional Patent Application No. 61/021,962, of the same title, filed on Jan. 18, 2008.

The '490 Application is a continuation-in-part of U.S. patent application Ser. No. 12/249,090, which relies on, for priority, U.S. Provisional Patent Application No. 60/979,113, entitled "Photo-Acoustic Flow Meter", filed on Oct. 11, 2007.

The '490 Application is a continuation-in-part of U.S. patent application Ser. No. 12/575,449, which relies on, for priority, U.S. Patent Provisional Application No. 61/103,271, filed on Oct. 7, 2008, for priority.

The '490 Application is a continuation-in-part of U.S. patent application Ser. No. 12/751,930, which relies on, for priority, U.S. Patent Provisional Application No. 61/165,389, filed on Mar. 31, 2009.

The '490 Application is a continuation-in-part of U.S. patent application Ser. No. 12/705,054, which relies on, for priority, U.S. Patent Provisional Application No. 61/151,912, filed on Feb. 12, 2009.

The '490 Application is a continuation-in-part of U.S. patent application Ser. No. 12/875,888, which is a divisional of U.S. patent application Ser. No. 12/238,055, which relies on, for priority, U.S. Patent Provisional Application No. 60/975,840, filed on Sep. 28, 2007.

The '490 Application is a continuation-in-part of U.S. patent application Ser. No. 12/210,080, which relies on, for priority, U.S. Patent Provisional Application No. 60/971,937, filed on Sep. 13, 2007.

The '490 Application is a continuation-in-part of U.S. patent application Ser. No. 12/351,969, filed on Jan. 12, 2009.

The '490 Application is a continuation-in-part of U.S. patent application Ser. No. 12/713,447, which relies on, for priority, U.S. Patent Provisional Application No. 61/155,548, filed on Feb. 26, 2009.

The '490 Application is a continuation-in-part of U.S. patent application Ser. No. 12/575,450, which relies on, for priority, U.S. Patent Provisional Application No. 61/103,274, filed on Oct. 7, 2008.

All of the above listed specifications are herein incorporated by reference in their entirety.

FIELD OF THE INVENTION

The present invention is directed to a portable dialysis system with improved structural and functional features. In particular, the dialysis system of the present invention is directed to a portable dialysis system with improved modularity, ease of use, and safety features.

BACKGROUND

Blood purification systems, which are used for conducting hemodialysis, hemodiafiltration or hemofiltration, involve the extracorporeal circulation of blood through an exchanger having a semi permeable membrane. Such systems further include a hydraulic system for circulating blood and a hydraulic system for circulating replacement fluid or dialysate comprising the certain blood electrolytes in concentrations close to those of the blood of a healthy subject. Most of the conventionally available blood purification systems are, however, quite bulky in size and difficult to operate. Further, the design of these systems makes them unwieldy and not conducive to the use and installation of disposable components.

Standard dialysis treatment, using an installed apparatus in hospitals, comprises two phases, namely, (a) dialysis, in which toxic substances and scoriae (normally small molecules) pass through the semi-permeable membrane from the blood to the dialysis liquid, and (b) ultrafiltration, in which a pressure difference between the blood circuit and the dialysate circuit, more precisely a reduced pressure in the latter circuit, causes the blood content of water to be reduced by a predetermined amount.

Dialysis procedures using standard equipment tend to be cumbersome as well as costly, besides requiring the patient to be bound to a dialysis center for long durations. While portable dialysis systems have been developed, conventional portable dialysis systems suffer from certain disadvantages. First, they are not sufficiently modular, thereby preventing the easy setup, movement, shipping, and maintenance of the systems. Second, the systems are not simplified enough for reliable, accurate use by a patient. The systems' interfaces and methods of using disposable components are subject to misuse and/or errors in usage by patients. For a portable dialysis system to be truly effective, it should be easily and readily used by individuals who are not health-care professionals, with disposable input and data input sufficiently constrained to prevent inaccurate use.

One conventional design of dialysis systems uses a single pass system. In single pass systems, the dialysate passes by the blood in the dialyzer one time and then is disposed. Single pass systems are fraught with a plurality of disadvantages, arising from the use of large amounts of water. First, assuming a 50% rejection rate by the R.O. (Reverse Osmosis) system, at least 1000 to 1500 ml/min of water is required. Second, a water purification system for providing a continuous flow of 100 to 800 ml/minute of purified water is required. Third, an electrical circuit of at least 15 amps is required, in order to pump 100 to 800 ml of water/minute, and, fourth, a floor drain or any other reservoir capable of accommodating at least 1500 ml/min of used dialysate and RO rejection water.

Conventional systems are also less reliable because of the necessity of using a myriad of tubes comprising the fluid circuits of the purification systems, thus increasing the risks of leakage and breakage. In addition to being difficult to transport due to their large size, conventional dialysis machines also suffer from a lack of flexibility. For example, sorbent based hemodialysis procedures have a particular set of hardware requirements that are not shared by the hemofiltration process. Thus, it would be beneficial to have common hardware components such as the pumping system, which can be used such that the dialysis system can be operated in hemofiltration as well as hemodialysis modes.

Additionally, there is a need for a portable system that can effectively provide the functionality of a dialysis system in a safe, cost-effective, and reliable manner. In particular, there is a need for a compact dialysis fluid reservoir system that can satisfy the fluid delivery requirements of a dialysis procedure while integrating therein various other critical functions, such as fluid heating, fluid measurement and monitoring, leak detection, and disconnection detection.

With respect to disconnection detection in particular, the effective detection of a return line disconnect is difficult, as most known methods are based on monitoring and detecting a change in pressure in the venous return line tubing. Return line disconnection usually occurs due to a needle pull out situation. Since a needle typically offers the highest fluidic resistance in an extracorporeal blood circuit, a pressure change in the return line due to needle disconnect is not significant and cannot be detected easily. The pressure drop is also very low in cases where a catheter disconnects from a patient's body, causing a return line disconnection. Hence, detection of a disconnection in a return venous blood circuit using pressure as an indicator or metric is unreliable and may result in serious injury. Further, methods using detection of air bubbles as an indication of a disconnect cannot be relied upon because a disconnect in a venous return line does not cause air to be drawn in the return line tubing. Consequently, there is need for an improved apparatus and method for detecting a disconnect in a venous return line. Further, there is also need for an apparatus and method which does not require any extra element, such as a moisture pad to be placed at the needle insertion site.

Additionally, there are no satisfactory mechanisms in the prior art for maintaining volumetric accuracy during the dialysis process that can be easily implemented at a reasonable cost. Most of the prior art methods for maintaining volumetric accuracy of replacement fluid and output fluid are not suited for use with disposable devices. One prior art approach for maintaining volumetric accuracy involves weighing both the replacement fluid and output fluid. However, this approach is difficult to implement in practice. Another prior art method comprises the use of volumetric balance chambers for dialysis systems. Such chambers are, however, complex and expensive to build and also not suitable for disposable devices. Volumetric flow measurements are another known method, but the accuracy of this method is not proven. Further, this method is very difficult to implement for a dialysis system in disposable form. Another prior art approach involves using two piston pumps to achieve volumetric accuracy. However, this approach is extremely difficult to implement at a reasonable cost in disposable form, and is also not economical to operate at the required pumping volumes, which are of the order of 200 ml/min. There is therefore a need for a method and a system that can be used to accurately maintain the volume of the fluid infused into and removed from the patient, and which can be implemented inexpensively.

Furthermore, there is a need for a multiple-pass sorbent-based dialysis system that lowers the overall water requirements relative to conventional systems. There is also a need for a manifold that can be used in a single pass sorbent-based dialysis system as well as in the multiple-pass system of the present invention, which offers a lightweight structure with molded blood and dialysate flow paths to avoid a complicated mesh of tubing.

It is also desirable to have a portable dialysis system that has a structural design configured to optimize the modularity of the system, thereby enabling the easy setup, movement, shipping, and maintenance of the system. It is further desirable to have system interfaces, through which patients input data or deploy disposable components, configured to prevent errors in usage and sufficiently constrained to prevent inaccurate use.

SUMMARY

In one embodiment, the specification discloses a dialysis machine comprising a controller unit wherein said controller unit comprises a door having an interior face, a housing with a panel wherein said housing and panel define a recessed region configured to receive said interior face of said door, and a manifold receiver fixedly attached to said panel and a base unit wherein said base unit comprises a planar surface for receiving a container of fluid, a scale integrated with said planar surface, a heater in thermal communication with said planar surface, and a sodium sensor in electromagnetic communication with said planar surface.

Optionally, the manifold receiver comprises at least one of contoured guides, pins, or latches. The panel is configured to provide access to a plurality of pumps. The panel is configured to provide access to four peristaltic pumps in substantially parallel alignment. The interior face comprises four pump shoes. When the door is received into said recessed region, each of said four pump shoes aligns with one of said four peristaltic pumps. At least one of said pump shoes is movably attached to said door by a member and spring. The member is a bolt.

Optionally, the controller unit further comprises a sensor for measuring movement of said member. The controller unit further comprises a controller for receiving a measure of the movement of said member from the sensor and determining a fluid pressure based on said measure.

Optionally, the machine is configured to perform a dialysis treatment using approximately six liters of water, wherein said water is from a non-sterile source. The manifold receiver is configured to receive a molded plastic substrate that defines a first flow path which is fluidically isolated from a second flow path. Each of said first and second flow paths has a hydraulic diameter in a range of 1.5 mm to 7.22 mm. The molded plastic substrate is bonded to a plurality of tubing and wherein said plurality of tubing is bonded to a dialyzer. The controller unit further comprises a member connected to an exterior of said housing, wherein said member is configured to physically receive said dialyzer.

Optionally, the base unit further comprises a member connected to an exterior of said base unit, wherein said member is configured to physically receive said dialyzer. The plurality of tubing is adapted to be removably attached to a sorbent cartridge. The base unit further comprises a member connected to an exterior surface of the base unit, wherein said member is configured to physically receive the sorbent cartridge. The controller unit comprises a bottom surface, wherein said bottom surface comprises a first physical interface and a first data interface.

Optionally, the base unit has a top surface and wherein said top surface comprises a second physical interface configured to complement said first physical interface and a second data interface capable of interfacing with said first data interface. The scale comprises a plurality of flexures and hall sensors, wherein each of said flexures is in physical communication with said planar surface and wherein each of said hall sensors is configured to sense a physical displacement. The sodium sensor comprises a conductivity sensor.

Optionally, the conductivity sensor comprises a coil having a plurality of turns, a capacitor in electrical communication with said coil, wherein said coil and capacitor define a circuit, and an energy source in electrical communication with said circuit. The conductivity sensor outputs a value indicative of a sodium concentration in said fluid based on an energy input required from said energy source to maintain the constant voltage across the capacitor.

Optionally, the base unit comprises at least one moisture sensor. The base unit comprises a door capable of being in an open state or in a closed state and wherein the door is physically blocked from being in the open state when said interior face of the door is received in the recessed region. The base unit comprises a door capable of being in an open state or in a closed state and wherein the door is physically locked into the closed state when said interior face of the door is in said recessed region. The controller unit comprises a plurality of sensors in communication with a molded plastic substrate when said interior face of the door is in said recessed region. At least one of said plurality of sensors comprises a pressure transducer. The pressure transducer is in pressure communication with a flexible membrane integrated into said molded plastic substrate.

Optionally, the controller unit comprises at least one valve component in communication with said molded plastic substrate. The controller unit comprises a plurality of programmatic instructions configured to activate the valve component and wherein activation of said valve component causes fluid flow to be directed through one of two separate fluid paths in said molded plastic substrate. The activation of the valve component is dependent upon a mode of operation of the blood purification system.

Optionally, the valve component has an open position and a closed position and wherein said valve component comprises an orifice closing member adjacent to an orifice through which fluid can flow, a displacement member having a first portion and a second portion, wherein said first portion is adjacent to the orifice closing member when a valve component is in said open position, a first magnet and a second magnet wherein said first and second magnets are sufficiently proximate to said displacement member to exert a magnetic force on said displacement member, and an actuator for generating a magnetic field to move said displacement member toward said first magnet, cause said first portion to press against the orifice closing member, and cause the orifice closing member to close said orifice.

Optionally, the first portion comprises a housing, elastic material, a rod and a gap between said elastic material and said rod. An optical sensor is positioned to sense if a gap in said valve component is present or absent. The first portion comprises a rod and said second portion of said displacement member is a metal body with a diameter greater than said rod. The rod is bonded to a cylinder. The first magnet is larger than said second magnet. The orifice closing member comprises at least one of a diaphragm, an elastic material, and a compressible material. The orifice closing member compresses against a valve seat to close said orifice.

Optionally, the valve component comprises an orifice closing member adjacent to an orifice through which fluid can flow wherein said orifice closing member compresses against a valve seat when the valve is in a closed position, a moveable member that is physically movable relative to said orifice closing member wherein said moveable member moves from a first position when said valve is in an open position to a second position when said valve is in said closed position and wherein, in said second position, the moveable member presses against the orifice closing member to cause said orifice closing member to compress against the valve seat, a first magnet and a second magnet having a separation wherein said first magnet and second magnet generate a magnetic field in the separation and wherein said magnetic field has a direction, and an actuator capable of generating an electromagnetic force, wherein said electromagnetic force reverses the direction of said magnetic field.

Optionally, the dialysis machine comprises an optical sensor positioned to sense if a gap is present or absent. The first magnet and second magnet provide a bearing surface for movement of said moveable member. The first magnet, having a first pole, is larger than said second magnet, having a second pole. The first pole and second pole repel each other and wherein the first magnet and second magnet are configured to have said first pole and second pole face each other.

Optionally, the controller unit further comprises a valve having a first stable state and a second stable state wherein said valve comprises magnets, wherein an input of energy into said valve creates a magnetic force which causes a displacement member to move within said controller unit, wherein the movement of said displacement member causes a change between the first state and the second state, and wherein maintenance of said first or second state does not require energy input.

Optionally, the molded plastic substrate has an orifice wherein said orifice is closed to fluid flow when said valve is in the first stable state and wherein said orifice is open to fluid flow when said valve is in the second stable state. The orifice is closed to fluid flow when said displacement member compresses a material into said orifice. At least one of said plurality of sensors is a flow meter.

Optionally, the flow meter comprises at least two probes, each of said probes having a body and a contact surface positioned on said molded plastic substrate, wherein a first of said at least two probes generates a thermal wave within fluid flowing through said molded plastic substrate in response to a first thermal signal and a second of said at least two probes senses said thermal wave within said fluid. The flow meter further comprises a reference signal generator, wherein said reference signal generator outputs a reference signal. The flow meter further comprises a heat source, wherein said heat source receives said reference signal from said reference signal generator, is configured to thermally engage with the first of said at least two probes, and generates said first thermal signal, having a phase derived from said reference signal. The flow meter further comprises a temperature sensor, wherein said temperature sensor is configured to thermally engage with said second probe, and generate a second thermal signal, having a phase derived from said thermal wave. The flow meter further comprises a multiplier for receiving an input signal from said reference signal generator and for receiving said second thermal signal and for outputting a third signal. The flow meter further comprises a low pass filter for receiving a signal derived from said third signal, and for receiving the reference signal from said reference signal generator, wherein said low pass filter modulates its cutoff frequency based upon the reference signal.

Optionally, the second probe is separated from said first probe by a distance of less than two inches. The dialysis machine further comprises an amplifier for amplifying said third signal and generating the signal derived from said third signal. The body of each of said at least two probes has a diameter in the range of 0.03 inches to 0.15 inches. The contact surface of each of said at least two probes has a diameter in the range of 0.025 inches to 0.2 inches. The second probe comprises a thermistor. The low pass filter generates a filtered signal and wherein the reference signal generator generates said reference signal based, at least in part, on said filtered signal. The flow meter dynamically adjusts said reference signal in order to maintain a constant frequency. The flow meter dynamically adjusts said reference signal in order to maintain a constant phase.

Optionally, the flow meter is configured to project an optical beam into fluid within said molded plastic substrate; detect a resultant acoustic signal at a first point upstream and at a second point downstream in the fluid; determine a phase difference between said acoustic signal detected upstream and said acoustic signal detected downstream in the fluid; and, compute the rate of flow of said fluid from said determined phase difference. The phase difference is determined by subtracting the signals representative of said acoustic signal phase detected upstream and downstream.

Optionally, the flow meter comprises an optical system for projecting an optical beam into fluid flowing through a transparent section of said molded plastic substrate; a first acoustic detector for detecting the acoustic signal at a first point upstream from said transparent section; a second acoustic detector for detecting said acoustic signal at a second point downstream from said transparent section; and, a processor for determining a phase difference between said acoustic signal detected upstream and said acoustic signal detected downstream and for computing from the determined phase difference a rate of flow of fluid in said molded plastic substrate.

The processor for determining the phase difference comprises a subtraction unit. The optical system is a pulsed laser system. The optical beam is projected perpendicular to the direction of flow of said fluid. The flow meter has an operative sensing range between 20 ml/min to 600 ml/min. The flow meter has an operative sensing range between 20 ml/min to 600 ml/min. The controller unit further comprises a reader for detecting identification data embedded in a molded plastic substrate. The controller unit further comprises a temperature sensor which is adapted to be in thermal communication with a molded plastic substrate when said door is in said recessed region.

Optionally, the controller unit comprises a disconnection monitor for determining if a blood line connection to a patient has been disconnected. The disconnection monitor comprises a pressure transducer in pressure communication with a blood flow path in said manifold wherein said pressure transducer generates a signal indicative of a pulse signal in said blood flow path, a cardiac reference signal generator, wherein said cardiac reference signal generator detects and generates a signal indicative of said patient's pulse, a pressure transducer data receiver, wherein said pressure transducer data receiver receives said signal indicative of the pulse signal in said blood flow path, a cardiac reference signal receiver, wherein said cardiac reference signal receiver receives said signal indicative of the patient's pulse, and a processor, wherein said processor cross-correlates said signal indicative of the pulse signal in said blood flow path and said signal indicative of the patient's pulse to generate data indicative of a disconnection of the blood line connection to the patient.

Optionally, the disconnection monitor further comprises a controller, wherein said controller triggers an alarm based upon said data indicative of a disconnection of the blood line connection to the patient. The disconnection monitor further comprises a controller, wherein said controller shuts down a dialysis pump based upon said data indicative of a disconnection of the blood line connection to a patient.

Optionally, the pressure transducer non-invasively generates a signal indicative of a pulse signal in said blood flow path. The processor cross-correlates said signal indicative of the pulse signal in said blood circuit and said signal indicative of the patient's pulse by computing a sum of products of corresponding pairs of points of the signal indicative of the pulse signal in said blood circuit and said signal indicative of the patient's pulse within a specified time frame.

Optionally, the disconnection monitor further comprises programmatic instructions for directing a patient to first attach said cardiac signal reference generator prior to starting a dialysis pump. The disconnection monitor further comprises programmatic instructions for directing the system to capture said signal indicative of the pulse signal in said blood flow path prior to starting a dialysis pump.

Optionally, the controller unit further comprises a display, a scale, a bar code reader, and a memory storing a plurality of programmatic instructions wherein, upon execution, said instructions generate a) a first graphical user interface for presentation on said display, wherein said first graphical user interface displays each additive required for use in a dialysis treatment, b) a second graphical user interface for presentation on said display, wherein said second graphical user interface prompts a user of said system to submit a plurality of additives to scanning using said bar code scanner and c) a third graphical user interface for presentation on said display, wherein said third graphical user interface prompts a user of said system to submit a plurality of additives to measurement using said scale.

Optionally, the scale is a digital scale. The bar code scanner provides a visual indication of a successful read. The memory further comprises a table associating a plurality of additive names with a plurality of bar codes. The memory further comprises a table associating a plurality of additives with a plurality of weight values. The first graphical user interface displays a visual representation of the additive packaging. The third graphical user interface only prompts the user of said system to submit an additive to measurement using said scale if a bar code of the additive is not recognized. The third graphical user interface only prompts the user of said system to submit an additive to measurement using said scale if a bar code for the additive is not available.

Optionally, the controller unit further comprises a display, a scale comprising a plurality of magnets, an electronic reader, and a memory storing a plurality of programmatic instructions wherein, upon execution, said instructions generate a) a first graphical user interface for presentation on said display, wherein said first graphical user interface prompts a user of said system to submit a plurality of additives to scanning using said bar code scanner and b) a second graphical user interface for presentation on said display, wherein said second graphical user interface prompts a user of said system to submit a plurality of additives to measurement using said scale.

Optionally, upon execution, the instructions further generate a third graphical user interface for presentation on said display, wherein said third graphical user interface displays each additive required for use in the dialysis treatment. The scale is a digital scale and wherein said digital scale generates data representative of a weight of an object placed on said digital scale. The digital scale further comprises at least three flexures. Each of said flexures comprises a magnet and a corresponding hall sensor.

Optionally, the dialysis system further comprises a molded plastic substrate wherein said molded plastic substrate comprises a first flow path and a second flow path defined therein and wherein said first flow path and said second flow path are fluidically separated by a valve. The controller unit further comprises a memory storing a plurality of programmatic instructions, wherein said programmatic instructions are configured to define a first state of said valve and a second state of said valve depending upon a selected mode of operation. The selected mode of operation is either a priming mode or a treatment mode. The first state of the valve places said first flow path in fluid communication with said second flow path. The second state of the valve places said first flow path in fluid isolation from said second flow path. The dialysis system further comprises a molded plastic substrate wherein said substrate comprises a first fluid circuit for infusing fluid into a patient and a second fluid circuit for removing fluid from the patient.

Optionally, the controller unit further comprises a first pump configured to alternately operate on said first circuit and said second circuit; a second pump configured to alternately operate on said second circuit and said first circuit; and a controller for causing said first pump to alternatively operate on said first circuit and said second circuit and for causing said second pump to alternatively operate on said first circuit and said second circuit, wherein each of the said first pump and second pump operate only one circuit at a given time.

Optionally, the first pump causes a higher amount of fluid to be pumped per unit time than the second pump. The first and second pumps alternately operate on said first and second circuits for a time interval, wherein said time interval is derived from an allowable difference in the amount of fluid pumped per unit time by the said first and second pumps. The first and second pumps are peristaltic pumps. The dialysis system further comprises a restrictor for equalizing a pressure differential between said first and second circuits. The restrictor is active and equalizes said pressure differential based upon a measured pressure differential derived from a first pressure sensor in said first circuit and from a second pressure sensor in said second circuit.

Optionally, the panel further comprises a funnel defined by two sloped surfaces leading to a channel and wherein said channel comprises at least one moisture sensor. When the door is received into said recessed region, the funnel is located below the manifold and configured to channel fluid leaking from said manifold toward said moisture sensor.

Optionally, the bottom surface of the controller unit is adapted to be removably attached to a top surface of said base unit. The controller unit is in electrical communication with the base unit. The controller unit is physically detached from the base unit. The controller unit is in data communication with the base unit. The controller unit is in fluid communication with the base unit.

In another embodiment, the present invention is directed toward a dialysis machine comprising a first unit wherein said first unit comprises a door having a first face, a housing attached to said door, wherein housing has a second face, at least one manifold receiver fixedly attached to said second face, and a display for displaying a graphical user interface, and a second unit wherein said second unit comprises a planar surface for supporting a container of fluid, a weighing means integrated with said planar surface, a heater in thermal communication with said planar surface, and a sodium sensor proximate to said planar surface. Optionally, the manifold receiver is configured to receive a molded plastic substrate that defines a first flow path which is fluidically isolated from a second flow path. The molded plastic substrate comprises a first layer; a second layer; a first flow path defined by a first surface of the first layer and a first surface of the second layer; a second flow path defined by a first surface of the first layer and a first surface of the second layer; and a valve in fluid communication with both said first flow path and said second flow path wherein said valve has a first state and a second state and wherein, when in said first state, the first flow path and second flow path are in fluid isolation and when in said second state, the first flow path and second flow path are in fluid communication.

Optionally, the molded plastic substrate comprises a first plurality of ports in opposing alignment to a second plurality of ports. At least one of said first plurality of ports and second plurality of ports comprises a member having an external cylindrical housing, wherein said member has an interior space defined by a central axis. The central axis is angled relative to a plane within which said plastic substrate lies. The angle is in a range of 5 degrees to 15 degrees. At least one of said first plurality of ports is defined by a cross-sectional area having a first diameter and a second diameter perpendicular to the first diameter. At least one of said first plurality of ports is connected to a port channel defined by a cross-sectional area having a third diameter and a fourth diameter perpendicular to the third diameter, wherein the third diameter is greater than the first diameter and wherein the fourth diameter is less than the second diameter. The port channel comprises at least one protruding member having a height less than the fourth diameter. The port channel is covered by a flexible membrane. The port channel comprises at least one protrusion configured to prevent a flexible membrane from collapsing into said port channel and completely occluding said port channel. The cross-sectional area of said port channel is different from said cross-sectional area of said port and the cross-sectional area of said port channel is configured to maintain a substantially constant velocity of fluid passing through said port and into said port channel.

Optionally, the molded plastic is defined by a first segment, second segment, and third segment; wherein said first segment is parallel to said second segment; wherein said third segment is perpendicular to, and attached to, each of said first segment and second segment; and wherein said first, second, and third segments define a first flow path that is fluidically isolated from a second flow path.

Optionally, the first segment has a first plurality of ports and said second segment has a second plurality of ports, and wherein said first and second plurality of ports are in alignment. At least one of said first plurality of ports and second plurality of ports comprises a member having an interior space defined by a central axis. The central axis is angled relative to a plane within which said first and second segments lie. The angle is in a range of 5 degrees to 15 degrees. At least one of said first plurality of ports is defined by a cross-sectional area having a first diameter parallel to a length of the first segment and a second diameter perpendicular to the first diameter. At least one of said first plurality of ports is connected to a port channel having a cross-sectional area with a third diameter parallel to the length of the first segment and a fourth diameter perpendicular to the third diameter, wherein the third diameter is greater than the first diameter and wherein the fourth diameter is less than the second diameter. The port channel comprises at least one protruding member having a height less than the fourth diameter. The port channel is covered by a flexible membrane. The port channel comprises at least one protrusion configured to prevent a flexible membrane from collapsing into said port channel. The cross-sectional area of said port channel is different from said cross-sectional area of said port and the cross-sectional area of said port channel is configured to maintain a substantially constant Reynolds number of fluid passing through said port and into said port channel.

Optionally, the third segment is attached to a center of the first segment and the second segment. The third segment is not attached to a center of the first segment or the second segment. The first segment has at least one port wherein a portion of an interior of said port is defined by a flat base. The first segment and said second segment have a length in a range of 4 to 7 inches and a width in a range of 0.5 to 1.5 inches. The third segment has a length in a range of 2.5 to 4.5 inches. The first segment has a first length and a first width, said second segment has a second length and a second width, and said third segment has a third length and a third width, and wherein said first length and said second length are greater than the third width and said first width and second width are less than the third length. The first segment has a first length and a first width and said second segment has a second length and a second width, and wherein said first length is equal to said second length and said first width is equal to said second width.

Optionally, the manifold receiver is configured to receive a molded plastic substrate and wherein a tubular segment connects said molded plastic substrate with a dialyzer. The dialysis machine comprises a receiver to removably attach said dialyzer to an external surface of said dialysis machine. The tubular segment comprises a disposable conductivity probe, having an internal volume, wherein said internal volume receives fluid flowing through said tubular segment. The disposable conductivity probe is adapted to removably connect to mating probes positioned on an external surface of said dialysis machine.

In another embodiment, the present invention is directed toward a dialysis machine comprising a first unit in data communication with a second unit, wherein said first unit comprises a door with a pressure plate positioned on an interior face of the door, a housing with a panel wherein said housing and panel define a recessed region configured to receive said interior face of said door, an alignment mechanism fixedly attached to said panel, wherein said alignment mechanism is configured to detachably receive a manifold on said panel and position said manifold against said pressure plate when the door is received into said recessed region and wherein said second unit comprises a planar surface for receiving a container of fluid, a weighing means integrated with said planar surface, a heater in thermal communication with said planar surface, and a sodium sensor proximate to said planar surface.

In another embodiment, the present invention is directed towards a multiple-pass, sorbent-based hemodiafiltration system, advantageously combining hemofiltration and hemodialysis in a multiple pass configuration.

In another embodiment, the present invention is directed toward manifold supports for blood purification systems, such as, but not limited to hemodiafiltration and ultrafiltration. In one embodiment, the manifold of the present invention comprises a composite plastic manifold, into which the blood and dialysate flow paths are molded. This plastic based manifold can be used with the multiple-pass sorbent-based hemodiafiltration system of the present invention.

In another embodiment, blood purification system components, such as sensors, pumps, and disposables are integrated into the molded manifold. Disposable items such as but not limited to dialyzer and sorbent cartridges, are detachably loadable on to, or in fluid communication with, the manifold. Disposable items such as but not limited to dialyzer and sorbent cartridges, are fixedly attached to tubing that is fixedly attached to, and in fluid communication with, the manifold.

In yet another embodiment, an ultrafiltration system is integrated into a manifold by molding both blood and ultrafiltrate flow paths in the manifold. In one embodiment, the manifolds disclosed herein comprise single, composite plastic structures, also referred to as substrates or housings, that can be made by combining two plastic substrate halves.

In another embodiment, the present invention is directed towards a dialysis system that supports an electronic-based lockout system. Accordingly, in one embodiment, a reader is mounted on the system housing(s) and/or manifold(s), such as but not limited to the hemodiafiltration and ultrafiltration manifolds, and reads identification indicia on disposable items that are loaded onto the dialysis housing(s) and/or manifolds. The reader communicates with a database over a network, such as a public network or private network, to check if the disposable items are valid, accurate, or of sufficient integrity to be safe and ready for use. This is done by querying information on the disposable items from the remote database, based on the identification indicia of the items. If the disposable item has an "invalid" or "compromised" status, (based on the information received from the database) the system "locks out" the use of the loaded disposable, and thus does not allow the user to proceed with using the system for treatment.

The present specification is also directed toward a diaphragm integrated into a disposable manifold for use in a dialysis machine and adapted to be compressed by components that are within said dialysis machine and external to said disposable manifold, said diaphragm comprising: a convex exterior surface protruding outward from the manifold and fixedly attached to said manifold at a first end and at a second end, wherein a distance between the first end and second end defines a length and height of said diaphragm, wherein the diaphragm at the first end and second end has the same height as the manifold, wherein the height of said convex exterior surface increases from said first end to a first height relative to the manifold, and wherein the height of said convex exterior surface decreases from said first height to the second end.

In one embodiment, the first height of said diaphragm is between 0.03 and 0.04 inches relative to the manifold.

In one embodiment, the diaphragm has a thickness along the length from the first end to the second end wherein said thickness is substantially constant along said length. In one embodiment, the thickness of said diaphragm is between 0.03 and 0.04 inches.

In one embodiment, the total length of said diaphragm is between 0.625 and 0.675 inches.

The present specification is also directed toward a manifold comprising one or more of the diaphragms having a convex exterior surface described directly above.

The present specification is also directed toward a diaphragm integrated into a disposable manifold for use in a dialysis machine and adapted to be compressed by components that are within said dialysis machine and external to said disposable manifold, said diaphragm comprising: a first substantially planar surface having a first end and a first bend wherein a distance between the first end and first bend defines a length and a height of said first planar surface, wherein said first end is fixedly attached to said manifold, further wherein said height of said first planar surface is substantially equal to the height of said manifold; a convex exterior surface continuing and protruding outward from said first bend of said first planar surface, said convex exterior surface continuing from said first bend to a second bend, wherein a distance between the first bend and second bend defines a length and height of said convex surface, wherein the convex surface at the first bend and the second bend has the same height as the first planar surface, wherein the height of said convex exterior surface increases from said first bend to a second height relative to the manifold, and wherein the height of said convex exterior surface decreases from said second height to the second bend; and, a second substantially planar surface, continuing from said second bend to a second end, wherein a distance between the second bend and second end defines a length and a height of said second planar surface, wherein said second end is fixedly attached to said manifold, further wherein said height of said second planar surface is substantially equal to said height of said first planar surface and said length of said second planar surface is substantially equal to said length of said first planar surface.

In one embodiment, the second height of said convex exterior surface is between 0.03 and 0.04 inches relative to said first substantially planar surface.

In one embodiment, the diaphragm has a thickness along a length from the first end to the second end wherein said thickness is substantially constant along said length. In one embodiment, the thickness of said diaphragm is between 0.03 and 0.04 inches.

In one embodiment, a total length of said diaphragm from said first end of said first planar surface to said second end of said second planar surface is between 0.625 and 0.675 inches. In one embodiment, the length of said convex exterior surface is between 0.125 and 0.15 inches and the length of said first planar surface and the length of said second planar surface are between 0.25 and 0.2625 inches.

The present specification is also directed toward a manifold comprising one or more of the diaphragms having first and second planar surfaces and a convex exterior surface described directly above.

The present specification is also directed toward a diaphragm integrated into a disposable manifold for use in a dialysis machine and adapted to be compressed by components that are within said dialysis machine and external to said disposable manifold, said diaphragm comprising: a first sloped surface having a first end and a first bend wherein a distance between the first end and first bend defines a length of said first sloped surface, wherein said first end is fixedly attached to said manifold, further wherein said first sloped surface has a first height at said first end and a second height at said first bend, wherein said second height of said first sloped surface is greater than said first height of said first sloped surface relative to said manifold, further wherein said first height of said first sloped surface is substantially equal to the height of said manifold; a convex exterior surface continuing and protruding outward from said first bend of said first sloped surface, said convex exterior surface continuing from said first bend to a second bend, wherein a distance between the first bend and second bend defines a length and height of said convex surface, wherein the height of the convex surface at the first bend and the second bend is the same as the second height of the first sloped surface, wherein the height of said convex exterior surface increases from said first bend to a second height of said convex surface relative to the second height of said first sloped surface, and wherein the height of said convex exterior surface decreases from said second height of said convex surface to the second bend; and, a second sloped surface, continuing from said second bend to a second end, wherein a distance between the second bend and second end defines a length of said second sloped surface, wherein said second end is fixedly attached to said manifold, further wherein said second sloped surface has a first height at said second bend and a second height at said second end, wherein said first height of said second sloped surface is greater than said second height of said second sloped surface relative to said manifold, further wherein said second height of said second sloped surface is substantially equal to said first height of said first sloped surface, said first height of said second sloped surface is substantially equal to said second height of said first sloped surface, and said length of said second sloped surface is substantially equal to said length of said first sloped surface.

In one embodiment, the second height of said convex exterior surface is between 0.01 and 0.02 inches relative to said second height of said first sloped surface and said first height of said second sloped surface and, the second height of said first sloped surface and said first height of said second sloped surface are approximately 0.02 inches relative to said manifold.

In one embodiment, the diaphragm has a thickness along a length from the first end to the second end wherein said thickness is substantially constant along said length. In one embodiment, the thickness of said diaphragm is between 0.03 and 0.04 inches.

In one embodiment, a total length of said diaphragm from said first end of said first sloped surface to said second end of said second sloped surface is between 0.625 and 0.675 inches. In one embodiment, the length of said convex exterior surface is between 0.125 and 0.15 inches and the length of said first sloped surface and the length of said second sloped surface are between 0.25 and 0.2625 inches.

The present specification is also directed toward a manifold comprising one or more of the diaphragms having first and second sloped surfaces and a convex exterior surface described directly above.

These, and other embodiments, are described in the Detailed Description section which should be read in light of the Figures.

BRIEF DESCRIPTION OF THE DRAWINGS

These and other features and advantages of the present invention will be appreciated, as they become better understood by reference to the following detailed description when considered in connection with the accompanying drawings, wherein:

FIG. 47 depicts a plurality of variables defining the operation of an exemplary thermal flow meter;

FIG. 49 depicts a plurality of variables defining the operation of an exemplary thermal flow meter;

FIG. 51 depicts a plurality of variables defining the operation of an exemplary thermal flow meter;

FIG. 52 depicts a plurality of variables defining the operation of an exemplary thermal flow meter;

FIG. 67 is a chart representing one embodiment of the use of pump swapping to achieve volumetric accuracy;

FIG. 79 is a chart representing one embodiment of a plurality of additives for use in the dialysis system;

DETAILED DESCRIPTION

Figure 1:
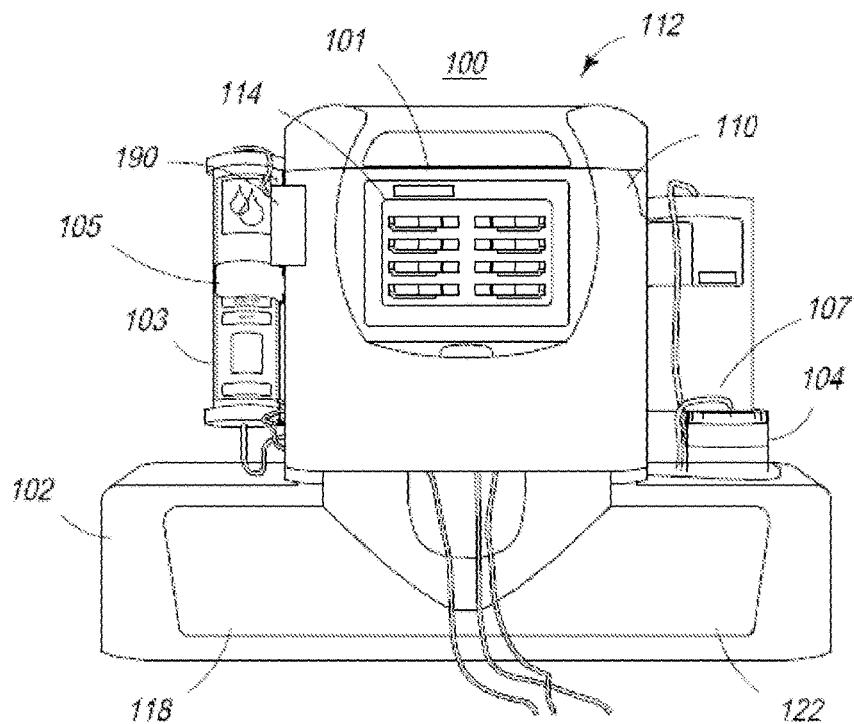
FIG. 1 is a front view of one embodiment of the dialysis system of the present invention.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a", "an", "the", "one or more", and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Device Structure

Figure 2:
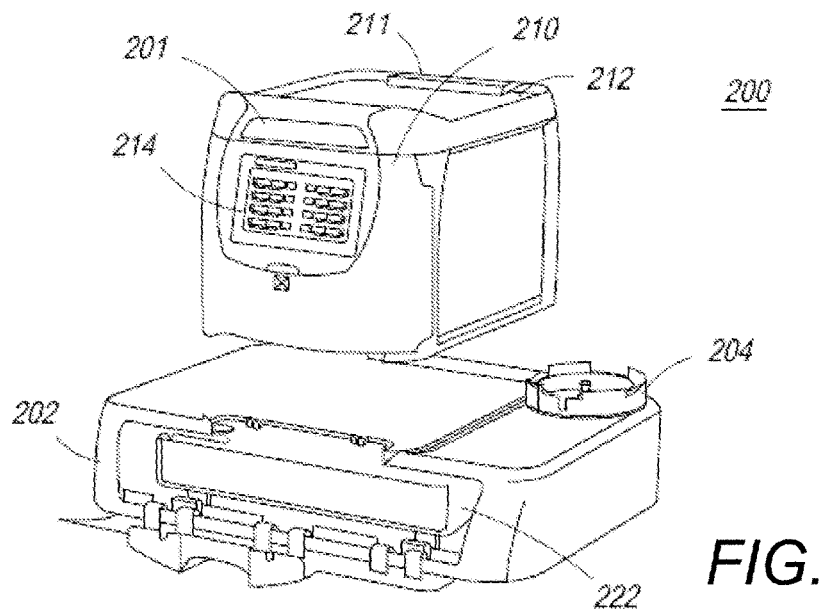
FIG. 2 is a view of one embodiment of the dialysis system showing the modularity of the system.

The present specification discloses embodiments of dialysis systems that are modular and portable, with improved safety and functionality. Referring to FIGS. 1 and 2, in one embodiment, the dialysis system 100, 200 comprises a top unit 101, 201 that is detachably affixed to a base 102, 202. The base 102, 202 comprises a reservoir 122, 222 for fluid storage, measurement, and monitoring. The top unit 101, 201, also referred to as the main unit or controller unit, comprises a graphical user interface 114, 214, pumping unit, and a door 110, 210 with a power lock and mechanical backup mechanism, as further discussed below.

Figure 3:
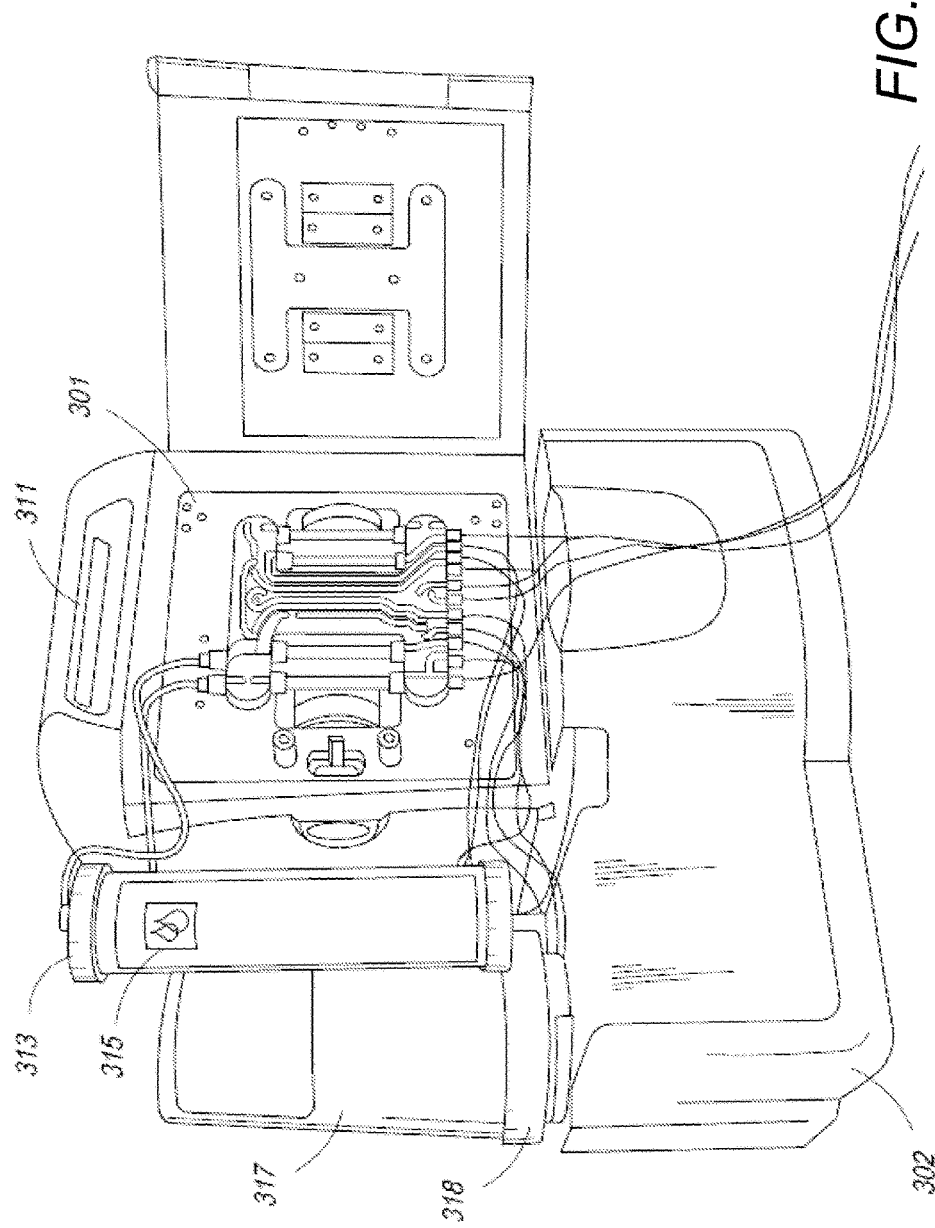
FIG. 3 is a view of the front of one embodiment of the dialysis system, with the door open.

To a first side of the top unit 101, 201 is a clasp 105 used to detachably affix a dialyzer 103. To a second, opposing side of the top unit 101, 201 is a sorbent cartridge locking base 104, 204 used to detachably affix a sorbent cartridge 107. It should be appreciated that the clasp 105, hemofilter 103, 315 sorbent cartridge locking base 104, 318 and sorbent cartridge 107, 317 can be positioned on the same side of the top unit 101, as shown in FIG. 3. In either case, the bottom unit has a sufficiently larger area relative to the top unit such that shelves are formed on either side of the top unit to hold the sorbent cartridge, to hold an infusate jar, to capture any spillage, and/or to channel any leaks into a leak detector.

Between the dialyzer 103 and door 110 are anti-coagulant pumps in the form of syringe pumps 190. Optionally, the top unit 101 can comprise a bottle holder that has a spiked base to receive a bottle, top-down, within the bottle holder housing. Infusion lines are connected to the inlet of the blood pump, outlet of the blood pump, or outlet of the dialyzer (blood side). The infusion lines could also 'thread' through air bubble detectors to sense if/when the anti-coagulant is emptied or blocked.

Figure 4:
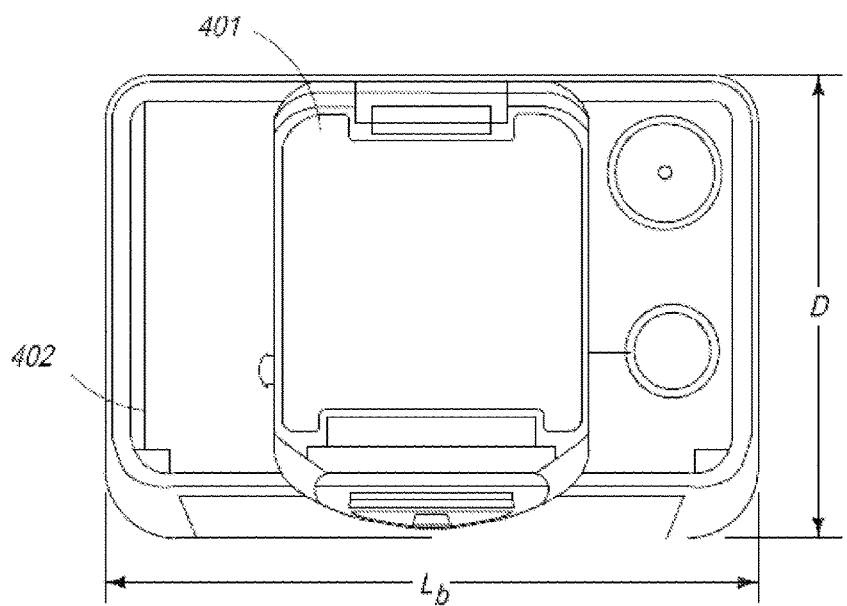
FIG. 4 is a top view of one embodiment of the portable dialysis system with exemplary dimensions denoted.
Figure 5:
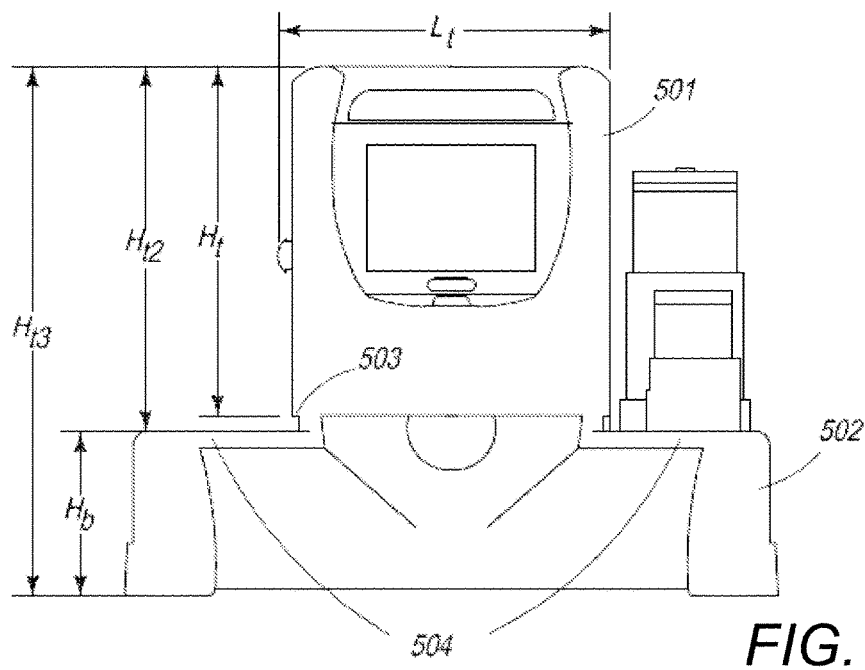
FIG. 5 is a front view of one embodiment of the portable dialysis system with exemplary dimensions denoted.

In one embodiment, referring to FIG. 4, the top unit 401, which comprises the user interface and controller, has the same depth, but a different length and height than the base unit 402, which comprises a reservoir integrated with a scale. In this exemplary embodiment, both the top unit 401 and bottom unit 402 have a depth D in the range of 10 to 30 inches, more preferably approximately 19 inches. Referring now to FIGS. 4 and 5 simultaneously, in this exemplary embodiment, the top unit 401, 501 has a length Lt in the range of 6 to 20 inches, more preferably approximately 14 inches, while the bottom unit 402, 502 has a length Lb in the range of 14 to 40 inches, more preferably 27 inches. In this exemplary embodiment, the top unit 401, 501 has a height Ht in the range of 7 to 21 inches, more preferably approximately 14.5 inches, while the bottom 402, 502 unit has a height Hb in the range of 3 to 11 inches, more preferably 7 inches.

As shown in FIG. 5, the base unit 402, 502 may further be defined by two shoulders 504, each extending outward, along the length of the base unit 502, from the sides of a centrally positioned top unit 501. The top unit is preferably positioned in the center of the base unit 502, as measured by length Lb in FIG. 4. Accordingly, the shoulder 504 can be defined as having a length in the range of 4 inches to 10 inches, more preferably approximately 7 inches. Extending upward from the surface of the base unit 502, where shoulders 504 physically meet top unit 501, is a lip 503 that defines a surface upon which top unit 501 is aligned and placed. The lip 503 is contiguous around the base of the top unit 501, having the same length and depth as the top unit 501, with a height defined as the difference between Ht2 and Ht. In one embodiment, the lip height is in the range of 0.1 to 3.5 inches, more preferably 0.6 inches. The overall height of the system, Ht3, is in the range of 10 to 35 inches, more preferably 22 inches.

The external housing structures defining the top unit 501 and base unit 502 may be characterized as rectangular parallelepipeds, cuboids, or boxes, each with four sides, a top, and a bottom. In an exemplary embodiment, for both the top unit 501 and base unit 502, two of the four sides, each having an exterior and interior surface, have the same height, length, and depth, while the top and bottom structures, each having an exterior and interior surface, have the same height, length, and depth.

It should be appreciated that the system configurations shown in FIGS. 1, 2, 3, 4, and 5 are exemplary and not limiting. For example, shown in FIG. 3, the top unit 301 may be positioned on one side of the base unit 302 (creating an asymmetric base), as opposed to being centrally positioned on top of the base unit 302 relative to the overall length of the base unit 302 (creating a symmetric base). While placement of the top unit 301 to one side of the base unit 302 has the advantage of placing all tubing connections and consumables on the same side of the system, sorbent cartridge 317 and dialyzer 313 are unnecessarily crowded together, making the machine more difficult to use.

Figure 6:
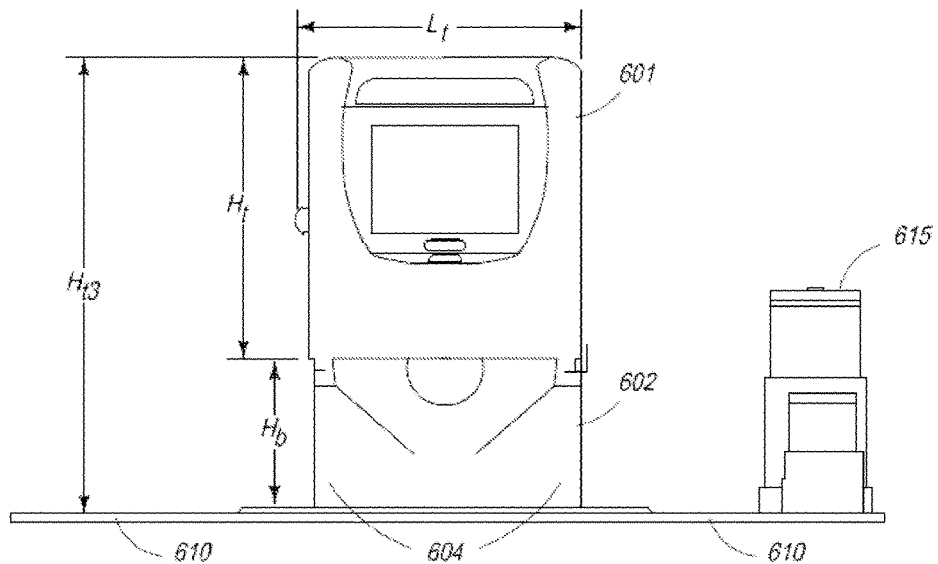
FIG. 6 is a front view of another embodiment of the dialysis system.

Referring to FIG. 6, in another embodiment, the top unit 601, which comprises the user interface and controller, has the same depth and length, but a different height than the base unit 602, which comprises a reservoir integrated with a scale 604. In this exemplary embodiment, both the top unit 601 and bottom unit 602 have a depth in the range of 16.0 to 20.0 inches, more preferably less than 24 inches and approximately 17.0 inches. In this exemplary embodiment, the top unit 601 and bottom unit 602 have a length Lt in the range of 10.0 to 15.0 inches, more preferably less than 18 inches or approximately 13.0 inches. In this exemplary embodiment, the top unit 601 has a height Ht in the range of 10.0 to 14.0 inches, more preferably less than 17 inches and approximately 12.0 inches, while the bottom unit 602 has a height Hb in the range of 9.0 to 11.0 inches, more preferably less than 13 inches and approximately 9.5 inches. The total height of both units together is denoted by Ht3. The base unit 602 and top unit 601 therefore have the same footprint, although different heights. It should be appreciated that the base unit 602 and top unit 601 could have the same footprint and same height as well.

Extending out from under the base unit 602 are flattened lateral wings 610 which comprise connectors for attaching the sorbent cartridge and infusate container 615. The surface of the lateral wings 610 may comprise a membrane that can electronically sense the presence of moisture and/or may be angled to direct any moisture to strategically placed sensors.

Figure 7:
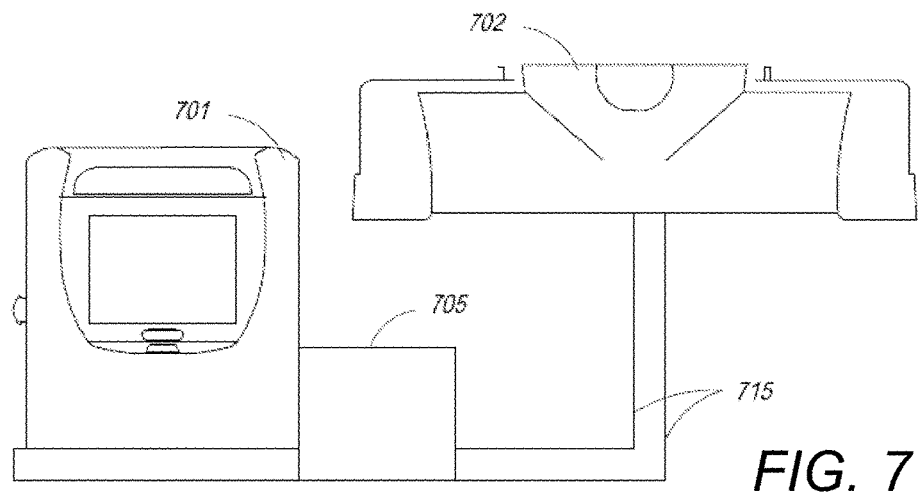
FIG. 7 is a view of another embodiment of the dialysis system demonstrating the modularity of the system.

Referring to FIG. 7, in another embodiment, the top unit 701 may physically interface with a docking station 705, which electronically and fluidically interfaces 715 with a remotely located base unit 702. While the reservoir located in the base unit 702 would still have to be in fluid communication with the controller 701, the use of a docking station 705 would allow for greater flexibility in switching out the size of the reservoir system being used, thereby allowing one controller design to be implemented under multiple use scenarios or for a wider range of patients, e.g. small vs. large patients.

Figure 8:
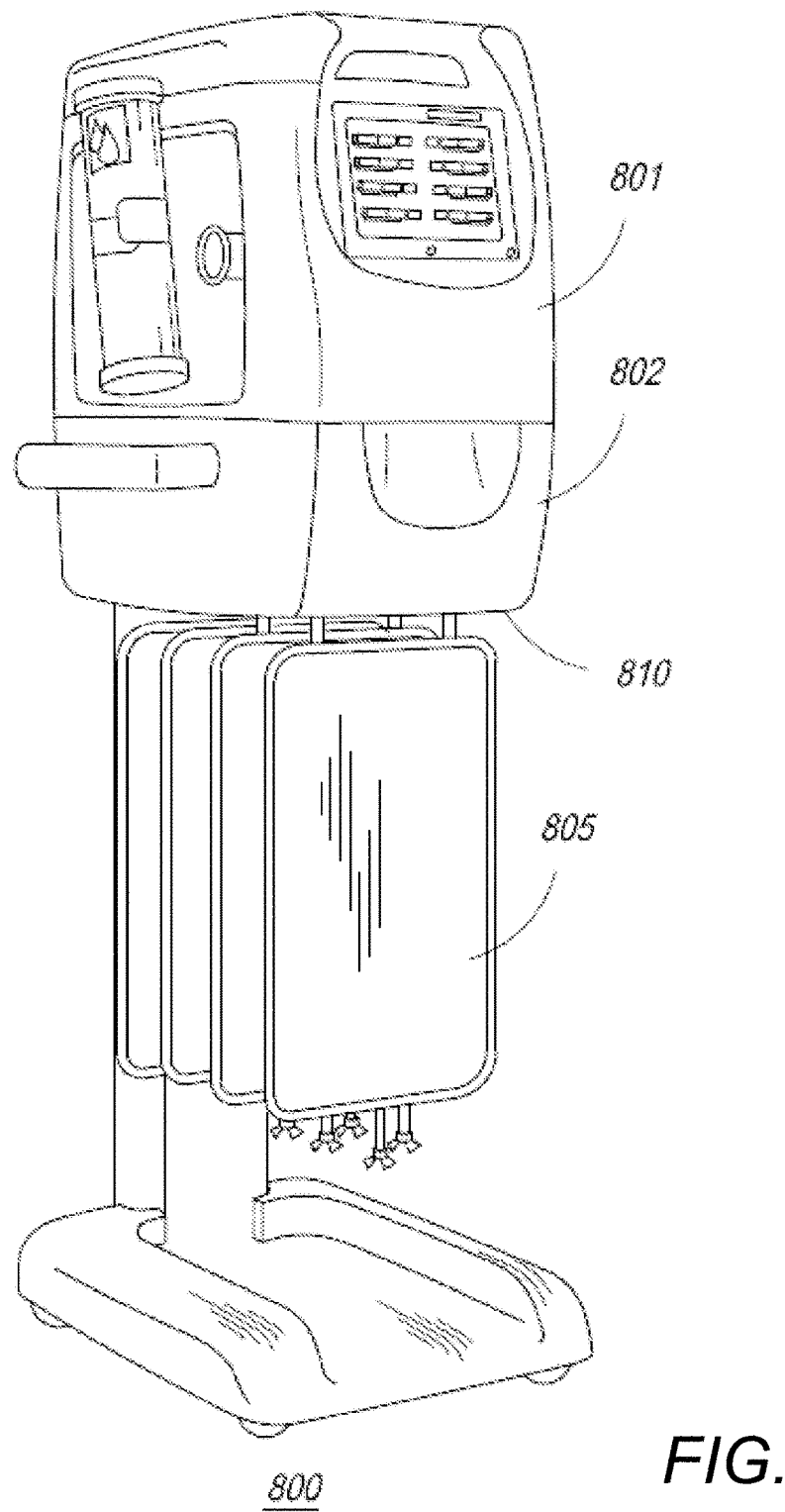
FIG. 8 is a front view of another embodiment of the dialysis system.

Referring to FIG. 8, in yet another embodiment, the portable dialysis system 800 incorporates an upper subsystem (pumping and control unit) 801, as previously described, with a lower assembly 802. The lower portion 802 of the system 800 comprises an independent, suspended bag of dialysate 805. That is, the dialysate bag 805 is not incorporated as a part of the lower assembly 802, as in the previously disclosed embodiments. Further, the lower assembly 802 is designed such that it incorporates a weighing mechanism integrated into the structures 810 that suspend the independent bags of dialysate 805. This arrangement is suitable when the dialysis system is configured to operate in hemofiltration mode because, in the hemofiltration mode, various sensors used in sorbent based dialysis, such as ammonia, pH and sodium sensors, are not required; therefore the entire reservoir assembly module can be removed, and the system 800 can simply be operated using a bag of dialysate 805. The modular and compact design of the lower subsystem 802 makes its removal easy, and simplifies the system operating in hemofiltration mode by taking away the unnecessary components. This is another advantage of integrating the major components of the dialysate circuit used during hemodialysis mode into a lower base unit 802.

The dialysis system of the present invention achieves functional and operational parameters that represent a substantial improvement over the prior art. Referring to the embodiments shown in FIGS. 1 through 6, the top unit is in the range of approximately 20-40 pounds, and more particularly 30 pounds, and the bottom unit is in the range of approximately 15-30 pounds, and more particularly 22 pounds, thereby weighing less than prior art systems. The top unit is in the range of approximately 1 to 4 cubic feet, and more particularly 2.3 cubic feet, and the bottom unit is in the range of approximately 1 to 4 cubic feet, and more particularly 2.8 cubic feet, thereby having a smaller volume than prior art systems.

Furthermore, the dialysis system uses less water than prior art systems. While conventional systems use approximately 120 liters per treatment, in one embodiment, the present system uses between 3 and 8 liters, and more particularly between 5 and 6 liters. Furthermore, the system does not require a home drain, supply connection, or separate outlet to address excess water.

Additionally, the system design is more compact, with low power requirements (only 300 at peak and 50 to 100 W during operation), no separate fluid bags required for priming or travel, and integrated pumps. The device operates using a blood flow range of 20-600 Qb (ml/min), a dialysate flow of 50-500 Qd (ml/min). The volumetric accuracy is also precise at less than +/−30 ml/hr.

As shown in FIG. 2, the dialysis system is modular. In one embodiment, the top unit 201 can be physically separated from the bottom unit 202. The top unit 201 contains the primary electronics of the system, including the graphical user interface, controllers, and pumps, integrally formed into a self-contained housing. The larger, bulkier bottom unit 202 contains the reservoir 222. Separation of the system electronics from the reservoir allows the portable dialysis system to be separated into multiple units for installation, service, and travel, with each subunit being easily handled, packaged and carried. The design specifically sizes components for shipping via UPS or other door to door carriers. It further provides flexibility in product growth. For example, if improvements are made to the controller unit or, separately, to the reservoir (such as reducing fluid volume or a change in volume scale measurement), an existing customer need only upgrade one of the two component parts, not both. Similarly, if only one of the two components breaks (e.g. the pump burns out), a customer need only send in one for repair or purchase one of the two components.

To enable the above described modularity, embodiments of the present invention employ a latching mechanism that, in a first configuration, securely attaches the bottom unit 202 to the top unit 201 and can be manipulated to removably detach the bottom unit 202 from the top unit 201. Even though the two systems could be simply stacked atop each other, without a latch, the presence and use of a latch reduces the likelihood of an accidental disconnection. Furthermore, when latched together the device is easier to move. The latch mechanism preferably uses no tools and is simply achieved using male/female mating connections present on the base of the top unit and top surface of the bottom unit. Further preferably, the latch mechanism is designed to ensure solid alignment between the top and bottom units, thereby enabling the use of electronic components (such as exposed electronic connectors on the bottom of the top unit and top of the bottom unit as further described below) which, when the units are properly aligned, automatically come into contact and complete a power circuit. This permits the use of a single power supply and simple connection/disconnection.

Figure 9:
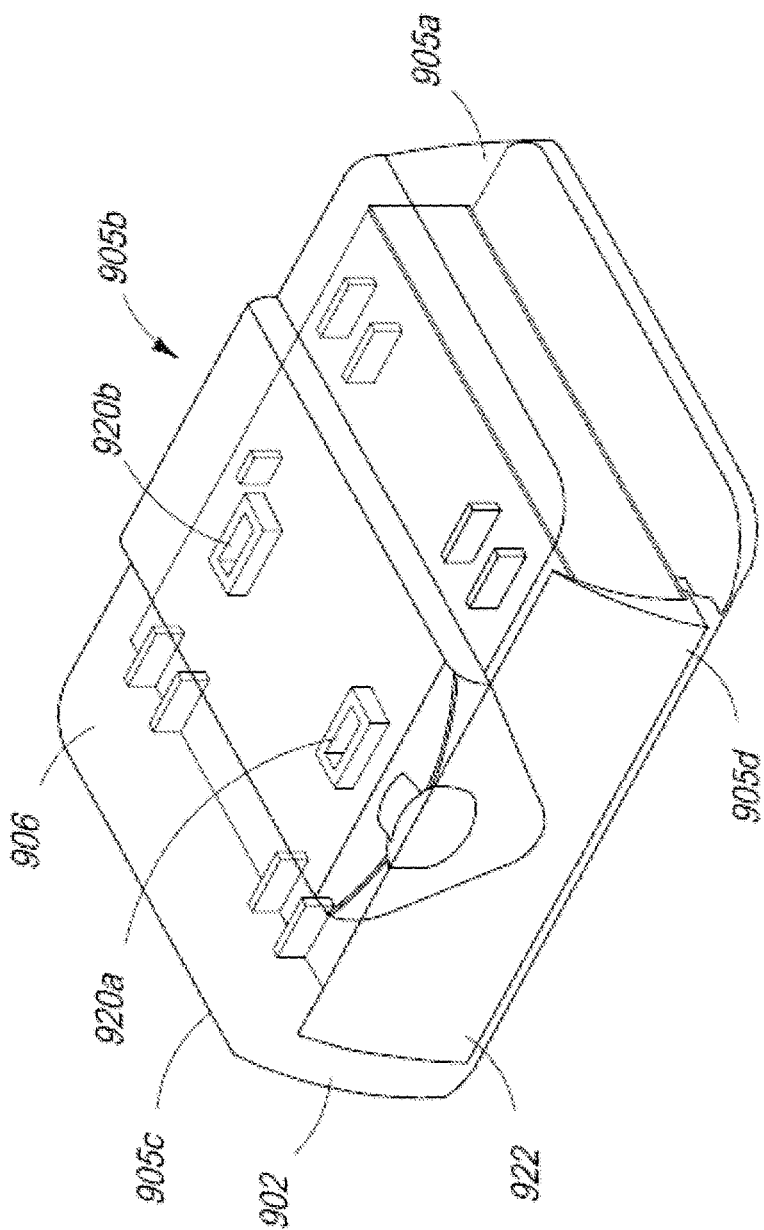
FIG. 9 is a top view of one embodiment of the reservoir unit of the dialysis system.

Referring to FIG. 9, the bottom unit 902 has four sides 905a, 905b, 905c, 905d, a base, a top surface 906, and a reservoir 922 accessible via first side 905d. The bottom unit 902 further comprises a plurality of latch mating structures 920a, 920b on its top surface 906. In one embodiment, the present invention comprises two latch mating structures 920a, 920b that, relative to the length of the bottom unit 902, are centrally positioned to ensure even weight distribution. The first latch mating structure 920a is preferably positioned a distance equal to one third of the width of the bottom unit 902, as measured from side 905d. The second latch mating structure 920b is preferably positioned a distance equal to one third of the width of the bottom unit 902, as measured from side 905b.

Figure 10:
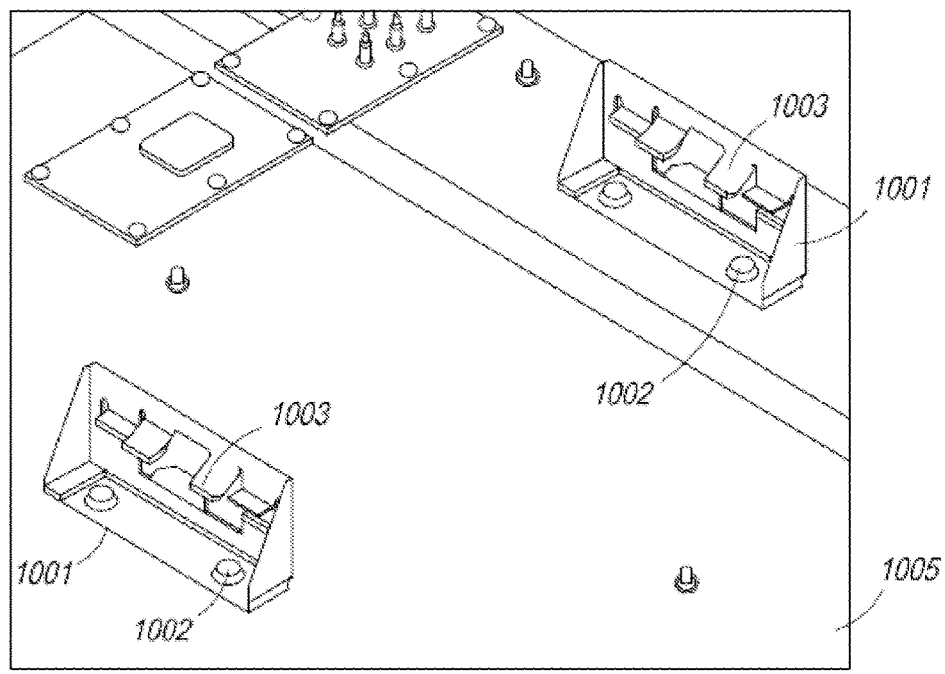
FIG. 10 is a schematic view of exemplary components positioned on the top surface of the reservoir unit of the dialysis system.

The latching mechanisms, as shown in FIG. 10, comprise a metal frame 1001 that is securely fastened using, for example, a bolt, screw, or other fastener 1002, to the top surface of the bottom unit 1005. The frame 1001 supports a protrusion or elongated member 1003 that can flexibly insert into, and be removed from, a corresponding latch.

To securely and removably attach the bottom unit to the top unit, the top unit comprises complementary mechanical sliding latches, which are securely attached to the base of the top unit. In one embodiment, the base of the top unit comprises a first latch that is preferably positioned in the center of top unit, relative to the length of the top unit, and a distance equal to one third of the width of the top unit, as measured from a first side. The base also comprises a second latch that is preferably positioned in the center of top unit, relative to the length of the top unit, and a distance equal to one third of the width of the top unit, as measured from a second side, which is opposite and parallel to the first side.

Figure 11:
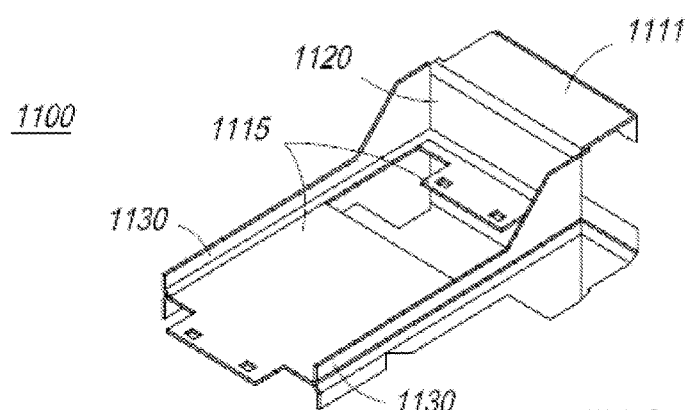
FIG. 11 is a schematic view of an exemplary attachment component positioned on the top surface of the reservoir unit of the dialysis system.

As shown in FIG. 11, the top unit comprises a latch 1100 with a sliding metal flat base 1120. Rails 1130 are slidably engaged with the bottom surface of the top unit, which has mating members to hold the rails 1130 in place. The latch 1100 has two latching tabs 1115 which are adapted to slide into, and out of, mating structures physically attached to the top surface of the base unit.

Latches 1100, attached to the top unit, mate with latch mating structures 920a, 920b on the top surface of the bottom unit 906. In operation, when the sliding latch 1100 is in a first position, the top unit will not effectively fit on top of, or align with, the base unit because the sliding latch 1100 will not properly physically mate with latch mating structures 920a, 920b . To prepare the top unit for secure placement on to the top surface of the base unit 906, the sliding latches are moved within the member holding structure positioned on the bottom of the top unit and placed into a second position. In the second position, the handle of the latch 1111 will protrude, thereby moving the tabs 1115 away from the latch mating structures 920a, 920b and allowing the top unit to sit correctly on the base unit.

Figure 12:
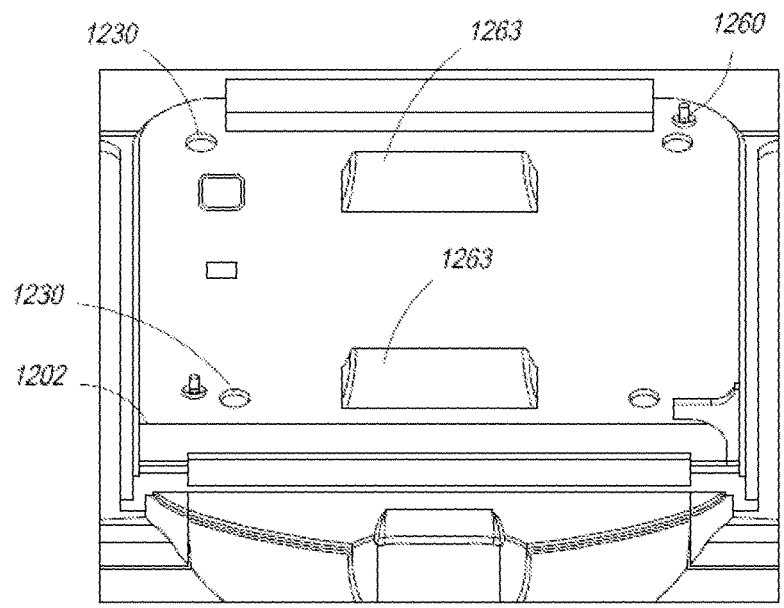
FIG. 12 is a schematic view of exemplary components positioned on the top surface of the reservoir unit of the dialysis system.
Figure 13:
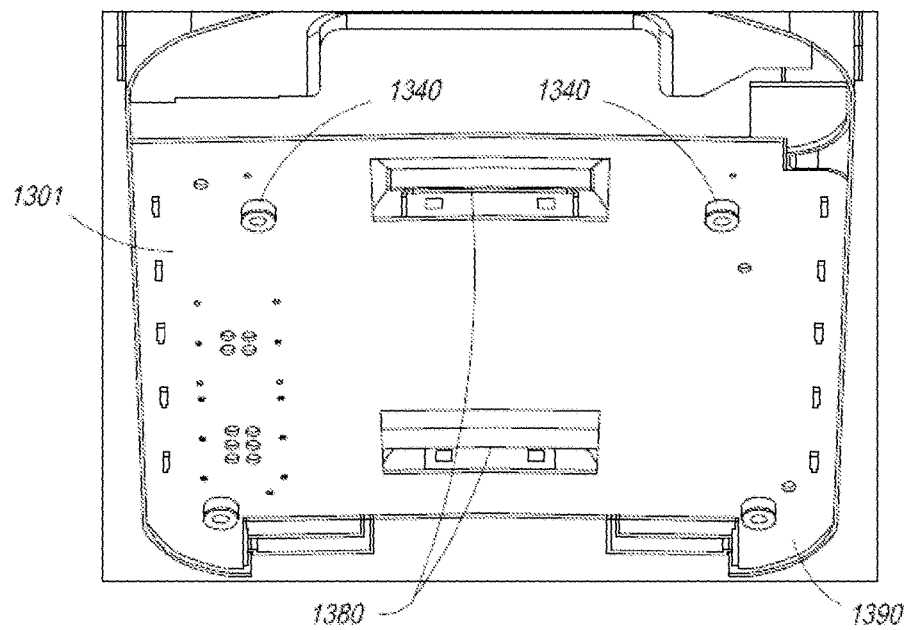
FIG. 13 is a schematic view of exemplary components positioned on the bottom surface of the controller unit of the dialysis system.

Referring to FIGS. 12 and 13, the top unit 1301, which has sliding latches 1380, is aligned to the bottom unit 1202 by four small rubber feet, or footing pads, 1340 on the bottom of the top unit 1301, which are configured or adapted to snugly and securely fit into four cavities or pockets 1230 located proximate to each corner on the top of the bottom unit 1202. Additionally, the top unit 1301 can be accurately aligned to the bottom unit 1202 using alignment pins 1260, or protrusions, on the top surface of the base unit 1202, which are configured or adapted to securely and snugly fit into corresponding cavities 1390 on the bottom surface of the top unit 1301. The bottom unit also has latch mating structures 1263, as described above.

Aligning the rubber footings 1340 into the cavities 1230 and the pins 1260 into the cavities 1390 ensures that latches 1380 on the top unit 1301 can be readily aligned and latched to the latch matching structures 1263 without excessive trial and error. Once aligned, the latch 1380 is mated with the latch mating structures 1263 by sliding the latches 1380 into the latch mating structures 1263, thereby creating a tight fit between the two units. Referring back to FIGS. 9 and 11, to unlatch, latch handles 1111 are pulled or otherwise manipulated, thereby releasing tabs 1115 from the base unit slots 920a, 920b, and allowing the top, upper unit to be lifted from the bottom, lower unit.

Furthermore, to enable the above described modularity, embodiments of the present invention also employ an electrical and communication connection mechanism that, in a first configuration, securely establishes electrical communication and/or data communication connection between the bottom unit and the top unit and, in a second configuration, terminates an electrical communication and/or data communication connection between the bottom unit to the top unit.

Figure 14:
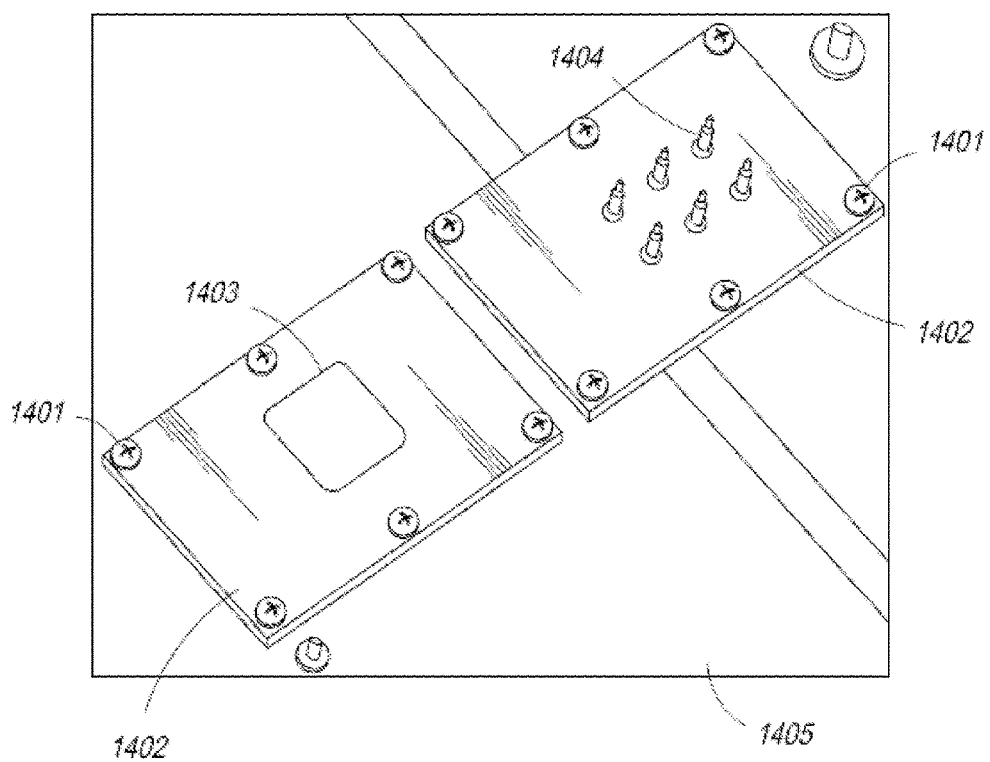
FIG. 14 is a schematic view of an exemplary interfacing component positioned on the top surface of the reservoir unit of the dialysis system.

Referring to FIG. 14, the electrical connections between the top and bottom units are created when the top unit is placed on the bottom unit. These connections are made through a non-contact infrared communications port 1403 and a push-pin power port 1404, which are integrally formed into plates 1402 and securely attached using fasteners 1401 to the top surface of the bottom unit 1405. It should be appreciated that the bottom surface of the top unit would then comprise, in proper alignment with the push-pins, an electrical contact pad. It should further be appreciated that the location of the push-pins and contact pads can be reversed, thereby placing the push-pins on the bottom surface of the top unit and the contact pad on the top surface of the bottom unit.

In one embodiment, a high current power connection is created by placing six spring loaded pins into electrical contact with contact pads, which are integrated into the bottom surface of the top unit. Three pins are for +24 volt DC current and three pins are for ground. In one embodiment, the pins or probes have the following characteristics: a) minimum center of 0.175 inches, b) current rating of 15 amps (continuous), c) spring force in the range of 6.2 oz to 9.0 oz at 0.06 inches to 0.067 inches of travel, d) typical resistance of less than 10 mΩ, e) maximum travel in the range of 0.09 to 0.1 inches, f) working travel in the range of 0.06 to 0.067 inches, g) barrel made of nickel/silver and gold plated, h) stainless steel spring (optionally gold plated), i) plunger made of full-hard beryllium copper and gold plated, and j) optionally a stainless steel bias ball. The spring force of the pins assists in preventing breakage by absorbing bending or other contortions. It should be appreciated that the term electrical pins represents any protrusion capable of transmitting electrical power and electrical contact pad represents any surface capable of receiving an electrical pin.

The non-contact infrared communication port 1403 employs two LED transmitters and two LED receivers which align to, and communicate with, two LED transmitters and two LED receivers on the bottom surface of the top unit. The distance between the transmit and receive ports is less than 0.3 inches. On both the top surface of the bottom unit and bottom surface of the top unit, the four LED units are divided into two pairs, a control pair (comprising one transmitter and one receiver) and one safety pair (comprising one transmitter and one receiver). These ports are placed in data communication when the top and bottom units are properly aligned.

In one embodiment, the LED transmitters are high speed infrared emitting diodes, 870 nm, made of GaAlAs double hetero technology. The LED transmitters are high speed diodes having the following characteristics: a) extra high radiant power, b) low forward voltage, c) suitable for high pulse current operation, d) angle of half intensity of approximately 17 degrees, e) peak wavelength of approximately 870 nm, f) reverse voltage of approximately 5 V, g) forward current of approximately 100 mA, h) a peak forward current of approximately 200 mA, i) surge forward current of approximately 0.8 A, j) power dissipation of approximately 190 mW) junction temperature of approximately 100 degrees Celsius, and l) an operating temperature range of −40 to 85 degrees Celsius. It should be appreciated that the non-contact infrared communication ports can be distributed in any functional manner across the top surface of the bottom unit or bottom surface of the top unit. It should be further appreciated that any other communication port or structure known to persons of ordinary skill in the art can be implemented herein.

In one embodiment, the LED receivers are high speed silicon photodiodes with extra fast response times, radiant sensitive area of approximately 0.25 $mm^2$ and an angle of half sensitivity of approximately 15 degrees. The receivers have the following characteristics: a) reverse voltage of approximately 60 V, b) power dissipation of approximately 75 mW, c) junction temperature of approximately 100 degrees Celsius, d) an operating temperature range of −40 to 85 degrees Celsius, e) forward voltage of approximately 1 V, f) minimum breakdown voltage of 60 V, and g) diode capacitance of approximately 1.8 pF.

Referring back to FIGS. 1, 2 and 3, atop the controller unit 201 are handles 211, 311 and a workspace in the form of a useable shelf 112, 212. The handles, located on the upper pumping portion of the system, are directly connected to the internal structure or frame of the system and are not simply an extension of the exterior plastic molding, housing, or skins surrounding the top unit 101, 201. The direct connection to the internal frame of the system permits using the handle to reposition the system in a manner that is safe and can reliably handle the load, particularly when the instrument is in operation with six liters of water (adding approximately 40 lbs).

Figure 15:
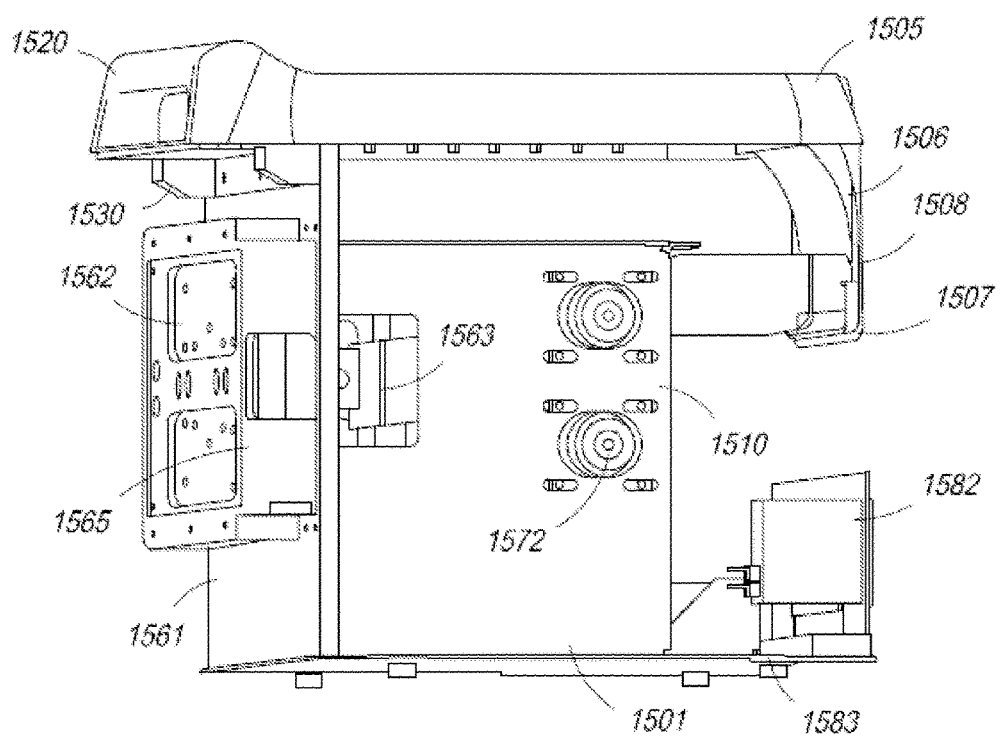
FIG. 15 is a schematic view of one embodiment of an internal frame of the controller unit of the dialysis system.

Referring to FIG. 15, in one embodiment, the top unit 1501 comprises an internal metal casing, frame or housing 1510 within which, and to which, the electronics, controller, and other top unit components are contained. The internal casing 1510 comprises a horizontal protruding arm 1507 that extends to the back side of the top unit 1501. The substantially horizontal top shelf 1505 comprises at least one handle 1520 that is integrally formed into the top shelf structure 1505, a base bracket 1530, and a vertical arm 1506, thereby creating a single, contiguous metal or molded plastic piece. The base bracket 1530 is securely attached to the internal casing 1510 at the front of the top unit 1501 and the vertical arm 1506 is securely attached to the protruding arm 1507 at point 1508 using screws. By securely attaching the shelf 1505 and handle 1520 structure to the internal casing 1510 of the top unit 1501, one avoids potential damage or breakage that would normally occur by placing large weight loads at the point of connection between a handle and an external or outside housing of the top unit.

Also attached to the internal frame or casing 1510 is a metal door 1562, with hinges 1565, which forms the internal frame of door 110, shown in FIG. 1. Door 1562 is securely attached to plate 1561 which is part of internal frame 1510. Structures 1563 and 1572 are structures that hold, and/or represent protrusions of, the internal motors and pulley assemblies. Protrusion 1583, which extends from the back of frame 1510, is used to connect various electronic components, including a power entry module and USB connections 1582. The top of the controller unit, or shelf 1505, is flat and has side-walls making it ideal for storage of supplies or a temporary working surface.

Figure 16A:
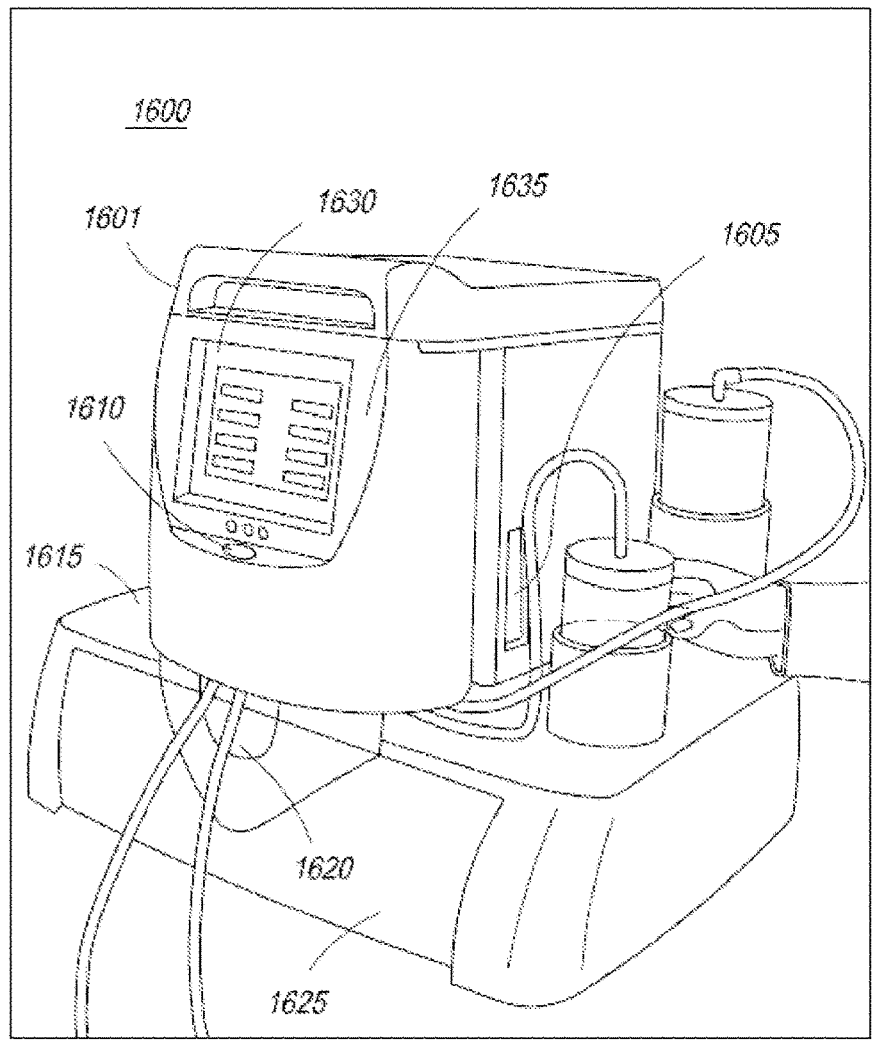
FIG. 16A is a front/side view of one embodiment of the dialysis system of the present invention.

Another structural feature of the controller unit 1601 is shown in FIG. 16A. Preferably, the unit 1601 has a built-in exposed reader, such as a bar code reader or RFID tag reader 1605, which can be used to read codes or tags on the disposable components. Operationally, a user would preferably swipe all of the codes/tags on the disposable components by the reader. Prompting the user can be effectuated through an initial GUI dialysis setup step which instructs the user to swipe each disposable component past the reader.

Upon doing so, the reader obtains identifying information about the disposable, transmits that identifying information to an internal table stored in memory, compares the identifying information to the contents of the internal table, and verifies (or does not verify) that the correct disposable components (particularly additives used in the dialysate) are present. The contents of the internal table can be generated by manual input of the identity and amount of the disposables or by remote access to a prescription that details the identity and amount of the disposables. This verification step has at least two benefits. The first is to ensure that the user has, in his or her possession, all of the required components and the second is to ensure that the correct components are being used (not counterfeit or unsuitable disposables). This component can be used to enable a variety of user interfaces, as further described below.

In another embodiment, the reader 1605 mounted on the side of the top unit is a specialized multi-function infrared camera that, in one mode, provides the ability to read bar codes and, in another mode, detects a level change in the infusate container. The camera emits an infrared signal that reflects off fluid level. The reflected signal is received by the camera's infrared receiver and processed, using a processor, to determine the location of the meniscus of the fluid level. In one embodiment, the camera can determine and monitor a change in the fluid level to a resolution of 0.02 mm. In one embodiment, the camera is a 1.3 megapixel single-chip camera module with one or more of the following characteristics: a) 1280 W×1024 H active pixels, b) 3.0 µm pixel size, c) ⅓ inch optical format, d) RGB Bayer color filter array, e) integrated 10-bit ADC, f) integrated digital image processing functions including defect correction, lens shading correction, image scaling, demosaicing, sharpening, gamma correction, and color space conversion, g) embedded camera controller for automatic exposure control, automatic white balance control, and back level compensation, h) programmable frame rate and output derating functions, i) up to 15 fps SXGA progressive scan, j) low power 30 fps VGA progressive scan, k) 8-bit parallel video interface, l) two-wire serial control interface, m) on-chip PLL, n) analog power supply from 2.4 to 3.0 V, o) separate I/O power supply, p) integrated power management with power switch, and q) 24 pin shield socket options. In one embodiment, the camera is a 1.3 megapixel camera made by ST Microelectronics, Model No. VL6624/V56624.

The top or bottom unit of the dialysis system also preferably has electronic interfaces, such as Ethernet connections or USB ports, to enable a direct connection to a network, thereby facilitating remote prescription verification, compliance vigilance, and other remote servicing operations. The USB ports permit direct connection to accessory products such as blood pressure monitors or hematocrit/saturation monitors. The interfaces are electronically isolated, thereby ensuring patient safety regardless of the quality of the interfacing device.

The front of the top unit has a graphical user interface 114 that provides for a simple user interface with the system 100. In a home setting, it is important that the device be easy to use. Maximal use of colors and the touch screen is ideally suited for the application. The touch screen allows multiple user input configurations, provides multiple language capability, and can be readily seen at night (particularly with brightness controls and night-vision colors).

The GUI further includes a feature for the automatic closing, opening, and locking of the door during operation. In one embodiment, the GUI opens the door to a first latch position and then a user must press a physical door-open button to fully open the door. In another embodiment, the device has a manual override which permits the user to open the door (e.g. by pressing the open door button twice or with extra force) to manually open the door. Referring to FIG. 16A, preferably, proximate to the GUI 1630, is a single mechanical button 1610, with lighted visual indication, that, if activated, provides a central stop button with a common function (such as stopping the system) regardless of the state of operation.

To provide further security and safety, the system 1600 controls the opening of the reservoir door 1625 in the base unit 1615 without requiring a door controller, button, or mechanical system that is independent from the door control system of the top unit 1601. In one embodiment, the reservoir door 1625 is physically blocked from opening by a protrusion 1620 that is physically attached to, connected to, or otherwise controlled by the front door 1635 of the top unit 1601. The protrusion 1620, which can extend over the reservoir door 1625 from any direction relative to the top unit 1601, serves to provide a physical barrier to opening the reservoir door 1625. Therefore, in this embodiment, one cannot open the reservoir door 1625 without first unlocking and opening the controller door 1635, which is controlled by the user interface.

Figure 16B:
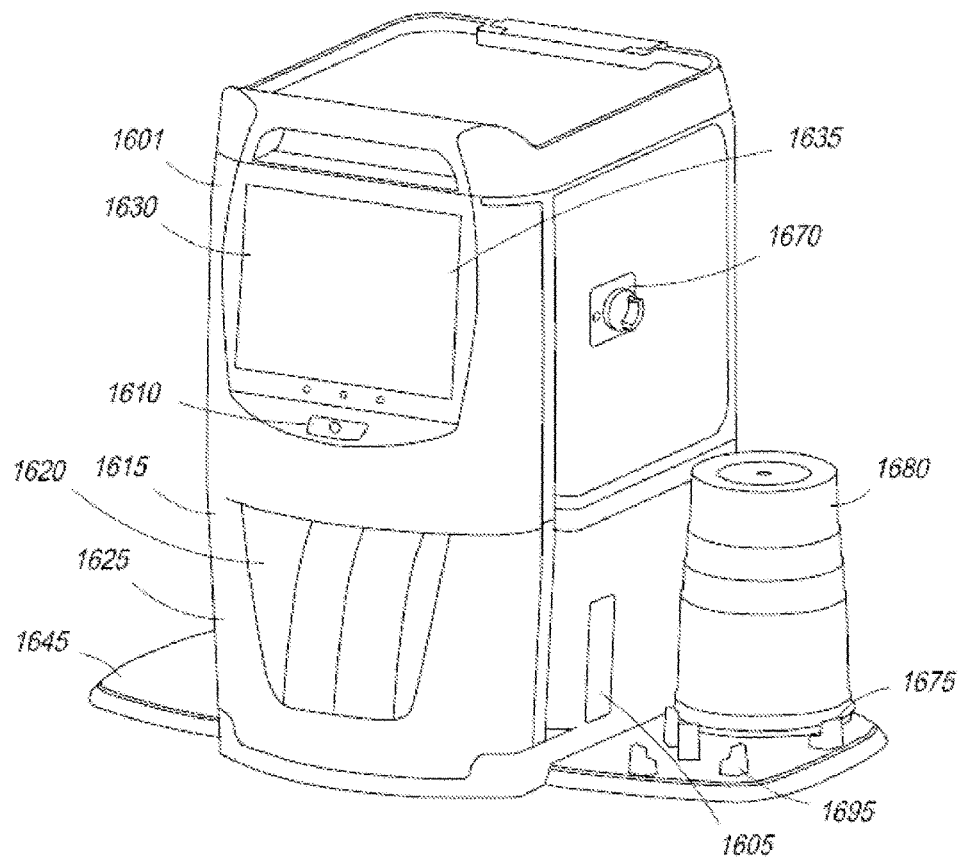
FIG. 16B is a front/side view of another embodiment of the dialysis system of the present invention.

In another view of one embodiment of the dialysis system, shown in FIG. 16B, the dialysis system 1600 comprises a controller unit 1601 with an ammonia sensor 1670, GUI 1630, and a single mechanical button 1610 for opening and closing the controller door 1635, and a base unit 1615 with a reservoir door 1625 that is physically blocked from opening by a protrusion 1620 that is physically attached to, connected to, or otherwise controlled by the front door 1635 of the top unit 1601 and built-in exposed reader, such as a bar code reader or RFID tag reader 1605. The controller unit 1601 and base unit 1615 are positioned atop a single continuous substantially planar base or partitioned planar base 1645 that has two attachment mechanisms 1675, 1695. The first attachment mechanism 1675, which is used to hold in place a sorbent cartridge 1680, is positioned adjacent to the second attachment mechanism 1695, which is used to hold in place a concentrate jar 1695, on the same side of the dialysis system 1600. The planar base 1645 preferably comprises a drip tray or other moisture catching or sensing surface.

Figure 16C:
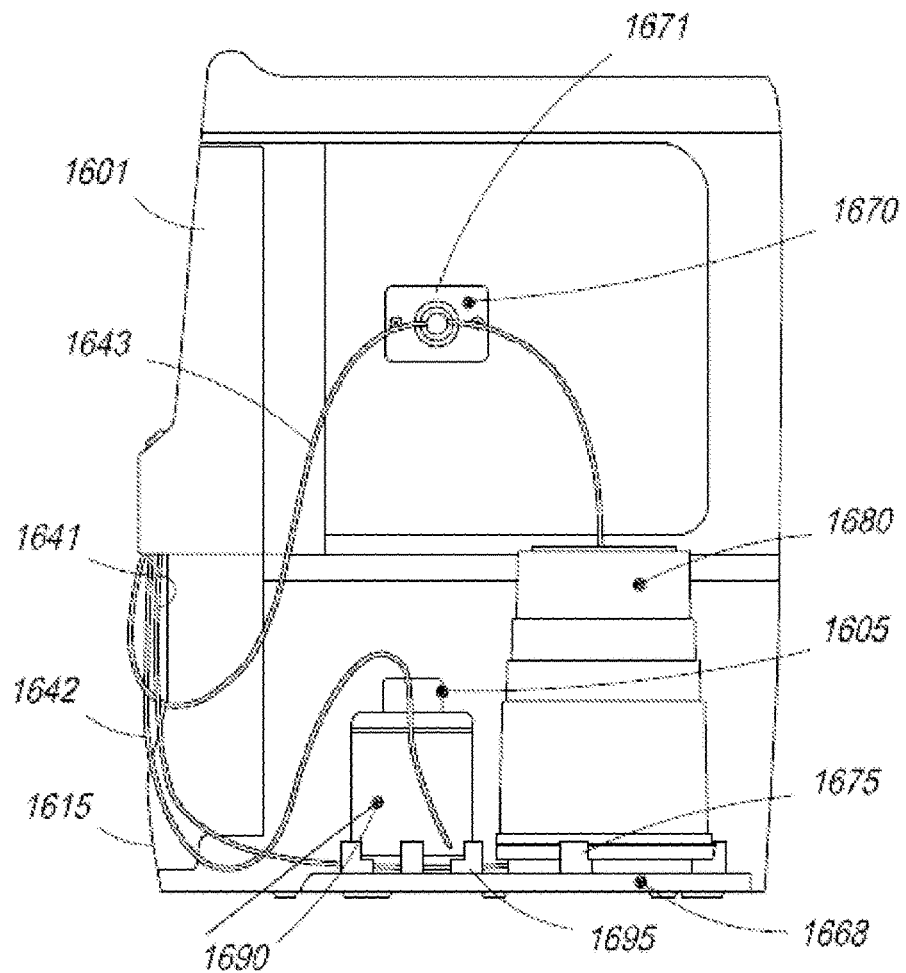
FIG. 16C is a side view of another embodiment of the dialysis system of the present invention.

Referring to FIG. 16C, the controller unit 1601 and base unit 1615 are shown in profile. The sorbent cartridge 1680 is held in place by attachment mechanism 1675 and concentrate jar 1690 is held in place by attachment mechanism 1695. Both the sorbent cartridge 1680 and concentrate jar 1690 are placed atop a planar surface, such as a drip tray 1668, to insure all moisture is captured. Scanner 1605 is positioned on the side of the base unit 1615 and in direct optical communication with the concentrate jar 1690. Fluids flow from the system 1600 to and from the sorbent cartridge 1680 and from the concentrate jar 1690 via three tubular or fluid segments 1641, 1642, 1643. Tube segment 1642 places the concentrate jar 1690 in fluid communication with the manifold through the concentrate manifold port. Tube segment 1641 places the sorbent cartridge 1680 in fluid communication with the manifold through the sorbent outflow port, thereby sending dialysate requiring regeneration to the sorbent cartridge 1680. Tube segment 1643 places the sorbent cartridge 1680 in fluid communication with the manifold through the sorbent inflow port, thereby receiving regenerated dialysate from the sorbent cartridge 1680. The tube segment 1643 is removably attached proximal to the ammonia sensor 1670 using mechanisms 1671 such as hooks, clips, clamps, or other means permitting a tube segment 1643 to be easily removed and placed in proximal contact with the ammonia sensor 1670 positioned on the side of the controller unit 1601 on the same side as the sorbent cartridge 1680. In one embodiment, the ammonia sensor 1670 comprises an optical sensor that uses a colorimetric measurement approach to determining the presence of ammonia and whether such ammonia exceeds a predefined threshold.

Figure 17A:
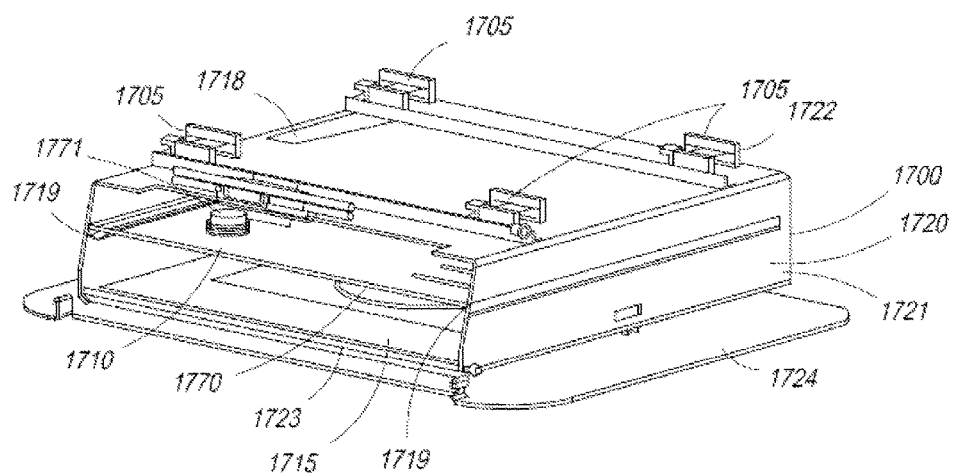
FIG. 17A is a schematic view of an internal structure of one embodiment of the reservoir unit of the dialysis system of the present invention.
Figure 17B:
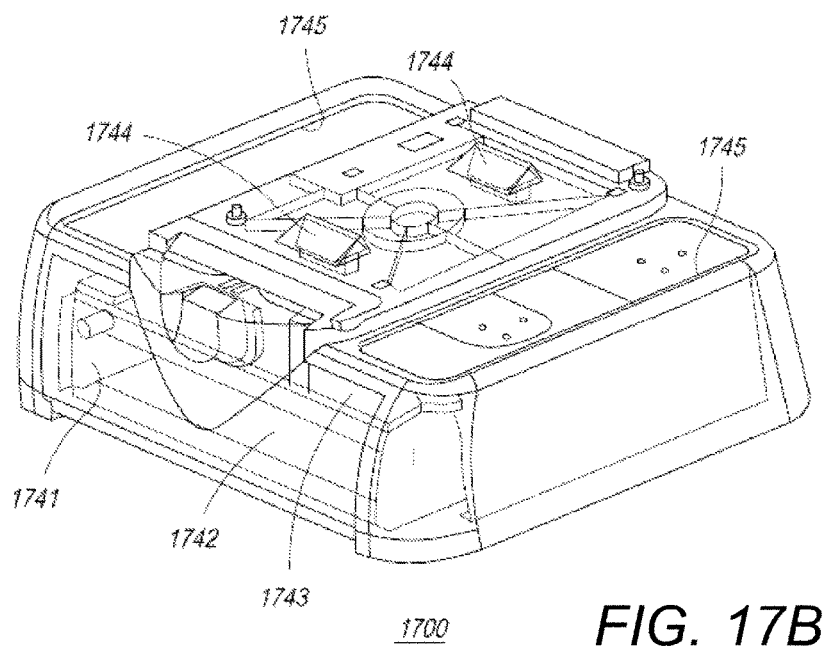
FIG. 17B is a schematic view of an internal structure of one embodiment of the reservoir unit of the dialysis system of the present invention.

Referring to FIG. 1, the reservoir system 102 has a door 118 which, when pulled and not blocked by any protrusion, slides the reservoir 122 out, or otherwise makes the reservoir 122 accessible to a user, to allow a user to insert or change fluids used for dialysis. The reservoir volume is monitored by a scale system. The scale-based fluid balance 604, depicted in FIG. 6 and more particularly in FIGS. 17A and 17B, is integrally formed with the reservoir and provides accurate fluid removal data and enables accurate balance calculations, thereby preventing hypotension and other ailments caused from fluid imbalances. Integrating the scale with the reservoir and enclosing them completely provides for a more robust system.

Referring to FIG. 17A, the internal structure 1700 of the reservoir system is shown. A metallic internal frame 1720 comprises two sides 1721, a back 1722, an open faced front 1723, and a base 1724. The internal structure or frame is shown without the external housing, as depicted as element 102 in FIG. 1. A scale 1718 is integrated into the reservoir internal structure 1700. The bottom surface 1715 of the scale 1718 comprises a metal surface or pan that, together with the rest of the scale 1718, is suspended from the external reservoir housing (shown as 102 in FIG. 1) by four flexures 1705. Below the bottom surface 1715 of the scale is preferably situated a heating pad, such as a square, rectangular, circular, or other shaped surface capable of incurring a temperature increase and conducting the increased temperature, as heat, to surface 1715. A conductivity coil 1770, capable of exerting a field and using changes in that field to measure conductivity, is integrated into base surface 1715. Accordingly, when a reservoir bag (not shown) is placed on bottom surface 1715, it can be heated by a heating pad and, because it is in contact with coil 1770, its conductivity can be monitored.

The internal surfaces of the sides 1721 comprise a plurality of rails, elongated members, or protrusions 1719 that serve to secure, hold, encase or attach to a disposable reservoir bag mounting surface, such as a plastic sheet, 1710 to which a reservoir bag can be attached. Specifically, a reservoir bag positioned on surface 1715 can have an outlet attached to conduit 1771 integrated into sheet 1710. Mounted in each of the four corners of the scale surface 1718 are flexures 1705 with each one comprising a hall sensor and magnet.

Accordingly, in one embodiment, components of the reservoir subsystem assembly include, but are not limited to a dialysate reservoir, including disposable reservoir liner or bag, dialysate heater, dialysate temperature monitor, reservoir weighing system, including magnetic flexures and tilt sensor, dialysate ammonia concentration and pH sensor, including disposable sensor elements and reusable optical reader, dialysate conductivity sensor (non contact type), and wetness or leak sensors.

One of ordinary skill in the art would appreciate that apart from the sensors listed above other components in the dialysate circuit, such as pumps and sensors such as pressure transducers may also be included within the reservoir module. Further, various sensors such as ammonia and pH sensors may be integrated as individual sensors into the reservoir module, or as a single 'sensor sub-module' that comprises all the sensors.

The inclusion of each of these components is designed in a manner that makes the reservoir assembly module specially suited for use in the operation of a recirculating sorbent based dialysis system. Further, the module is also designed such that during other forms of dialysis, such as single pass hemofiltration, any unnecessary elements of the module that are specific only to sorbent based dialysis can be removed.

FIG. 17B illustrates one embodiment of the reservoir assembly module, with the outer skins or covers rendered transparent, thereby revealing the internal arrangement. An opening 1741 is provided in the front of the reservoir subsystem module 1700. The main function of the reservoir subassembly is containment of the dialysate. The opening 1741 allows a disposable reservoir bag, which can be a conventional IV bag with dialysate contained therein, to be inserted. The reservoir module 1700 is also provided with a pan 1742 inside the front opening for containing the reservoir bag. In one embodiment, a flat film heater and temperature sensor are both located underneath the bottom of the reservoir pan 1742, and help maintain the temperature of dialysate fluid at body temperature or close to it. In one embodiment, the temperature of the dialysate fluid can be set by the user.

In one embodiment, the reservoir pan 1742 is suspended in a scale mechanism 1743, as further described below. The scale mechanism 1743 can be used for accurate measurement of the weight of the dialysate fluid in the reservoir bag prior to start of the dialysis, and for maintaining volumetric balance of the dialysate fluid in the circuit during dialysis.

On the top of reservoir assembly module 1700, features 1744 for attachment to the pumping unit of the dialysis system are provided, as previously discussed. These features help in easy coupling and removal of the reservoir assembly module from the pumping unit, which in one embodiment may be mounted on the top of the reservoir assembly. As further discussed below, the top of the reservoir assembly module is also equipped with drain gutters 1745 on either side of the module. Individual wetness sensors (not shown) are provided in each of the gutters. As known in the art, wetness sensors are optical devices that sense moisture on account of increased coupling of light into fluid as opposed to air, by virtue of the difference of index of refraction between air and fluid. The wetness sensors in the drain gutters 1745 keep track of moisture and indicate any leaks in the pumping system when it is mounted on top of the reservoir assembly. By having a separate wetness sensor in the drain gutter on either side, leaks can be localized and specific guidance given to the user regarding any corrections that may be required.

Figure 17C:
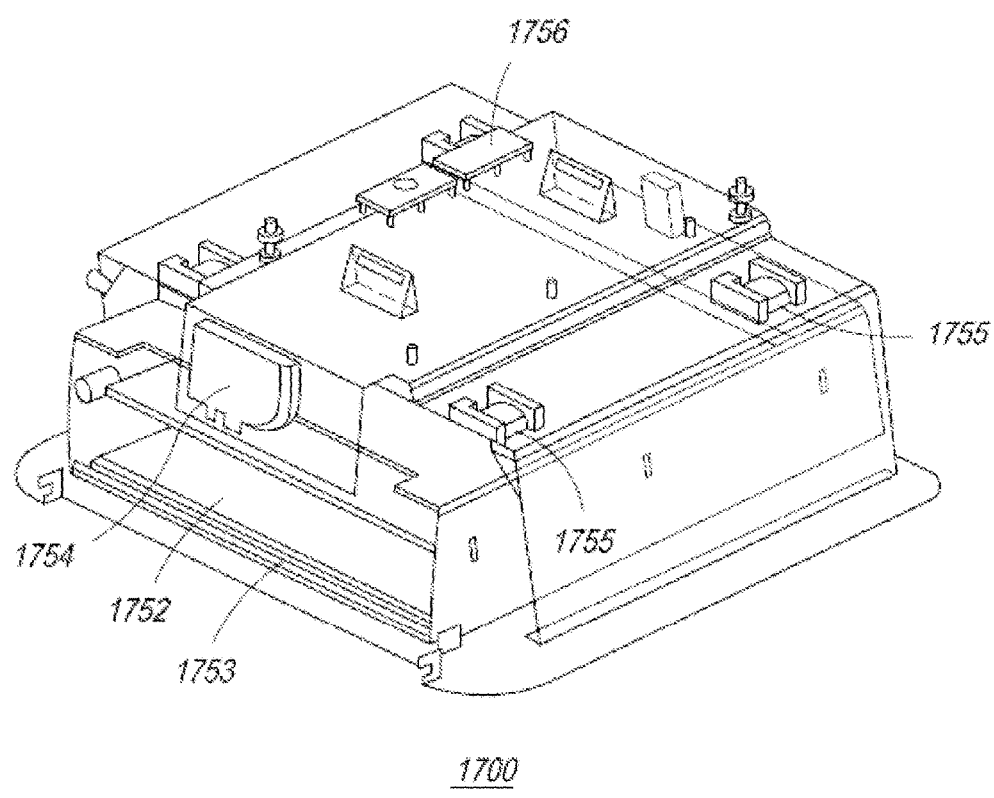
FIG. 17C is a schematic view of an internal structure of one embodiment of the reservoir unit of the dialysis system of the present invention.

FIG. 17C illustrates another view of the reservoir assembly module, wherein the outer covers of the module 1700 are totally removed and some internal components rendered transparent. Referring to FIG. 17C, the reservoir pan 1752 is provided with an internal gutter 1753. The gutter 1753 is further equipped with a wetness sensor, which is located just under the dialysate pan 1752, to which flexures are attached 1755, so that it can sense a leak inside the reservoir assembly 1700.

The reservoir assembly module 1700 further comprises a sensor pod 1754 or sub-module, which comprises a collection of various sensors on the same circuit board. The sensor board comprises sensors specifically related to sorbent based dialysis, such as ammonia and pH sensors. In one embodiment, the ammonia sensor comprises disposable color sensitive strips, which are made up of a material that exhibits a visible change in color in response to the level of ammonia present in the dialysate. For example, the color of the indicator strip may change gradually from blue to yellow, depending on the ammonia level present around that strip. Such visual color indication makes it easier to keep track of ammonia levels and to identify if ammonia breakthrough occurs. In one embodiment, for a more precise assessment of color change in ammonia indicator strips, an optical sensor is used. The optical sensor is also located in the sensor module 1754, and can be used for converting the general visible color reading into an accurate indication of ammonia level.

With respect to the dialysate sodium concentration, it should be appreciated that, to perform kidney dialysis properly and cause correct diffusion across the dialyzer, the concentration of sodium must be maintained within a certain range. A conventional method of determining the sodium concentration of a fluid is to measure the fluid's electrical conductivity and the fluid's temperature and then calculate the approximate sodium concentration. An improved method and system for measuring sodium concentration in dialysate in a non-contact manner uses a non contact conductivity sensor built in to the bottom of the reservoir pan 1752.

In one embodiment, the non-contact conductivity sensor is an inductive device utilizing a coil. Change in sodium concentration changes the conductivity of the dialysate solution, which in turn changes the impedance of the coil. By placing the conductivity sensor in the bottom of the reservoir pan 1752, and thus under the dialysate bag in the reservoir, a large surface area is presented to the coil. This ensures high accuracy of measurement, in addition to requiring no physical contact of the sensor with the dialysate fluid.

Figure 17D:
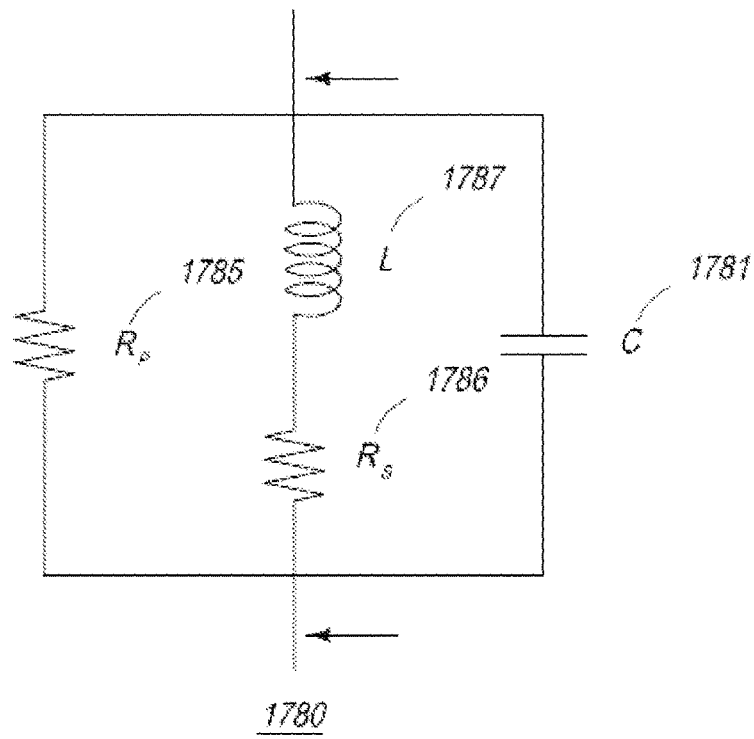
FIG. 17D is a circuit diagram of an exemplary conductivity sensor.
Figure 17E:
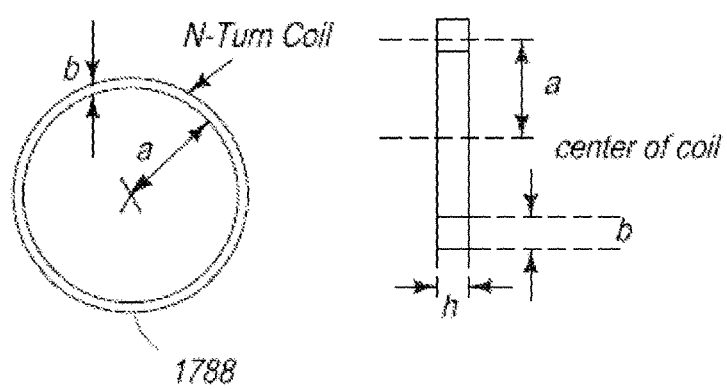
FIG. 17E is a diagram of an exemplary coil used in a conductivity sensor.

Referring to FIGS. 17D and 17E, components of a non-contact electrical conductivity sensor are shown, including a coil 1788 with n-turns defining the generation of a magnetic field when properly energized and a diagram of the resulting resonant LCR tank circuit 1780 created when the coil, defined by resistance elements Rs 1786 and Rp 1785 and inductor element L 1787, is electrically coupled with a capacitor 1781.

The coil 1788 is a multi-layer, circular, flat coil used as an energy storage device in conjunction with a capacitor 1781. The coil 1788 has loss elements, which comprises the electrical resistance of the coil wire Rs 1786 and a magnetic field loss element Rp 1785, the electrical conductivity of the fluid in the bag.

The coil 1788 diameter is a function of magnetic field penetration into the fluid. Another factor for fluid penetration is operating frequency. Low operating frequency will penetrate deeper into the fluid, but with a cost of lower losses. A larger coil will have small effect cause by dimensional tolerances. A defining equation is provided below:

$$L = \frac{0.31(aN)^2}{6a + 9h + 10b} \; (\mu H)$$

Where a=average radius of the coil in centimeters, N=number of turns, b=winding thickness in centimeters, h=winding height in centimeters. In one embodiment, the radius of the coil is in the range of 2 to 6 inches and, more particularly, 2, 3, 4, 5, and 6 inches and all increments in between.

Referring to the circuit 1780, the physical coil 1788 is represented by L 1787 and Rs 1786, with L being the inductance of the coil and Rs being the electrical resistance of the coil wire. Energy loss of the magnetic field produced by L 1787 is represented by Rp 1785. Energy loss Rp arises from, and is directly related to, the conductivity fluid which is proximate to the coil 1788. Therefore, if the coil 1788 is placed in the reservoir pan, integrated into the surface of the reservoir pan, or otherwise placed at a distance such that the magnetic field generated by the coil 1788 can be affected by the presence of dialysate within a bag, or, more particularly, the conductivity of the dialysate within a bag, changes in the bag's sodium concentration, and therefore conductivity, can be monitored and measured by tracking the corresponding changes to the magnetic field generated by the coil 1788.

Circuit 1780 enables the accurate measurement of changes in the magnetic field generated by the coil 1788. When the circuit 1780 is driven at its resonant frequency, energy is transferred back and forth between inductive element L 1787 and capacitor 1781. At resonance, energy losses are proportional to the $I^2R$ losses of $R_S$ and $R_P$. To maintain a constant AC voltage across C 1781, energy must be supplied to the circuit 1780 and the supplied energy must equal the energy loss of $R_P$ 1785 and $R_S$ 1786. When the L 1787 and C 1781 elements are placed in a Pierce oscillator with automatic gain control, the control voltage will be proportional to the electrical conductivity of the fluid being sensed, since the oscillator will require more energy to oscillate with higher resistive field losses due primarily to changes in dialysate conductivity arising from changes in sodium concentration levels.

As mentioned previously with reference to FIG. 17B, the reservoir pan is suspended in a scale mechanism for accurate measurement of the weight and for maintaining volumetric balance of the dialysate fluid in the circuit during dialysis. The suspension points 1755 for the scale mechanism are illustrated in FIG. 17C. In one embodiment, four suspension points 1755 are provided, each of which includes a weighing mechanism, as previously described. In addition to the four suspension points 1755, the reservoir assembly subsystem 1700 also includes a level sensor. The level sensor allows for computation of accurate weight even if the reservoir bag is not level. FIG. 17C also illustrates pins 1756 on the top of the reservoir assembly module 1700, which can be used to provide electrical connection to a control and/or pumping unit which, as mentioned earlier, may be mounted on the top of the reservoir assembly.

Figure 18:
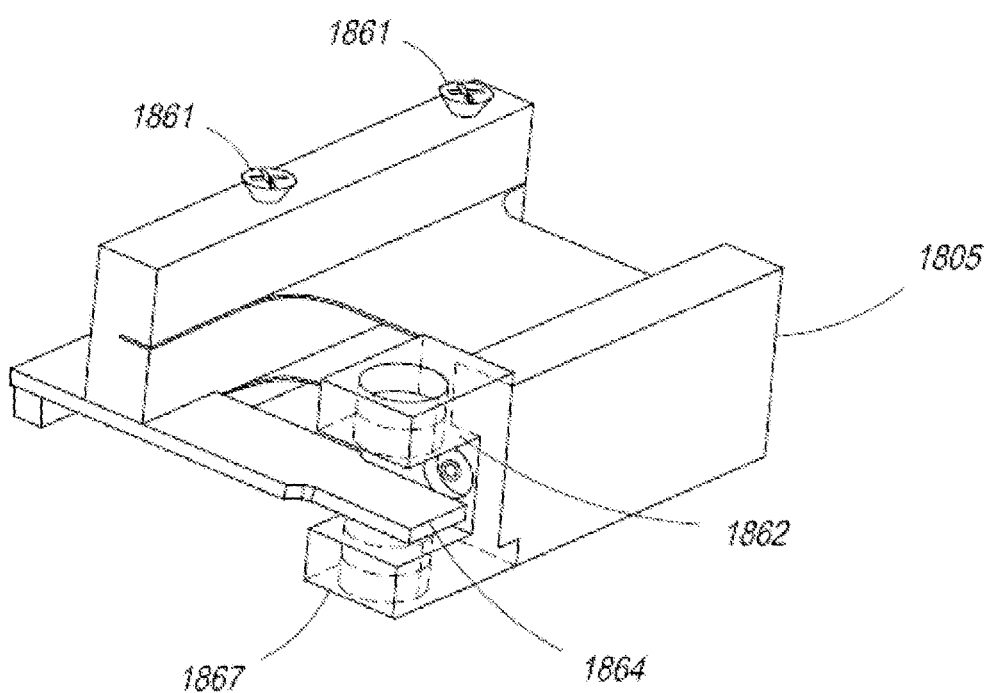
FIG. 18 is a schematic view of a flexure used in one embodiment of the reservoir unit of the dialysis system of the present invention.

Referring to FIG. 18, the flexure 1805 comprises a plurality of attachment points 1861 where the flexure is secured to the external reservoir housing. The flexure further comprises magnetic bodies 1862, such as two magnets, and a hall sensor 1864. The base 1867 of the flexure 1805 is attached to the top surface 1715 of scale 1718. As the scale 1718 displaces due to the application of a weight load (e.g. when the reservoir bag fills with dialysate the bag presses on surface 1715, thereby pulling scale 1718 downward), the flexure 1805, which is connected to the scale at one end and the external housing at another end, will flex and the magnet 1862, mounted on the one end of the flexure 1805, will track that change by virtue of changes to the magnetic field generated by the magnetic body 1862. The hall sensor 1864 detects changes in the magnetic field strength. One of ordinary skill in the art would understand how to translate this sensed magnetic field change into a measure of the applied weight load.

The front door opens widely (approximately 100 degrees), for loading a disposable manifold. Having a wide opening facilitates manifold loading and easy cleaning of the faces of the machine and inside of the door. Having the door close and cover the moving parts of the device makes it safer and more robust, which is particularly important for home use. Additionally, having the front door house the display saves space and re-enforces the important point that the device is not to be operated unless the disposables are in place and the door is closed. The door provides the necessary occlusion force on the manifold and its pump segments. The door also contains a touch screen, audio alarm, and manual stop button in the face of the door.

In one embodiment, the door is held in a fully closed position by an electric stepper motor. This motor is operated via the user interface and, in particular, by a user pressing a button when the door is ready to be fully closed or opened. To ensure proper pressure is placed on the manifold structures by the door and pump shoes, it is preferred to have an electronic mechanism by which the door is closed and sufficient closing door force is generated. In one embodiment, a closing door force of 90 to 110 lbs is generated.

Figure 19:
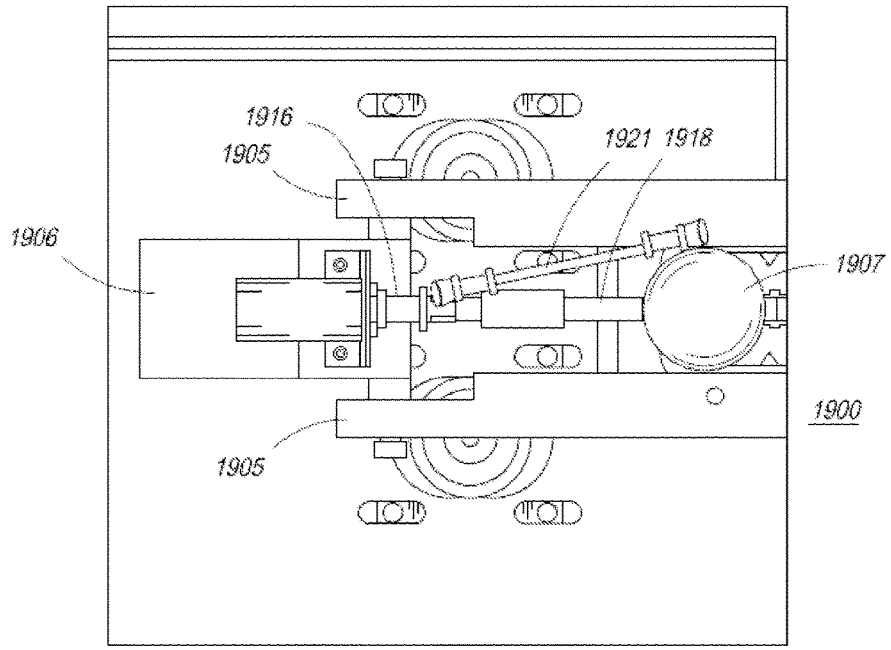
FIG. 19 is a schematic view of a door locking mechanism implemented in one embodiment of the controller unit of the dialysis system of the present invention.
Figure 20:
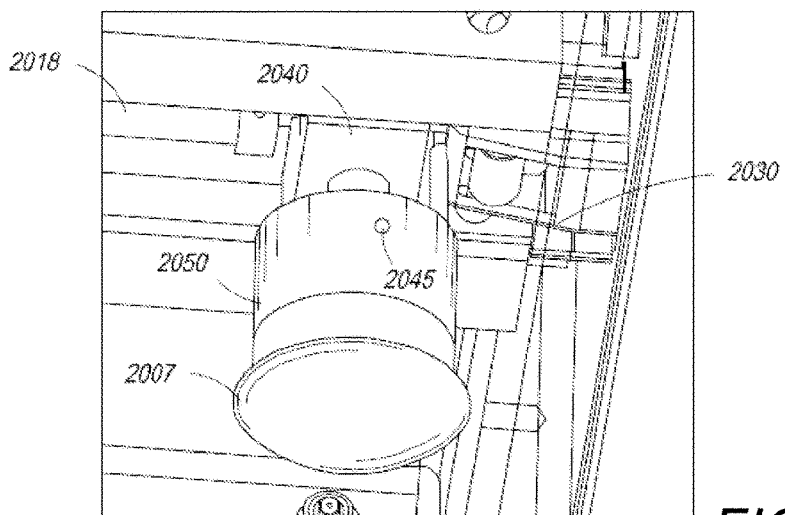
FIG. 20 is a schematic view of a door locking mechanism implemented in one embodiment of the controller unit of the dialysis system of the present invention.

Referring to FIGS. 19 and 20, one embodiment of the power door closing mechanism 1900 is shown. A stepper motor 1906 is mechanically engaged with a lead screw 1916, such that, when actuated by a controller, the stepper motor 1906 causes the lead screw 1916 to turn and, consequently, to cause rod 1918, 2018 to apply a motive force to a hook. The hook, located under member 2040, serves to latch onto U-latch 2030 and, when pulled, turned, or otherwise moved inward toward stepper motor 1906, pull the U-latch 2030 further closed, thereby applying the requisite closing door force. The hook is physically engaged with rod 1918, 2018 and can be manipulated to pull the U-latch 2030 tightly closed or to loosely engage with the U-latch 2030. The power closing system is mounted and kept in proper orientation by mounting brackets 1905.

Figure 21:
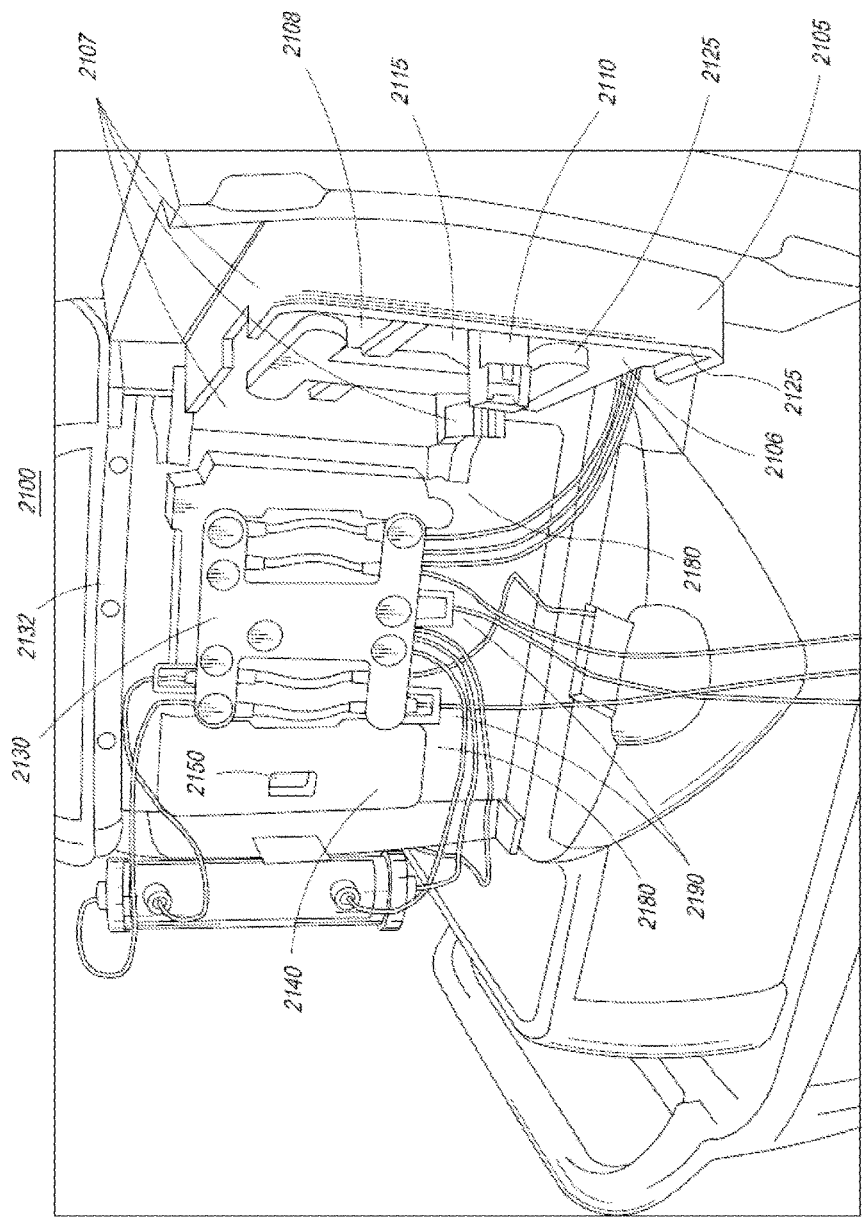
FIG. 21 is a view of the front of one embodiment of the dialysis system, with the door open and a manifold installed.

Referring to FIG. 21, operationally, a user closes the door sufficiently to engage the U-latch 2110 on the door with the hook 2150 inside the internal volume of the controller unit. A user then indicates to the portable dialysis machine a desire to close the door, preferably through a mechanical button or graphical user interface icon, which, when pressed, sends a signal to a controller that, in turn, actuates the stepper motor. The stepper motor applies a motive force to the hook 2150, which then pulls the engaged U-latch 2110 tightly closed. In one embodiment, a controller monitors the torque force being applied by the motor and, when it reaches a pre-defined limit, deactivates the stepper motor. In another embodiment, a hall device positioned proximate to the lead screw senses the extension of the lead screw and determines the extent of movement of the screw. If the screw has sufficiently moved in the direction of creating greater closing door force, the hall sensor transmits a signal to the controller to deactivate the motor. Alternatively, the sensor constantly transmits a signal indicative of the extension of the screw, which is then interpreted by the controller to determine if sufficient motive force has been applied, and whether the stepper motor should be deactivated. In any of these embodiments, if the motor over torques, a pre-set distance is exceeded, or the door does not reach its fully closed position in a predetermined time, a controller can actuate the motor to stop and reverse to a fully open state. The controller can also cause a visual and/or auditory alarm to sound.

When a user wishes to open the door, a mechanical button or graphical user interface icon is activated, sends a signal to a controller that, in turn, actuates the stepper motor in reverse. The hook then becomes loosely engaged with the U-shaped latch. A mechanical release button is then pressed to disengage the loosely engaged hook from the U-shaped latch.

In addition to providing the requisite closing force, this power door closing mechanism has several important features. First, it is designed to avoid obstructions from being caught in the door and subject to the powerful door closing force. Referring to FIG. 21, the area recessed into the door 2105 for accepting a manifold 2130 is surrounded by a four sided edge guard 2107 which prevents a door latch from engaging with a latch receiver on the top unit if a blockage, such as person's finger or improperly installed disposable, is between the door 2105 and the top unit's base plate. Door 2105 comprises an internal surface 2106 to which a metallic casing 2125 is attached. In one embodiment, the top surface of the internal surface 2106 of the door 2105 is securely attached to an external surface of the casing 2125. The casing 2125 is substantially rectangular and defines a cavity with four sides 2107 and a base 2108 creating an internal volume. The cavity opens toward the manifold structure 2130 of the dialysis system 2100 and encompasses and surrounds the manifold structure 2130 and guard 2140, which is preferably a plastic shroud that surrounds the manifold structure 2130 at its top and sides. Attached to the surface of the base 2108 are the pump shoes 2115 and at least one U-shaped latch 2110, which protrudes toward the back plate. Integrated within, and extending out of, the guard is a hook 2150 which is configured to securely engage and disengage the U-shaped latch 2110. If the door is correctly closed and nothing is caught between the door and the guard, then the U-shaped latch will be mechanically hooked by the power-door lock hook mechanism. If an obstruction is in the door pathway, the metal casing 2125 will be unable to extend into the internal volume of the top unit (and encompass the guard) and, therefore, the U-shaped latch will be unable to engage the hook, thereby preventing the mechanical hooking and accidental power closing of the door when an obstruction is in place.

Second, the mechanical button release can only be actuated when the power closing door force has been dissipated through the reverse motion of the stepper motor, thereby preventing an accidental release of, and rapid opening of, the door. Referring to FIGS. 19 and 20, when the door is closed and locked, a collar 2050 on the button shaft 1907, 2007 turns 90 degrees moving a push pin away from the power-door locking hook. The collar 2050 is turned by virtue of rod 1921, which is connected to the collar at point 2045 and in mechanical engagement with lead screw 1916. The collar 2050 is spring loaded and locked by a small pin solenoid. If the user presses the button when in the locked position the button will move into the machine but, because of the displacement caused by the turning of the collar, will not disengage the hook, thereby preventing the door from opening.

If the power is lost or unintentionally terminated, then the pin solenoid will release, allowing the collar to turn back 90 degrees and placing the push-pin in proper alignment. Then when the user presses the button the push pin will contact the power-door hook and release the door latch. This mechanism provides the convenience and safety back up of a mechanical door release without concern that the mechanical door release can accidentally be activated to cause the door to swing open with tremendous force. It should be appreciated that the term "hook" or "latch" should be broadly defined as any protrusion or member capable of physically or mechanically engaging with another protrusion or member. It should further be appreciated that the term "U-shaped latch" is not limiting and any latching or hooking mechanism, as defined above, can be used.

As discussed above, shelving space formed by the bottom unit and surrounding the top unit employs drainage paths with fluid sensors, in multiple locations internal and external to the device, in order to enable zoned leak detection. Specifically, by building in drainage paths, with optical leak sensors, into the external body of the device, the system captures and routes fluids potentially leaked from the external components (like the sorbent canister) to the optical leak sensors. For example, in one embodiment, the surface 2132 of the top unit upon which the manifold 2130 is mounted and against which the casing 2125 rests and forms a cavity, comprises angled surfaces 2190 that form angled edges which serve to capture moisture emitted or leaked from the manifold 2130, and areas around the manifold 2130, and direct the moisture, through force of gravity, to a centrally positioned moisture sensor 2180. Preferably, the angled surfaces 2190 are sufficiently inclined to cause moisture landing on the angled edges to move downward toward one or more moisture sensors 2180 positioned to receive the moisture. In one embodiment, one moisture sensor 2180 is centrally located, relative to the position of the manifold 2130, and equidistant from the ends of each angled surface 2190.

Figure 22:
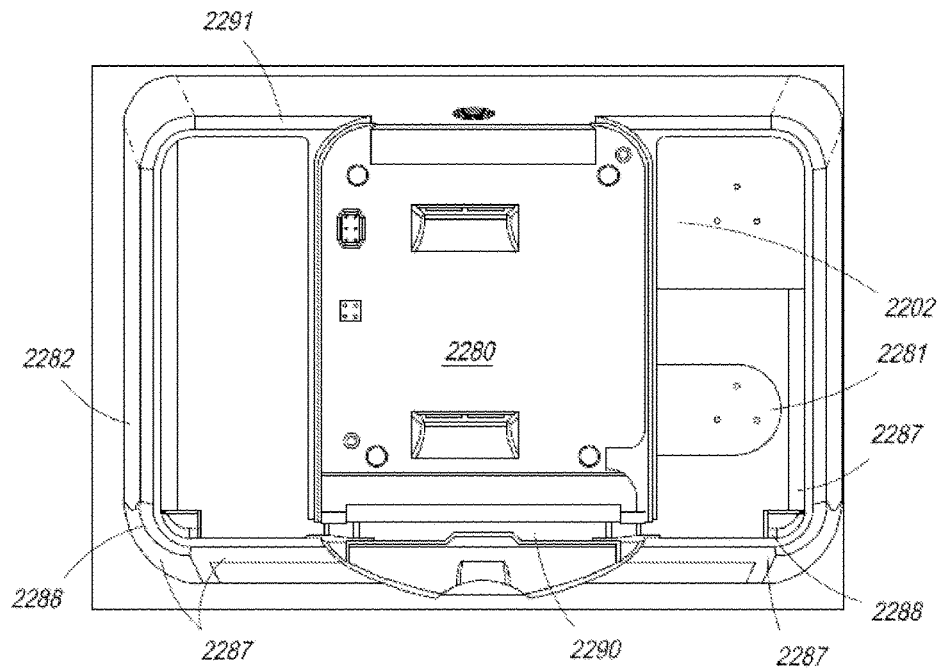
FIG. 22 is a schematic view of one embodiment of moisture sensors positioned on the reservoir unit of the dialysis system.

In one embodiment, integrated within the external housings of the bottom unit are at least three different optical leak detectors. Referring to FIG. 22, the top surface of bottom unit 2202 is slightly angled, with center 2280 raised relative to sides 2281 and 2282. In one embodiment, the surface tilts downward, from center area 2280 to sides 2281 and 2282, by an angle of 1 to 10 degrees, preferably 3 degrees. Channels 2287 encircle the top surface of the bottom unit, extend around the periphery, extend through the center of the top surface, and/or extend through any other portion of the top surface. By virtue of the angled top surface of the bottom unit 2202, the channels 2287 are also angled from the center 2280 to the sides 2281, 2282. In another embodiment, the top surface is also slightly angled downward from back side 2291 to front surface 2290. The angled channels 2287 cause fluids to be directed away from the center and/or back of the system forward and to the sides where leak detectors 2288 are positioned and are in fluid communication with the channels 2287.

Figure 23:
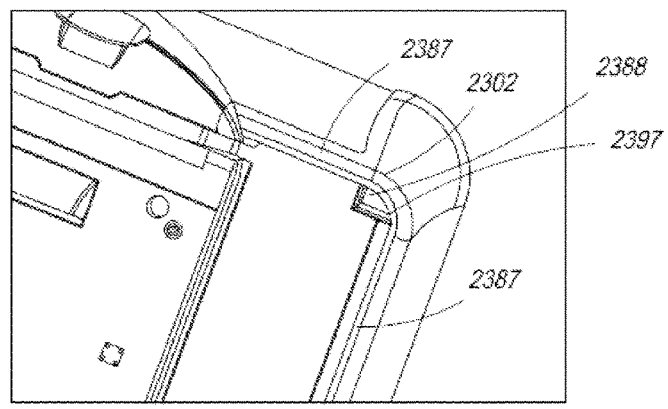
FIG. 23 is a close-up schematic view of one embodiment of moisture sensors positioned on the reservoir unit of the dialysis system.

A first optical leak detector 2288 is located on the front right corner of the top surface of the bottom unit 2202. A second optical leak detector 2288 is located on the front left corner of the top surface of the bottom unit 2202. Each leak detector is positioned within a well or cavity and comprises an optical sensor, which is located in the side of the well. The optical sensor detects fluids that have drained and/or been channeled to the wells and transmits a detected signal to a controller in the top unit. The detected signal is processed by a processor to determine if a leak has occurred. Detected signals are then stored and, if required, the processor causes an alarm or alert to display on the GUI. The well or cavity preferably comprises a rounded base to permit the user to easily wipe the well dry. FIG. 23 shows a more detailed view of the top surface of the bottom unit 2302 with channels 2387 and leak detector 2388 positioned within well 2397.

Figure 24:
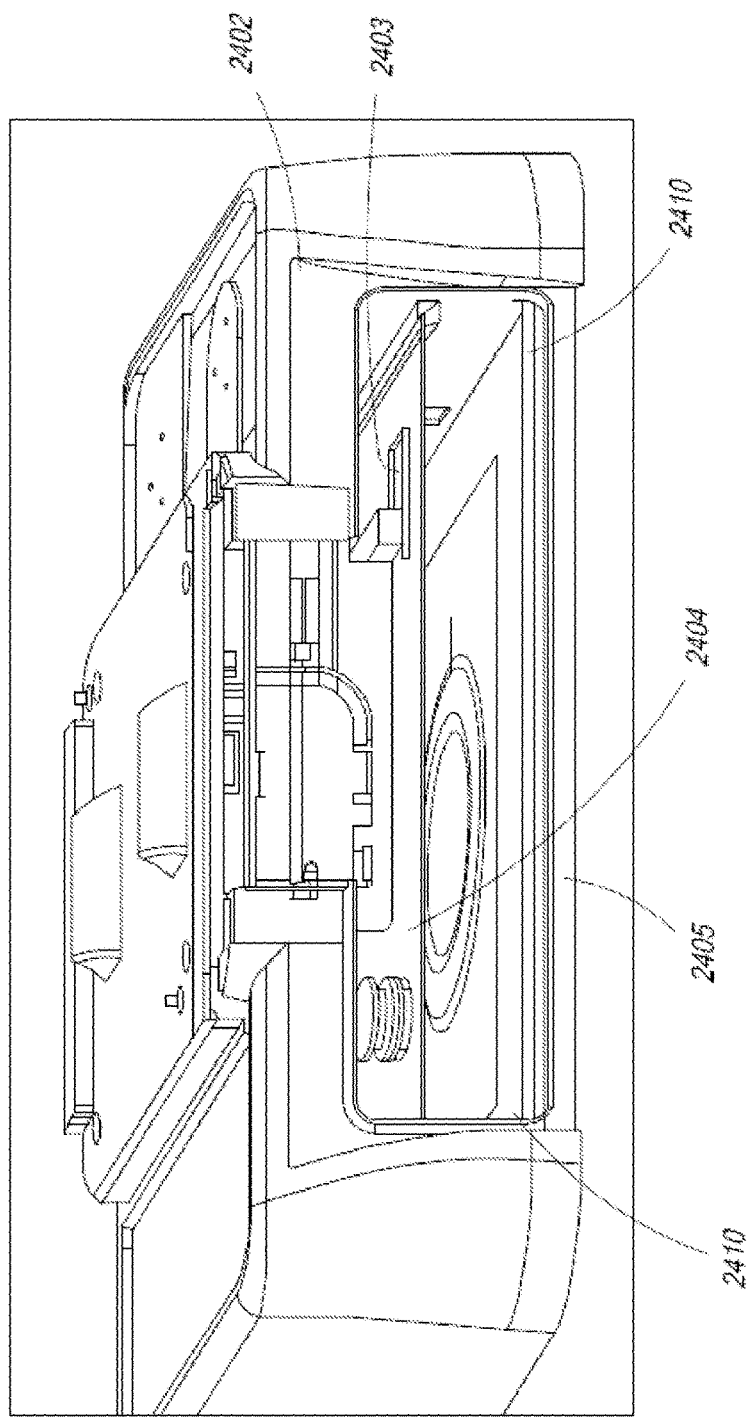
FIG. 24 is a front view of one embodiment of the reservoir unit of the dialysis system with the door open.

Referring to FIG. 24, at least one additional leak detector is located within the bottom unit 2402 and, more particularly inside the reservoir 2403, within which a scale 2404 is integrated. Channels 2405 are integrated into the reservoir structure, such as the internal housing or metal bag holder, and are preferably angled from one side to the other side or from the center to either side. In one embodiment, the angle is in the range of 1 to 10 degrees and more particularly 3 degrees. A well 2410 housing a leak detector is integrated into the reservoir housing and in fluid communication with the channels 2405 in one or both sides of the reservoir housing. If a leak occurs in the disposable bag, fluid will drain to the corner of the metal pan or reservoir housing via channels 2405 and be directed into at least one well with a leak sensor 2410.

The drainage paths serve two functions: a) to make sure fluid does not enter the instrument and b) to make sure that a leak is quickly contained and routed to a sensor which can trigger an alert or alarm. Additionally, the device preferably also includes fluid drainage channels leading to wells with optical sensors on the interior of the device. So, for instance, if there is a leak in the internal reservoir, the fluid is routed away from critical components and an optical sensor warns of the leak. Based on the sensor activated, the GUI can present an alarm to the user and can specifically identify the location of the fluid leak. By providing several independent zones of leak detection (several fluid sensors and drainage paths), the instrument can guide the user to find the leak quickly. Having multiple channels and sensors allows the system to partially, automatically, identify the source of the leak and offer graphic assistance, toward remedy of the problem, to the user.

Figure 25:
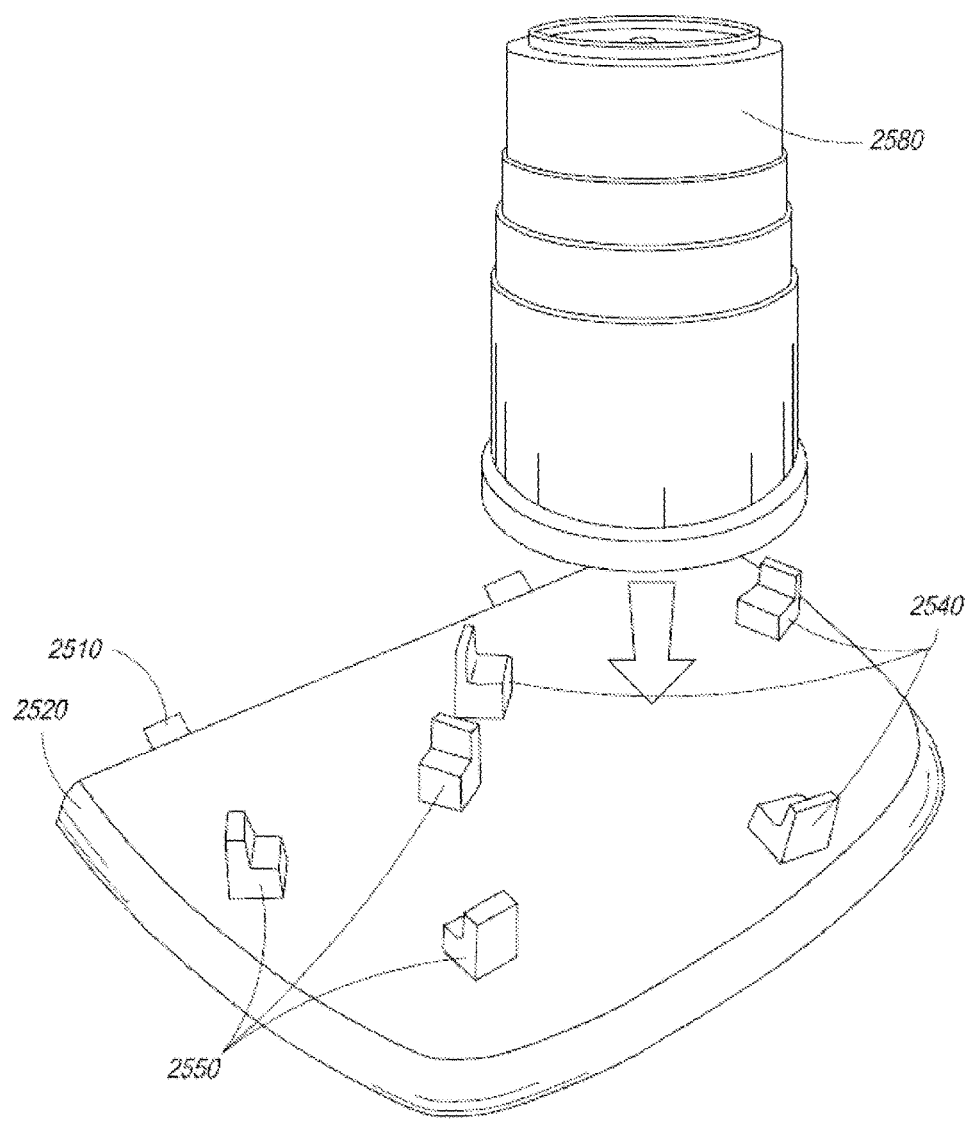
FIG. 25 is a schematic view of one embodiment of a connector mechanism for attaching a sorbent cartridge and/or concentrate jar to the dialysis system.

Referring now to FIG. 25, when a sorbent cartridge 2580 fills with waste material, it expands and, if not properly anchored to the base, can tip over. In one embodiment, the sorbent cartridge 2580 is anchored to the base 2520, and temporarily physically attached thereto, by a plurality of connectors 2540. The base 2520 is a planar structure having connectors 2510 that are configured to removably attach to mating connectors on the base of the dialysis system. In one embodiment, the base unit 2520 comprises two mating connectors 2510 having complementary mating connectors on the base unit. The connectors 2540 comprise at least two, preferably three, or optionally more than three L-shaped members. In a three connector configuration 2540, the connectors are equally distributed around a circumference that is slightly larger than the periphery of the base of the sorb ent cartridge 2580. When the sorbent cartridge 2580 is placed within the connectors, it fits snugly therein and is kept in place by the weight of the cartridge 2580. The planar surface 2520 further comprises a second set of connectors 2550 that comprise at least two, preferably three, or optionally more than three L-shaped members. In a three connector configuration 2550, the connectors are equally distributed around a circumference that is slightly larger than the periphery of the base of a concentrate jar. When the concentrate jar is placed within the connectors 2550, it fits snugly therein and is kept in place by the weight of the jar 2550.

Exemplary Blood and Dialysate Fluid Paths

Figure 26:
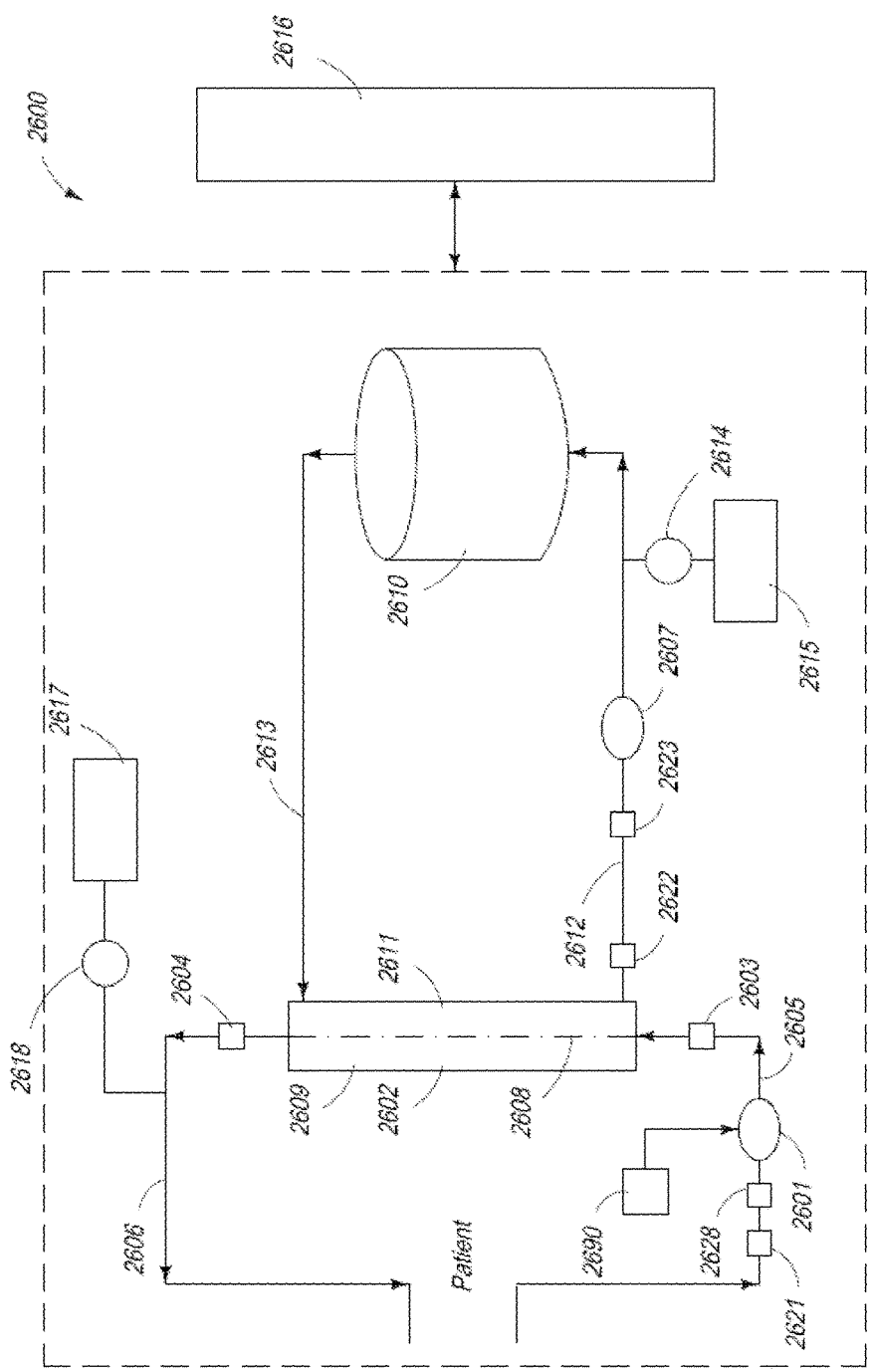
FIG. 26 is a first exemplary fluid circuit diagram.

The disclosed embodiments can be used to provide dialysis treatments to a patient. FIG. 26 is a functional block diagram of one embodiment of a multiple-pass sorbent-based dialysis system of the present invention. In one embodiment, dialysis system 2600 employs a dialyzer cartridge 2602 comprising a high flux membrane to remove toxins from the blood both by diffusion and by convection. The removal of toxins by diffusion is accomplished by establishing a concentration gradient across the semi-permeable membrane by allowing a dialysate solution to flow on one side of the membrane in one direction while simultaneously allowing blood to flow on the other side of the membrane in the opposite direction. To enhance removal of toxins using hemodiafiltration, a substitution fluid is continuously added to the blood either prior to the dialyzer cartridge (pre-dilution) or after the dialyzer cartridge (post-dilution). An amount of fluid equal to that of the added substitution fluid is "ultra-filtered" across the dialyzer cartridge membrane, carrying the added solutes with it.

Figure 27:
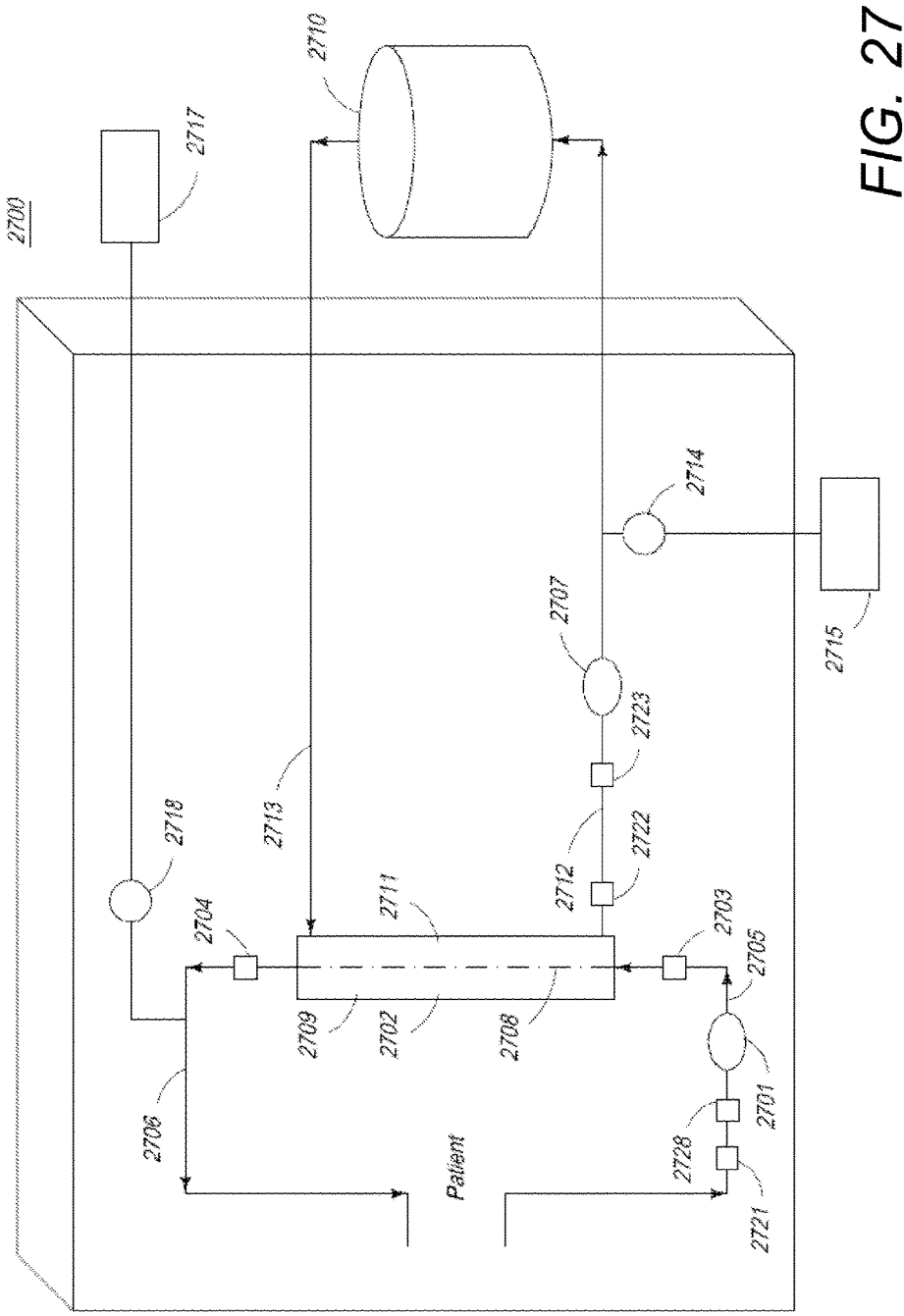
FIG. 27 is a second exemplary fluid circuit diagram.

Referring to both FIGS. 26 and 27 simultaneously, in one embodiment, the blood containing toxins is pumped from a blood vessel of a patient by a blood pump 2601, 2701 and is transferred to flow through dialyzer cartridge 2602, 2702. Optionally, inlet and outlet pressure sensors 2603, 2604, 2703, 2704 in the blood circuit measure the pressure of blood both before it enters the dialyzer cartridge 2602, 2702 via the blood inlet tube 2605, 2705 and after leaving the dialyzer cartridge 2602, 2702 via the blood outlet tube 2606, 2706. Pressure readings from sensors 2603, 2604, 2628, 2703, 2704, 2728 are used as a monitoring and control parameter of the blood flow. A flow meter 2621, 2721 may be interposed in, or otherwise in pressure communication with, the portion of blood inlet tube 2605, 2705 that is located directly upstream from the blood pump 2601, 2701. The flow meter 2621, 2721 is positioned to monitor and maintain a predetermined rate of flow of blood in the impure blood supply line. A substitution fluid 2690 may be continuously added to the blood either prior to the dialyzer cartridge (pre-dilution) or after the dialyzer cartridge (post-dilution).

In one embodiment, referring to both FIGS. 26 and 27, dialyzer cartridge 2602, 2702 comprises a semi-permeable membrane 2608, 2708 that divides the dialyzer 2602, 2702 into a blood chamber 2609, 2709 and a dialysate chamber 2611, 2711. As blood passes through the blood chamber 2609, 2709, uremic toxins are filtered across the semi-permeable membrane 2608, 2708 due to convective forces. Additional blood toxins are transferred across the semi-permeable membrane 2608, 2708 by diffusion, primarily induced by a difference in concentration of the fluids flowing through the blood and dialysate chambers 2609, 2709 and 2611, 2711 respectively. The dialyzer cartridge used may be of any type suitable for hemodialysis, hemodiafiltration, hemofiltration, or hemoconcentration, as are known in the art. In one embodiment, the dialyzer 2602, 2702 contains a high flux membrane. Examples of suitable dialyzer cartridges include, but are not limited to, Fresenius® F 60, F 80 available from Fresenius Medical Care of Lexington, Mass., Baxter CT 110, CT 190, Syntra® 160 available from Baxter of Deerfield, Ill., or Minntech Hemocor HPH® 1000, Primus® 1350, 2000 available from Minntech of Minneapolis, Minn.

In one embodiment of the present invention, dialysate pump 2607, 2707 draws spent dialysate from the dialyzer cartridge 2602, 2702 and forces the dialysate into a dialysate regeneration system 2610, 2710 and back 2613, 2713 into the dialyzer cartridge 2602, 2702 in a multiple pass loop, thus generating "re-generated" or fresh dialysate. Optionally, a flow meter 2622, 2722 is interposed in the spent dialysate supply tube 2612, 2712 upstream from dialysate pump 2607, 2707 which monitors and maintains a predetermined rate of flow of dialysate. A blood leak sensor 2623, 2723 is also interposed in spent dialysate supply tube 2612, 2712.

The multi-pass dialysate regeneration system 2610, 2710 of the present invention comprises a plurality of cartridges and/or filters containing sorbents for regenerating the spent dialysate. By regenerating the dialysate with sorbent cartridges, the dialysis system 2600, 2700 of the present invention requires only a small fraction of the amount of dialysate of a conventional single-pass hemodialysis device.

In one embodiment, each sorbent cartridge in the dialysate regeneration system 2610, 2710 is a miniaturized cartridge containing a distinct sorbent. For example, the dialysate regeneration system 2610, 2710 may employ five sorbent cartridges, wherein each cartridge separately contains activated charcoal, urease, zirconium phosphate, hydrous zirconium oxide and activated carbon. In another embodiment each cartridge may comprise a plurality of layers of sorbents described above and there may be a plurality of such separate layered cartridges connected to each other in series or parallel in the dialysate regeneration system. Persons of ordinary skill in the art would appreciate that activated charcoal, urease, zirconium phosphate, hydrous zirconium oxide and activated carbon are not the only chemicals that could be used as sorbents in the present invention. In fact, any number of additional or alternative sorbents, including polymer-based sorbents, could be employed without departing from the scope of the present invention.

The sorbent-based multiple-pass dialysis system of the present invention provides a plurality of advantages over conventional single-pass systems. These include:

No requirement of a continuous water source, a separate water purification machine or a floor drain as the system of present invention continuously regenerates a certain volume of dialysate. This allows for enhanced portability.

The present system requires a low amperage electrical source, such as 15 amps, because the system recycles the same small volume of dialysate throughout the diafiltration procedure. Therefore, extra dialysate pumps, concentrate pumps and large heaters used for large volumes of dialysate in single pass dialysis systems are not required.

The present system can use low volumes of tap water, in the range of 6 liters, from which dialysate can be prepared for an entire treatment.

The sorbent system uses sorbent cartridges that act both as a water purifier and as a means to regenerate used dialysate into fresh dialysate.

While the current embodiment has separate pumps 2601, 2701, 2607, 2707 for pumping blood and dialysate through the dialyzer, in an alternate embodiment, a single dual-channel pulsatile pump that propels both blood and dialysate through the hemodiafiltration system 2600, 2700 may be employed. Additionally, centrifugal, gear, or bladder pumps may be used.

In one embodiment, excess fluid waste is removed from the spent dialysate in the spent dialysate tube 2612, 2712 using a volumetric waste micro-pump 2614, 2714 and is deposited into a waste collection reservoir 2615, 2715 which can be periodically emptied via an outlet such as a tap. An electronic control unit 2616 comprising a microprocessor monitors and controls the functionality of all components of the system 2600.

In one embodiment, diafiltered blood exiting dialyzer cartridge 2602, 2702 is mixed with regulated volumes of sterile substitution fluid that is pumped into the blood outlet tube 2606, 2706 from a substitution fluid container 2617, 2717 via a volumetric micro-pump 2618, 2718. Substitution fluid is typically available as a sterile/non-pyrogenic fluid contained in flexible bags. This fluid may also be produced on-line by filtration of a non-sterile dialysate through a suitable filter cartridge rendering it sterile and non-pyrogenic.

Figure 28:
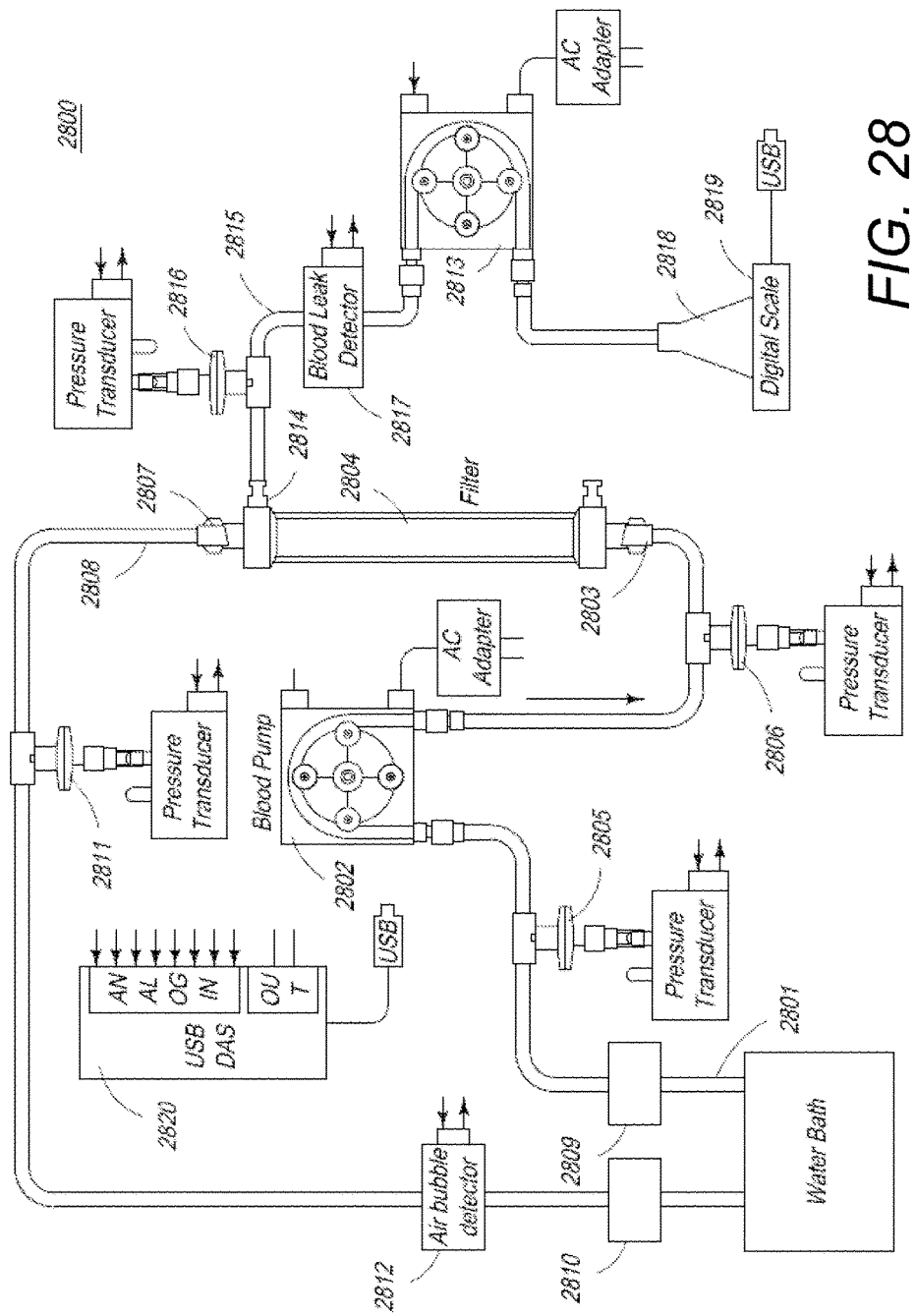
FIG. 28 is a third exemplary fluid circuit diagram.

FIG. 28 is a functional block diagram showing one embodiment of an ultrafiltration treatment system 2800 of the present invention. As shown in FIG. 28, blood from a patient is drawn into blood inlet tubing 2801 by a pump, such as a peristaltic blood pump, 2802 that forces the blood into a hemofilter cartridge 2804 via blood inlet port 2803. Inlet and outlet pressure transducers 2805, 2806 are connected in-line just before and after the blood pump 2802. The hemofilter 2804 comprises a semi-permeable membrane that allows excess fluid to be ultrafiltrated from the blood passing therethrough, by convection. Ultrafiltered blood is further pumped out of the hemofilter 2804 through blood outlet port 2807 into blood outlet tubing 2808 for infusion back to into the patient. Regulators, such as clamps, 2809, 2810 are used in tubing 2801 and 2808 to regulate fluid flow therethrough.

A pressure transducer 2811 is connected near the blood outlet port 2807 followed by an air bubble detector 2812 downstream from the pressure transducer 2811. An ultrafiltrate pump, such as a peristaltic pump, 2813 draws the ultrafiltrate waste from the hemofilter 2804 via UF (ultrafiltrate) outlet port 2814 and into the UF outlet tubing 2815. A pressure transducer 2816 and a blood leak detector 2817 are transposed into the UF outlet tubing 2815. Ultrafiltrate waste is finally pumped into a waste collection reservoir 2818 such as a flask or soft bag, attached to the leg of an ambulatory patient and equipped with a drain port to allow intermittent emptying. The amount of ultrafiltrate waste generated can be monitored using any measurement technique, including a scale 2819 or flow meter. The microcontroller 2820 monitors and manages the functioning of the blood and UF pumps, pressure sensors as well as air and blood leak detectors. Standard luer connections such as luer slips and luer locks are used for connecting tubing to the pumps, the hemofilter and to the patient.

Figure 29:
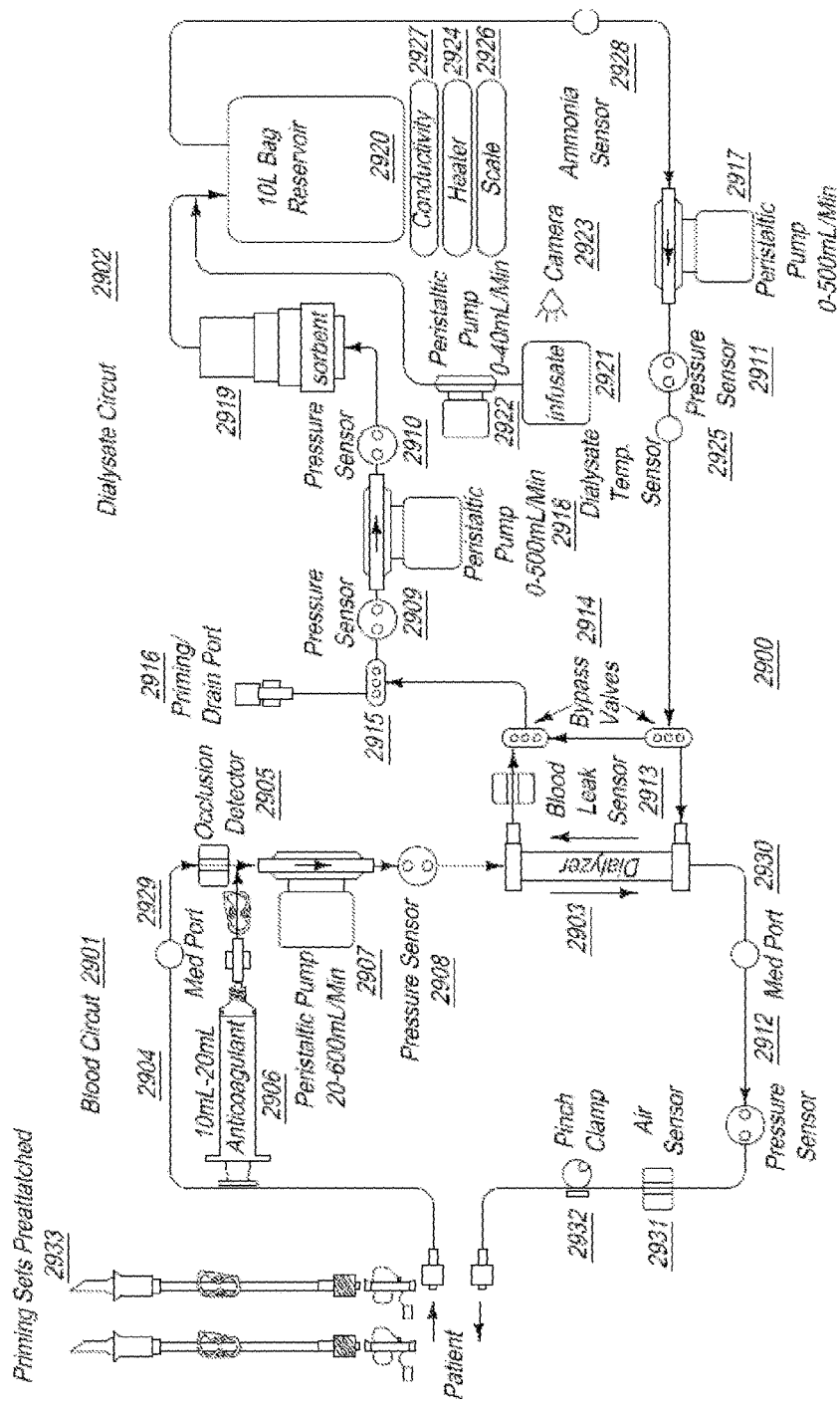
FIG. 29 is a fourth exemplary fluid circuit diagram.

Another blood and dialysate circuit capable of being implemented or used in the embodiments of the dialysis systems is shown in FIG. 29. FIG. 29 depicts the fluidic circuit for an extracorporeal blood processing system 2900 used for conducting hemodialysis and hemofiltration. In one embodiment of the present invention, the system 2900 is implemented as a portable dialysis system which may be used by a patient for conducting dialysis at home. The hemodialysis system comprises two circuits—a Blood Circuit 2901 and a Dialysate Circuit 2902. Blood treatment during dialysis involves extracorporeal circulation through an exchanger having a semi permeable membrane—the hemodialyzer or dialyzer 2903. The patient's blood is circulated in the blood circuit 2901 on one side of the membrane (dialyzer) 2903 and the dialysate, comprising the main electrolytes of the blood in concentrations prescribed by a physician, is circulated on the other side in the dialysate circuit 2902. The circulation of dialysate fluid thus provides for the regulation and adjustment of the electrolytic concentration in blood.

The line 2904 from the patient, which transports impure blood to the dialyzer 2903 in the blood circuit 2901 is provided with an occlusion detector 2905 which is generally linked to a visual or audible alarm to signal any obstruction to the blood flow. In order to prevent coagulation of blood, delivery means 2906, such as a pump, syringe, or any other injection device, for injecting an anticoagulant—such as heparin, into blood is also provided. A peristaltic pump 2907 is also provided to ensure flow of blood in the normal (desired) direction.

A pressure sensor 2908 is provided at the inlet where impure blood enters the dialyzer 2903. Other pressure sensors 2909, 2910, 2911 and 2912 are provided at various positions in the hemodialysis system to track and maintain fluid pressure at desired levels at specific points within the respective circuits.

At the point where used dialysate fluid from the dialyzer 2903 enters the dialysate circuit 2902, a blood leak sensor 2913 is provided to sense and warn of any leakage of blood cells into the dialysate circuit. A pair of bypass valves 2914 is also provided at the beginning and end points of the dialysate circuit, so that under conditions of start up, or at other times as deemed necessary by the operator, the dialyzer can be bypassed from the dialysate fluid flow, yet the dialysate fluid flow can still be maintained, i.e. for flushing or priming operations. Another valve 2915 is provided just before a priming/drain port 2916. The port 2916 is used for initially filling the circuit with a dialysate solution, and to remove used dialysate fluid after, and in some instances during, dialysis. During dialysis, valve 2915 may be used to replace portions of used dialysate with high concentrations of, for instance, sodium with replenishment fluid of appropriate concentration so that overall component concentration of the dialysate is maintained at a desired level.

The dialysate circuit is provided with two peristaltic pumps 2917 and 2918. Pump 2917 is used for pumping dialysate fluid to the drain or waste container, as well as for pumping regenerated dialysate into the dialyzer 2903. Pump 2918 is used for pumping out spent dialysate from the dialyzer 2903, maintaining fluid pressure through the sorbent 2919, and pumping in dialysis fluid from port 2916 to fill the system or maintain component concentration in the dialysate.

A sorbent cartridge 2919 is provided in the dialysate circuit 2902. The sorbent cartridge 2919 contains several layers of materials, each having a role in removing impurities, such as urea and creatinine. The combination of these layered materials allows water suitable for drinking to be charged into the system for use as dialysate fluid. It also allows closed loop dialysis. That is, the sorbent cartridge 2919 enables regeneration of fresh dialysate from the spent dialysate coming from the dialyzer 2903. For the fresh dialysate fluid, a lined container or reservoir 2920 of a suitable capacity such as 0.5, 1, 5, 8 or 10 liters is provided.

Depending upon patient requirements and based on a physician's prescription, desired quantities of an infusate solution 2921 can be added to the dialysis fluid. Infusate 2921 is a solution containing minerals and/or glucose that help replenish minerals like potassium and calcium in the dialysate fluid at levels after undesired removal by the sorbent. A peristaltic pump 2922 is provided to pump the desired amount of infusate solution 2921 to the container 2920. Alternatively, the infusate solution 2921 can be pumped into the outflow line from reservoir 2920. A camera 2923 may optionally be provided to monitor the changing liquid level of the infusate solution as a safety check warning of infusate flow failure and/or function as a bar code sensor to scan bar codes associated with additives to be used in a dialysis procedure. Optionally, an ammonia sensor 2928 may be provided.

A heater 2924 is provided to maintain the temperature of dialysate fluid in the container 2920 at the required level. The temperature of the dialysate fluid can be sensed by the temperature sensor 2925 located just prior to the fluid's entry into the dialyzer 2903. The container 2920 is also equipped with a scale 2926 for keeping track of the weight, and therefore volume, of the fluid in the container 2920, and a conductivity sensor 2927, which determines and monitors the conductivity of the dialysate fluid. The conductivity sensor 2927 provides an indication of the level of sodium in the dialysate.

A medical port 2929 is provided before blood from the patient enters the system for dialysis. Another medical port 2930 is provided before clean blood from the dialyzer 2903 is returned to the patient. An air (or bubble) sensor 2931 and a pinch clamp 2932 are employed in the circuit to detect and prevent any air, gas or gas bubbles from being returned to the patient.

Priming set(s) 2933 is/are attached to the dialysis system 2900 that help prepare the system by filling the blood circuit 2901 with sterile saline before it is used for dialysis. Priming set(s) may consist of short segments of tubing with IV bag spikes or IV needles or a combination of both pre-attached.

It should be appreciated that, while certain of the aforementioned embodiments disclose the incorporation and use of a port that receives an injection or administration of an anticoagulant, thereby creating an air-blood interface, such a port can be eliminated if the device can operate with minimal risk of blood clotting at ports of entry and exit. As further discussed below, the manifold design, particularly with respect to the internal design of the manifold ports, minimizes the risk of blood clotting, thereby creating the option of eliminating air-blood interfaces for receiving an injection or administration of an anticoagulant.

One of ordinary skill in the art would infer from the above discussion that the exemplary fluidic circuits for a hemodialysis and/or hemofiltration system are complex. If implemented in a conventional manner, the system would manifest as a mesh of tubing and would be too complicated for a home dialysis user to configure and use. Therefore, in order to make the system simple and easy to use at home by a patient, embodiments of the present invention implement the fluidic circuits in the form of a compact manifold in which most components of the fluidic circuit are integrated into a single piece of molded plastic or multiple pieces of molded plastic that are configured to connect together to form a single operative manifold structure.

Exemplary Manifolds

It should be appreciated that the multi-pass dialysis treatment processes, represented by the blood and dialysate circuits described above, can be implemented within, and by, a plurality of blood and dialysate circuits molded into a disposable manifold. As shown in FIG. 21, the embodiments of the dialysis system disclosed herein operate using a manifold 2130 that defines a plurality of blood and dialysate circuits and places the fluid into pressure, thermal, and/or optical communication with various sensors, meters, and pumps.

In one embodiment, the manifold of the present invention comprises a composite plastic manifold, into which the blood and dialysate flow paths are molded. Blood purification system components, such as sensors and pumps, are placed into pressure, thermal, and/or optical communication within the fluid flow contained within the molded manifold.

Figure 30:
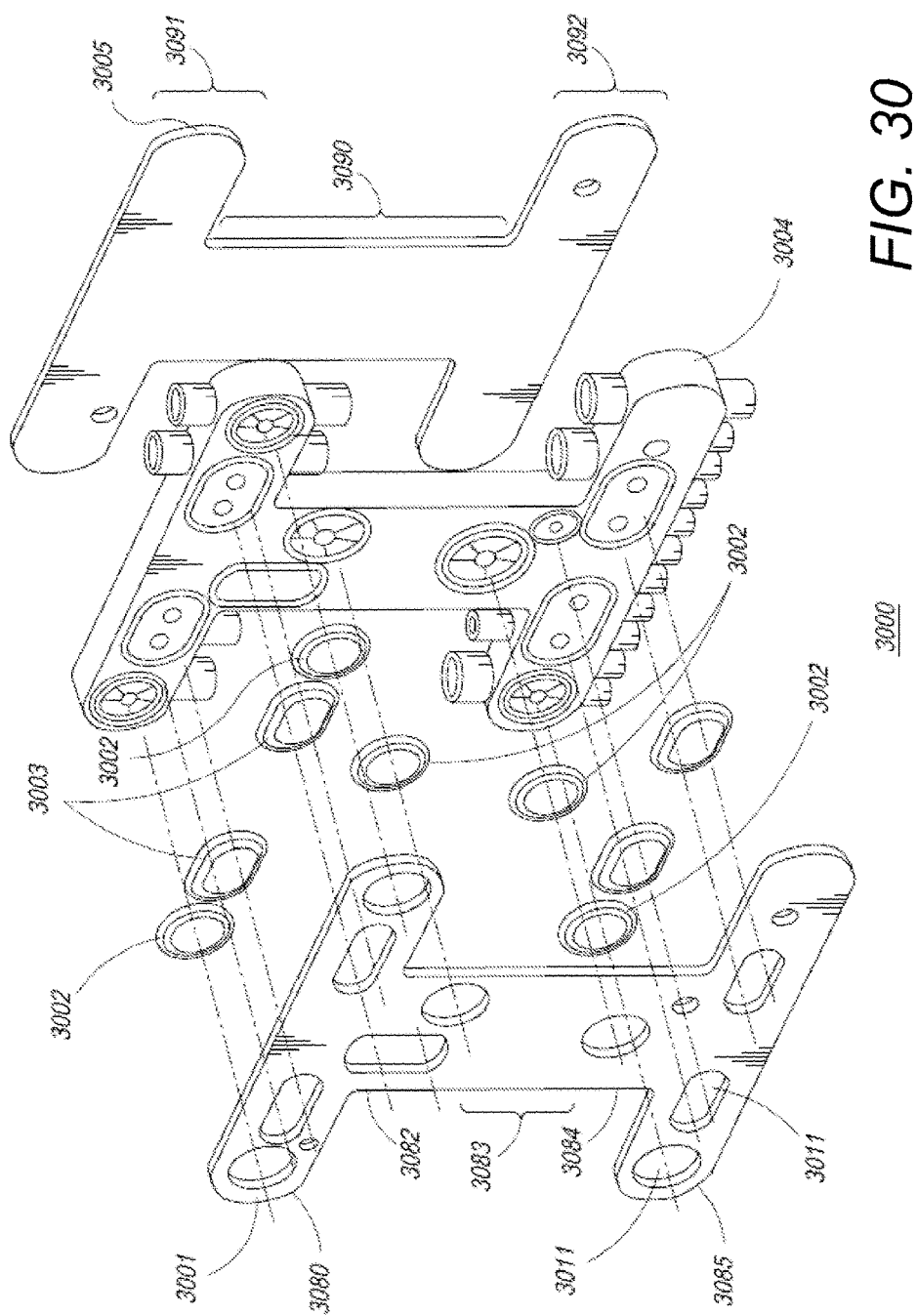
FIG. 30 is a schematic view of one embodiment of an exemplary manifold.

FIG. 30 illustrates the structural elements of a compact manifold, according to one embodiment of the present invention. The disposable manifold pumps and directs fluid flow while measuring pressure in key areas. Those fluids include blood, dialysate, infusate and anticoagulant. In addition, the manifold provides features for detecting blood leakage from the dialyzer, detecting occlusion in the arterial line, and detecting air in the venous line.

Referring to FIG. 30, in one embodiment, the compact manifold 3000 comprises a plurality of plastic layers with components fixedly attached therein. More specifically, the manifold 3000 comprises the following elements:
Back Cover 3001
Pressure Transducer Membranes 3002
Valve Membranes 3003
Mid Body 3004
Front Cover 3005
Pump tube segments (not shown in FIG. 30)

The mid-body layer 3004 contains molded in channels on one side. These channels are completed by the front cover layer which is fixedly attached to the mid-body by any number of methods, including ultrasonic welding. This combined front cover-mid-body structure forms the major part of the fluid pathways within the manifold. On the opposite side of the mid-body 3004 there are features that form surfaces for valving and pressure sensing, which communicate to the fluid pathways on the front cover side of the manifold. The manifold includes elastomeric components for valving and pressure sensing. These elastomeric components are captured between the back cover layer and mid-body layer through the use of ultrasonic welding and complete the fluid pathways throughout the manifold.

Referring to FIG. 30, in one embodiment, the manifold 3000 comprises five pressure transducer membranes 3002 and three to four membranes 3003 for two-way valves. In one embodiment, the two covers 3001 and 3005, and mid body 3004 of the manifold 3000 are molded of a polycarbonate material or ABS (acrylonitrile butadiene styrene). The pressure transducer membranes 3002 and valve membranes 3003 are molded of a common material, such as Santoprene, or more preferably Sarlink, which is a medical grade elastomeric polymer. In one embodiment, front and back covers 3005 and 3001 may be molded of optically clear material, at least transparent to certain preselected wavelengths of light, to allow for spectroscopic analysis of the fluid(s) contained within.

Additionally, the manifold preferably includes four pumping components. These pumping components are segments of extruded PVC tubing formulated and dimensioned to have properties optimized for pump use, particularly roller pump use. This tubing is bonded to barbed fittings that are integrally molded to the manifold mid-body. One of the four pumping components is for drawing blood from the patient's artery and pumping it through a dialyzer and back to the patient's vein. Two pumping components are for dialysate flow and one is for infusate delivery to the dialysate fluid circuit. A separate syringe pump can be used for pumping anticoagulant into the arterial blood pathway, pre-dialyzer.

In one embodiment, the manifold further incorporates tubing ports, preferably in the range of 10-14 and more preferably 12 ports, for connecting all the fluid pathways within the manifold to other components in the disposable set including dialyzer, sorbent cartridge, bag reservoir, infusate container, patient blood lines, anticoagulant, sensors, priming line and drain, as further discussed below.

Figure 32:
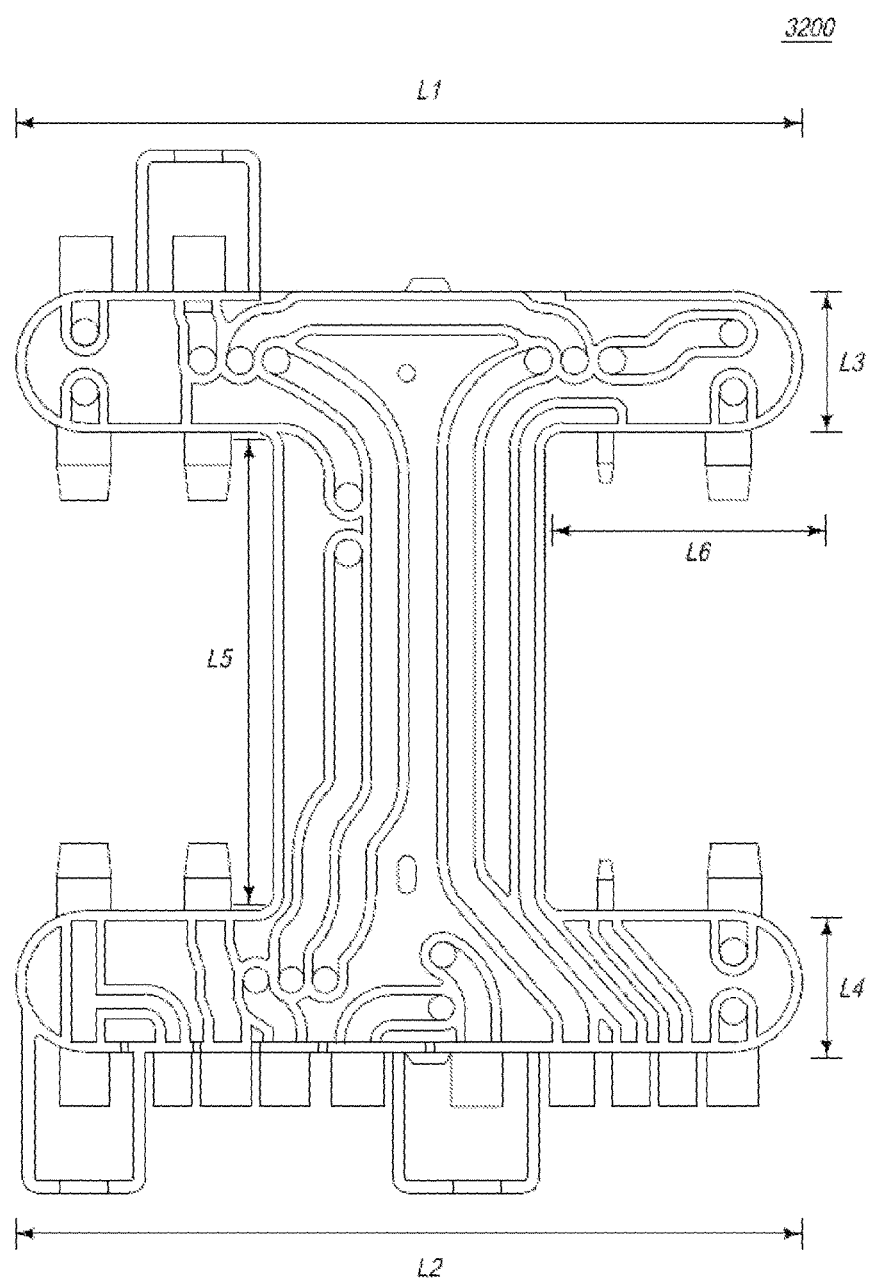
FIG. 32 is a schematic view of another embodiment of an exemplary manifold with dimensions associated therewith.

In one embodiment, the manifold is shaped like a capital "T", with a first segment and a second segment parallel to each other and a connecting segment that a) is perpendicular to the first segment and second segment and b) serves to connect the first and second segments. In one embodiment, the connecting segment connects the middle of the first segment to the middle of the second segment, thereby making the distance between the connecting segment and each end of the first and second segments equidistant. It should be appreciated that the connecting segment can be placed at the ends of the first and second segment, thereby making a capital "C" or backwards "C". The manifold can also be rotated relative to the dialysis system and need not be positioned as a capital "I", e.g. it can be positioned on its side or at an angle. As shown in FIG. 32, in an exemplary embodiment, the manifold 3200 has dimensions as follows: L1 and L2 are in the range of 4 to 7 inches, and preferably approximately 5.7 inches, L3 and L4 are in the range of 0.5 to 1.5 inches, and preferably approximately 1 inch, L5 is in the range of 2.5 to 4.5 inches, and preferably approximately 3.5 inches, and L6 is in the range of 1 to 3 inches, and preferably approximately 1.8 inches. While dimensions have been provided, it should be appreciated that the inventions disclosed herein are not limited to any specific dimension, or set of dimensions.

In one embodiment, the assembly process of the manifold 3000 comprises mating the back cover 3001 to the mid-body 3004 while affixing the membranes 3002 and 3003 into place by having a first side of the membranes physically attach or touch the mid-body and having a second side of the membranes pass through holes, spaces, or voids 3011 in the back cover 3001. Cover 3001 may be divided into two portions, a top portion and a bottom portion, wherein the top portion comprises a top portion of the central vertical portion 3082 and top horizontal section 3080 and the bottom portion comprises a bottom portion of the central vertical portion 3084 and bottom horizontal section 3085. In this embodiment, the top and bottom portions of the cover 3001 can be separately attached to the mid-body 3004 and, relative to a contiguous cover 3001, may not include material in the mid section area 3083 of the central vertical portion to save material costs. Preferably, the second side of the membranes has a tiered structure which permits a first tier to pass through the void 3011 while the second tier remains between the back cover 3001 and mid-body 3004. This affixes the membranes 3002, 3003 into the back cover 3001. Furthermore, it is preferred for the mid-body 3004 to contain recesses into which the first side of the membranes 3002, 3003 rest, thereby affixing them to the mid-body 3004. In an alternate configuration, the membranes 3002 and 3003 may be co-molded to the back cover 3001 in a multi-shot molding process.

One of ordinary skill in the art would appreciate that the various components of the manifold can be bound or affixed together using any suitable means. In one embodiment, the seal between the mid-body and back cover is achieved via ultrasonic welding or adhesive. Alternately laser welding may be employed. The front cover is bonded to the other side of the mid body in a similar manner. Pump tubing segments are solvent bonded into place in one embodiment, or in an alternate embodiment, the segments may be laser welded using a laser absorbing additive in the plastic.

In one embodiment, the front cover is molded from BASF Terlux 2802HD, ABS, which is clear and will provide visibility to the fluid pathway. The clarity of the ABS will also provide a means for inspecting the integrity of the ultrasonically welded surfaces. ABS is preferred for its biocompatibility as well as compatibility to ultrasonic welding. Additionally, the front cover can include a molded in textured surface to help facilitate a better bond between the front cover and the mid-body. This textured surface is a chemical etching process that is known to persons of ordinary skill in the art. One preferred texture depth is 0.0045". Other suitable textures can be laser etched as well. The surface to be welded on the front cover is designed with a 0.003" recess which translates to a 0.003" raised surface on the mold. This provides an accurate surface to receive the texturing. Once the texturing takes place on the mold, the height of this 0.003" surface is lowered. Because of the peaks and valleys of the 0.0045" texture depth it is assumed that the average would be half that amount or 0.00225". The result would leave the mold in a steel safe condition of 0.00075". Cover 3005 may also be in the form of just the central vertical portion 3090 and not include top and bottom horizontal portions 3091, 3092. Central vertical portion 3090 can be attached to the mid-body 3004 by placing it in a recessed area, defined by raised edges on the surface of the mid-body 3004 opposing the surfacing facing cover 3001, and bonding the portion 3090 within the recessed region.

In one embodiment, the front cover provides blood flow directors in both the arterial and venous pathways. These features are designed to minimize hemolysis. The blood flow directors provide for a consistent cross-sectional area throughout the pathway and minimize sharp edges to which the blood would come in contact without their presence. The wall on the opposite side of the blood flow directors has been relieved to provide a more consistent wall thickness in the molded plastic part. This will prevent sinks in this area, which could affect the surrounding welded surfaces. In one embodiment, the front cover wall thickness is 0.075".

Optionally, the front cover has alignment holes provided for assembly purposes to ensure that the front cover and mid-body are accurately aligned during the ultrasonic welding process. The raised bosses around the alignment holes help maximize contact with the alignment pins of the welding fixture so that the plastic does not melt as easily due to friction. These bosses do not touch and are not welded to the mid-body to ensure that the hole is patent.

Figure 31:
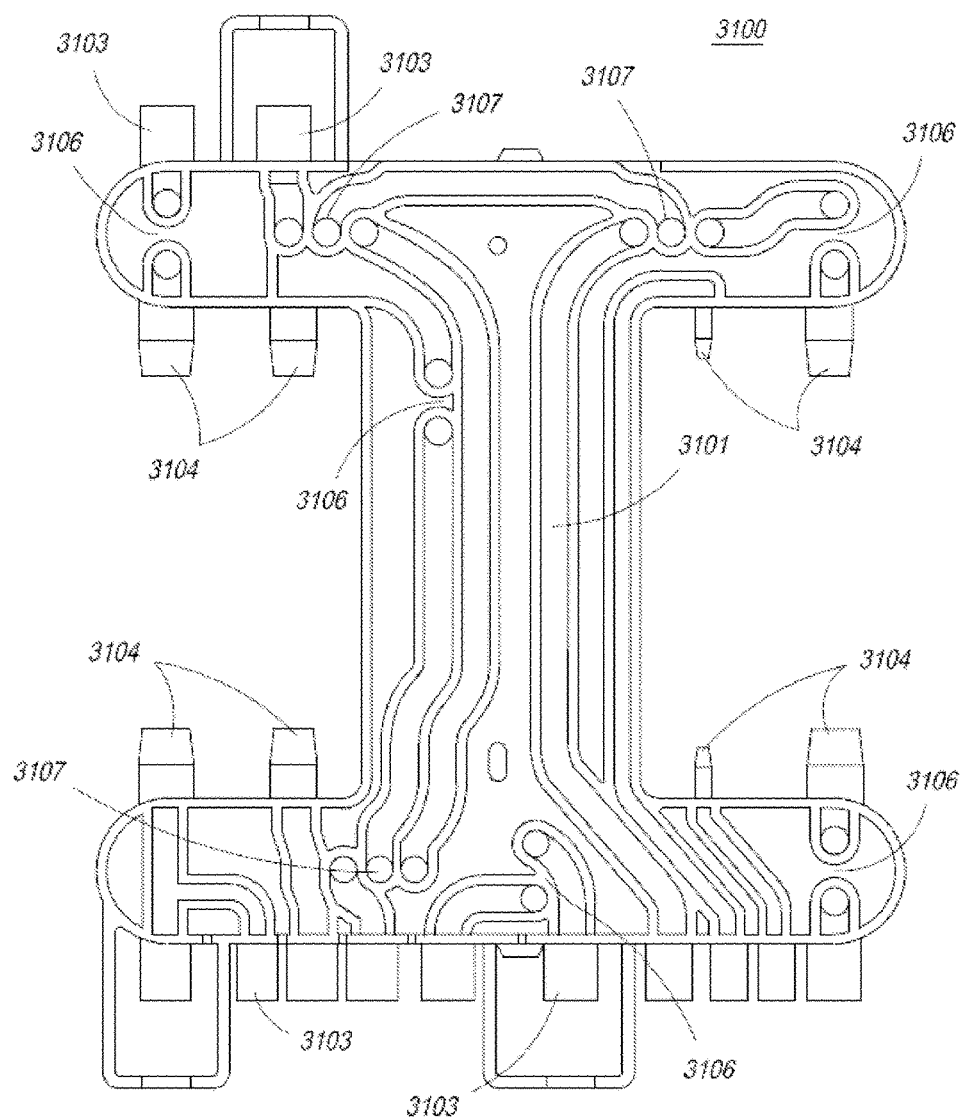
FIG. 31 is a schematic view of another embodiment of an exemplary manifold.

FIG. 31 provides a perspective view of the mid-body component of the compact manifold of the present invention. As is shown in FIG. 31, the complete blood and dialysate flow paths 3101 of the hemodialysis/hemofiltration system are molded into the mid-body. Accommodations for the various functional elements of the blood purification system, such as pumps, valves and sensors are also integrated into the mid-body section of the compact manifold.

The mid-body can be molded from BASF Terlux 2802HD, ABS. Another alternative ABS is Lustran 348, White. ABS was chosen for its biocompatibility as well as compatibility to ultrasonic welding. The mid-body along with the front cover provides the fluid path channels for the manifold. The mid-body contains the energy directors for the butt joint style ultrasonic welding. In one embodiment, the energy director's dimensions are 0.019" tall with a 0.024" wide base. This results in a cross-sectional area of 0.00023 square inches. The width of the welding surface is 0.075" resulting in a weld volume of about 0.003"×0.075". A butt joint style energy director is preferred over other styles, like shear joints, tongue and groove, step joint, due to its simplicity and ability to control the molded part geometry. Vents are provided in the weld geometry to prevent trapped gases from being forced through the welds resulting in a poor weld that may leak.

The back cover side of the mid-body preferably provides a molded in textured surface to help facilitate a better bond between the back cover and the mid-body. This textured surface is a chemical etching process that is known to persons of ordinary skill in the art. The preferred texture depth is 0.0045". Other suitable textures can be laser etched as well. The surface to be welded on the mid-body is designed with a 0.003" recess which translates to a 0.003" raised surface on the mold. Once the texturing takes place on the mold, the height of this 0.003" surface is lowered. Because of the peaks and valleys of the 0.0045" texture depth it is assumed that the average would be half that amount or 0.00225". The result would leave the mold in a steel safe condition of 0.00075".

The size of the components being welded can have a major impact on the successfulness of the ultrasonic welding process. The larger the surface area, the more difficult the welding process becomes. It is important that the welding surfaces are accurately controlled. Consistent thickness in the front and back covers is more important than flatness because a cover that is off slightly on flatness will be pressed flat during the welding process. Flatness on the mid-body is important due to the structural design that would prevent it from being flattened during the welding process. Due to these issues it is very important that the parts are designed correctly and not prone to anomalies like warpage, sinks, dimensional variations, etc. In addition, the mold construction and quality needs to match high standards that the parts will need to meet. It would follow that the molding process controls would require the highest of standards as well.

The back cover can be molded from BASF Terlux 2802HD, ABS. The back cover contains the energy directors for the butt joint style ultrasonic welding. The energy director's dimensions are 0.019" tall with a 0.024" wide base. This results in a cross-sectional area of 0.00023 square inches. The width of the welding surface is 0.075" resulting in a weld volume of about 0.003"×0.075". This 0.003" weld volume should be considered when determining the geometry of the assembled components. Vents are provided in the weld geometry to prevent trapped gases from being forced through the welds resulting in a poor weld that may leak. The alignment holes in the back cover are provided for assembly purposes to ensure that the back cover is accurately aligned to the mid-body during the ultrasonic welding process. The alignment holes in the back cover also provide accurate alignment of the manifold and instrument when properly loaded. The raised bosses around the alignment holes are designed to maximize contact with the alignment pins of the welding fixture so that the plastic does not melt as easily due to friction. These bosses do not touch and are not welded to ensure that the hole is patent.

Ultrasonic welding was chosen as the method for bonding the manifolds three major components because of the low cost of this manufacturing process. The relatively low equipment costs and cycle times to create the weld attribute to this lower manufacturing cost. Once the parts are loaded into the fixture, the welding cycle with horn travel and removal, can be accomplished in seconds. The actual weld time is about one second. Other bonding methods include hot plate, laser, and UV adhesive.

Referring to FIG. 31, in one embodiment, the mid-body section 3100 has integrated within it three 2-way valves 3107, five pressure transducers 3106, an occlusion detector, an air bubble detector and a blood leak detector. One of ordinary skill in the art would appreciate that the number and type of functional components that are integrated within the mid-body section 3100 may be varied according to the requirement and application of the blood purification system and, therefore, can include 1, 2, 3, 4, 6, 7, 8, 9, 10 or more pressure transducers, 1, 2, 4, 5, 6, or more 2-way valves, 0, 2, 3, 4, or more occlusion detectors, 0, 2, 3, 4, or more air bubble detectors, 0, 2, 3, 4 or more blood leak detectors. Additionally, the mid-body section 3100 comprises a plurality of ports 3103, 3104.

The ports include internal ports 3104 through which fluid flows via pump segments (not shown) from and between the first and second segments of the manifold 3100. In one embodiment, the first segment has four internal ports 3104, two on each side of the point where the first segment and connecting segment connect. It should be appreciated that the first segment can have 1, 2, 3, 5, 6, 7, or more internal ports. In one embodiment, the second segment has four internal ports 3104, two on each side of the point where the first segment and connecting segment connect. It should be appreciated that the second segment can have 1, 2, 3, 5, 6, 7, or more internal ports. Additionally, it is preferred that the position and location of the internal ports of the first segment mirrors the position and location of the internal ports of the second segment. The ports also include external ports 3103 to elements external to the manifold 3100. In one embodiment, the first segment has two external ports 3103. In one embodiment, the second segment has ten external ports 3104. In one embodiment, the first segment has 1, 3, 4, 5, 6, 7, 8, 9, 10, 11, 12, 13, 14, 15, or more external ports 3103. In one embodiment, the second segment has 1, 2, 3, 4, 5, 6, 7, 8, 9, 11, 12, 13, 14, 15, or more external ports 3104.

Incorporating fluid contacting elements into the manifold, as described above, enables the design of systems where reusable sensors are mounted in the dialysis machine to which the manifold is mated while necessarily disposable fluid contacting elements are separated out and placed in the manifold. To ensure proper readings and measurements are made, the fluid contacting elements and reusable sensors need to be aligned. Mating and alignment between the manifold and dialysis machine is critical with respect to positioning and pressure applied. Typically such mating precision must provide for 0.001" to 0.010" tolerance in X, Y and Z directions and apply a mounting force in the range of 10-100 PSI to oppose fluid forces with the manifold. Such critical positioning is accomplished by means of specially designed positioning surfaces on the manifold registering with complimentary positioning surfaces on the dialysis machine. Required forces are delivered by analysis and design of dialysis machine structure to allow for X and Y positions and Z direction deflections of less than about 0.001" to 0.010" under all fluidic and mechanical pressures developed within the manifold during operation. Because the manifold contains many structures on one monolithic substrate such critical alignment need only be done once serving to position all features of the manifold with all mating features of the dialysis machine.

The mid-body channel size is nominally in the range of 0.190" deep by 0.190" wide with 0.020" radiuses at the bottom corners of the channel on the mid-body side. The radius at the bottom corners of the channel should be the maximum to prevent sinks from occurring under the channel walls. These channel walls have valve and pressure diaphragm geometry on the opposite side of the mid-body, which could be adversely affected by sink in these areas. In one embodiment, the fluid pathways are square. General design rule to prevent sink is that the wall thickness of a rib (channel wall in this case) should not be more than 50-60% of the adjacent wall, to which it is attached. The channel wall is 0.075" and the adjacent wall (main manifold structure) is 0.130" resulting in 58%. The 0.190"×0.190" dialysate channels transition to the 0.155" tubing port through holes. This minimizes the accuracy required to align the front cover to the mid-body and minimizes the potential for sinks created by the thicker walls which could affect sealing features on the opposite side of the mid-body. The same approach was taken for anticoagulant and infusate channels. Gentle curves are designed into the channels to maximize laminar flow and minimize turbulent flow. In one embodiment, the anticoagulant and infusate channels, as discussed below, measure 0.190" deep by 0.100" wide.

In one embodiment, the mid-body has alignment holes for assembly purposes to ensure that both the front cover and back cover are accurately aligned to the mid-body during the ultrasonic welding process. The raised bosses around the alignment holes maximize contact with the alignment pins of the welding fixture so that the plastic does not melt as easily due to friction. These bosses do not touch and are not welded to ensure that the hole is patent.

Figure 33:
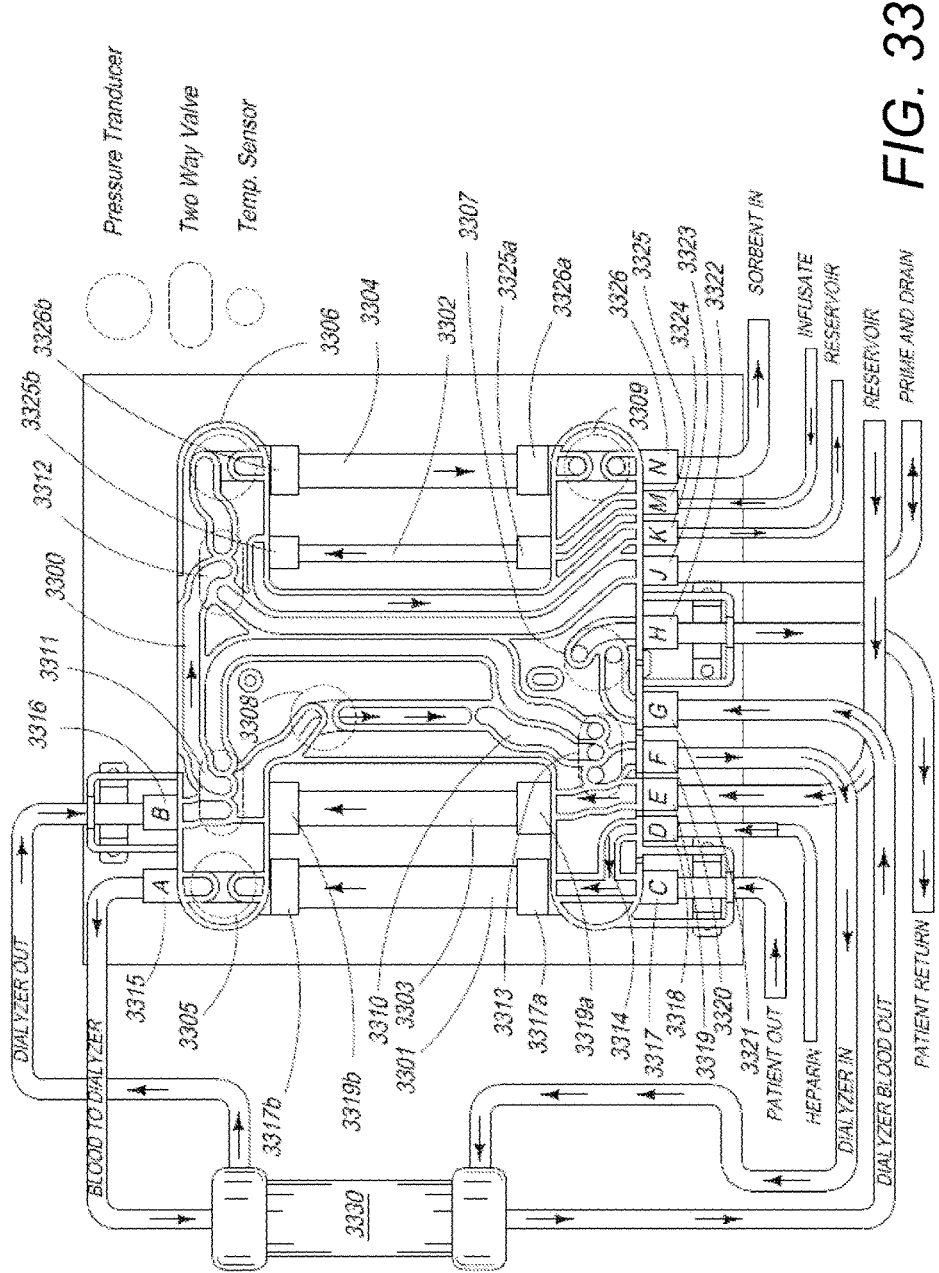
FIG. 33 is a schematic view of another embodiment of an exemplary manifold.

FIG. 33 is a diagram detailing the fluidic circuit for the compact manifold according to one embodiment of the present invention. The fluidic circuit comprises four pump tube segments P1 3301, P2 3302, P3 3303 and P4 3304 in pressure communication with pumps within the top controller unit and pump shoes in the top controller unit door. It further comprises five pressure membranes in pressure communication with pressure sensors S1 3305, S2 3306, S3 3307, S4 3308 and S5 3309, and an area in thermal or optical communication with a temperature sensor S6 3310. In the embodiment illustrated in FIG. 33, three pairs of membranes, VIA and V1B 3311, V2A and V2B 3312 and V3A and V3B 3313, are integrated into the manifold. The membranes function as valves when they are occluded by a pin, member or protrusion from the controller unit.

Grouped in this manner the pairs of six one way valves, 3311 A,B, 3312 A,B, 3313 A,B form three two way valve assemblies 3311, 3312, 3313. The two-way valves provide greater flexibility in controlling the configuration of a circuit. When conventional two-way valves are used to occlude portions of a fluid pathway, they are typically configured to enable two different fluid pathways, one for a first valve state and one for the second valve state. Certain valve embodiments, as disclosed below, used in combination with the valve membranes or pressure points integrated into the manifold, enable more nuanced control, enabling the creation of four distinctly different fluid flow paths.

Pump tube segments 3301, 3302, 3303, 3304 are bonded into the compact manifold. A number of ports are provided in the manifold, which connect with tubes external to the manifold to allow the flow of various fluids in and out of the manifold. These ports are connected to various tubes in the blood purification system for carrying fluids as follows:

Port A 3315—blood to the dialyzer 3330;
Port B 3316—dialyzer output (used dialysate);
Port C 3317—blood from the patient;
Port D 3318—heparin for mixing in the blood;
Port E 3319—reservoir output (fresh dialysate);
Port F 3320—dialyzer input (fresh dialysate);
Port G 3321—dialyzer output (blood);
Port H 3322—patient return (clean blood);
Port J 3323—connects to prime and drain line;
Port K 3324—reservoir infusate input;
Port M 3325—infusate in from infusate reservoir;
Port N 3326—dialysate flow into sorbent.

In one embodiment, a tube segment, formed as a pathway molded into the manifold structure 3300, connects the fluid flow of heparin 3314, entering via Port D 3318, to the fluid flow of blood, entering via Port C 3317. The combined heparin and blood flow through port 3317a, via pump segment 3301, and into port 3317b of the manifold 3300. A pressure transducer is in physical communication with a membrane 3305, formed in the manifold structure 3300, which, in turn, passes the blood and heparin fluid through Port A 3315. Fluid flow out of the manifold 3300 at Port A 3315 passes through dialyzer 3330, which is external to the manifold 3300. The dialyzed blood passes back into the manifold 3300 through Port G 3321 and into a segment 3307, formed as a pathway molded into the manifold structure 3300 that is in physical communication with a pressure transducer. Fluid then passes from the segment through Port H 3322 and into a patient return line.

Separately, dialysis fluid enters the manifold 3300 from a reservoir via Port E 3319. Fluid in the reservoir has infusate in it, which first enters the manifold 3300 via Port M 3325, passes through a segment, formed as a pathway molded into the manifold structure 3300, through another port 3325a, through a segment 3302 in communication with a pump, and back into the manifold 3300 via port 3325b. The infusate passes through a segment, formed as a pathway molded into the manifold structure 3300, and out the manifold 3300 at Port K 3324, where it passes into the reservoir. The dialysis fluid which entered the manifold via Port E 3319 passes through a segment, formed as a pathway molded into the manifold structure 3300, through another port 3319a, through a segment 3303 in communication with a pump, and back into the manifold 3300 via port 3319b.

The dialysate fluid passes into a segment, formed as a pathway molded into the manifold structure 3300, which is in physical communication with a pair of valves 3311. A segment, formed as a pathway molded into the manifold structure 3300, passes the dialysate fluid to another pair of valves 3313. The segment is in physical communication with pressure transducers 3308 and optional temperature sensor 3310. The dialysate fluid passes out of the manifold 3300 through Port F 3320, and into a line that passes into the dialyzer 3330.

A line out of the dialyzer 3330 passes fluid back into the manifold 3300 through Port B 3316 and into a segment, formed as a pathway molded into the manifold structure 3300, that is in physical communication with a first pair of valves 3311, a second pair of valves 3312, and a pressure transducer 3306. The used dialysate fluid passes out of the manifold 3300 through port 3326b, through segment 3304 in communication with a pump, and back into the manifold via port 3326a. A segment in fluid communication with port 3326a is in physical communication with pressure transducer 3309 and passes fluid through Port N 3326 and to a sorbent regeneration system.

The ports are designed for circuit tubing 0.268"×0.175" tubing or anticoagulant and infusate tubing 0.161"×0.135". Preferably, the tubing ports are bonded with a suitable solvent.

Figure 86:
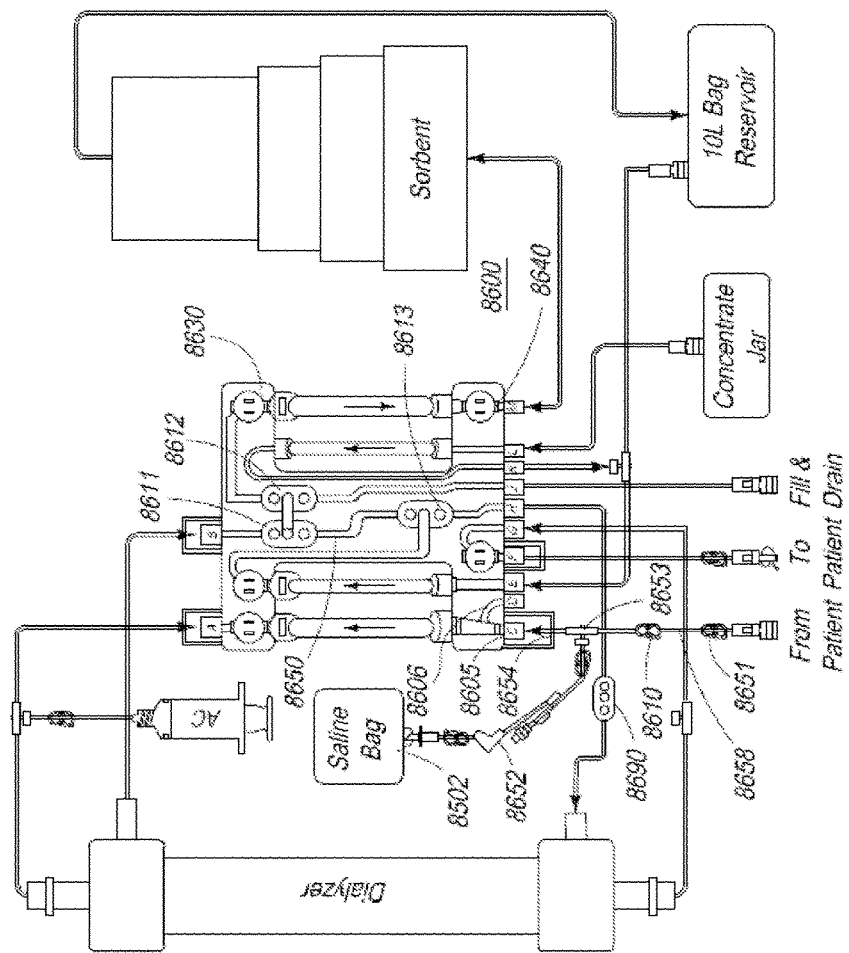
FIG. 86 is a schematic of another embodiment of an exemplary manifold.

It should be appreciated that the valves 3311, 3312, 3313 shown in FIG. 33 can be positioned in different locations within the manifold. Referring to FIG. 86, valve 8611 (valve 3311 in FIG. 33) can be positioned in the central vertical portion 8650 of the manifold 8600 adjacent to and parallel to valve 8612 (valve 3312 in FIG. 33). Also on the central vertical portion 8650 of the manifold 8600, which connects the top horizontal portion 8630 and bottom horizontal portion 8640 together, is valve 8613 (valve 3313 in FIG. 33). Valve 8613 is on the bottom portion of the central vertical portion 8650 and positioned substantially below and centered between valves 8611, 8612.

In one embodiment, the 2-way valves operate by having valve actuators, which are mounted on the instrument, compress an elastomeric diaphragm over a volcano seal to prevent dialysate flow through its respective pathway, as described in further detail below. The volcano seal opening is approximately 0.190" diameter to match the channel geometry. The cross-sectional pathway through the interior of the valve is at least equivalent to 0.190" diameter when valves are open. When the valve is in the closed position the valve actuator and elastomeric diaphragm consume most of the fluid path space around the volcano seal minimizing the potential for air entrapment. There are raised plastic features on the mid-body that minimize dead space within the fluid path as well as help prevent the diaphragm from collapsing around the center fluid path under negative pressure conditions. The elastomeric diaphragm has an o-ring feature around its perimeter that fits into a groove on the mid-body surface. The o-ring is compressed between the mid-body and back cover to form a fluid tight seal. The design provides for approximately 30% compression on the o-ring. The 2-way valves control the direction of dialysate flow through the manifold.

The manifold contains structures that allow for fluid pressure monitoring across diaphragms through the use of sensors in the instrument. Fluid is allowed to flow from channels on the front cover side of the mid-body through inlet and outlet holes underneath the diaphragm on the back cover side. The cross-sectional pathway through the interior of the pressure sensing structure is at least equivalent to 0.190". The interior pathway is designed to minimize air entrapment while providing adequate fluid contact with the diaphragm. The elastomeric diaphragm has an o-ring feature around its perimeter that fits into a groove on the mid-body surface. The o-ring is compressed between the mid-body and back cover to form a fluid tight seal. The design provides for a 30% compression on the o-ring.

The valves and diaphragms can be made from a variety of different materials and by different processes. In one embodiment, the elastomeric components are made from silicone. In another embodiment, the elastomeric components are made from a variety of thermoplastic elastomers. Two shot molding may be used to attach the valves and diaphragms to the back cover. Two shot molding of valves and diaphragms would remove the need to individually assemble these parts into the manifold therefore reducing labor costs and improving quality of the manifold assembly.

Pumping components in the manifold design have been defined as PVC header tubing. These headers combined with the rotary peristaltic pumping system of the instrument provide the flow of blood, dialysate, and infusate. The circuit tubing material for dialysate, infusate, and anticoagulant is preferably kink resistant, such as the tubing referred to as Colorite, Unichem PTN 780, (80 A durometer) extruded by Natvar, and all TEKNIplex companies. The tubing dimensions for the dialysate lines range from 0.268"×0.189" to 0.268"×0.175".

Figure 34:
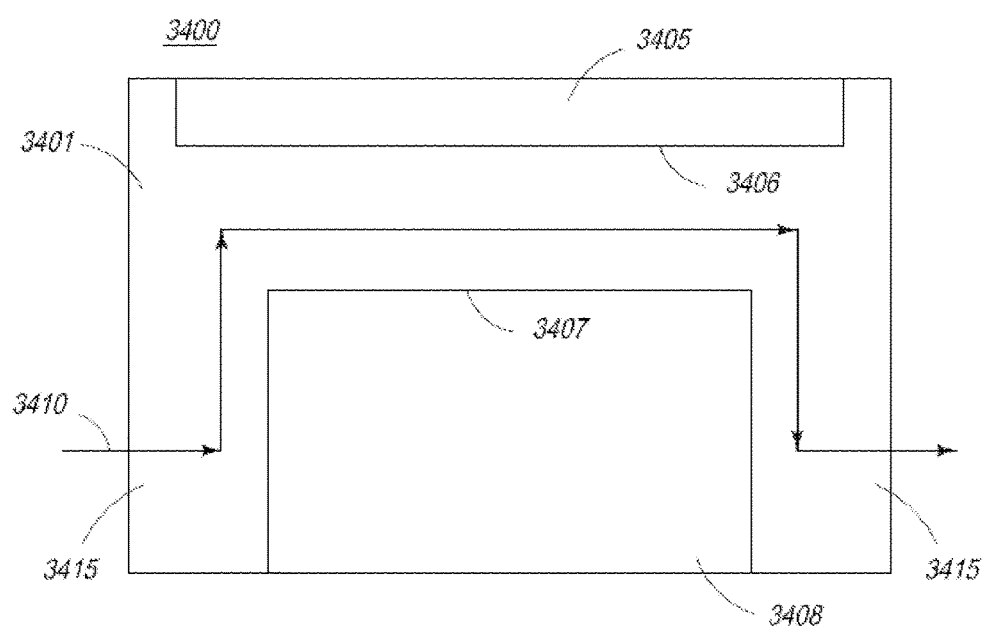
FIG. 34 is a diagram depicting a first exemplary fluid flow through a port.

In order to bring manifold segments into effective thermal, optical or pressure communication with one or more sensors through elastic membranes, it is important to create a sufficiently proximate exposure of the fluid flow to the sensing apparatus. One way of doing so is shown in FIG. 34. Manifold segment 3400 receives a fluid flow 3410 that is caused to move upward due to the blocking and redirecting position of a protrusion, member, or other structure 3408 within the fluid path 3410. The fluid moves upward and is concentrated in between the membrane 3405 and structure 3408, thereby enabling improved sensing. However, such an embodiment has the potential of resulting in blood clots forming in bends 3401, 3415 or occlusions caused by the adherence of the base 3406 of membrane 3405 to the top 3407 of structure 3408 due to negative pressure.

Figure 35A:
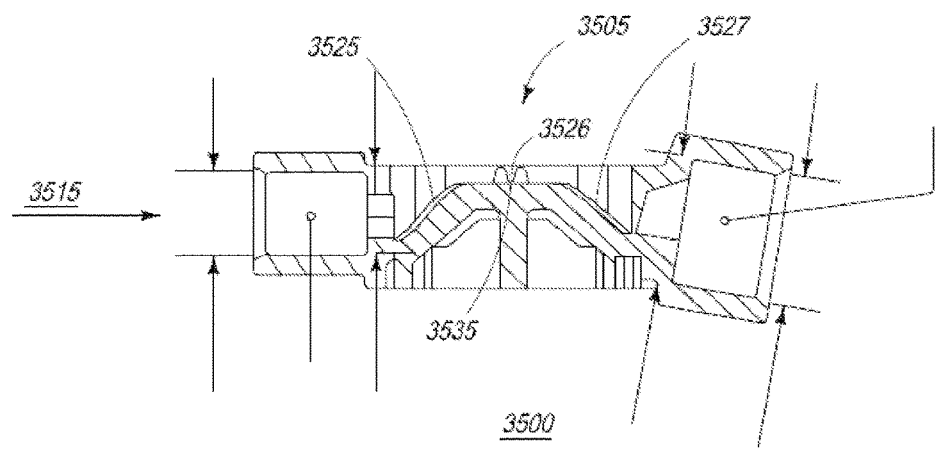
FIG. 35A is a diagram depicting a second exemplary fluid flow through a port.
Figure 35B:
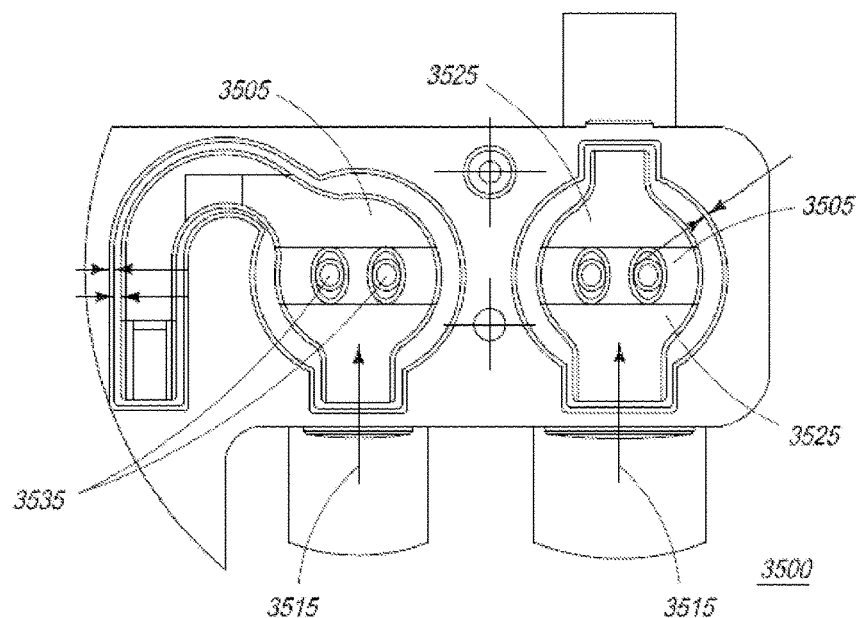
FIG. 35B is a diagram depicting a membrane structure over a port.

Referring now to FIGS. 35A and 35 B simultaneously, to minimize the potential of blood clots or occlusions, it is therefore preferred that the structure of the manifold segments 3500 that are in thermal, optical or pressure communication with one or more sensors through elastic membranes 3505, also referred to as sensing segments, are designed in a manner that avoids creating sharp turns, bends, or U-shaped paths which could increase the likelihood of clotting or occlusions, yet still provide sufficient contact between flowing fluid and a sensor located over or proximate to the segment. Referring to FIGS. 35A and 35B, the internal fluid pathway 3515 is now defined by a top surface comprising a membrane 3505 through which a sensor can be placed in thermal, optical or pressure communication occurring through pathway 3515 and a bottom surface defined by a) a first upward sloping wall 3525 that decreases the height of the pathway 3515 from a first height to a second height along the length of the wall 3525, b) a planar segment 3526 that maintains the same pathway height 3515 at the second height, and c) a downward sloping wall 3527 that increases the pathway 3515 height across the length of the wall 3527 from a second height down to the first height again. The angled inclination/declination of the walls 3525, 3527 cause the fluid pathway 3515 to narrow. Concurrently, however, the width of the segment, defined by the angled walls 3525, 3527 and planar segment 3526, widens relative to the manifold portions before and after this sensing segment. The sensing segment's height decrease and width increase relative to the manifold segments before and after the sensing segment provides for a substantially constant velocity of fluid, thereby avoiding velocity changes that could hemolyze the blood, eliminating dead spaces, and maintaining a low Reynolds number, while still providing the requisite contact area for the flexible membrane 3505, through which sensors conduct measurements. In one embodiment, one or more posts 3535 are incorporated into the fluid pathway 3515, atop the planar surface 3526, and below the membrane 3505 to prevent a complete collapse of the membrane 3505 due to negative pressure.

Figure 36:
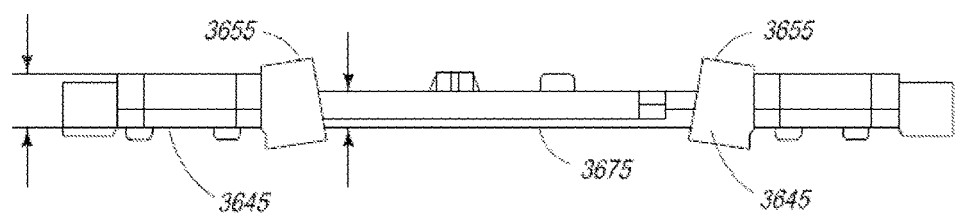
FIG. 36 is a diagram depicting one embodiment of an angled manifold port structure.
Figure 37:
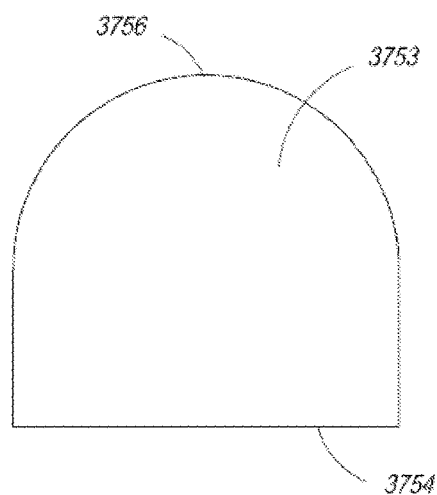
FIG. 37 is a diagram of one embodiment of a molded fluid path having a substantially planar base.

As would be appreciated from the above discussion, the blood and dialysis circuits of the manifold may be defined by a single piece of molded plastic, rather than a plurality of plastic components that are welded together. However, when the blood and dialysis circuits are defined by a single unitary piece of material, certain challenges arise. In particular, ports 3317b, 3317a, 3319b, 3319a, 3325a, 3325b, 3326a, and 3326b in FIG. 33 are challenging to cost-effectively and reliably mold if the cylindrically shaped protrusions defining each port extend directly perpendicular from the manifold surface or, stated differently, are angled at substantially zero degrees from the side of the portion of the manifold to which the cylindrical protrusion is attached. If the ports are manufactured in a fully perpendicular configuration, the pins from the molding machine cannot be readily removed. Referring to FIGS. 33 and 36 simultaneously, it would be preferred to manufacture ports 3317b, 3317a, 3319b, 3319a, 3325a, 3325b, 3326a, and 3326b by having the cylindrical protrusion defining the port structure 3655 be angled relative to the side of the manifold 3645 to which the protrusion 3655 attaches, as defined by surface 3675. Therefore, in one embodiment, the internal manifold ports will be at an angle relative to the manifold surface. This angle further reduces stress on any pump tube segment which is inserted between the two angled ports. It further positions the pump tube segment to be in a slightly curved, bent, or otherwise non-linear shape to better conform to a pump header contact surface. In one embodiment, an angle, which is defined by a line normal to the center of the angled port and a line normal to the side of manifold, is less than 20 degrees and preferably less than 10 degrees. In one embodiment, the angle is approximately 10 degrees. In one embodiment, the internal manifold ports 3317*b*, 3317*a*, 3319*b*, 3319*a*, 3325*a*, 3325*b*, 3326*a*, and 3326*b* are manufactured at the aforementioned angle while the remaining ports are at an angle approximately equal to zero. In another embodiment, the protrusions 3655, while described as cylindrical, have interior areas or volumes 3753 in which the base 3754 is substantially planar and not curved while the rest of the internal structure defining the volume 3753 remains curved 3756, as shown in FIG. 37. In another embodiment, all the ports or fluid pathways have interior areas or volumes 3753 in which the base 3754 is substantially planar and not curved.

Figure 38:
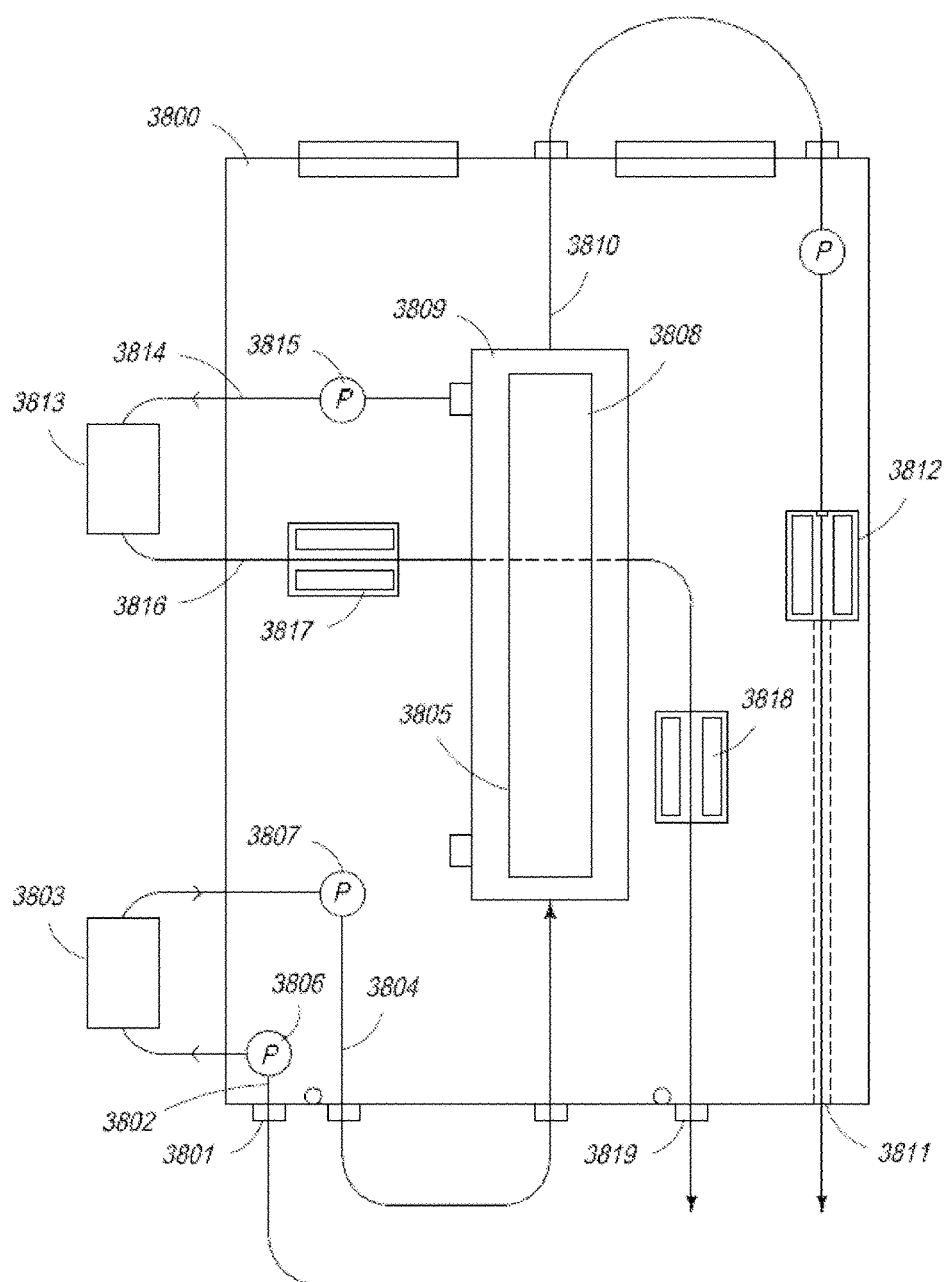
FIG. 38 is a fifth exemplary fluid circuit diagram.
Figure 39:
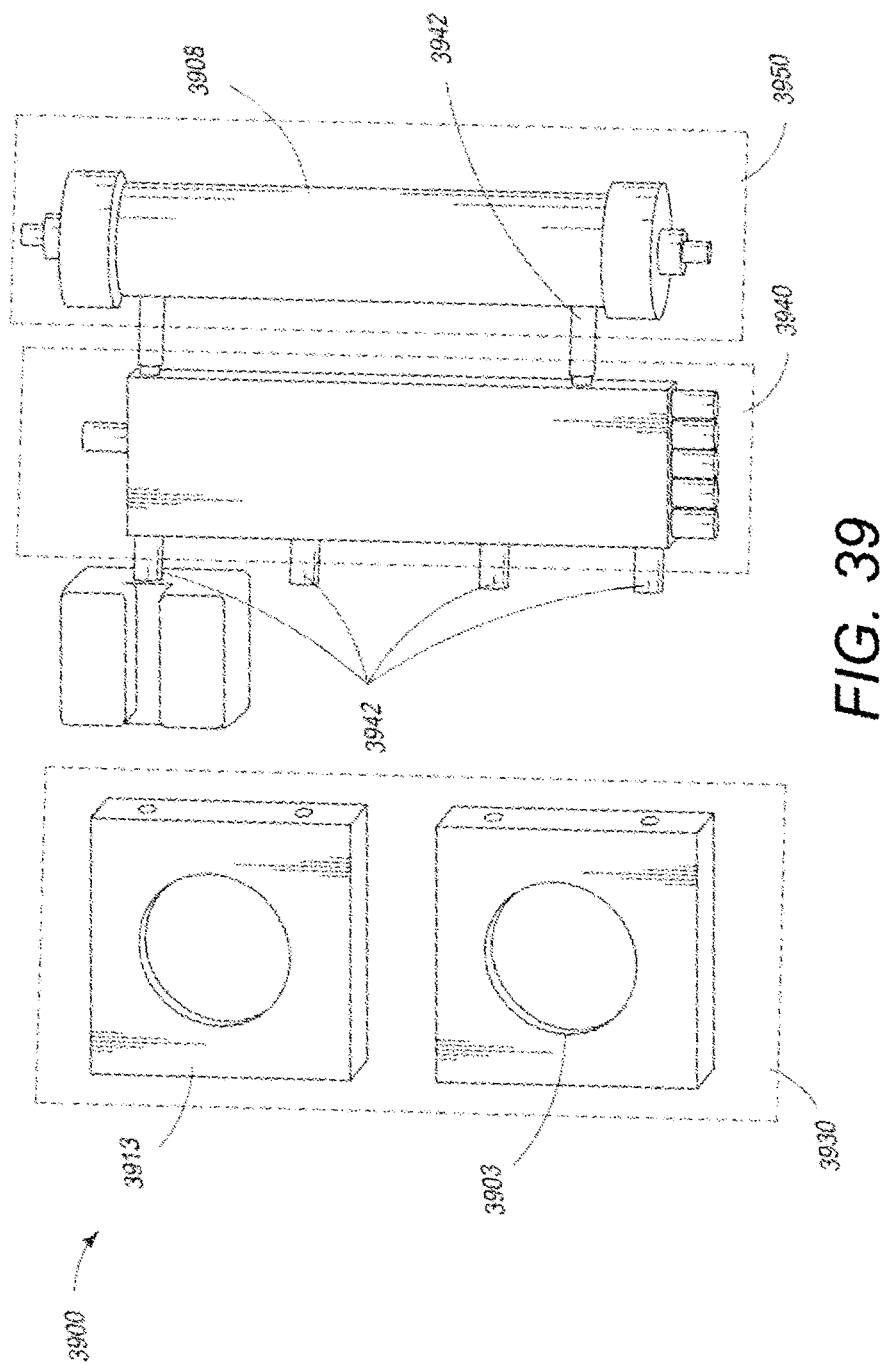
FIG. 39 is a schematic of another embodiment of an exemplary manifold used in association with other dialysis components.
Figure 40:
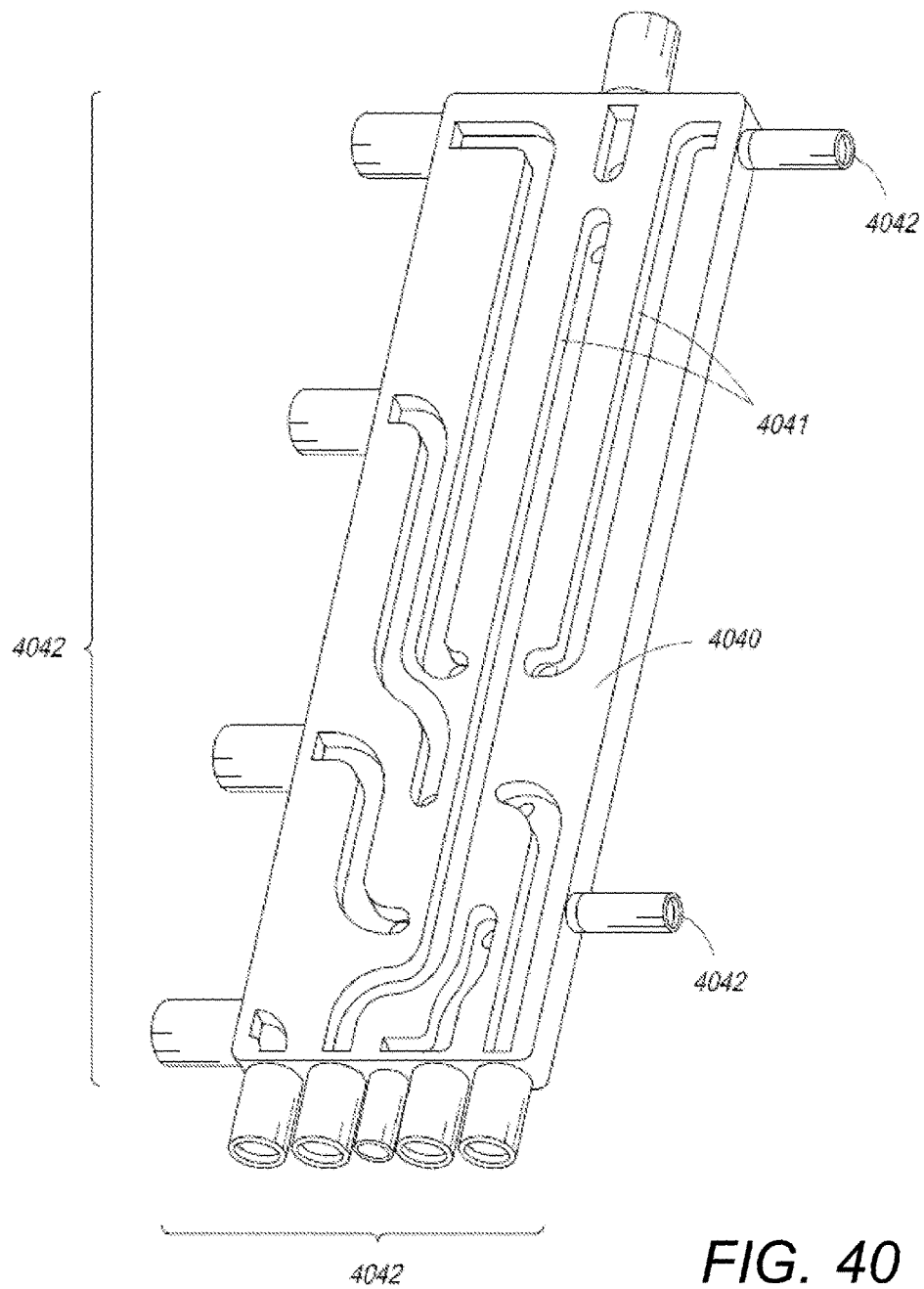
FIG. 40 is a schematic of another embodiment of an exemplary manifold.

Another embodiment of a manifold is shown in FIGS. 38 to 40, with blood and dialysate flow paths molded in a single compact plastic unit. In one embodiment, the manifold 3800 is an easy to assemble compact plastic unit that has built-in molded blood and waste flow paths. Optionally, the sensors, pumps and hemofilter cartridges can also be integrated with the compact plastic unit by insertion into concave moldings in the unit. In one embodiment, the dialysis system of the present invention is capable of operating more than 8 hours per treatment and for up to 72 hours continuously. It should be appreciated that fluid flows in and out of the manifold through defined inlet and outlet ports, such as to and from external pumps, to a waste UF reservoir, or to a patient return line.

FIG. 39 shows a modular assembly of a manifold 3900 in one embodiment of the present invention. Pumping section 3930 comprises blood and waste pumps 3903, 3913 respectively. Module 3940 comprises molded flow paths 3942 for blood and ultrafiltrate wastes and a hemofilter module 3950 comprising a hemofilter cartridge 3908. This modular design allows quick and easy assembly of various modules into a single compact structure.

FIG. 40 shows an enlarged view of a mid-body module 3940 of FIG. 39. In one embodiment, mid-body module 4040 comprises built-in molded flow paths 4041 for carrying blood and waste. Connection ports 4042 are also molded into the mid-body module for connecting (via luer connectors and tubing) to pumps at one end of mid-body module 4040 and to a hemofilter cartridge at the other end of mid-body module 4040.

Referring back to FIG. 38, blood is drawn into the manifold 3800 via blood inlet port 3801 and molded flow path 3802 using a blood volumetric pump 3803 in pressure communication with a manifold tube segment. Blood volumetric pump 3803 pumps blood into hemofilter cartridge 3808 via the molded flow path 3804. Inlet pressure sensor areas 3806, 3807 are also integrated into manifold 3800 in molded flow paths 3802, 3804.

Referring back to FIG. 38, waste from the permeate region 3809 is drawn out by waste volumetric pump 3813 through molded flow path 3814, which, in one embodiment, has an integrated pressure sensor area 3815 located in-line of flow path 3814. The waste is pumped through molded flow path 3816, which, in one embodiment, has an integrated blood leak detector area 3817 and waste flow meter 3818, in-line with flow path 3816 leading out of the manifold 3800 through a waste outlet port 3819.

In one embodiment, the hemofilter cartridge 3808 is disposable and can be removably integrated into the corresponding molded concavity in the manifold 3800 to complete the ultrafiltration circuit. The manifold 3800 also provides an interface to a redundant pinch valve to prevent air from entering the patient's vascular system. The pinch valve is designed such that it is in a closed (occluded) position when no electrical power is applied.

The molded flow paths 3802, 3804, 3810, 3814 and 3816 define the blood and ultrafiltrate flow circuits of the manifold 3800. In one embodiment, these flow paths comprise disposable tubing and a plurality of interfacing components, such as joints, that are suitable for blood and ultrafiltrate contact for at least 3 days. The joints preferably are designed to have at least 5 lbs. strength and seal to 600 mmHg (that is, greater than hemofilter maximum trans-membrane pressure). In one embodiment, the blood set tubing corresponding to flow paths 3802, 3804 and 3810 have suitable length and internal diameter for supplying a blood flow of 50 ml/minute. In one embodiment the prime volume of the blood set tubing, including the hemofilter, is less than 40 ml. The blood set tubing interfaces with the blood volumetric pump 3803. Blood pump 3803 tubing, in one embodiment, is of Tygon brand, formulation S-50-HL, size ⅛" ID×³⁄₁₆" OD×¹⁄₃₂" Wall.

Similarly, in one embodiment, the ultrafiltrate set tubing corresponding to flow paths 3814 and 3816 are capable of supplying an ultrafiltrate flow of 500 ml/Hr (8.33 ml/minute). The ultrafiltrate set tubing also interfaces with the waste volumetric pump 3813. Waste pump 3813 tubing, in one embodiment, is of Tygon brand, formulation S-50-HL, size ³⁄₃₂" ID×⁵⁄₃₂" OD×¹⁄₃₂" Wall.

Since the manifolds of the present invention comprise molded flow paths for blood, dialysate, waste fluids, and substitution fluids, the entire flow path can be easily manufactured as portable composite manifolds. The manifolds are also easy to handle since all flexible tubing outside the manifolds are attached on one side of the manifolds. Use of manifolds with built-in molded flow paths enhances fail-safe treatment as the chances of disconnection, misassembly and leakage are minimized in comparison to prior art systems that use a myriad of flexible tubing. Use of the novel manifolds also enhances ease of use leading to enhanced portability.

In one embodiment the dialysis manifolds are standalone compact units such that they can be individually and separately used to process blood from a patient. In another embodiment the two manifolds are connectable to each other to function as a dual stage blood processing system. In one example, blood is drawn from an arterial site in a patient and passed through a dialyzer where a large amount of waste fluid is convected out. The manifold is used to return an equal amount of fluid back to the blood, before the blood is reinfused. The manifold measures and dumps the waste fluid into a waste bag.

As known to persons of ordinary skill in the art, the hemofilter, or dialyzer, cartridge 3808 comprises a hollow tube further comprising a plurality of hollow fiber tubes whose walls act as a semi-permeable membrane. The plurality of semi-permeable, hollow fiber tubes divide the hemofilter cartridge 3808 into blood flow regions 3805 within the hollow fiber tubes and a filtrate or permeate region 3809 outside the hollow fiber tubes. As blood passes through blood regions 3805, plasma water passes across the semi-permeable membranes of the hollow fiber tubes. The hemofilter cartridge 3808 is a small hemofilter. More concentrated blood flows out from the cartridge 3808 through molded flow path 3810 and out of the manifold 3800 through a blood outlet port 3811. An air detector area 3812 is also integrated into blood return flow path 3810.

The following are exemplary physical specifications of a hemofilter, or dialyzer, 3808 in accordance with one embodiment of the present invention:

| | |
|---|---|
| Membrane Surface Area (m$^2$) | ≤0.1 |
| Prime Volume (ml) | ≤10 |
| Molecular Weight cut-off (Daltons) | 65,000 |
| Pressure Drop3 (mmHg) | ≤50 (Qb = 50 ml/min |
| Maximum Transmembrane Pressure (mmHg) | ≥500 |
| Overall Unit Length (cm) | 12-15 |
| Filtration rate | 8-10 ml/min @100 mmHg @ 50 ml/min Qb |
| Tubing Connections | |
| Blood | Male Luer |
| Filtrate | Slip fit (straight) |
| Sterilization | ETO or gamma |
| Membrane Material | Polysulfone (preferred) |
| Housing material | Polycarbonate |
| Potting material | Polyurethane |
| Sieving coefficients | |
| Urea | 1.00 |
| Creatinine | 1.00 |
| Vit B12 | 0.98 |
| Middle molecule/size | ≥0.20 17,000 |
| Albumin | ≤.03 |

Figure 41:
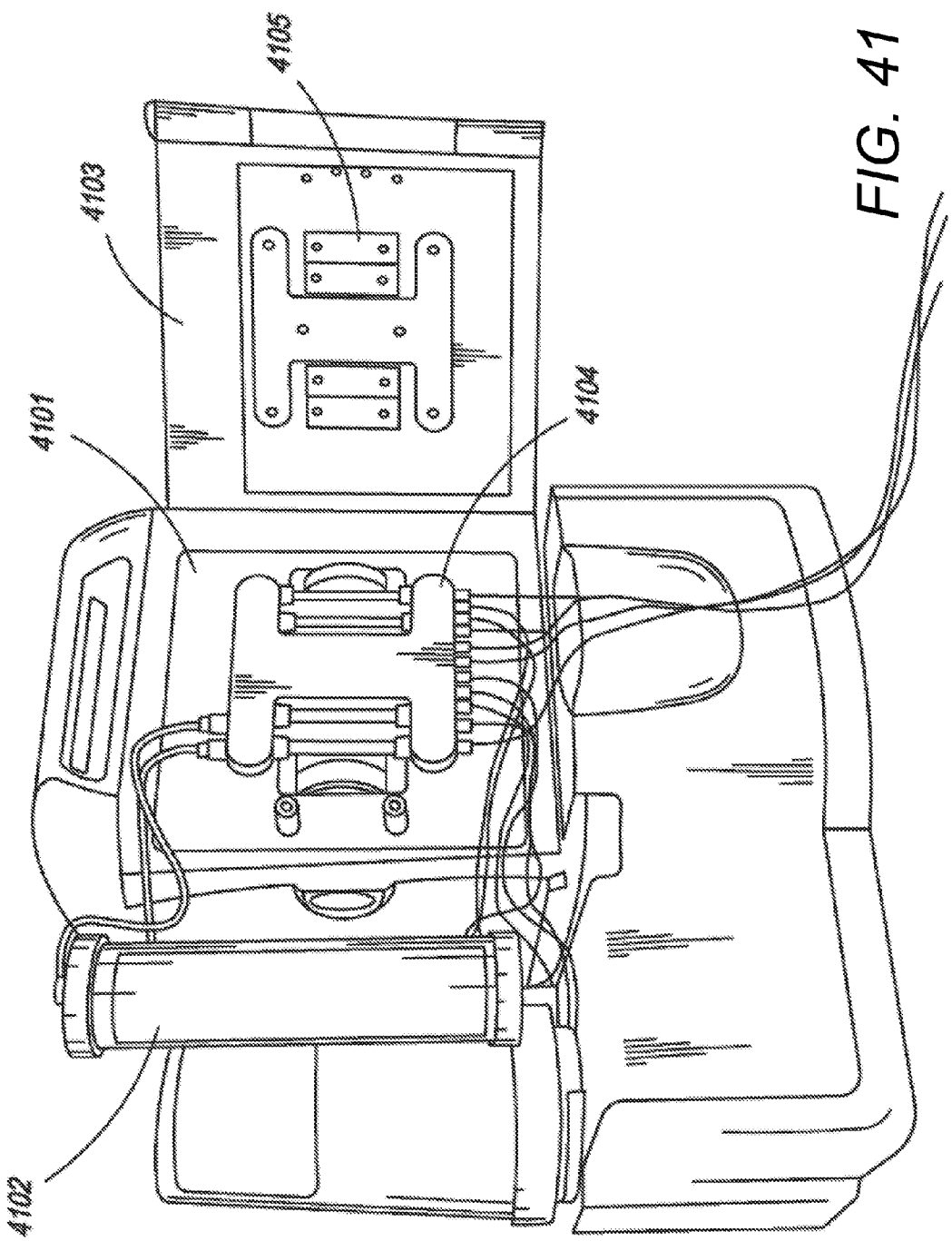
FIG. 41 is a front view of one embodiment of the controller unit of the dialysis system with the door open and manifold installed.

During dialysis treatment, a patient or healthcare provider installs one of the above described manifolds in the dialysis machine. Referring to FIG. 41, the dialysis machine 4101 has a front door 4103 which can be widely opened to install the disposable components. For installation, the manifold 4104 simply needs to be inserted in the space provided for the purpose in the dialysis unit 4101, as previously discussed above. Installing the dialyzer 4102 also involves a simple insertion in a designated recess. The front door 4103 is provided with pump shoes 4105 that makes loading of disposable components very easy, as no pump tubing needs to be thread between roller and shoes. Further, this arrangement allows installing the dialyzer 4102 and the manifold 4104 in a manner that ensures proper alignment against non-disposable components such as pressure readers, sensors, and other components. This packaged, simple approach enables easy disposables loading and cleaning of the system. It also ensures that the flow circuitry is properly configured and ready for use.

Figure 42:
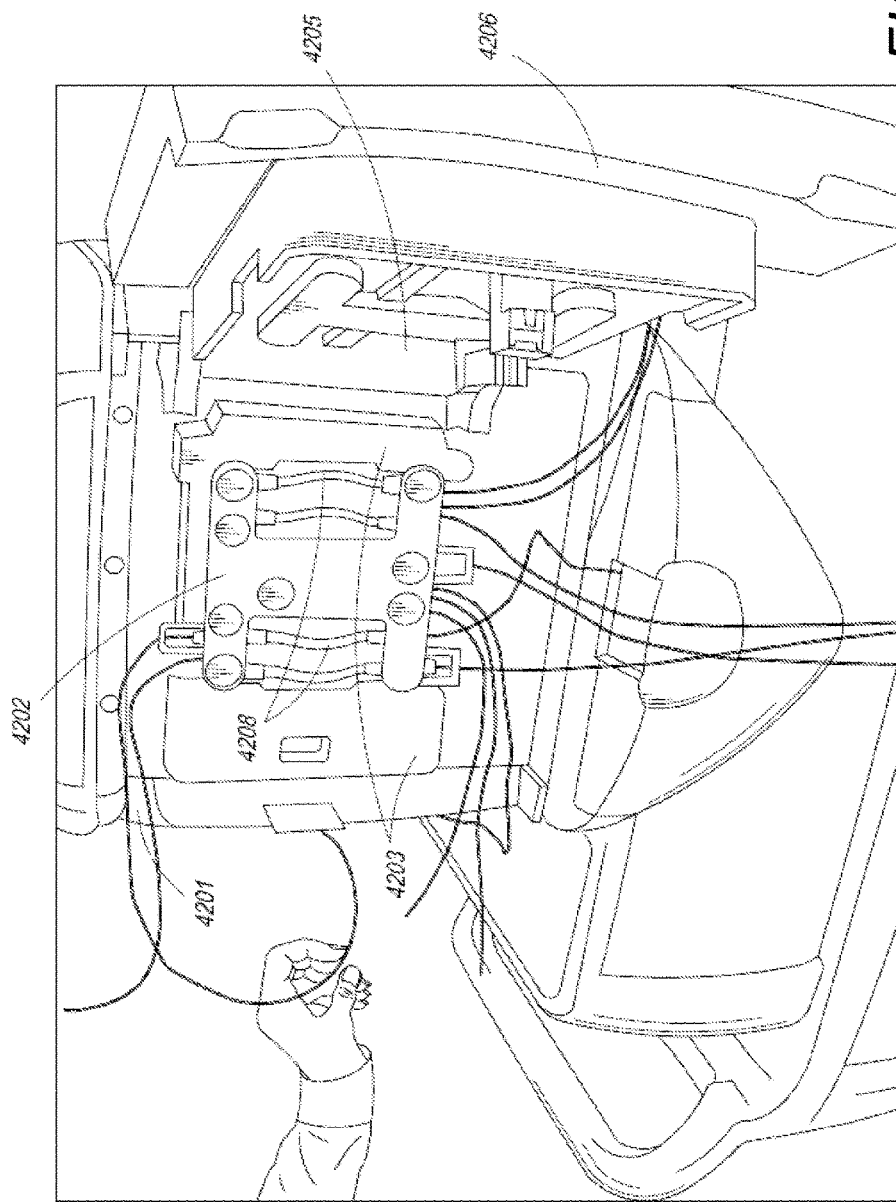
FIG. 42 is a front view of one embodiment of the controller unit of the dialysis system with the door open and manifold installed using attachment guides.

Referring to FIG. 42, in one embodiment, the manifold 4202 is mounted on the vertical front panel 4203 of the dialysis system 4201. The manifold 4202 is accurately located on this panel 4203 by a plurality of alignment mechanisms. The first alignment mechanism comprises a plurality of alignment pins in the panel 4203 that engage alignment holes in the manifold 4202. The second alignment mechanism comprises at least one latch that maintains the manifold 4203 in a specific mounted position until the door 4206 is closed and the final accurate position is obtained. In one embodiment, the back cover of the manifold 4202 has two designed-in tabs at top and bottom. These tabs latch the manifold 4202 in a first holding position prior to the door 4206 closure and subsequent placement of the manifold's 4202 accurate position. The tabs enable a latching mechanism that can be manually released or by ball detents that require forcibly removing the manifold 4202 by hand. In another embodiment, the latch mechanism comprises a spring loaded insertion and release mechanism at the top of the back cover. This mechanism had a connecting rod between the top latch and a bottom latch. When the release mechanism at the top was activated the bottom latch released as well.

The third alignment mechanism comprises contoured guides 4208 that direct the general position and configuration of the manifold 4202. The contoured guides 4208 are preferably shaped to mate with, match, or otherwise complement the physical structure of the manifold 4202. In one embodiment, the guides 4208 are generally rectangular and configured to fit inside the space bounded by the sides of the first segment, second segment, and connecting segment of the manifold 4202, as described above. The fourth alignment mechanism comprises a door 4206 having at least one spring loaded pressure plate 4205 that captures the manifold 4202 between the door 4206 and front panel 4203, thereby applying adequate pressure for valving and pressure sensing. The door 4206 also includes four pressure shoes that apply adequate pressure to the pumping components for rotary peristaltic delivery of fluids.

It should be appreciated that one or more of the alignment mechanisms can be used, either alone or in combination, to achieve the requisite aligned and pressurized position for the manifold. It should further be appreciated that the alignment mechanisms are attached to the surface of a recessed region within the dialysis device enclosure. The recessed region comprises the front panel 4203 that is recessed relative to the dialysis device housing and is bounded by four walls (a first wall, a second wall, a third and a fourth wall) that extends upward from the front panel 4203 to meet and fixedly attach to the dialysis device enclosure. The recess is sufficiently deep and configured to receive the door 4206.

Sensing Systems

As stated above, the dialysis system, and particularly the top controller unit, comprises sensing systems that interact with portions of the manifold, and particularly clear portions of the manifold or membranes embedded in the manifold structure, to sense certain parameters or states, such as flow rates, temperature, pressure, the presence of sodium, the presence of ammonia, pH levels, leaking blood, occlusion or air bubbles. For example, sensing for blood leakage, air bubbles, and/or occlusion is achieved by including optical sensors in the dialysis machine which attach to, and around, pre-defined areas of the manifold. The manifold may comprise a plurality of tubing support brackets which facilitate accurately placing the circuit tubing into optical sensors, such as Optek sensors, that are separately mounted in the instrument when the manifold is installed and the door is shut. The sensors provide means for detecting occlusion in the arterial line, blood leak in the blood line downstream of the dialyzer and air detection in the venous blood line. The brackets restrain the tubing on one side of the sensor while the tubing port does the restraining on the other side of the sensor. These optical sensors are U shaped devices into which the tubing is forced when the manifold is installed. The tubing support brackets provide support for the tubing so that all three of these sensors are loaded with the same motion as loading the manifold, with no extra effort on the user's part. Sensing systems for flow rate, temperature, disconnection, central venous pressure, among other systems, are further described below.

Flow Rate

In one embodiment, the dialysis system comprises a non-invasive or non-contact type acoustic flow meter that has the ability to generate an acoustic signal directly in the fluid to be monitored without physical contact, thereby providing flow measurement with improved accuracy based on the measurement of acoustic wave transit time. It is further contemplated the present flow meter can be used with one of the above described manifolds to non-invasively measure flow within the manifold.

Figure 43:
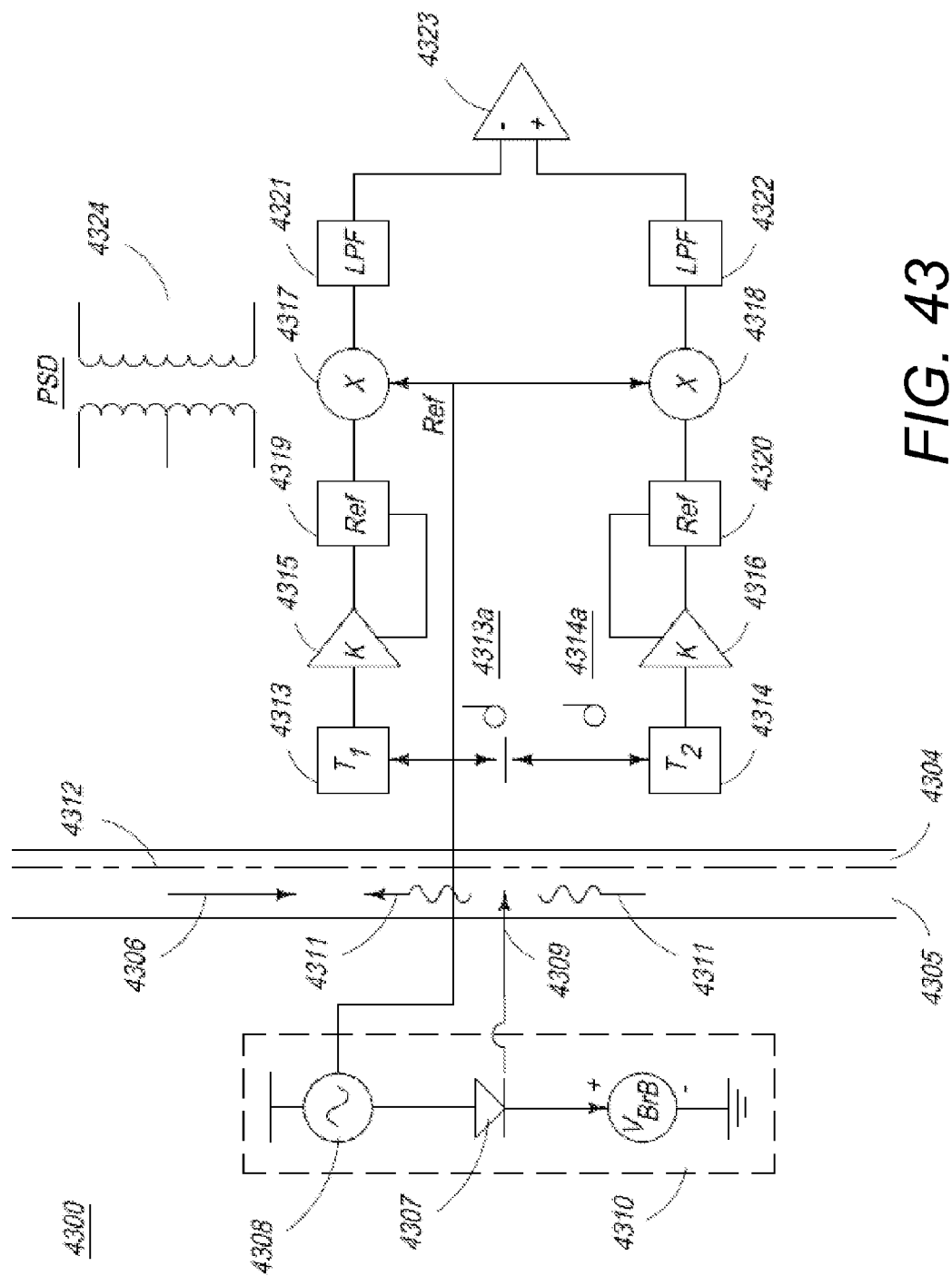
FIG. 43 is a circuit diagram depicting an exemplary photo-acoustic flow meter.

FIG. 43 is a circuit diagram depicting an exemplary photo-acoustic flow meter 4300. The fluid 4304 for which the flow rate is to be measured, is carried by a fluid-bearing passageway 4305, such as a pipe, tubing, or manifold segment, in the direction indicated by the arrow 4306. The photo-acoustic pulse flow meter 4300 comprises a light emitting system 4310. In one embodiment, the system 4310 further comprises an LED or solid state laser 4307, which is excited in a sinusoidal manner by a signal source 4308. In another embodiment, a Q-switched ruby laser may be used in place of system 4310. Persons of ordinary skill in the art would appreciate that any other suitable optical generation system known in the art may be used for the purpose.

The optical generation system 4310 projects a beam 4309 into the fluid 4304 through an optical aperture, or an optically transparent section formed in the wall of the passageway 4305 (i.e. manifold segment). In one embodiment, the projected optical beam 4309 traverses through the fluid 4304 in a direction perpendicular to the direction of the axis 4312 of the fluid-bearing passageway 4305. The optically transparent section of tube 4305 should be transparent to the particular wavelength of optical source 4310. The wavelength of optical source 4310 must be selected so that the light is readily absorbed by the fluid 4304, whose flow rate the system is intended to measure. It should further be appreciated that, when the present system 4300 is used with a manifold, the optical generation system 4310 is preferably contained in the dialysis machine into which the disposable manifold is loaded and aligned with the manifold such that the generated optical beam 4309 passes through a transparent section of the manifold.

As the optical beam 4309 passes into the fluid 4304, heat energy associated with the optical beam is absorbed into the fluid. The absorption of heat occurs along the direction of the beam 4309 and causes thermal fluctuations in the fluid 4304. These thermal fluctuations manifest as localized fluid heating and cause thermal expansion in the fluid. As a result of this thermal expansion, an acoustic signal 4311 is produced. The nature of this signal, in terms of pressure variations in the fluid 4304, replicate the waveform generated in signal source 4308 used to power the optical signal generation element 4307. This pressure variation propagates both downstream and upstream with respect to the location of the optical beam 4309 in the passageway 4305.

As is known to persons skilled in the art, the acoustic signals received upstream and downstream by sensors 4313 and 4314 respectively will be out of phase with one another. The amount of the phase difference between the acoustic signals received upstream and downstream is directly proportional to the flow rate. It should be further appreciated that, when used in conjunction with a disposable manifold, the sensors 4313 and 4314 are positioned proximate to the manifold tubing or embedded within the manifold tubing.

Accordingly, in one embodiment acoustic detectors T1 4313 and T2 4314 are placed upstream and downstream respectively, equidistant from the optical beam 4309, such that d1 4313a and d2 4314a are equal. In another embodiment, the upstream and downstream placement of 4313 and 4314 need not be equidistant from 4309. Detectors T1 and T2 may be either pressure transducers or acoustic transducers such as microphones. A microphone cartridge such as Model WM-55A103 manufactured by Panasonic Corporation is suitable for this application.

The detectors T1 4313 and T2 4314 interrogate the fluid flow to detect the acoustic signal 4311 at the points where the detectors T1 4313 and T2 4314 are located. Interrogation occurs acoustically as the pressure variations (sound) of acoustic signal 4311 are transferred through the walls of conduit 4305 to sensors 4313 and 4314.

A first receiving amplifier 4315 is connected to the detector T1 4313 and a second receiving amplifier 4316 is connected to receive the output from the detector T2 4314. The outputs of the first and second amplifiers 4315 and 4316 are connected to the inputs of first and second phase sensitive detectors 4317 and 4318 respectively, through gain control elements 4319 and 4320. One implementation of phase sensitive detectors 4317 and 4318 is known in the art as a "lock in amplifier". After the signals are processed by the amplifiers 4315, 4316 and phase sensitive detectors 4317, 4318, the outputs of 4317 and 4318 are passed through low pass filters 4321 and 4322 to eliminate high frequency noise components, or ripples left over from the phase sensitive detection process 4324, from the signals. The resultant outputs of filters 4321 and 4322 are steady signals representative of the relative phase, with respect to the original signal of generator 4308, of the acoustic signals detected by 4313 and 4314 respectively. Thus, the photo-acoustic flow meter provides an indication of the phase angle of the upstream and downstream acoustic signals, with respect to a reference signal.

After processing and phase detection by the phase sensitive detector elements, the upstream and downstream phase angle signals are supplied to addition/subtraction unit 4323. The output of the addition/subtraction unit 4323 represents the phase difference between the acoustic signal received upstream by the acoustic detector T1 4313 and downstream by the acoustic detector T2 4314. This phase difference between these acoustic signals is directly proportional to the flow rate of the fluid and, as one of ordinary skill in the art would appreciate, can be used as the basis to calculate the actual flow rate or changes to the flow rate. All means for calculating the flow rate comprise a processor and software algorithms for deriving the flow rate or changes in the flow rate, from at least the phase difference data. Therefore, the output of the addition/subtraction unit 4323 provides a measurement of the flow rate of the fluid 4304.

Thus, as described above, in one embodiment output voltage signals of the first and second low pass filers 4321 and 4322 are sampled and, in the unit 4323, are subjected to a subtraction to determine a phase difference signal indicative of the rate of flow of the fluid in the passageway 4305. One of ordinary skill in the art would appreciate that any other suitable means for computing the phase difference from the outputs of the acoustic detectors may be employed. All such means comprise a processor and either hard coded or soft coded software algorithms for calculating a phase difference.

Figure 44:
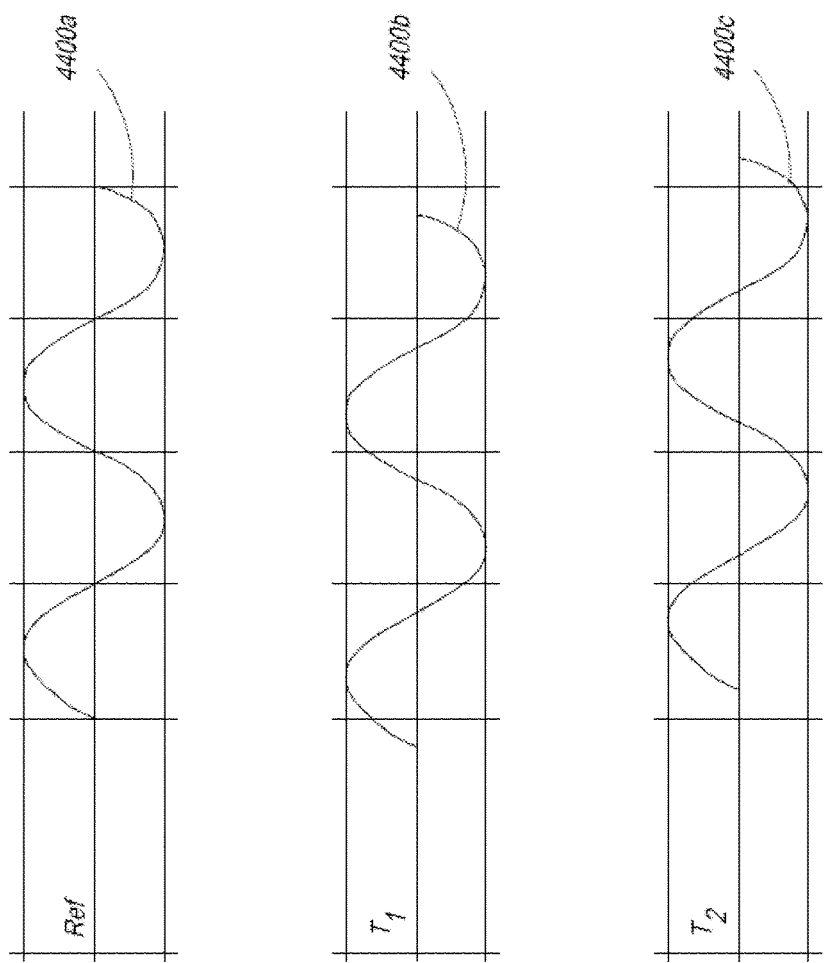
FIG. 44 depicts a plurality of propagating signals generated by the exemplary photo-acoustic flow meter.

As mentioned previously, the signal generated by the source 4308 acts as a reference signal for the upstream and downstream acoustic transducers T1 4313 and T2 4314. FIG. 44 depicts the reference signal 4400a generated by source 4308 of FIG. 43. FIG. 44 depicts the acoustic wave signals, 4400b and 4400c respectively, after undergoing signal processing at the outputs of gain control amplifiers 4315 and 4316 of FIG. 43, respectively.

In one embodiment, the photo-acoustic pulse flow meter is utilized to non-invasively monitor the rate of flow of fluids in a dialysis system such as a hemodialysis, hemofiltration and/or a hemodiafiltration system known to persons of ordinary skill in the art. The fluids for which flow rate measurement during dialysis is required are primarily blood and dialysate, in blood and dialysate circuits respectively; however one of ordinary skill in the art would appreciate that flow rate of other fluids such as infusate or concentrate may also be measured with the flow meter of the present invention. Persons of ordinary skill in the art would also appreciate that the flow meter of the present invention is also capable of indicating when there is a non-flow of fluid in a conduit/passageway.

Thus, referring back to FIG. 43, if the difference between signal outputs of low pass filters 4321 and 4322 is null, this would imply that there is no flow of fluid. In a dialysis system application, this detection of non-flow of fluid is very useful, as it might be indicative of a serious problem such as the disconnection of an arterial/venous catheter connected to the patient.

Figure 56:
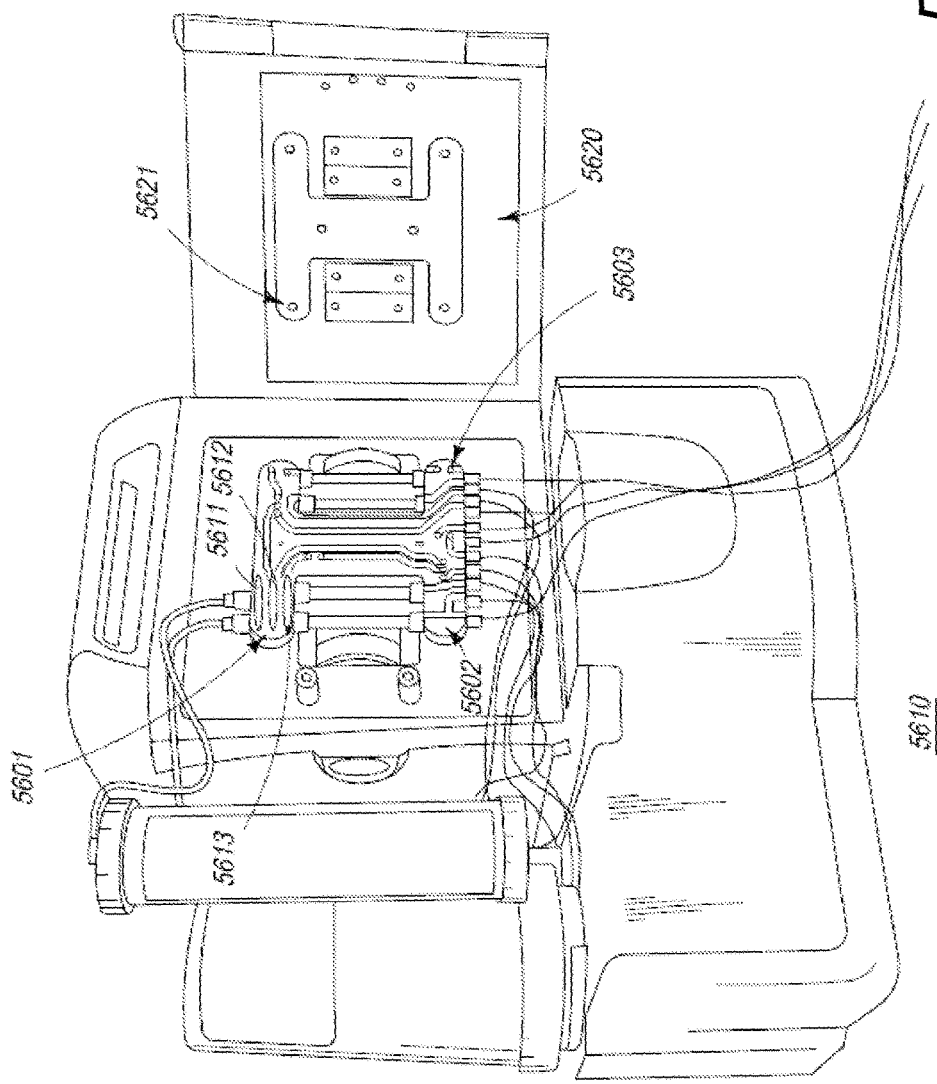
FIG. 56 is a front view of one embodiment of the controller unit of the dialysis system with the door open and manifold installed.

In another embodiment, flow within the manifold can be measured by a thermal flow meter. FIG. 56 illustrates the thermal fluid flow measurement device 5601 of the present invention installed with the manifold 5602 in the dialysis machine 5610. As mentioned earlier, the manifold 5602 has fluid flow paths or tubing circuit 5603 embedded within. The dialysis machine 5610 has a front door 5620 which can be opened to install the disposable manifold 5602. Further, the front door 5620 is equipped with pins 5621 that, when the door 5620 is closed, can make contact with electrical points on the manifold 5602 to read information or provide electrical input.

The thermal fluid flow measurement device 5601 further comprises a series of contacts 5611, 5612 and 5613. Operationally, as fluid (such as blood, dialysate or other fluids) flows during dialysis through the fluid flow path 5603, it passes the first contact 5611 which is embedded in the plastic pathway. The contact 5611 makes electrical contact with an electrical source, which in one embodiment is a pin 5621 on the machine front door 5620. The electrical source or pin is controlled by a controller in the dialysis machine 5610. The electrical source provides an electrical stimulus to the contact 5611, which acts to micro heat the contact based on a sine-wave method.

In one embodiment, the micro heating process effectuates a temperature increase between 0.1 and 1.0 degrees Celsius in the fluid being measured. This is effectuated by means of micro heaters located at the first contact 5611, which produce heat on receiving the electrical stimulus. Micro heaters for the thermal fluid flow measurement device of the present invention can be manufactured using any design suitable for the application. In one embodiment for example, the micro heater is made up of 10 turns of 30 g copper wire wound around a pin located at the first contact position 5611.

As the contact 5611 gets micro-heated, the resulting thermal energy acts to create a thermal wave, which propagates downstream from the first contact 5611. A plurality of contacts, which in one embodiment are two in number—5612 and 5613 are located downstream from the first contact 5611, and are used to measure the time of flight of the thermal wave. The measured phase of the wave is then compared with the initial wave generated by the first contact 5611. The phase difference thus determined provides an indication of the flow rate.

Figure 45:
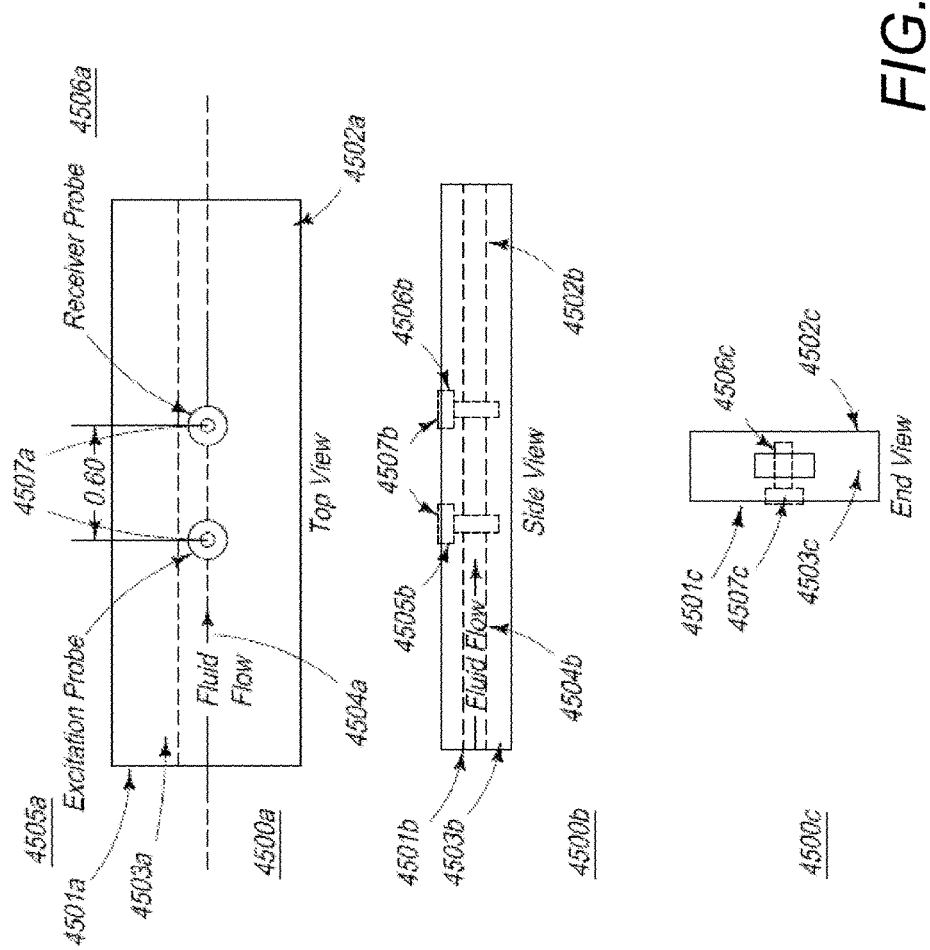
FIG. 45 is a circuit diagram depicting an exemplary thermal flow meter.

FIG. 45 illustrates one embodiment of a flow meter 4500a with probes that can be used for flow measurement. A channel 4501a encompasses a volume 4502a through which fluid, such as water or saline solution (0.9 N) 4503a flows. In one embodiment, the channel has a height in the range of 1 mm to 5 mm (preferably 3 mm), a width in the range of 3 mm to 13 mm (preferably 8 mm), a length in the range of 10 mm to 100 mm (preferably 50 mm), a channel area in the range of 3 $mm^2$ to 65 $mm^2$ (preferably 24 $mm^2$), and/or a hydraulic diameter in the range of 1.5 mm to 7.22 mm (preferably 4.36 mm).

The direction of the fluid flow is shown by arrow 4504a. An excitation probe 4505a is positioned proximate to a receiver probe 4506a. The relative distance of the probes is an important feature of the design, as the excitation frequency at which the electrical stimulus needs to be delivered by the excitation pin or probe 4505a depends on the spacing between the probes 4505a and 4506a. In one embodiment, the excitation probe and receiver probe are positioned less than 2 inches, preferably less than 0.8 inches, and more preferably approximately 0.6 inches, or approximately 15 mm, from each other. In this embodiment, excitation and measurement only requires two contacts, each contact having a contact surface 4507a. One of ordinary skill in the art would appreciate that, in such a case, only two contact points would be required, rather than three, as shown above relative to a disposable manifold and dialysis machine.

An excitation pin or probe 4505a is embedded in the channel 4501a and acts to provide a thermal stimulus (in the form of a thermal wave) to the flowing fluid, which is then sensed and measured by the receiving probe 4506a. In one embodiment, the body diameter of the pin or probe is in the range of 0.03 inches to 0.15 inches (preferably 0.08 inches), the diameter of the top contact surface is in the range of 0.025 inches to 0.2 inches (preferably 0.125 inches), and is made of gold plated brass or any other material having a density of approximately 8500 kg/$m^3$, a thermal conductivity of approximately 1.09 W/mK and/or a specific heat of approximately 0.38 J/KgK.

In one embodiment, the bodies of both the excitation pin or probe 4505a and the receiving pin or probe 4506a are molded into the manifold (such that the pin or probe is not in physical contact with the fluid and its top contact area is exposed to one surface of the manifold). The body of the pin or probe is centered in the cell and fluid passes by it. The top of the pin is exposed so a spring loaded contact, from the instrument panel, can make thermal contact, thereby enabling the transfer of thermal energy between the spring loaded contact and the contact surface of the pin.

For example, referring to FIG. 45, a side view of one embodiment of the thermal flow meter 4500b of the present invention is shown with the contact surface 4507b exposed so that a spring loaded contact from the instrument panel of the dialysis machine (shown in FIG. 56) can make thermal contact and thermal energy can be exchanged between the spring loaded contact and the excitation pin or probe 4505b. A channel 4501b encompasses a volume 4502b through which fluid 4503b flows. The direction of the fluid flow is shown by arrow 4504b. An excitation probe 4505b is positioned proximate to a receiver probe 4506b, each of which has a contact surface 4507b.

FIG. 45 further shows thermal flow meter 4500c from the end of the flow channel 4501c, which contains a volume 4502c through which fluid 4503c flows. Here, only the receiver probe 4506c and its contact surface 4507c are shown. In one embodiment, the receiving contact or pin 4506c has a structure similar to that of the excitation pin 4505b and its top 4507c is also exposed. In one embodiment, the receiver pin surface 4507c is also designed as a low thermal mass spring loaded contact. The excitation 4505a as well as receiver 4506a probes or pins are made up of a suitable material which has high thermal and electrical conductivity, which in one embodiment is gold plated brass.

In one embodiment, a low thermal mass spring loaded contact in the instrument, such as a dialysis machine, is temperature controlled using a heater and a thermistor. The temperature control function then generates a cosine temperature wave form in the probe which is reflective of the temperature wave created in the spring loaded contact. The resultant excitation signal characteristic of the excitation pin may be defined as:

$e_s = E_s \cos(\omega t)$, where $\omega t$ is the excitation frequency.

The thermal response of the receiver pin may be characterized by the following equation:

$r_r = R_r \sin(\omega t + \theta)$, where $\omega t$ is the excitation frequency and $\theta$ is the phase.

Figure 46:
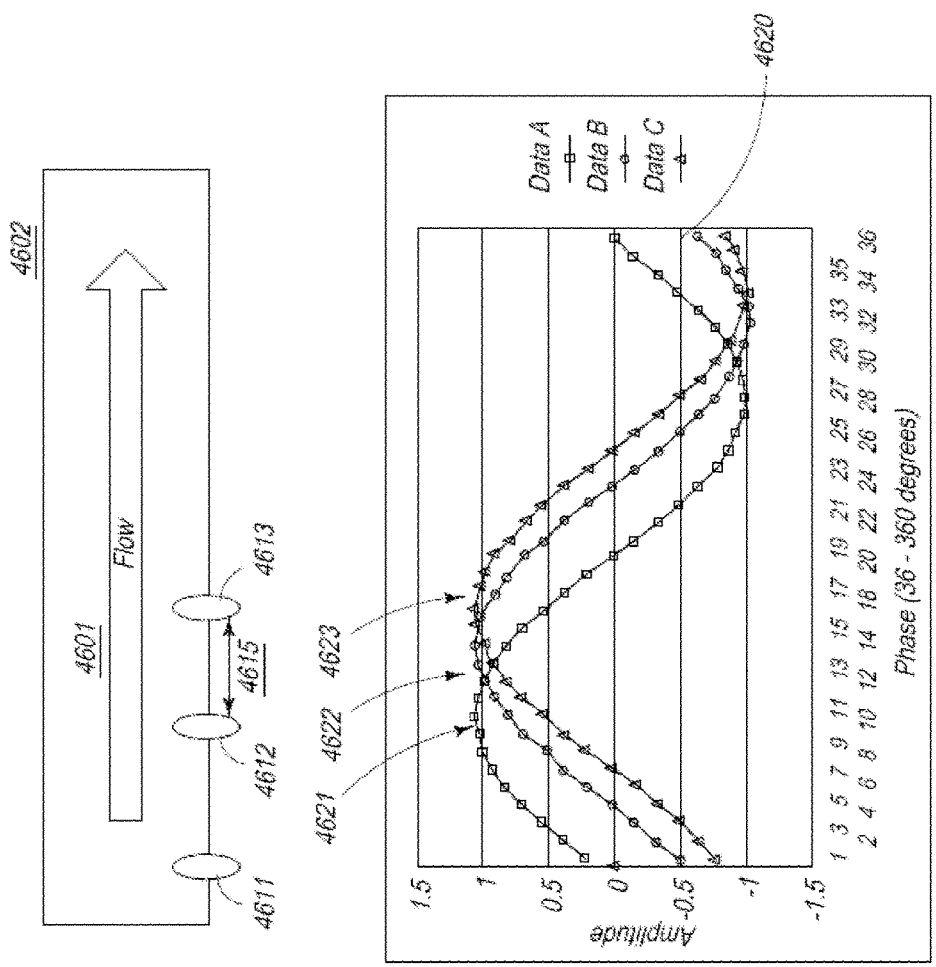
FIG. 46 depicts a plurality of propagating signals generated by the exemplary thermal flow meter.

One representation of the propagation of a thermal wave is shown in FIG. 46. Referring to FIG. 46, the arrow 4601 represents the direction of flow of fluid (and hence the direction of propagation of a thermal wave) in a fluid pathway 4602 in a channel. Measurement contacts are represented by 4611, 4612 and 4613. Since the micro heater is located proximate to the first contact 4611, the thermal wave originates at the first contact, and then propagates towards the second and third contacts 4612 and 4613 respectively, which are located downstream from the first contact 4611. The distance between the second 4612 and third 4613 contacts is 4615.

FIG. 46 further illustrates exemplary wave measurements 4620 at the three contacts 4611, 4612 and 4613. The thermal wave generated at the first contact 4611 is represented by the first curve 4621. Given that the flow is from left to right, this thermal wave will reach contact 4612 at the second location slightly ahead of the time than when it reaches the contact 4613 at the third location. The outputs of the second and third contacts 4612 and 4613 are represented by the curves 4622 and 4623, respectively.

The phase shift between the second 4622 and third 4623 signals can be measured by comparing the points of the zero crossing for each. The distance 4615 between the second 4612 and third 4613 contacts divided by the time between the respective zero crossings (also called time of flight) is equal to the flow velocity of the fluid. Further, multiplying the computed flow velocity by the diameter of the fluid pathway yields the volume flow rate.

The thermal wave can be monitored by using temperature sensors, which in one embodiment are constructed of thermistors, such as Cantherm, part number, CWF4B153F3470, and are placed in physical contact with contacts located at the second and third positions. In one embodiment, the contacts are monitored/measured using thermal measuring devices (which are in contact with the two metal contacts) in the dialysis machine itself. This eliminates the need for separate temperature measuring devices to be integrated in the manifold. It should be appreciated that, in a preferred embodiment, a dialysis machine, or non-disposable instrument, contains a processor and a memory which record a) the excitation frequency communicated to the spring loaded contact which, upon installation of a disposable manifold, physically communicates with the contact surface of the excitation probe and b) the frequency of the temperature wave sensed by the receiver probe and communicated, through the contact surface of the receiver probe, to a spring loaded contact in the dialysis machine, or non-disposable instrument. The processor implements the derivations, described herein, to determine the temperature levels and changes based upon the above-listed stored data. It should be further appreciated that this temperature information is then communicated to a display driver which causes the information to be visually displayed, or audibly communicated, via a user interface.

In one embodiment, the detection circuit examines the phase shift by mixing the excitation signal and receiver signal, performing a comparison, and subjecting the result to a low pass filter in order to get the phase shift information. More specifically, in one embodiment, phase detection is accomplished by multiplying the excitation frequency by the receiver signal. The results yield a signal with two components, one at twice the frequency and one being a DC signal proportional to the phase shift between the excitation reference signal and the receiver signal. This is represented by the following equation:

$$\text{Phase Detection: } e_s r_r = \frac{E_s R_r}{2}[\sin(2\omega t + \theta) + \sin\theta]$$

Where $e_s$ is the excitation signal, $r_r$ is the receiver signal, $\omega t$ is the excitation frequency and $\theta$ is the phase.

As described above, the present invention relies on a wave for time of flight measurement and not a thermal pulse. This method offers a significant advantage because a thermal pulse disperses, resulting in uncertainty over where the pulse edge begins, and substantially increases the measurement noise. Waves disperse as well but the phase shifts of a sine wave, even after dispersion, remain more distinct. Therefore relying on sine wave for measurement introduces less noise.

Another advantage of the present invention lies in integrating the thermal flow rate sensor in the disposable manifold. The plastic used in the manifold acts as a thermal insulator, which beneficially affects measurements. As mentioned previously, in one embodiment spring-loaded probes are used for the thermal flow measurement device, which makes it low cost and disposable.

The design of the device of present invention is optimized in accordance with three parameters: a) thermal excitation (frequency of the thermal input signal), b) the expected flow rate (a slower flow rate requires a different frequency than a higher flow rate because a slower flow rate experiences dispersion more), and c) amount and extent of thermal dispersion. In one embodiment, in order to minimize noise and improve detection accuracy, one can set a key parameter as being constant, e.g. constant phase shift, constant frequency, or constant flow area.

In one embodiment, the constant phase shift method is implemented by using a phase sensitive detector and a digitally controlled frequency generator. As described above, the time of flight causes a physical delay between the excitation probe and the receiver probe. At high flow rates the physical delay is small, while at low flow rates, the physical delay is large. Therefore, in order to maintain a constant phase shift the excitation frequency is controlled via feedback from the phase sensitive detector. A feedback loop is included in the system so that important parameters such as excitation frequency can be dynamically adjusted such that the phase shift remains constant.

Figure 53:
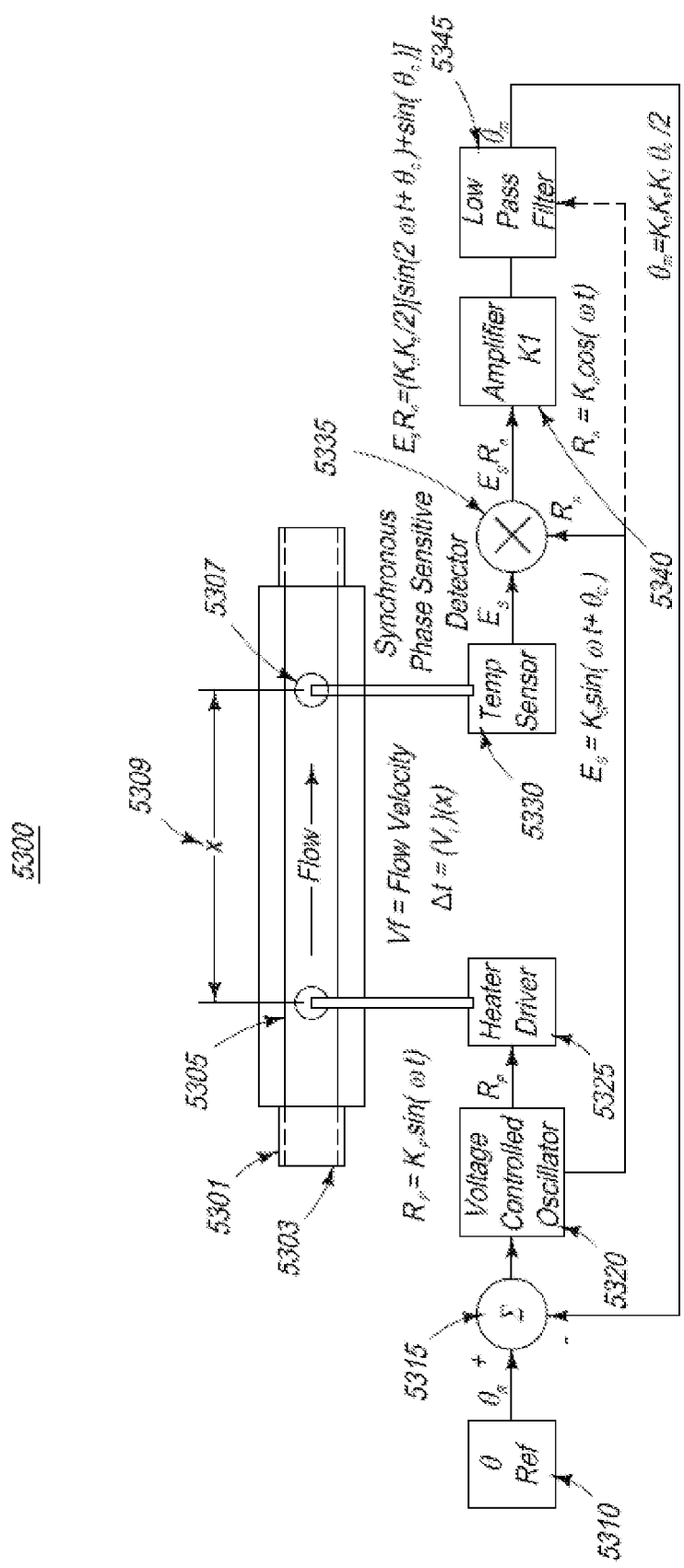
FIG. 53 is a schematic diagram depicting an exemplary thermal flow meter.

Referring to FIG. 53, a schematic of one embodiment of the present invention employing a constant phase shift mode of operation is shown. Liquid 5303 flowing through a channel 5301 passes by excitation probe 5305 and receiver probe 5307, which are separated by a distance 5309, as described above. In one embodiment, the channel 5301 is part of a manifold which is designed to be inserted into, and used within, a dialysis machine. Once installed within the dialysis machine, the contact surface of the excitation probe 5305 is made to thermally contact a heater driver 5325 and the contact surface of the receiver probe 5307 is made to thermally contact a temperature sensor 5330. The heater driver 5325 and temperature sensor 5330 are in electrical contact with a circuit, embodied in and/or integrated within, the dialysis machine.

On the excitation probe side, the circuit comprises a reference signal source 5310 which transmits a signal having a phase Or to a summation device 5315, which also receives a signal input θm from a low pass filter, as described below. The two signals are summed, processed, or otherwise compared to yield an output which is transmitted to a voltage controlled oscillator 5320. The voltage controlled oscillator 5320 outputs a signal, Rp where Rp=Kp sin(ωt), that is received by a heater driver 5325 and used to drive the heater driver 5325 to yield the excitation wave which is thermally communicated to probe 5305.

The thermal wave propagates through the channel 5301 as a function of the fluid 5303 flow rate. The receiver probe 5307 thermally communicates the sensed thermal wave to the temperature sensor 5330. The thermal sensed wave can be expressed as a function as follows:

$$Es=Ks\ \sin(\omega t+\theta c).$$

As stated above, the temperature sensor 5330 is in electrical contact with a circuit embodied within, or integrated into, the dialysis machine. The sensed thermal wave (Es) is communicated to a synchronous phase sensitive detector employing a multiplier component 5335, which multiplies the sensed thermal wave (Es) with an input signal from the voltage controlled oscillator 5320 (Rn, where Rn=Kn cos(ωt)), yielding an output signal EsRn. Output signal EsRn (which can be expressed as EsRn=(KnKs/2)[sin(2ωt+θc)+sin(θc)]) is input into the amplifier 5340 and amplified by constant K1. The amplified signal is then input into a low pass filter 5345, which receives an input signal from the voltage controlled oscillator 5320. The input signal from the voltage controlled oscillator 5320 is used to vary the filter threshold, or cutoff, of the low pass filter 5345. The output from the low pass filter 5345 (θm which can be expressed as a function of KnKsK1θc/2) is a signal that is indicative of the flow rate of the fluid, which can be derived by any means known to persons of ordinary skill in the art, and is communicated back to said summation device 5315 for use in generating the reference signal from the voltage controlled oscillator 5320.

FIG. 47 is a table which illustrates the range of excitation frequency that is dynamically adjusted to maintain a constant phase shift. Referring to FIG. 47, the determination process takes into account the values of various parameters such as flow rate 4701, which varies between 25 to 600 ml/min and flow velocity 4702 which ranges from 17.36 mm/s to 416.67 mm/s. Using a 15 mm value for probe separation 4703, the excitation frequency 4705 will vary from ~1.16 Hz @25 ml/min flow rate to 27.78 Hz @600 ml/min flow rate. The corresponding values of travel time and receiver amplitude are detailed in rows 4704 and 4706, respectively. Note that receiver amplitude is maintained at zero for a constant phase shift.

Figure 48:
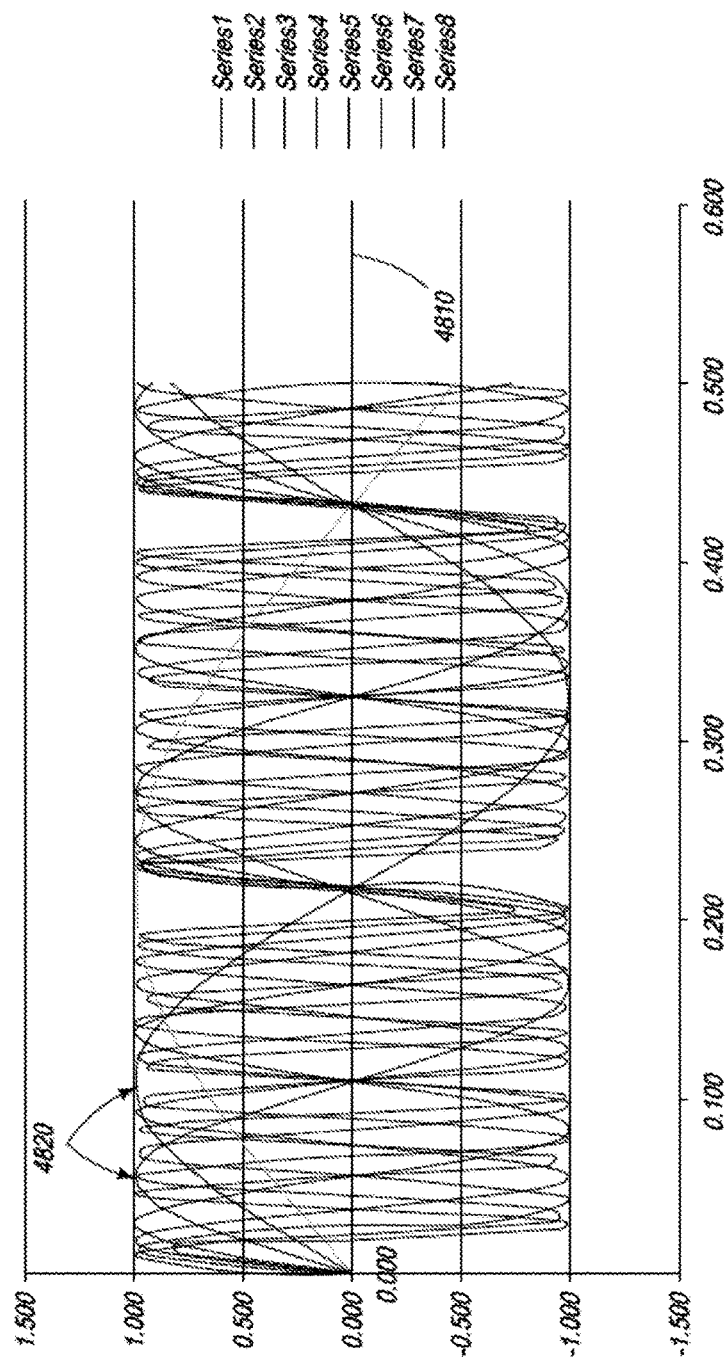
FIG. 48 depicts a plurality of propagating signals generated by the exemplary thermal flow meter.

FIG. 48 illustrates the output of the phase sensitive detector plotted against time axis 4810. The various curves 4820 represent a series of outputs of the phase sensitive detector for different values of flow rate. The graphs in FIG. 48 have been plotted for the values given in the table of FIG. 47; accordingly, the flow rate ranges from 25 to 600 ml/min and the corresponding excitation frequency varies from ~1.16 Hz to 27.78 Hz.

Figure 50A:
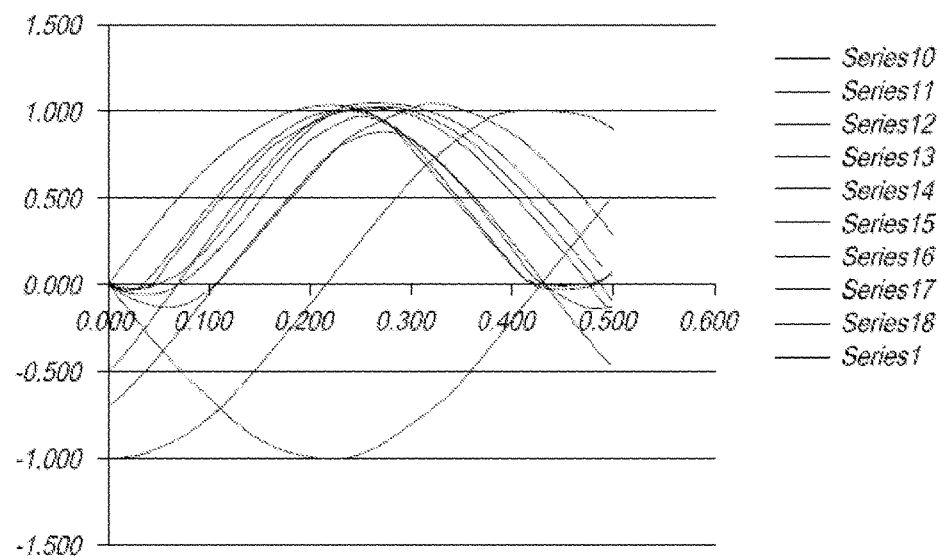
FIG. 50A depicts a plurality of propagating signals generated by the exemplary thermal flow meter.
Figure 50B:
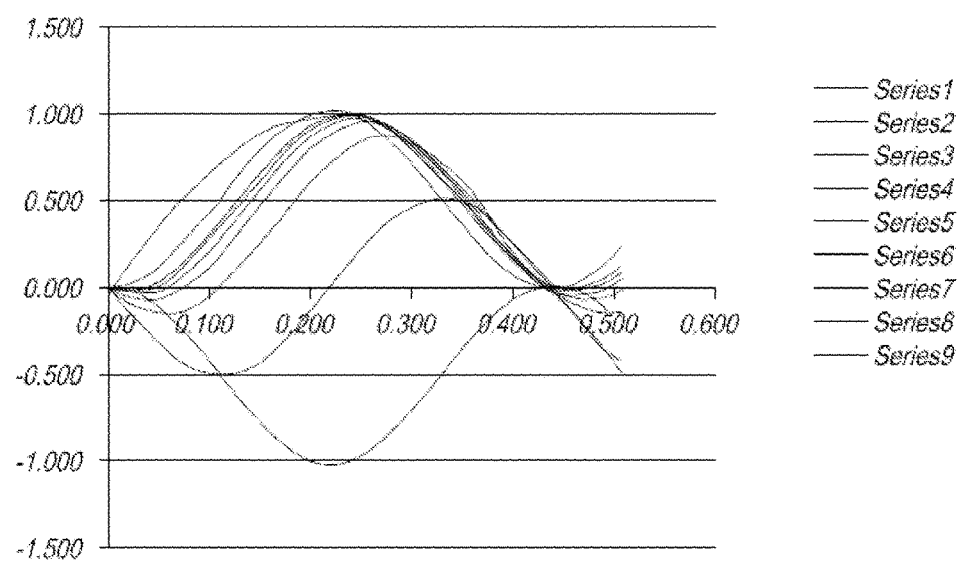
FIG. 50B depicts a plurality of propagating signals generated by the exemplary thermal flow meter.

In another embodiment, phase shift may be allowed to vary while the frequency excitation remains constant. Constant frequency excitation is employed along with a phase sensitive detector, while a feedback mechanism is not used. FIG. 49 illustrates a table detailing values of various parameters when the excitation frequency 4906 is maintained at 1.157 Hz. This value is for flow rate 4901 varying between 25 to 600 ml/min and flow velocity 4902 ranging from 17.36 mm/s to 416.67 mm/s. While the probe separation 4903 is set at 15 mm, the corresponding values of travel time 4904 range from 0.0360 sec (for Harmonic 4905 value of 1.000) to 0.864 sec. Varying phase shift is reflected in the corresponding receiver amplitude values detailed in row 4907. Receiver amplitude 4907 is shown in the final row. FIGS. 50A and 50 B illustrate two sets of outputs (for the range of flow rates specified in FIG. 49) of the phase sensitive detector plotted against time axis.

Figure 54:
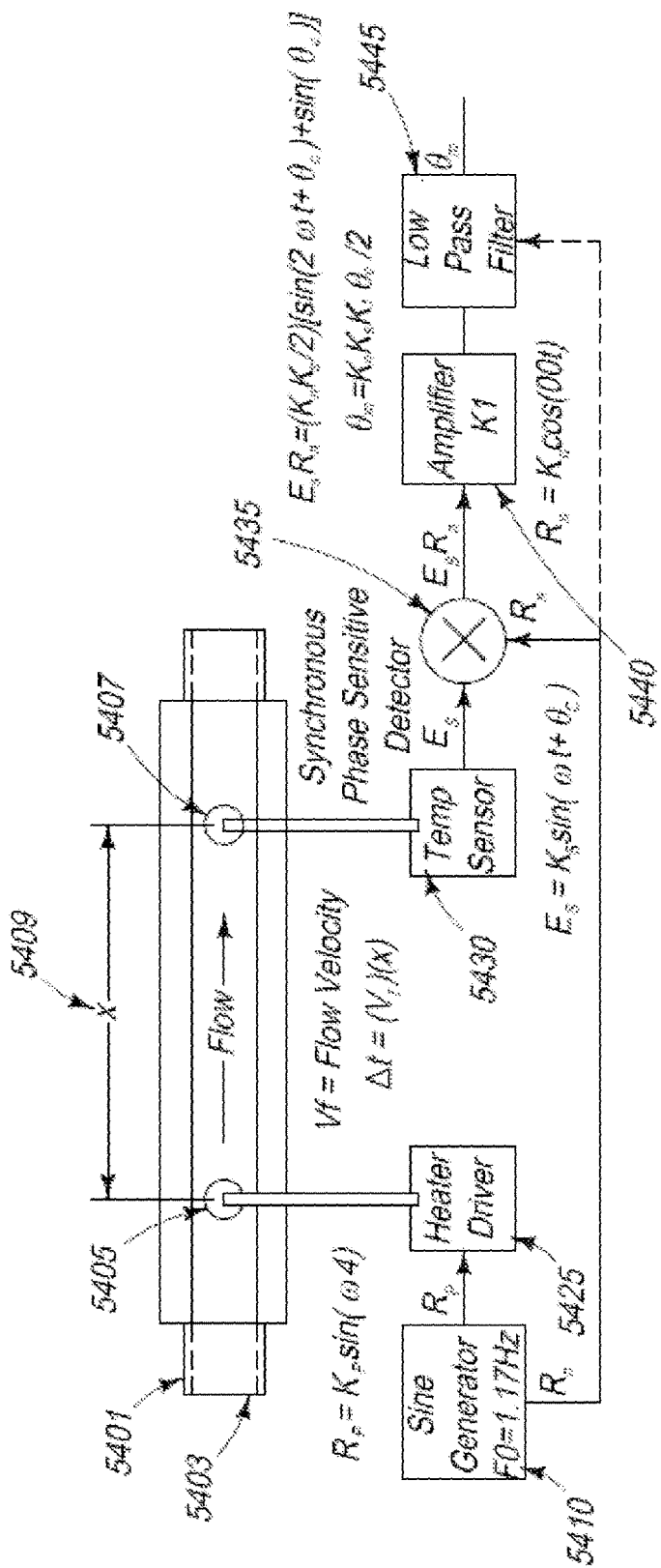
FIG. 54 is a schematic diagram depicting an exemplary thermal flow meter.

Referring to FIG. 54, a schematic of one embodiment of the present invention employing a constant frequency mode of operation is shown. Liquid 5403 flowing through a channel 5401 passes by excitation probe 5405 and receiver probe 5407, which are separated by a distance 5409, as described above. In one embodiment, the channel 5401 is part of a manifold which is designed to be inserted into, and used within, a dialysis machine. Once installed within the dialysis machine, the contact surface of the excitation probe 5405 is made to thermally contact a heater driver 5425 and the contact surface of the receiver probe 5407 is made to thermally contact a temperature sensor 5430. The heater driver 5425 and temperature sensor 5430 are in electrical contact with a circuit, embodied in and/or integrated within, the dialysis machine.

On the excitation probe side, the circuit comprises a reference signal source 5410, such as a sine generator, which transmits a signal having a frequency (e.g. at or about 1.17 Hz) to a heater driver 5425. The sine generator 5410 outputs a signal, Rp where Rp=Kp sin(ωt), that is received by a heater driver 5425 and used to drive the heater driver 5425 to yield the excitation wave which is thermally communicated to probe 5405. It is preferred that the excitation frequency is low enough so at low flow rates the phase shift is less than 80 degrees. The sine generator 5410 also outputs a signal, Rn where Rn=Kn cos(ωt), that is received by a multiplier 5435 and low pass filter 5445, as further described below.

The thermal wave propagates through the channel 5401 as a function of the fluid 5403 flow rate. The receiver probe 5407 thermally communicates the sensed thermal wave to the temperature sensor 5430. The thermal sensed wave can be expressed as a function as follows: Es=Ks sin (ωt+θc). The temperature sensor 5430 is in electrical contact with a circuit embodied within, or integrated into, the dialysis machine. The sensed thermal wave (Es) is communicated to a synchronous phase sensitive detector employing a multiplier component 5435, which multiplies the sensed thermal wave (Es) with an input signal from the sine generator 5410 (Rn, where Rn=Kn cos(ωt)), yielding an output signal EsRn. Output signal EsRn (which can be expressed as EsRn=(KnKs/ 2)[sin( 2ωt +0 c)+sin( 0 c)]) is input into the amplifier 5440 and amplified by constant Ki. The amplified signal is then input into a low pass filter 5445, which receives an input signal from the sine generator 5410. The input signal from the sine generator 5410 is used to vary the filter threshold, or cutoff, of the low pass filter 5445. The output from the low pass filter 5445 (Om which can be expressed as a function of KnKsK1θc/2) is a signal that is indicative of the flow rate of the fluid, which can be derived by any means known to persons of ordinary skill in the art. It should be appreciated that the frequency cutoff of the low pass filter is approximately ¹⁄₂₀ of the frequency of the excitation frequency. The low pass filter should attenuate the 2ωt signal by at least 80 db.

Figure 55:
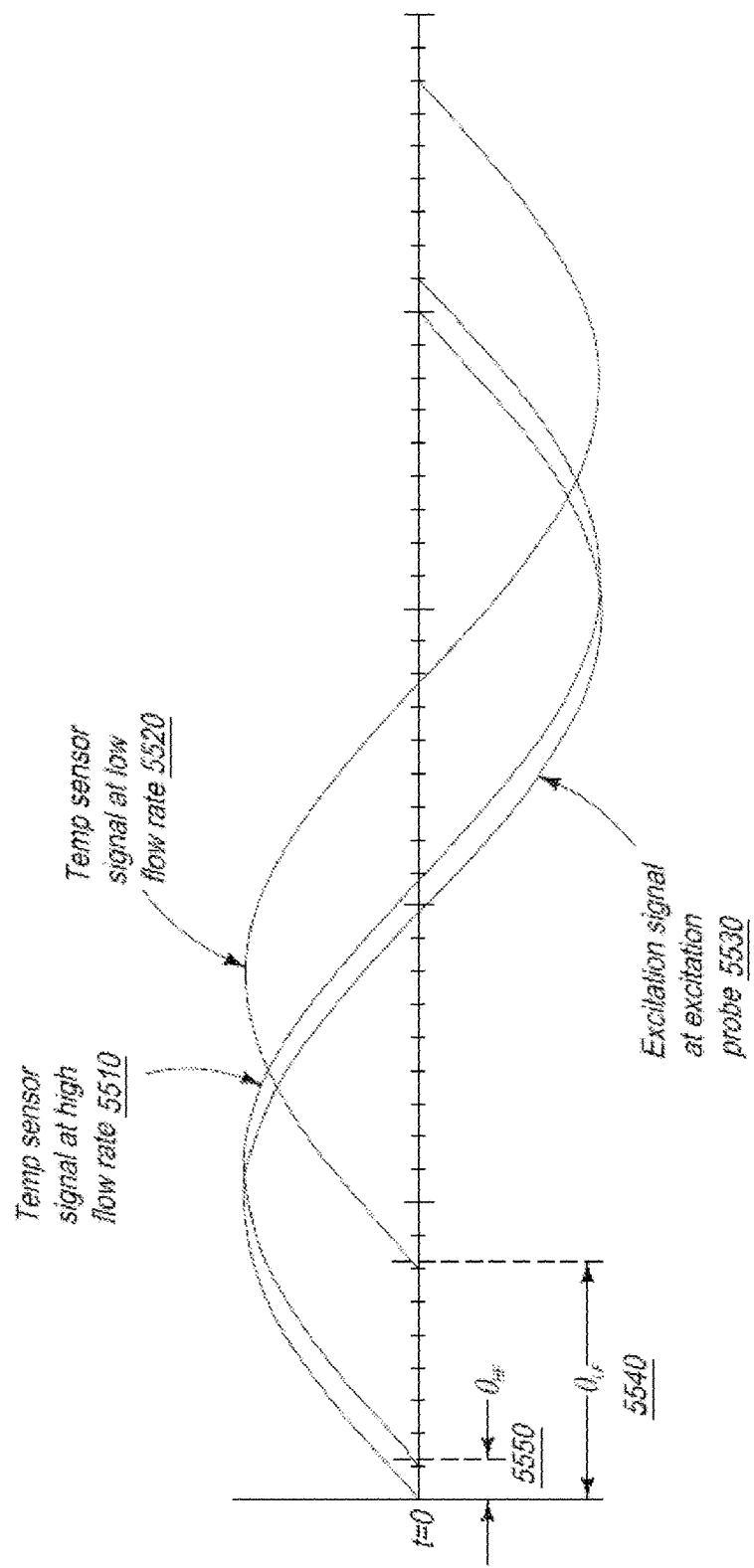
FIG. 55 depicts a plurality of propagating signals generated by the exemplary thermal flow meter.

FIG. 55 shows the relative phase shifts of signals generated in the constant frequency mode with a low flow rate and a high flow rate. An excitation signal 5530 is generated at time 0. In a low flow rate scenario, the sensed signal 5520 is offset from the excitation signal 5530 by a phase shift of $\theta_{LF}$ 5540 while, in a high flow rate scenario, the sensed signal 5510 is offset from the excitation signal 5530 by a phase shift of $\theta_{hF}$ 5550.

Regardless of whether constant or varying phase shift method is employed for measurement, using phase shift as the basis of flow measurement is advantageous as compared to using amplitude, since amplitude can get affected by external factors such as external temperature influences, which should not affect the phase shift.

In one embodiment, the non-invasive thermal fluid flow meter of the present invention provides a measurement range of 20 ml/min to 600 ml/min. Besides the factors listed previously, other factors that are important for designing the thermal flow meter for optimum performance include flow characteristics such as flow regime, maximum Reynolds number and flow velocity; and physical characteristics of the flow cell, such as channel height, width and length.

FIG. 51 comprises a table delineating an exemplary set of design parameters optimized such that the flow regime is kept laminar and Reynolds number 5109 is maintained under 2000, for a maximum flow rate 5101 of 600 ml/min. For keeping the flow regime laminar, channel size—including channel height 5102, width 5103, length 5104, area 5105 and hydraulic diameter 5106 are optimized. Reynolds number 5109 is computed after taking into account values of flow velocity 5107, hydraulic diameter 5106 and properties of water 5108, such as density, dynamic viscosity and kinematic viscosity.

In one embodiment, the flow cell is designed for turbulent flow regime instead of laminar. Such a design of the flow cell entails a constant flow area, which in turn would involve the flow area being widened around the probes (which is reduced around the probes for laminar flow). When the area at the probes widens, the fluid increases in velocity around the probes and the increased velocity causes the flow regime to move into the turbulent regime.

FIG. 52 is a table illustrating another set of exemplary design parameters for the excitation and receiver probes, which in one embodiment are sized to have a thermal time constant 5205 under 1 millisecond for optimum performance. The factors taken into account for this purpose are the material—which in this case is brass, and its properties 5201 such as density, thermal conductivity and specific heat, as well as convection coefficient 5204. Accordingly the size 5202 and exposed surface area 5203 of the probes is determined.

Temperature Sensing

As mentioned above, the compact manifold for the dialysis system also includes a temperature sensor. In one embodiment, the temperature sensor is located in the reservoir assembly. However, the temperature sensor may also be located outside the reservoir assembly, and in such embodiments, it can be integrated into the manifold.

There are three major approaches using temperature sensing which can be integrated into the manifold. One of ordinary skill in the art would appreciate that variations are possible with each approach, without effecting any significant change in the overall design of the manifold. These approaches are discussed as follows:

High Conductivity Fluid Contact

In a high conductivity direct fluid contact approach, a metal disk is built into the wall of the manifold with a thermistor or any other suitable temperature sensor known in the art placed in contact with the disk on the dialysis machine side, and with fluid on the patient side. Fluid temperature may thus be monitored through the metal disk.

Conventionally, the temperature is monitored by placing a thermistor directly in the fluid stream. Use of a metal disk for monitoring temperature in the present invention provides an advantage that lowers the risk of contamination, and hence the need for cleaning of the thermistor is avoided.

A person of ordinary skill in the art would appreciate that a metal disk of any suitable metal, such as type 316 Stainless Steel, may be used for the purpose. Further, a thermistor of any make appropriate for the current application may be employed. An exemplary thermistor is part number 10K 3A1A manufactured by BetaTherm.

In one embodiment, the metal disk is for single patient use and disposable, and the thermistor is part of the dialysis machine and is reused.

Medium Conductivity Fluid Contact

The pressure transducer membranes of the compact manifold are relatively thin and constructed of a medium thermal conductivity material. Thickness of typically 0.040" is used and can vary from 0.005" to 0.050" The thinner the material and the higher the thermal conductivity, the more accurately the pressure transducer membranes will transmit temperature of the dialysis fluid to the pressure transducer mounted inside the dialysis machine. By design they are in direct contact with the pressure transducer on the machine side and the fluid on the patient side. Placing a suitable temperature sensor inside the pressure transducer allows monitoring of the fluid temperature. Certain pressure transducers known in the art already include a temperature sensor for correction of the transducer due to temperature drift. Such pressure transducers with temperature sensing feature can be used for the purpose of the present application. An exemplary combination pressure—temperature sensor is model MPT40 manufactured by Micron Instruments. Employing such a combination of sensors avoids direct contact of the fluid measured and reduces the number of components in the manifold. This provides an alternative to the metal disk, as used in the previous approach.

Indirect Optical Temperature Measurement

If the plastic wall of the manifold fluid path is of limited thickness, such as approximately 0.020", then the plastic wall will equilibrate in temperature to the fluid inside the manifold. Under such conditions a non-contact optical temperature measurement can be made from outside of the thinned wall, and fluid temperature within can be determined. An exemplary non-contact optical temperature sensor is part number MLX90614 manufactured by Melexis. The non-contact approach provides the advantage that it requires no additional parts in the manifold. The only requirement is a thin section in the fluid path walls. This approach provides low cost and still maintains single patient use safety features.

Figure 57:
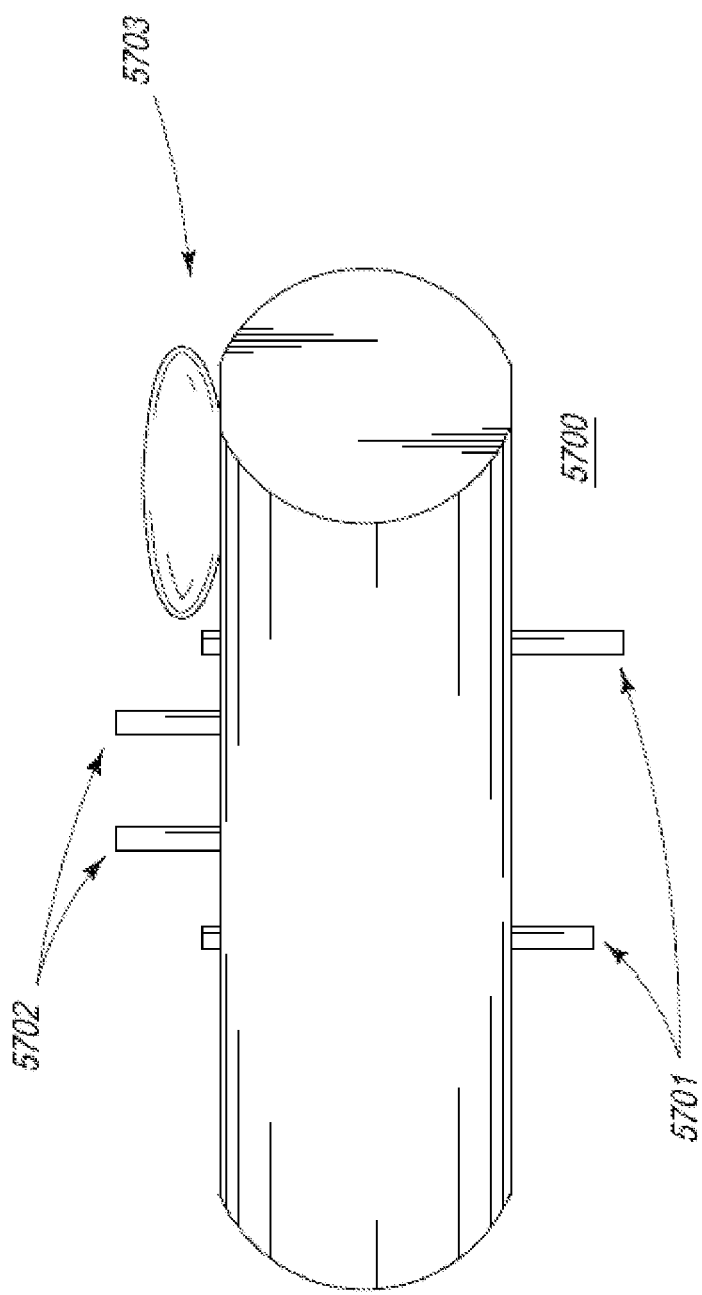
FIG. 57 is a diagram of an exemplary temperature probe.

One possible implementation for an integral conductivity sensor in the manifold is as a conductivity cell with electrical pins contacting the dialysate fluid. The technical details of an exemplary conductivity cell are shown in FIG. 57. Referring to FIG. 57, the conductivity cell 5700 comprises bias pins 5701 for applying a small, constant current to the fluid. Sensing pins 5702 detect the voltage in the fluid, wherein the magnitude of the detected voltage is dependent on the conductivity and temperature of the fluid. The temperature is measured using a thermistor 5703 placed next to the conductivity cell 5700. Alternately the temperature can be determined by one of the means disclosed above. Knowing the values of the measured temperature and voltage at the sensing pins 5702, conductivity of the fluid can be determined.

The current applied through the bias pins 5701 can be DC or an AC signal and is generally in the 50-100 kHz frequency range. In one embodiment, the magnitude of the applied current is of the order of 10 mA. Sensing pins 5702 are generally depth positioned during manufacture of the conductivity cell, typically to a depth of +/−0.001 inch with cal solution in the cell. The thermistor 5703 has a typical accuracy of 0.5 Deg C. The conductivity cell can be built into a dialysate fluid passage of the compact manifold by driving or molding in place conductive pins (bias pins and sensing pins) into the manifold body such that they come in contact with the dialysate but do not allow dialysate to leak out of the manifold.

Disconnection Detection

Embodiments of the disclosed dialysis system further incorporate an apparatus and method for the detection of disconnection in an extracorporeal blood circuit being used for any blood processing treatment routine. Examples of blood processing treatment routines include hemodialysis, hemofiltration, ultrafiltration, or apheresis. Vascular access for establishing an extracorporeal blood circuit is typically obtained by using a transdermal needle or a luer connected catheter. The disconnection apparatus and method uses the pressure pulse produced by a patient's beating heart as an indicator of an intact needle or catheter connection to the vasculature. The pressure pulse produced by a patient's heart is small; more so, in the venous return line of an extracorporeal blood circuit. In order to detect the small pressure pulse the present invention uses cross correlation methodology wherein a reference cardiac signal is cross correlated to the pressure pulse signal.

Figure 58:
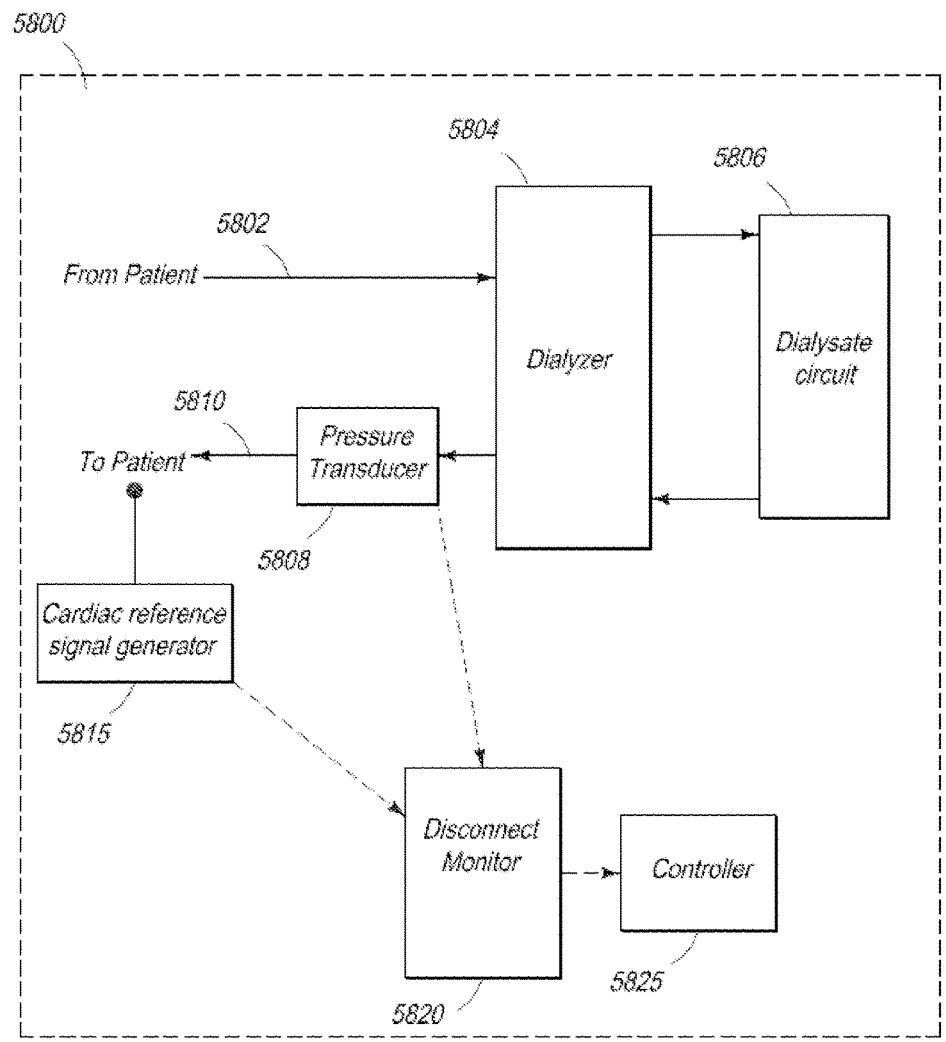
FIG. 58 is a diagram of an exemplary disconnect monitoring system.

FIG. 58 is a block diagram of a system 5800 for detecting a patient's disconnection from an extracorporeal blood circuit, in accordance with an embodiment of the present invention. System 5800 comprises an incoming arterial blood circuit 5802, a dialyzer 5804, a dialysate circuit 5806, a patient pulse pressure transducer 5808, a patient cardiac signal generator 5815 for reference, a disconnect monitor 5820, a controller 5825 and a return venous blood circuit 5810. In various embodiments of the present invention, blood drawn from a patient is passed through the dialyzer 5804 via the arterial blood circuit 5802 and cleansed blood from the dialyzer 5804 is returned to the patient via the venous blood circuit 5810. Contaminated dialysate expelled from the dialyzer 5804 is purified or regenerated within the dialysate circuit 5806 and is pumped back into the dialyzer 5804. In various embodiments of the present invention, cleansed blood is returned to a patient's body via a transdermal needle or a luer connected catheter. Blood flow rates in the return venous blood circuit 5810 are typically in the range of 300-400 ml/min. It should be appreciated that any suitable dialysis circuit can be deployed.

The pressure transducer 5808 measures the pressure pulse of a patient undergoing the blood processing treatment routine and communicates the pulse pressure substantially continuously to the disconnect monitor 5820. In one embodiment the transducer 5808 is an invasive or non-invasive venous pressure sensor located anywhere in the dialysis blood line (the incoming arterial blood circuit 5802 or the return venous blood circuit 5810). In another embodiment, the transducer 5808 is an invasive or non-invasive venous pressure sensor located specifically in a dialysis blood line between the dialyzer 5804 and the patient, that is, in the return venous blood circuit 5810. A non-invasive air bubble detector and/or pinch valve (not shown) are optionally located between the transducer 5808 and the luer connection to the patient. In an embodiment of the present invention, the pressure transducer 5808 is located in close proximity to the needle or catheter inserted in the patient's body for providing vascular access corresponding to the return venous blood circuit 5810. The pressure transducer 5808 is located in close proximity to the needle or catheter in order to preserve waveform fidelity. In other embodiments, the pressure transducer 5808 may be connected anywhere in the return venous blood circuit 5810. In an embodiment of the present invention, the pressure signal produced by the pressure transducer 5808 is an alternating current (AC) signal which is not an accurate measure of vascular pressure. Hence, the pressure transducer 5808 is not a high accuracy transducer.

The reference signal generator 5815 communicates the patient's cardiac signal substantially continuously to the disconnect monitor 5820 for reference. In an embodiment of the present invention, the reference cardiac signal is obtained from a plethysmograph connected to the same body part (such as an arm) to which the needle or catheter supplying processed blood to a patient is connected. In another embodiment of the present invention, the reference cardiac signal is obtained from a finger pulse sensor/oximeter. In various other embodiments of the present invention, the reference cardiac signal may be obtained via an electrocardiogram (ECG) signal, a real time blood pressure signal, stethoscope, arterial pressure signal from the blood withdrawal line, oximeter pulse signal, alternate site plethysmograph signal, transmissive and/or reflective plethysmograph signals, acoustic cardiac signals, wrist pulse or from any other cardiac signal source known to persons of ordinary skill in the art.

The disconnect monitor 5820 detects a disruption in the return venous blood circuit 5810 caused by the disconnection of a needle or catheter from the body of a patient undergoing blood processing treatment. To detect a disconnection, the monitor 5820 processes the patient pulse pressure transducer and cardiac reference signals. Persons of ordinary skill in the art would appreciate that such disconnection may be caused by the needle or catheter being pulled out of the patient's body due to any reason such as a sudden movement of the patient. The disconnect monitor 5808 is described in detail with reference to FIG. 59. Controller 5825 is any microprocessor known to persons of ordinary skill in the art. The function of the controller 5825 is to receive processed inputs from the monitor 5820 and accordingly trigger appropriate actions, when required.

Persons of ordinary skill in the art should appreciate that the pressure transducer and reference signals are communicated to the disconnect monitor 5820 through transmitters incorporated into the reference signal generator and pressure transducer. The transmitter can enable a wired or wireless communication to a corresponding receiver. Similarly, data from the disconnect monitor 5820 is communicated to the controller 5825 through a wired or wireless connection. In one embodiment, such signal communication is enabled using an appropriate wired or wireless public and/or private network such as LAN, WAN, MAN, Bluetooth networks, and/or the Internet. Also, in one embodiment the disconnect monitor 5820 and controller 5825 are located in proximity to each other and to the pressure transducer 5808 and the cardiac reference signal generator 5815. In an alternate embodiment, both or either of the disconnect monitor 5820 and the controller 5825 are/is located remotely from each other and/or from the rest of the components of the system 5800.

Figure 59:
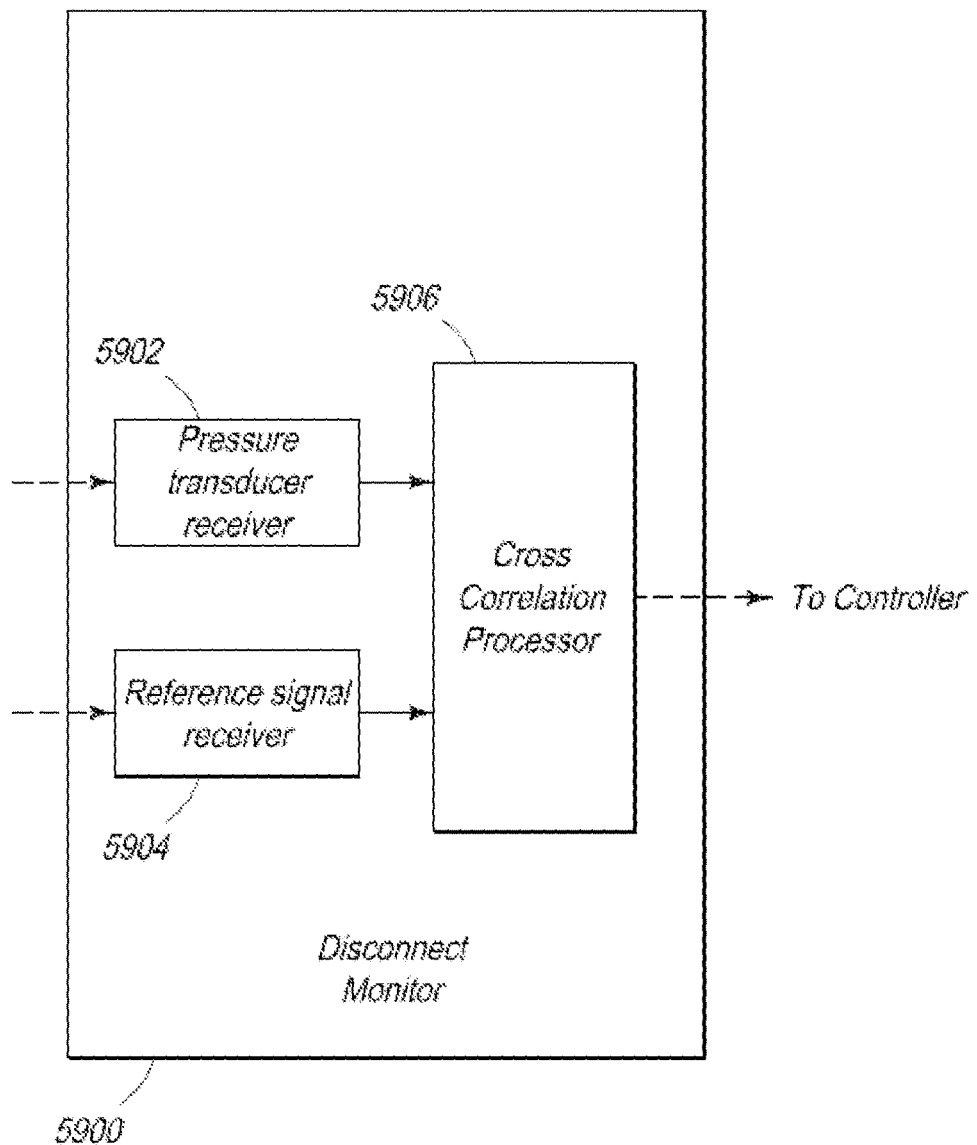
FIG. 59 is a diagram of an exemplary disconnect monitor.

FIG. 59 is a block diagram illustration of an apparatus 5900 for detection of a disconnection in a return venous blood circuit, in accordance with an embodiment of the present invention. The disconnect monitor 5900 comprises a pressure transducer receiver 5902, a reference signal receiver 5904, and a cross correlation processor 5906. The transducer receiver 5902 and the reference signal receiver 5904 receive input signals from the pressure transducer 5808 and cardiac reference signal generator 5815, respectively, of FIG. 58.

The pressure pulse signal obtained by the pressure transducer receiver 5902 and the reference cardiac signal obtained by the reference signal receiver 5904 are stored in a local memory and further fed to the cross correlation processor 5906, which in turn, computes a correlation between the two signals. The output of the processor 5906 is fed into the controller 5825 of FIG. 58. If the output produced by the cross correlation processor 5906 indicates a correlation between the two input signals, it is inferred that the return venous blood circuit is intact. If the output produced by the cross correlation processor 5906 does not indicate a correlation between the two input signals, it is inferred that the return venous blood circuit is broken due to a needle or catheter pull out, and the controller 5825 of FIG. 58 triggers appropriate actions, such as sounding an indicative alarm and/or shutting down the dialysis system completely or partially.

Persons of ordinary skill in the art should note that the present invention envisages use of any cross correlation processor that links, corresponds, or otherwise creates a measurable, quantifiable, and/or predictable relationship between the pressure transducer signal and reference signal. In one embodiment of the present invention cross correlation is performed by using a lock in amplifier, such as SR810 Lock-In Amplifier manufactured by Stanford Research Systems, California. Various known techniques for cross correlation detection of very low signal to noise ratio systems, and cardiac signals may be incorporated in the cross correlation processor 5906.

In various embodiments of the present invention, the cross correlation function, computed by the cross correlation processor 5906, is used to measure the similarities between the two input signals, i.e. the reference cardiac signal and the pressure pulse signal. Computation of the cross correlation function comprises computation of a sum of the products of corresponding pairs of points of the two input signals, within a specified time frame or window. The computation also takes into consideration any potential phase differences between the two input signals by including a lead or lag term. The mathematical formula corresponding to a cross correlation function is represented as:

$$r_{(12)}(j) = \frac{1}{N}\sum_{n=0}^{N-1} x_1(n)x_2(n+j)$$

where N represents a number of samples, j represents a lag factor and x1 and x2 represent the two input signals respectively.

Figure 60:
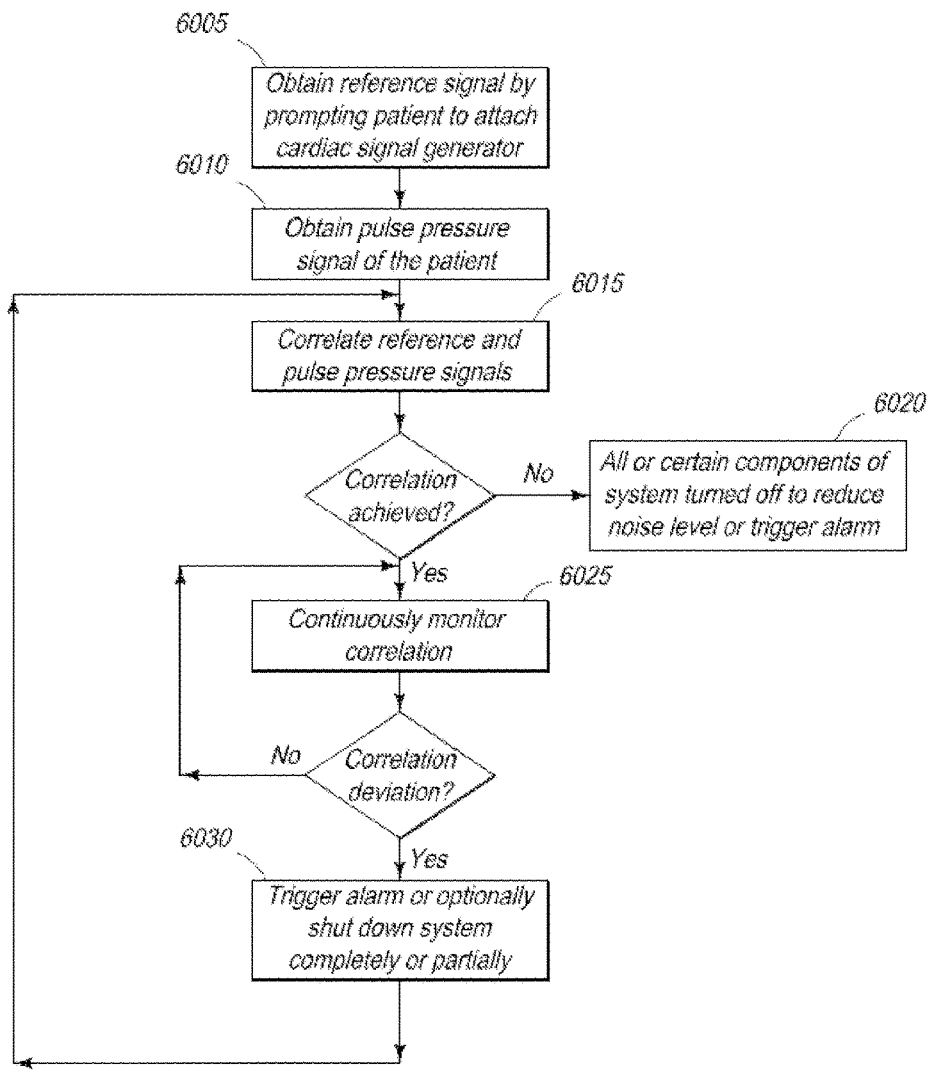
FIG. 60 is a flowchart defining an exemplary disconnection detection process.

FIG. 60 is a flow diagram showing exemplary steps of a method of ascertaining a patient's disconnection from an extracorporeal blood circuit, in accordance with an embodiment of the present invention. In operation, dialysis system software, comprising a plurality of instructions and executing on a processor, prompts a patient to first attach a cardiac signal generator (such as a finger pulse oximeter) to obtain 6005 a reference signal. At this point the patient may or may not be connected to a dialysis system. Thereafter or concurrent to capturing the cardiac reference signal, the dialysis system software, comprising a plurality of instructions and executing on a processor, prompts a patient to connect to the system 5800 of FIG. 58 as a result of which patient pulse pressure transducer signal is also obtained 6010. Next, a cross correlation processor attempts to correlate 6015 the reference and transducer signals. If no correlation can be achieved at start-up, in one embodiment, the patient is prompted to turn off 6020 all or certain components or, in another embodiment, the controller 5825 of the system 5800 of FIG. 58 does this automatically to lower noise level. For example, shutting off the pumps of the dialysis system can lower the noise and make it easier to capture and correlate the two signals. In another embodiment, a cross-correlation is attempted before noise-generating system components, such as pumps, are turned on. Thus, lock down of a correlation is attempted before complete system start-up can be completed. In one embodiment, if no correlation is locked down, an alarm is triggered, indicating the patient dialysis system may have an anomaly.

However, if a correlation is obtained, then that correlation is substantially continually monitored 6025. If there is any deviation in that correlation, an alarm is triggered 6030, indicating a possible leak or, optionally, the system is shut down (completely or partially) and an attempt to re-establish the correlated signal is attempted again. In one embodiment, if the nature of the correlation changes or deviates beyond or within a predefined threshold, certain system components, such as pumps, are shut down and the cross correlation processor attempts to re-establish the correlation. If the correlation cannot be re-established, then an alarm is triggered. In another embodiment, if the nature of the correlation changes or deviates beyond or outside the range of a predefined threshold, certain system components, such as pumps, are shut down and an alarm is immediately triggered, before any additional attempt to re-establish the correlation.

This approach to monitoring disconnection provides certain distinct improvements over the prior art. First, unlike the prior art, the present invention is responsive if the needle is just barely pulled out or if it is removed and pulled quite some distance from the insertion site. Second, the present invention does not need any extra apparatus placed at the insertion site, such as a moisture pad. Third, by cross correlating the patient's own cardiac signal, the false negatives are greatly diminished. Fourth, the combination of pressure pulse sensing and cross correlation renders the present invention unique and capable of detecting low signal to noise ratio signals. Fifth, continuously monitoring the cross correlation status enables the system to detect small signal deviations which could potentially indicate a disconnection. Therefore, an apparatus and method for detection of disconnection in an extracorporeal blood circuit being used for any blood processing treatment routine, is provided by the present invention.

Central Venous Pressure Monitoring

Embodiments of the dialysis system disclosed herein further incorporate methods and systems for monitoring and controlling the ultrafiltration (UF) rate, such that the volume of fluid within a patient undergoing dialysis/ ultrafiltration remains within a desired range. This invention integrates central venous pressure (CVP) monitoring into a dialysis system and uses CVP measurements to control the rate of ultrafiltration (UF). CVP feedback data helps prevent over-removal of fluids as a safety measure and provides a means for titrating the UF rate for improving therapy.

Figure 61:
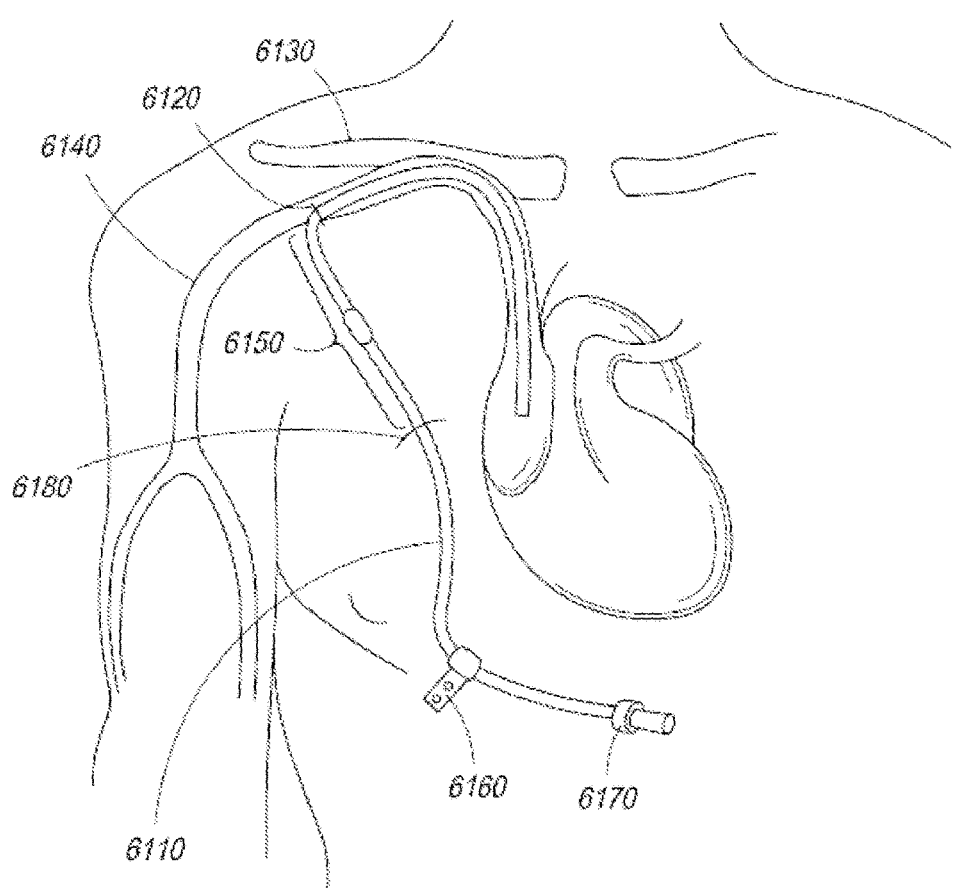
FIG. 61 is a diagram showing an exemplary placement of a catheter to measure CVP.

CVP measurement entails measuring the average pressure present in the central venous line used for dialysis, thereby integrating CVP measurement with dialysis. In order to measure CVP, an appropriate catheter needs to be inserted in the patient's body, such that the tip of the catheter is placed intrathoracically. FIG. 61 depicts an exemplary location of a central venous catheter for hemofiltration and CVP measurement. Referring to FIG. 61, a Central Venous Catheter (CVC) 6110 is used to provide vascular access for UF. In this particular embodiment, the entrance site 6120 chosen for the CVC 6110 is below the collarbone (clavicle) 6130, at the subclavian vein 6140. One of ordinary skill in the art would appreciate that any other large vein in the patient's body may be selected as an alternate site for inserting the CVC, while keeping its tip intrathoracic. The CVC 6110 passes through a subcutaneous tunnel 6150, and is secured with the help of a clamp 6160 and a standard luer-lock 6170. Pressure at the tip of the CVC at the exit site 6180 is equal to the Central Venous Pressure.

In one embodiment of the present invention, the CVC 6110 is used for accessing blood during hemofiltration, and the central venous pressure may be measured using sensors inside the hemofiltration machine. In this case, no additional equipment is required for CVP measurement. In another embodiment, a dual lumen CVC is used for hemofiltration. In this case, the proximal lumen can be used for blood withdrawal and the distal lumen (at the tip) can be used for returning blood. Either lumen or port can provide a CVP measurement. In both cases, when a CVC is used for blood access, the system of present invention provides that prior to taking a CVP measurement, blood flow is momentarily stopped to enable the accurate measurement of pressure. Therefore, in one embodiment, the present invention integrates into conventional dialysis machines programmatic controls for stopping blood flow through the device based upon a predetermined CVP measurement rate.

Figure 62:
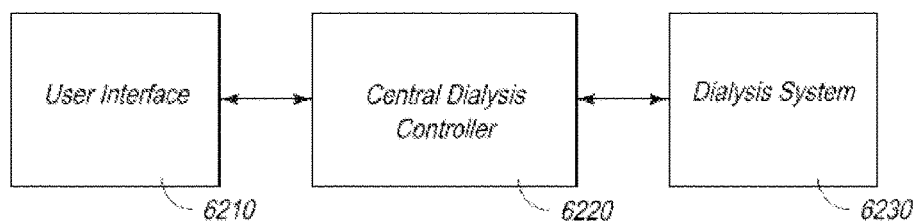
FIG. 62 is a diagram showing an exemplary dialysis system using CVP measurements.

FIG. 62 is a block diagram illustrating the dialysis control system of the present invention. Referring to FIG. 62, a user interface 6210 is provided that receives inputs from the user (clinician) indicating the preferred frequency of CVP measurement and the preferred range of CVP values. These inputs are supplied to the central dialysis controller 6220. The central dialysis controller 6220 is a programmable system that can be used to regulate CVP monitoring, and the rate of hemodialysis/ultrafiltration based on the monitored CVP. Depending on the frequency of CVP measurement determined by the user, the central dialysis controller 6220 communicates a signal to the blood pump in the dialysis system 6230 to stop the blood flow whenever a CVP measurement is to be recorded. Following this, a CVP sensor in the dialysis system 6230 takes the measurement and communicates it to the central dialysis controller 6220, which may transmit it to the user interface 6210 for display. After a CVP measurement is complete, the central dialysis controller 6220 communicates another signal to the dialysis system 6230, causing the blood flow to resume. The central dialysis controller 6220 also keeps track of the measured CVP values to determine if they are in the user-defined range. A decrease in CVP below the defined range would indicate hypovolemia. In such a case, the central dialysis controller 6220 halts the process of ultrafiltration, so that no additional fluid can be removed until CVP is restored to the desired range. In one embodiment the central dialysis controller 6220 titrates the ultrafiltrate removal to the range of 2-6 mm Hg, which keeps the CVP in the desired range.

Figure 63:
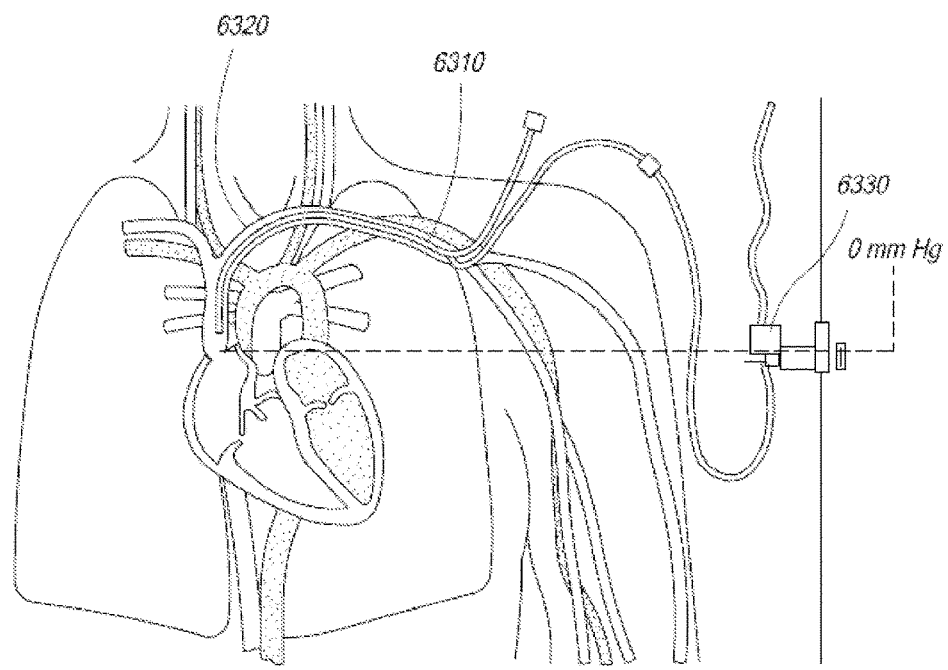
FIG. 63 is a diagram showing an exemplary placement of a catheter and measurement of CVP.

The CVP monitoring and UF regulation system contemplates a wide range of CVP measurement systems, integrated with conventional dialysis machines. Measuring CVP can be accomplished in a number of ways. In one embodiment, CVP may be measured with a sensor located at the tip of an appropriate catheter. In another embodiment, CVP may be measured with a dedicated pressure transducer located remote from the catheter, with the transducer being held at the same level as the heart. FIG. 63 is an exemplary illustration of the latter embodiment. Referring to FIG. 63, a catheter 6310 used for accessing blood is shown. The catheter 6310 is placed in the Central Vena Cava 6320. The pressure transducer 6330 measures the central venous pressure at the heart level. The CVP measurement in this case is used to control the rate of hemofiltration in the same manner as when a CVC is used.

Figure 64:
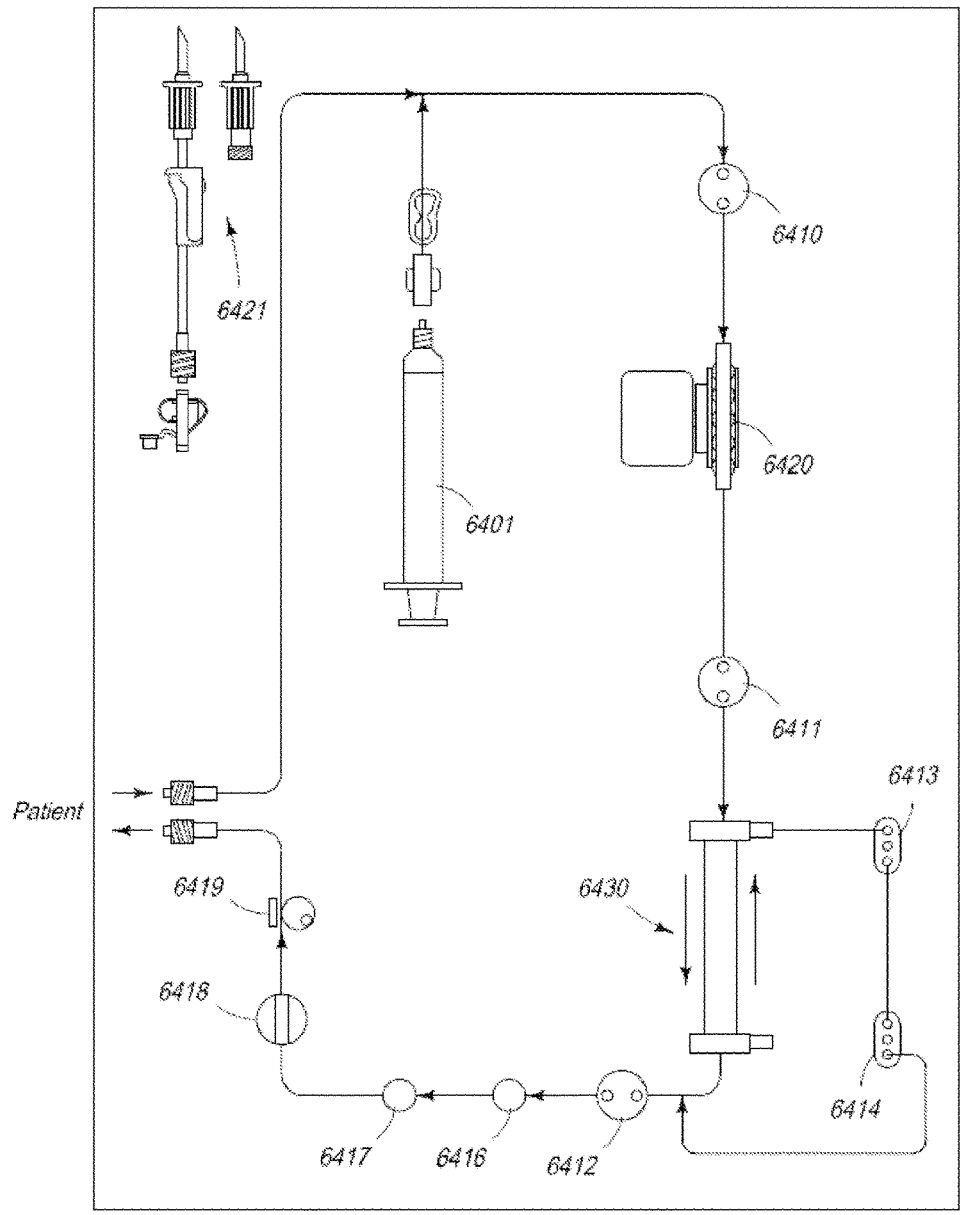
FIG. 64 is a sixth exemplary fluid circuit diagram.

In another embodiment, CVP is measured with a remote sensor inside the hemofiltration machine. Referring to FIG. 64, an exemplary blood circuit 6400 with the provision of CVP measurement is illustrated. As blood enters into the circuit 6400 from the patient, an anticoagulant is injected into the blood using the syringe 6401 to prevent coagulation. A pressure sensor PBIP 6410 is provided which is used for the measurement of central venous pressure. A blood pump 6420 forces the blood from the patient into the dialyzer 6430. Two other pressure sensors PBI 6411 and PBO 6412 are provided at the inlet and the outlet, respectively, of the dialyzer 6430. The pressure sensors PBI 6411 and PBO 6412 help keep track of and maintain fluid pressure at vantage points in the hemodialysis system. A pair of bypass valves B 6413 and A 6414 is also provided with the dialyzer, which ensures that fluid flow is in the desired direction in the closed loop dialysis circuit. The user can remove air at the port 6417 if air bubbles have been detected by sensor 6418. A blood temperature sensor 6416 is provided prior to the air elimination port 6417. An AIL/PAD sensor 6418 and a pinch valve 6419 are employed in the circuit to ensure a smooth and unobstructed flow of clean blood to the patient. A priming set 6421 is pre-attached to the hemodialysis system that helps prepare the system before it is used for dialysis.

For taking CVP measurements, blood flow in the circuit 6400 is stopped by stopping the blood pump 6420. At this point, the pressure in the catheter used for accessing blood (not shown) will equilibrate, and the pressure measured at pressure sensor PBIP 6410 in the hemofiltration machine will be equal to the pressure at the catheter tip. This measured pressure (CVP) is then used to regulate the rate of ultrafiltration and the volume of fluid removed from the patient.

Thus, operationally, the system of present invention modifies a conventional dialysis system such that ultrafiltration is conducted at a rate preset by the physician. Periodically, the blood flow is stopped and the average CVP is measured using one of the various measurement methods described above. In one embodiment, a safety mode is provided, wherein if CVP drops below a preset limit, hemofiltration is discontinued and an alarm sounded.

In another application, a hypervolemic patient such as a patient with Congestive Heart Failure (CHF) may be given ultrafiltration to remove fluids. It is known in the art that while the ultrafiltration process removes fluid from the blood, the fluid that is intended to be removed is located in the interstitial spaces. Further, the rate of fluid flow from the interstitial spaces into the blood is unknown. Without the system of present invention, a physician can only guess at the interstitial fluid removal rate that will balance fluid removal from the blood stream with the fluid flow back into the blood from the interstitial space, and sets the dialysis machine for that rate. In such a scenario, constant monitoring on the part of the physician is required to make sure that the fluid removal rate does not over- or under- hydrate the patient. With the system of present invention, a physician can pre-set the total amount of fluid he wants removed—typically computed from patient weight, and the minimal average CVP allowed. The system then removes fluid at the maximum rate that automatically maintains the desired CVP. That is, the system of present invention automatically balances the fluid removal rate with the fluid flow rate from the interstitial spaces into the blood.

It should be appreciated that normal CVP levels is between 2 and 6 mm Hg. Elevated CVP is indicative of over-hydration, while decreased CVP indicates hypovolemia. Using the present invention, a patient may begin an ultrafiltration session with a CVP above normal, e.g. 7-8 mm Hg, and end the session at a final CVP target of 3 mm Hg through, for example, a 6 hour treatment session. However, if midway through the treatment session, CVP has fallen more than 50% of the desired drop, while the fluid removed has only reached 50% of the final target for removal, the system can be reprogrammed to reduce the goal for fluid removal or reduce the rate of fluid removal. Other actions can be taken based on more complicated algorithms. The net result is that hypovolemia is avoided by monitoring the rate and actual value of CVP. It should be appreciated that this approach may also be useful in controlling fluid removal rates not only during hemofiltration, but for all types of renal replacement therapies.

Monitoring and Maintaining Volumetric Accuracy

Embodiments of the dialysis system disclosed herein further incorporate methods and systems for maintaining volumetric accuracy of replacement fluid and output fluid in a hemodialysis system. In one embodiment, the method involves swapping pumps used at the replacement fluid side and on the output side such that an equal quantity of fluid is pumped at each side. The pump-swapping system of the present invention provides an accurate means for maintaining the fluid volumes during the dialysis procedure, and can be inexpensively implemented, for reusable as well as disposable devices.

Figure 65:
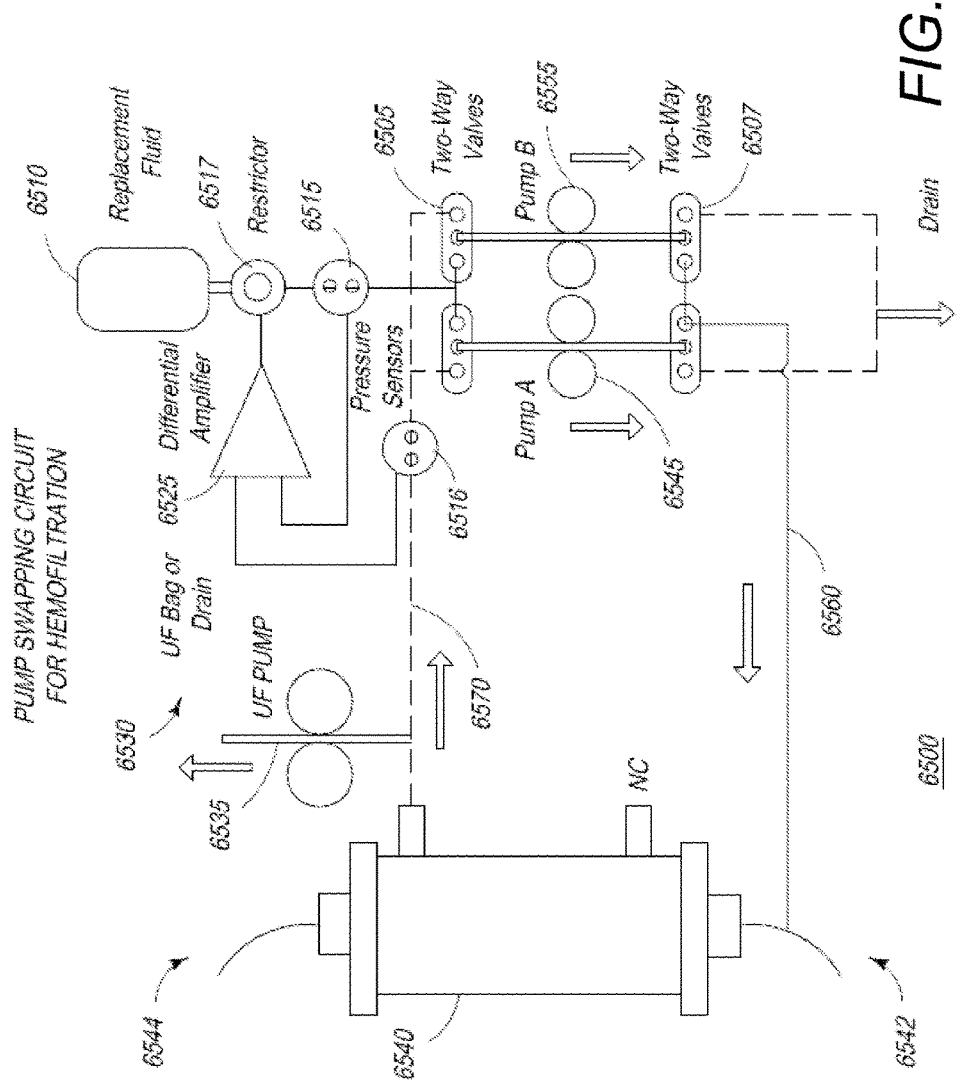
FIG. 65 is a seventh exemplary fluid circuit diagram.

FIG. 65 illustrates an exemplary pump swapping circuit as employed in one embodiment. A pump swapping circuit 6500 for hemofiltration comprises two pumps, Pump A 6545 and Pump B 6555. These two pumps are in fluid communication with the replacement fluid circuit R 6560 and the output fluid circuit O 6570. The fluid communication is facilitated by means of two pairs of two-way valves 6505 and 6507. For the replacement fluid circuit R 6560, a replacement fluid source 6510 provides fluid through a restrictor 6517 to the pair of two-way valves 6505. Thereafter, depending on which of the two valves in the pair 6505 is open, the replacement fluid is pumped by either Pump A 6545 or Pump B 6555 to the second set of two-way valves 6507. This set of two-way valves 6507 channelizes the replacement fluid to the replacement circuit R 6560, which is in fluid communication with the output 6542 of the dialyzer 6540. In the present embodiment, the communication with the output 6542 of the dialyzer 6540 is a post-dialyzer infusion configuration. In another configuration known in the art, the communication is with the input 6544 of the dialyzer instead. One of ordinary skill in the art would appreciate that either configuration may be used, without impacting the scope of the invention.

The pair of two-way valves 6505 can be configured to alternatively open such that any of the following fluid communication paths may be established:

Between output fluid circuit O 6570 and Pump A 6545;
Between replacement fluid circuit R 6560 and Pump B 6555;
Between replacement fluid circuit R 6560 and Pump A 6545; and,
Between output fluid circuit O 6570 and Pump B 6555.

The system 6500 also comprises two pressure sensors 6515 and 6516. The sensor 6516 is located on the output circuit O 6570 while the sensor 6515 is located proximate to the replacement fluid source 6510. The pressure sensors 6515 and 6516 are used for monitoring pressure. The pressure data from these sensors is provided to the active restrictor 6517 via a differential amplifier 6525. Depending on the pressure measurements, the restrictor 6517 variably restricts the flow of replacement fluid as required.

During dialysis, additional fluid may be removed from the patient, if required, in the form of ultrafiltrate (UF). For this purpose, a UF pump 6535 is provided that pumps the UF to a bag or drain 6530. Since UF fluid is removed prior to the point of pressure measurement in the output fluid sub-circuit O 6570, volumetric accuracy is maintained irrespective of how much or how little UF is removed.

Operationally, volumetric accuracy in the hemodialysis system of the present invention is achieved by swapping the pumps 6545 and 6555 used on the replacement fluid side and on the output side so that same quantity of fluid is pumped at each point after an even number of swaps. The two pairs of two-way valves 6505 and 6507 facilitate the use of each of the pumps alternatively with the replacement fluid circuit R 6560 and the output fluid circuit O 6570.

In one embodiment, the pumps used are peristaltic pumps. One of ordinary skill in the art would appreciate that other types of pumps may also be used, since volumetric balance in renal dialysis is achieved by the use of a pump-swapping technique, and is not dependent on the type of pump. In one embodiment, Pump A 6545 delivers more fluid per unit time than pump B 6555. Therefore, this would result in more replacement fluid being pumped than output fluid in any given period of time.

One of ordinary skill in the art would appreciate that pumps that include a disposable element can have a pumping rate differential since volumes across disposable elements are not equal, even if they are of the same size and type. For example, the volumes of two disposable syringes of nominally the same size inserted within two syringe-pump assemblies will not be exactly the same. One of ordinary skill in the art would also appreciate that two pumps that do not have disposable elements can usually be tuned so there will be no differential in pumping rate between the two. Examples of pumps using disposable elements that can be implemented with the present invention include, but are not limited to, rotary or linear peristaltic pumps, syringe pumps, rotary vane pumps, centrifugal pumps, and diaphragm pumps.

To achieve volumetric balance between the replacement fluid and output fluid, the pumps 6545 and 6555 are swapped every T minutes. At the end of the first 'T' minute interval, owing to the pumps' specific characteristics, pump A 6545 would deliver more volume than pump B 6555. The fluid volume delivered by pump A 6545 is termed as 'Q'. Thus, if during the first pumping interval 'T', replacement fluid is routed through Pump A 6545 and output fluid is routed through Pump B 6555, then at the end of time interval T, 'Q' more replacement fluid would have been pumped in the replacement fluid circuit R 6560 than output fluid in the circuit O 6570.

Thereafter, pumps A 6545 and B 6555 are swapped in the next time interval and output fluid in circuit O 6570 is pumped by Pump A 6545 and replacement fluid in circuit R 6560 is pumped by pump B 6555. In this interval, 'Q' less replacement fluid in R 6560 will be pumped than output fluid in O 6570. Therefore, at end of the second interval (and at the end of an even number of swaps), the difference in volume pumped during each interval would be: Q–Q=0. Thus, the net volume difference is zero after an even number of swaps, thereby achieving volumetric balance between the replacement fluid infused and the output fluid coming back from the patient through the dialyzer. One of ordinary skill in the art would appreciate that there may be a minute change in the flow rate through a pump over time, and consequently, in the volume delivered per unit time. In that case, the net volume difference may not be exactly zero, but very close to zero.

The volume pumped by a peristaltic pump depends on head pressure. Head pressure for the pumps is a function of the sub-circuit, not the pump, and is systematically different in the replacement fluid circuit R 6560 versus the output circuit O 6570. It is thus necessary to equalize head pressures experienced by Pump A 6545 and Pump B 6555.

In one embodiment, head pressures are equalized by modulating the restrictor 6517 on the input circuit from the replacement fluid source 6510. The restrictor modulation is achieved based on the output of a differential amplifier 6525, which calculates pressure differentials between the pressure values measured by head pressure sensors 6515 and 6516 located between the pumps 6545 and 6555. The amount of compensation required will depend on how much a pump is influenced by head pressures in the replacement fluid circuit R 6560 and the output fluid circuit O 6570. The head pressure in circuit O 6570 will typically be negative. The head pressure in circuit R 6560 will be positive if the replacement fluid bags (source) 6510 are elevated above the level of the pumps and negative if the bags are vertically positioned below the level of the pumps. For pumps utilizing heavy duty pump tube segments, the differences may be relatively small.

As mentioned, head pressures are equalized by measuring the pressures in the sub-circuits R 6560 and O 6570, providing those pressures as input to a differential amplifier 6525, and modulating the inflow from the replacement fluid bag 6510 with a variable restrictor 6517 in sub-circuit R 6560 that is regulated by the output of the differential amplifier 6525. Since the head pressure is a function of the sub-circuit rather than the pump, therefore, it is necessary to regulate the average difference between the head pressures of the two sub-circuits in an unregulated state. The pressures in the unregulated state can be measured initially and at desired intervals during operation by briefly turning off regulation. This recalibration does not require stopping pumping.

In one embodiment, pump head pressures can vary from zero to over several hundred mm Hg, depending on the dialyzer incorporated, the height of the replacement fluid relative to the dialysis machine and the dialysate flow rate setting. For example, for a dialysate flow of 200 ml/min and replacement fluid bags hung 5-10 inches above the dialysis machine, the pressure differentials are in the range of 10 mm Hg. In general, when the pressure in replacement circuit R 6560 is higher than the pressure in circuit O 6570, the flow restrictor 6517 will restrict flow from the replacement fluid source 6510 in order to compensate for the pressure differential.

Figure 66:
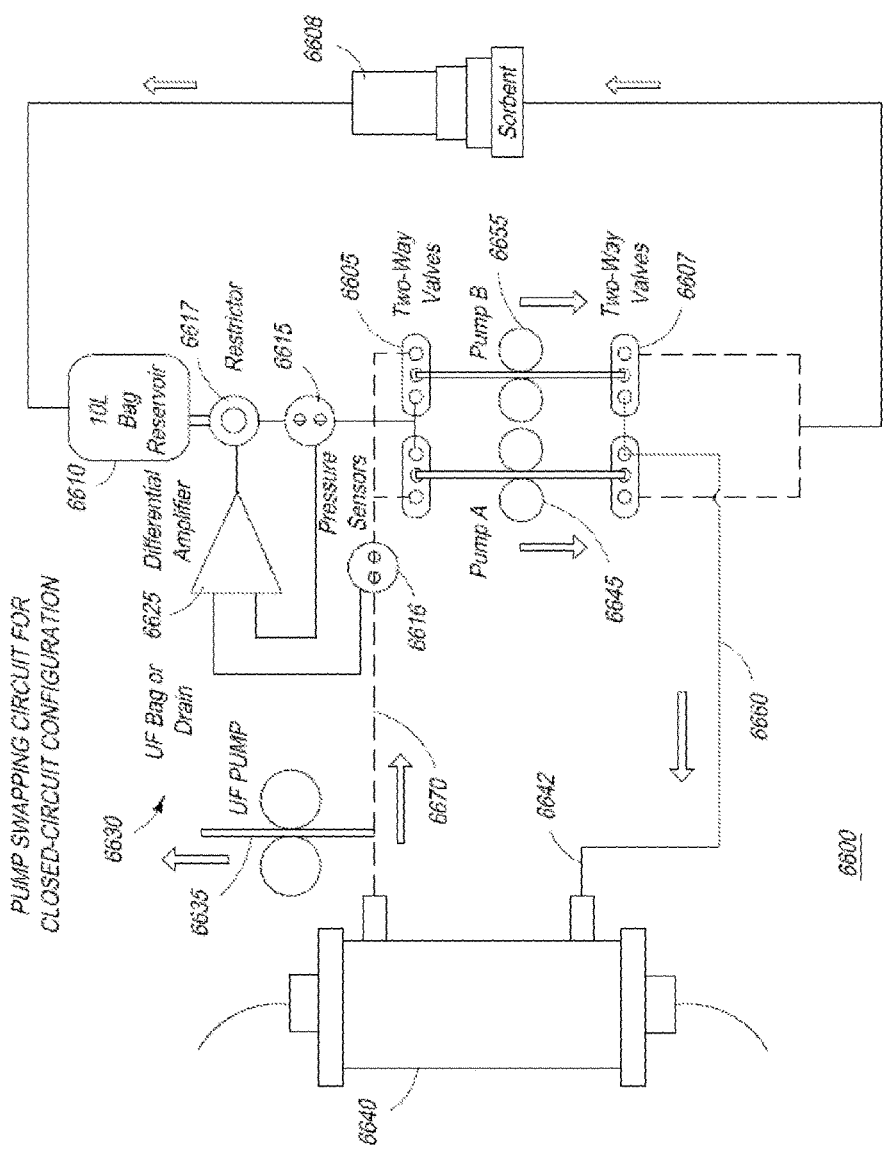
FIG. 66 is an eighth exemplary fluid circuit diagram.

For a dialysis system that uses a closed-loop dialysate circuit where the dialysate fluid is being constantly recycled passing through a sorbent cartridge, FIG. 66 presents an alternative pump swapping circuit. The pump swapping circuit 6600 for hemofiltration comprises two pumps, Pump A 6645 and Pump B 6655. These two pumps are in fluid communication with the return fluid circuit R 6660 and the sorbent fluid circuit S 6670. The fluid communication is facilitated by means of two pairs of two-way valves 6605 and 6607. For the return fluid circuit R 6660, a reservoir fluid source 6610 provides fluid through a restrictor 6617 to the pair of two-way valves 6605. Thereafter, depending on which of the two valves in the pair 6605 is open, the replacement fluid is pumped by either Pump A 6645 or Pump B 6655 to the second set of two-way valves 6607. This set of two-way valves 6607 channelizes fluid through a sorbent cartridge 6608 and through the reservoir 6610 to the return circuit R 6660, which is in fluid communication with the input port 6642 of the dialyzer 6640.

The pair of two-way valves 6605 can be configured to alternatively open such that any of the following fluid communication paths may be established:

Between sorbent fluid circuit S 6670 and Pump A 6645;
Between return fluid circuit R 6660 and Pump B 6655;
Between return fluid circuit R 6660 and Pump A 6645; and,
Between sorbent fluid circuit S 6670 and Pump B 6655.

The system 6600 also comprises two pressure sensors 6615 and 6616. The sensor 6616 is located on the sorbent circuit S 6670 while the sensor 6615 is located proximate to the reservoir fluid source 6610. The pressure sensors 6615 and 6616 are used for monitoring pressure. Pressure data from these sensors is provided to the active restrictor 6617 via a differential amplifier 6625. Depending on the pressure measurements, the restrictor 6617 variably restricts the flow of reservoir fluid as required.

As in the previous embodiment, this embodiment has a provision for a UF (ultrafiltrate) pump 6635, so that additional fluid in the form of (UF) may be removed from the patient during dialysis, if required. The UF pump 6635 pumps the ultrafiltrate to a bag or drain 6630. Since UF fluid is removed prior to the point of pressure measurement in the sorbent fluid sub-circuit S 6670, volumetric accuracy is maintained irrespective of how much or how little UF is removed.

Operationally, volumetric accuracy in the hemodialysis system of the present invention is achieved by swapping the pumps 6645 and 6655 used on the return fluid side and on the sorbent side so that the same quantity of fluid is pumped at each point after an even number of swaps. The two pairs of two-way valves 6605 and 6607 facilitate the use of each of the pumps alternatively with the return fluid circuit R 6660 and the sorbent fluid circuit S 6670.

In one embodiment, the pumps used are peristaltic pumps. One of ordinary skill in the art would appreciate that other types of pumps may also be used, since volumetric balance in renal dialysis is achieved by the use of a pump-swapping technique, and is not dependent on the type of pump. In one embodiment, Pump A 6645 delivers more fluid per unit time than pump B 6655. Therefore, this would result in more return fluid being pumped than sorbent fluid in any given period of time.

One of ordinary skill in the art would appreciate that pumps that include a disposable element can have a pumping rate differential since volumes across disposable elements are not equal, even if they are of the same size and type. One of ordinary skill in the art would also appreciate that two pumps that do not have disposable elements can usually be tuned so there will be no differential in pumping rate between the two.

To achieve volumetric balance between the return fluid and sorbent fluid, the pumps 6645 and 6655 are swapped every T minutes. At the end of the first 'T' minute interval, owing to the pumps' specific characteristics, pump A 6645 would deliver more volume than pump B 6655. The fluid volume delivered by pump A 6645 is termed as 'Q'. Thus, if during the first pumping interval 'T', reservoir fluid is routed through Pump A 6645 and sorbent fluid is routed through Pump B 6655, then at the end of time interval T, 'Q' more reservoir fluid would have been pumped in the return fluid circuit R 6660 than sorbent fluid in the circuit S 6670. Thereafter, pumps A 6645 and B 6655 are swapped the next time interval and sorbent fluid in circuit S 6670 is pumped by Pump A 6645 and return fluid in circuit R 6660 is pumped by pump B 6655. In this interval, 'Q' less reservoir fluid in R 6660 will be pumped than sorbent fluid in S 6670. Therefore, at end of the second interval (and at the end of an even number of swaps), the difference in volume pumped during each interval would be: Q−Q=0. Thus, the net volume difference is zero after an even number of swaps, thereby achieving volumetric balance between the return fluid infused and the sorbent fluid coming back from the patient through the dialyzer. Again, since there may be some, usually small, change in the flow rate through a pump over time, so that the volume delivered per unit time changes, the net volume difference may not be exactly zero at times, but substantially close to zero.

As is true for the embodiment shown in FIG. 65, the volume pumped by a peristaltic pump in the embodiment illustrated in FIG. 66 depends on head pressure. Further, since head pressure for the pumps is a function of the sub-circuit, not the pump, and is systematically different in the return fluid circuit R 6660 versus the sorbent circuit S 6670, it is necessary to equalize head pressures experienced by Pump A 6645 and Pump B 6655.

In one embodiment, head pressures are equalized by modulating the restrictor 6617 on the input circuit from the reservoir fluid source 6610. The restrictor modulation is achieved in a similar manner as with the embodiment of FIG. 65, and is based on the output of a differential amplifier 6625. The differential amplifier 6625 calculates pressure differentials between the pressure values measured by head pressure sensors 6615 and 6616 located between the pumps 6645 and 6655. The amount of compensation required will depend on how much a pump is influenced by head pressures in the return fluid circuit R 6660 and the sorbent fluid circuit S 6670. The head pressure in circuit S 6670 will typically be negative. The head pressure in circuit R 6660 will be positive if the reservoir 6610 is elevated above the level of the pumps and negative if the reservoir is vertically positioned below the level of the pumps. For pumps utilizing heavy duty pump tube segments, the differences may be relatively small.

As mentioned, head pressures are equalized by measuring the pressures in the sub-circuits R 6660 and S 6670, providing those pressures as input to a differential amplifier 6625, and modulating the inflow from the reservoir 6610 with a variable restrictor 6617 in sub-circuit R 6660 that is regulated by the output of the differential amplifier 6625. Since the head pressure is a function of the sub-circuit rather than the pump, therefore, it is necessary to regulate the average difference between the head pressures of the two sub-circuits in an unregulated state. The pressures in the unregulated state can be measured initially and at desired intervals during operation by briefly turning off regulation. This recalibration does not require stopping pumping.

In one embodiment, pump head pressures may vary from zero to over several hundred mm Hg, depending on the dialyzer incorporated, the height of the reservoir relative to the dialysis machine and the dialysate flow rate setting. For example, pressure differentials are in the range of 10 mm Hg for a dialysate flow of 200 ml/min. and with the reservoir located 5-10 inches above the pumps of the dialysis machine. When pressure in circuit R (return) 6660 is higher than pressure in circuit S 6670 (from dialyzer), the flow restrictor 6617 restricts flow from the reservoir 6610 to compensate.

In either the configuration in FIG. 65 or the one in FIG. 66, at times there may be increased outflow into the dialysate circuit segment (O 6570 or S 6670, respectively), due to increased dialyzer trans-membrane pressure (TMP). This may happen, for example, because of an outflow obstruction of the dialyzer (6540 or 6640, respectively). In such a case, there may be the possibility of the restrictor (6517 or 6617, respectively) not being able to open up sufficiently to regulate, for example, if the replacement fluid source 6510 or reservoir 6610 is located below the level of the pumps. To counter this, a booster pump may be inserted in the circuit after the replacement fluid source 6510 or the reservoir 6610. The booster pump may be configured to be turned on automatically in case the differential amplifier (6525 or 6625, respectively) and/or the restrictor (6517 or 6617, respectively) is unable to regulate the system.

Since a time gap is created during a pump swap, it is necessary to calculate the time interval between swaps. This calculation is a function of the maximum allowable difference in the amount of fluid pumped, as determined by two functions, at any given time. The calculation must compensate, however, for differences in head pressure presented to the pumps for fluid coming from the replacement-fluid containers and that coming back from the patient through the dialyzer.

The frequency at which the pumps are swapped depends on the maximum acceptable increase or decrease in fluid volume in a patient during the dialysis process for any given interval T. For example, if the allowable net gain or loss is 200 ml and the replacement fluid is being input at a rate of 200 ml/min, then the pump swapping frequency for various levels of differences in the pumping rate of the two pumps are detailed in a table 6700 in FIG. 67.

The following description refers to the components in the embodiment shown in FIG. 65, but is also applicable in the same manner to the embodiment illustrated in FIG. 66. Referring to FIG. 67, the first row 6701 of the table illustrates that when the percentage difference in the pumping rates of the two pumps—pump A 6545 and pump B 6555—is 1%, which amounts to a fluid volume difference of 2 ml (for an allowable net gain or loss of 200 ml), then swapping the pumps at a time interval of 200 ml/2 ml=100 minutes would achieve zero volumetric difference. Similarly, for a pumping rate difference of 2%, swapping the pumps at an interval of 200 ml/4 ml=50 minutes would achieve volumetric balance, and so on. This is illustrated in the subsequent rows of table 6700.

Even if a much more stringent limit was to be put on the maximum volume of fluid that can be infused into or removed from a patient, such as ±30 ml as opposed to ±200 ml in the above example, the swap interval for the case when the pumping difference is 5% would be 30 ml/10 ml=3 minutes. Since only switching the two-way valves (shown as 6505 in FIG. 65) is needed for swapping the pumps and starting and stopping the pumps is not required, even a short interval of 3 minutes (or shorter) is practically implementable.

Swapping the pumps more frequently can also mitigate any divergence in pump tube performance. Since in the system of the present invention, the tubes of both pumps are subject to the same number of impacts, the performance of the pumps tends not to diverge.

When using the pump-swapping approach, if the process does not stop at an even number of swaps it could result in a differential error in the volumetric balance of the replacement fluid and the output fluid. Therefore, in one embodiment, the system is configured to stop only when an even number of swaps are completed, unless the system is overridden. The potential impact of the problem ending in a net differential error can also be reduced by swapping the pumps more frequently. In any case, it can be guaranteed that any net difference will not be outside the originally set boundary for maximum allowable net fluid loss or gain, such as ±200 ml. Therefore, in one embodiment, the present invention comprises a controller in data communication with all operative pumps. The controller comprises software with a counter that tracks, by increment, the number of pump swaps. Where the number of pump swaps is uneven, the controller implements a blocking signal which prevents the system from being shut down. The controller releases the blocking signal when the counter is an even number, thereby permitting a shutdown of the system. The controller is further responsible for transmitting the swapping signal which causes the appropriate valves to open and close, thereby effectuating the pump swap.

During the process of pump swapping, there will be a small amount of residual fluid that will shift from one sub-circuit to the other. For example, if the peristaltic pump tubing is 0.8 ml/inch and the pump-tube segment length is 3 inches, the residual would be 2.4 ml (3 inch×0.8 ml/in=2.4 ml) per each time period. In an exemplary time period of 50 minutes, and with a pumping rate of 200 ml/min, 10 liters of fluid (50 min×200 ml/min=10,000 ml) will be pumped. Therefore, the percentage of residual to the total fluid pumped in liters is only 0.024% (2.4 ml/10,000 ml=0.024%). The effect of even this small percentage of residual will be nullified because a shift between the sub-circuits occurs due to pump swapping, which cancels out the net effect.

With regards to the issue of residual fluid from one sub-circuit coming into the other, the fluid coming out of the dialyzer comes from the patient only, and therefore, it is perfectly safe to put that fluid back into the patient along with the sterile replacement fluid.

As mentioned previously, during dialysis, additional fluid may be removed from the patient if required, in the form of ultrafiltrate (UF), and a UF pump is provided for this purpose in the system of present invention. Further, volumetric accuracy is maintained irrespective of how much or how little UF is removed.

When pumping out ultrafiltrate to remove excess fluid from the patient, if the system has a lower pump rate, such as of the order of 10 ml/min, as opposed to a high rate such as 200 ml/min, achieving a defined overall volumetric accuracy is easier. For example if the accuracy required is ±30 ml, then over a time period of 60 minutes, 600 ml will be pumped with a pump rate of 10 ml/min. This implies that the percentage accuracy achieved is 30 ml/600 ml=0.05 or 5%, which is reasonable to obtain. One of ordinary skill in the art would, however, appreciate that the system of the present invention is capable of achieving the desired volumetric accuracy regardless of the pump rate of the UF pump in the dialysis device.

Disposable Conductivity Sensor

FIG. 86 depicts, among other elements, a disposable conductivity sensor 8690 comprising a tubular section with a first end for receiving a first disposable tubing segment and a second end for receiving a second disposable tubing segment. The tubular section comprises a first plurality of probes that extend into the interior volume defined by the tubular section and constitute the fluid flow path. In one embodiment, at least three separate, elongated probes are employed. In another embodiment, at least four separate, elongated probes are employed.

The disposable conductivity sensor 8690 is adapted to attach to a complementary, mating second plurality of probes that are fixedly and/or permanently attached to the exterior side of the control unit. Preferably, the site of attachment comprises a portion of the exterior surface of the control unit proximate to, or on the same side as, the dialyzer, as previously described in relation to FIG. 1. Operationally, disposable conductivity sensor 8690 is snapped into a temporary, but attached, relation to the complementary, mating non-disposable plurality of probes. Therefore, the second plurality of probes is received into, and positioned in communication with, the first plurality of probes. The probes then operate by emitting and detecting signals within the fluid flow path defined by the first disposable tubing segment, tubular section of the conductivity sensor, and second disposable tubing segment, as previously discussed herein and then transmitting detected signals to a memory and processor within the control unit for use in monitoring and controlling the dialysis system.

Valve Systems

Figure 68:
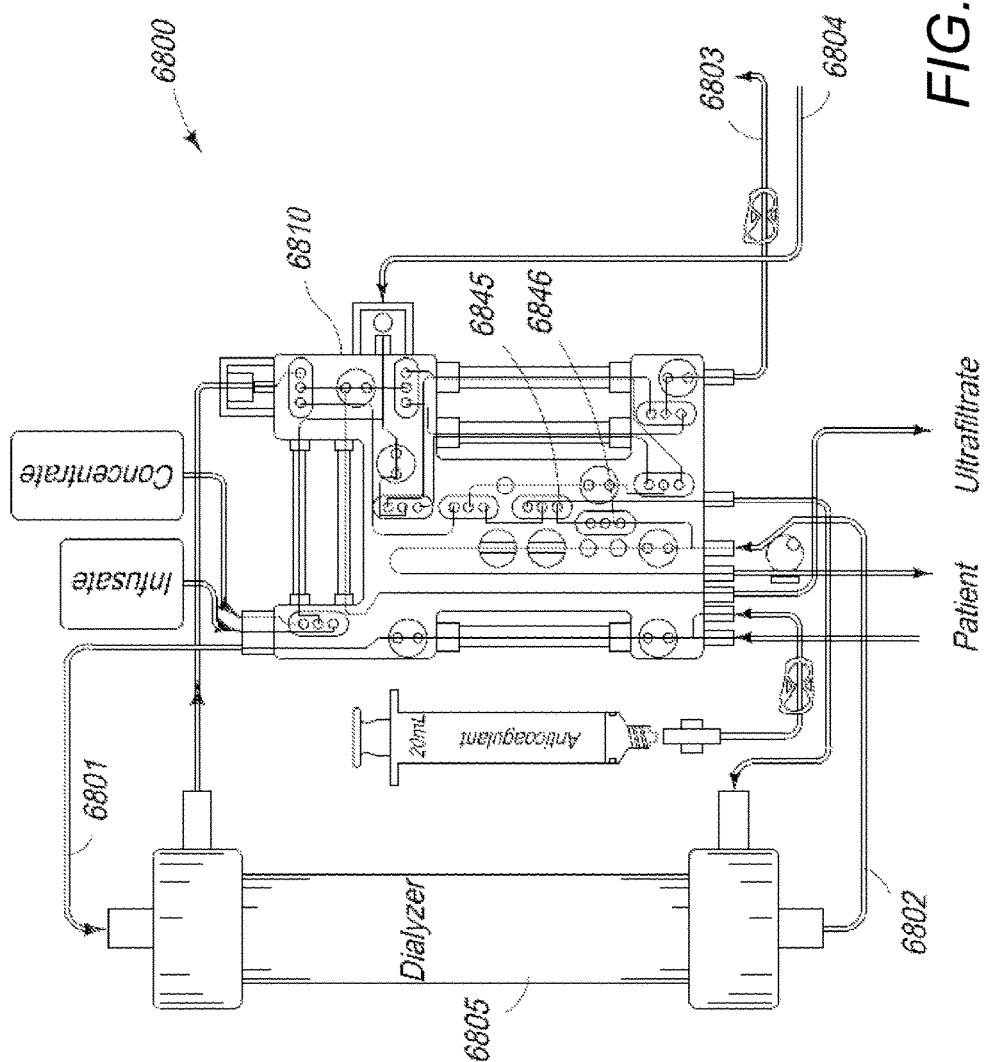
FIG. 68 is a ninth exemplary fluid circuit diagram.

To allow a control flow through the blood and dialysate circuits and to select the desired mode of operation (hemodialysis or hemofiltration), in one embodiment the system is provided with two-way valve(s), as described above. These valves can be actuated by a user to direct dialysate flow either through the dialyzer in one mode of operation or to deliver infusate grade dialysate flow directly to a patient, in a second mode of operation. These two-way valves can also be integrated with the compact manifold of the dialysis circuit. This is illustrated in FIG. 68. It should be noted that in FIGS. 68 through 70, for the purpose of clarity, corresponding elements have the same numbers.

Referring to FIG. 68, the extracorporeal blood processing system 6800 comprises a plastic molded compact manifold 6810 that encapsulates a plurality of molded blood and dialysate fluidic paths as well as a plurality of sensor areas, valves and fluidic pump segments. The dialyzer 6805 when connected to the arterial blood tube 6801 and venous blood tube 6802 of manifold 6810 completes the blood circuit of system 6800. In one embodiment, the dialyzer 6805 is disposable. Two lines, 6803 and 6804, are used for circulating spent and fresh dialysate respectively. For operating the system 6800 in either of the two modes (hemodialysis and hemofiltration), a two-way valve 6845 and a backup two-way valve 6846 are provided.

Back up valve 6846 is employed because the dialysate used in hemodialysis is not sterile and not infusion grade while the fluid used in hemofiltration is. If operating in hemodialysis mode or if there is a leak or other failure of valve 6845, valve 6846 provides double protection against that fluid being pumped into the patient blood stream. Inclusion of backup valve 6846 allows the use of one manifold for both hemodialysis and hemofiltration safely. As noted above, two way valves such as backup valve 6846 are composed of two single valves. In this case both one way valves are in series and so by closing both ports of two way valve 6846 double protection is afforded preventing dialysate from entering the blood stream. In an alternate embodiment, a manifold can be made that is only intended for hemodialysis, having no connection between dialysis fluid circuit and blood circuit, thereby permitting valve 6846 to be safely eliminated.

Figure 69A:
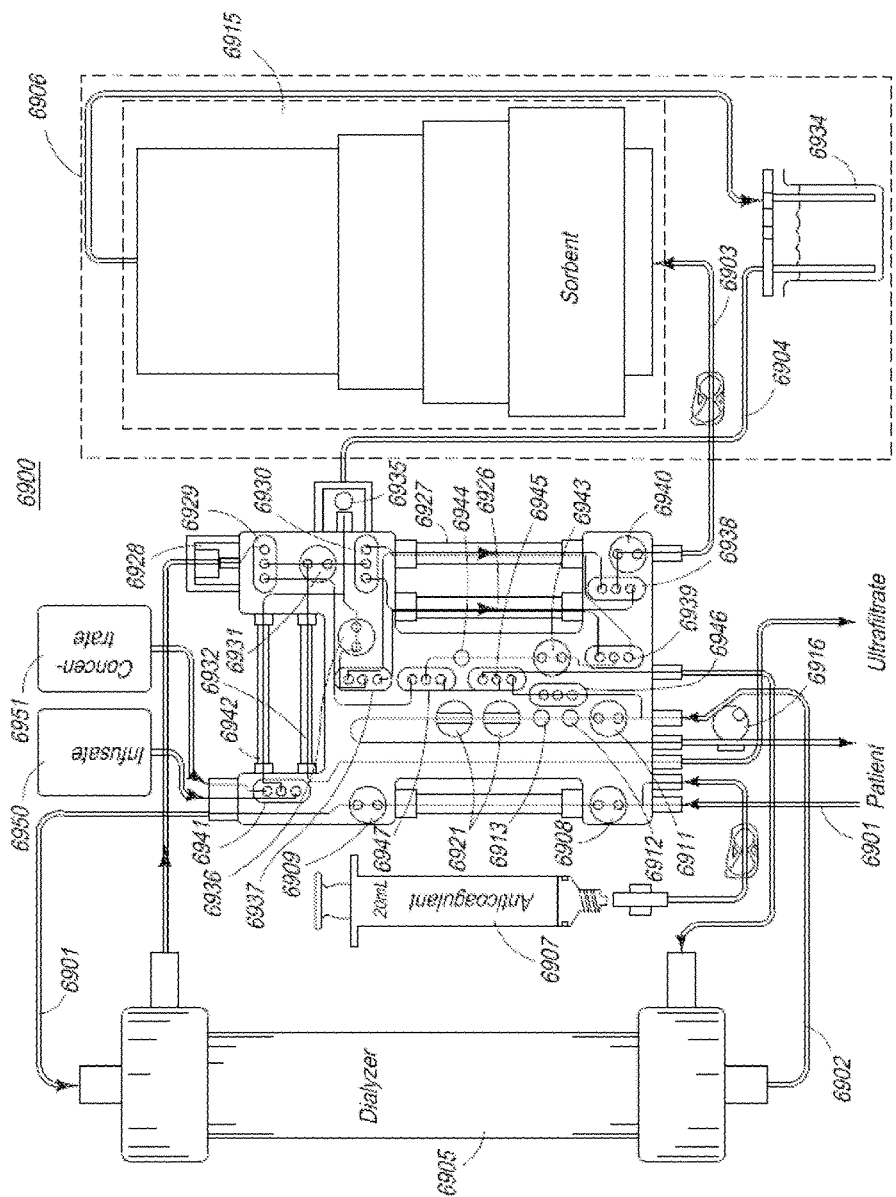
FIG. 69A is a tenth exemplary fluid circuit diagram.
Figure 69B:
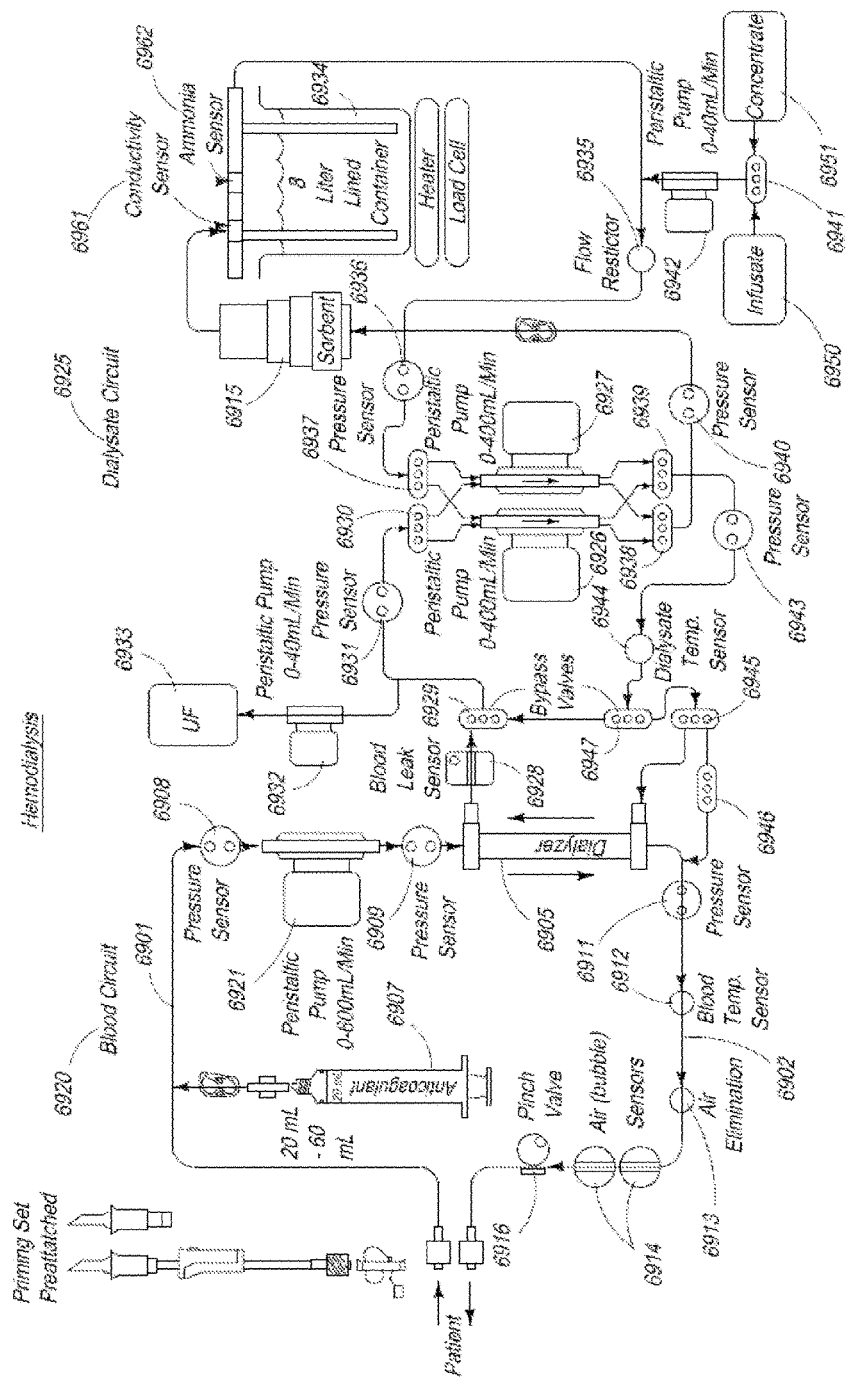
FIG. 69B is an eleventh exemplary fluid circuit diagram.

FIG. 69A illustrates in further detail the circuit for a hemodialysis/hemofiltration system according to one embodiment of the present invention. Spent dialysate and fresh dialysate tubes 6903 and 6904 respectively are connected to a dialysate regeneration system 6906, thereby completing the dialysate circuit of the system 6900. The dialysate regeneration system 6906 further comprises disposable sorbent cartridges 6915 and a reservoir 6934 to hold dialysate cleansed by cartridges 6915. Other components of the system shown in FIG. 69A are explained with reference to FIG. 69B, which shows an exploded view of the extracorporeal blood processing system 6900 configured to operate in hemodialysis mode. Corresponding elements in FIGS. 69A, 69B, and 69C have the same numbers.

Blood circuit 6920 comprises a peristaltic blood pump 6921 that draws a patient's arterial impure blood along the tube 6901 and pumps the blood through dialyzer 6905. A syringe device 6907 injects an anticoagulant, such as heparin, into the drawn impure blood stream. Pressure sensor 6908 is placed at the inlet of the blood pump 6921 while pressure sensors 6909 and 6911 are placed upstream and downstream of the dialyzer 6905 to monitor pressure at these vantage points.

As purified blood flows downstream from the dialyzer 6905 and back to the patient, a blood temperature sensor 6912 is provided in the line to keep track of temperature of the purified blood. An air eliminator 6913 is also provided to remove accumulated gas bubbles in the clean blood from the dialyzer. A pair of air (bubble) sensors (or optionally a single sensor) 6914 and a pinch valve 6916 are employed in the circuit to prevent accumulated gas from being returned to the patient.

The dialysate circuit 6925 comprises two dual-channel pulsatile dialysate pumps 6926, 6927. Dialysate pumps 6926, 6927 draw spent dialysate solution from the dialyzer 6905 and the regenerated dialysate solution from reservoir 6934 respectively. At the point where used dialysate fluid from the dialyzer 6905 enters the dialysate circuit 6925, a blood leak sensor 6928 is provided to sense and prevent any leakage of blood into the dialysate circuit. Spent dialysate from the outlet of the dialyzer 6905 then passes through the bypass valve 6929 to reach two-way valve 6930. A pressure sensor 6931 is placed between the valves 6929 and 6930. An ultrafiltrate pump 6932 is provided in the dialysate circuit, which is operated periodically to draw ultrafiltrate waste from the spent dialysate and store it in an ultrafiltrate bag 6933, which is emptied periodically.

As mentioned previously, spent dialysate is regenerated using sorbent cartridges. The dialysate regenerated by means of sorbent cartridge 6915 is collected in a reservoir 6934. The reservoir 6934 includes conductivity and ammonia sensors 6961 and 6962 respectively. From the reservoir 6934, regenerated dialysate passes through flow restrictor 6935 and pressure sensor 6936 to reach a two-way valve 6937. Depending upon patient requirement, desired quantities of infusate solution from the reservoir 6950 and/or concentrate solution from the reservoir 6951 may be added to the dialysis fluid. Infusate and concentrate are sterile solutions containing minerals and/or glucose that help maintain minerals like potassium and calcium in the dialysate fluid at levels prescribed by the physician. A bypass valve 6941 and a peristaltic pump 6942 are provided to select the desired amount of infusate and/or concentrate solution and to ensure proper flow of the solution into the cleansed dialysate emanating from the reservoir 6934.

The dialysate circuit comprises two two-way valves 6930 and 6937. The valve 6930 directs one stream of spent dialysate to a first channel of dialysate pump 6926 and another stream of spent dialysate to a first channel of dialysate pump 6927. Similarly, valve 6937 directs one stream of regenerated dialysate to a second channel of dialysate pump 6926 and another stream of regenerated dialysate to a second channel of dialysate pump 6927.

Streams of spent dialysate from pumps 6926 and 6927 are collected by two-way valve 6938 while streams of regenerated dialysate from pumps 6926 and 6927 are collected by two-way valve 6939. The valve 6938 combines the two streams of spent dialysate into a single stream that is pumped via pressure sensor 6940 and through sorbent cartridges 6915 where the spent dialysate is cleansed and filtered, then collected in the reservoir 6934. The valve 6939 combines the two streams of regenerated dialysate into a single stream, which flows to the two-way valve 6945 through a bypass valve 6947. A pressure sensor 6943 and a dialysate temperature sensor 6944 are provided on the dialysate flow stream to the two-way valve 6945.

By reversing the state of two way valves 6930, 6937, 6938 and 6939 the two pumps 6926 and 6927 are reversed in their action of one withdrawing dialysis fluid from the dialyzer 6905 and the other supplying dialysis fluid to the dialyzer 6905. Such reversal, when done periodically over short periods of time relative to the dialysis session, insures that over the longer period of the entire dialysis session the dialysate fluid volume pumped into the dialyzer equals the amount of fluid pumped out and the only total fluid volume lost by dialysis circuit 6925 is that removed by ultrafiltrate pump 6932, as discussed above.

In hemodialysis mode, two-way valve 6945 allows the regenerated dialysate to enter dialyzer 6905 to enable normal hemodialysis of the patient's blood. One side of valve 6945 is closed leading to the patient's blood return line. Another two-way valve 6946 acts as a backup, keeping dialysate form the patient's blood line with both ports of valve 6946 closed even if valve 6945 leaks or fails.

Figure 69C:
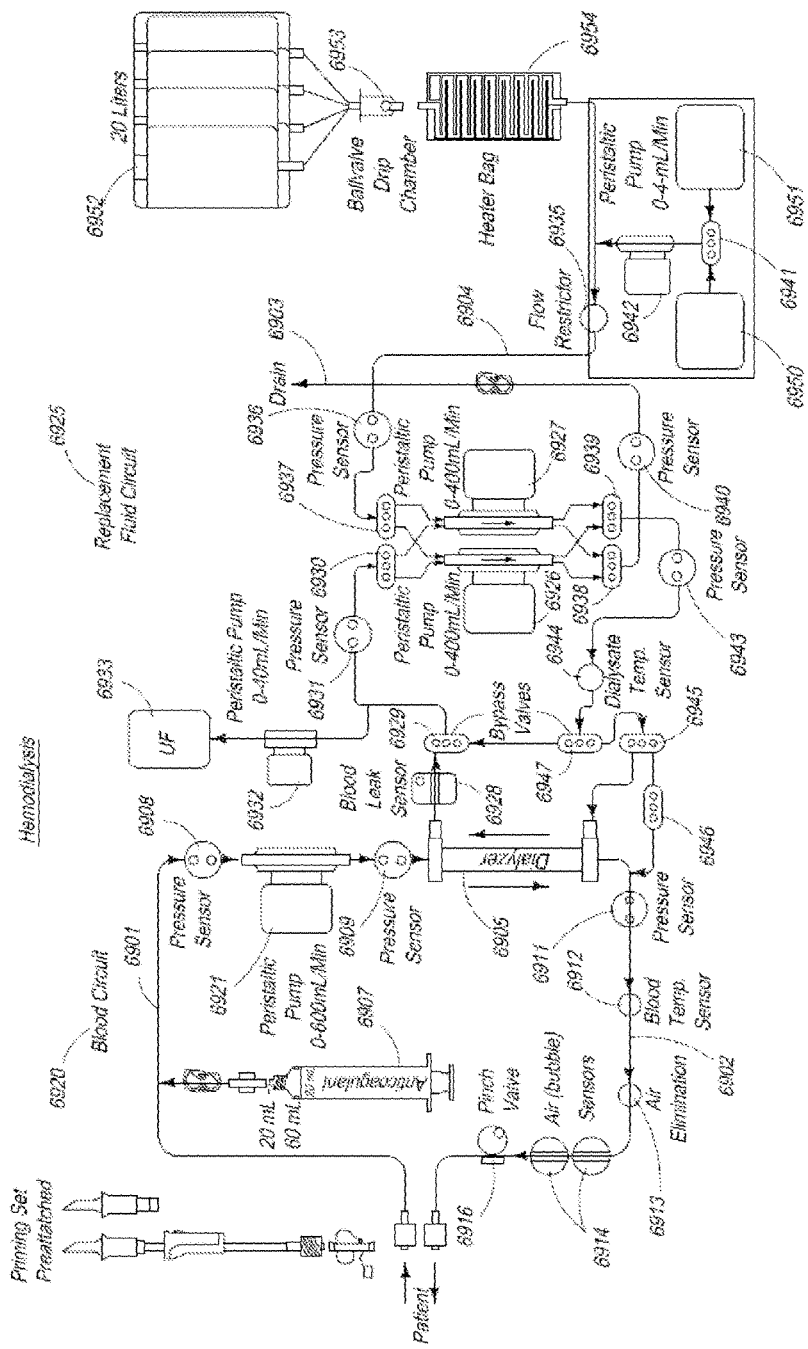
FIG. 69C is a twelfth exemplary fluid circuit diagram.

Referring to FIG. 69C, in hemofiltration mode, the two-way valve 6945 can be actuated to direct a stream of fresh ultrapure dialysate from reservoir 6952 through valve 6946, now with both ports open to directly enter the stream of purified blood emanating from the dialyzer and flowing back to the patient.

It should be noted by persons of ordinary skill in the art that the backup two-way valve 6946 is a redundant safety valve to ensure that in hemodialysis mode failure of one valve 6945 does not result in infusion of regenerated dialysate directly into the patient. That is, both the valves 6945 and 6946 are capable of being actuated by the system to allow fluid to be directed to the patient's venous blood line as a safety consideration. In one embodiment the two-way back-up valve 6946 is a single valve to allow or stop fluid flow.

It should be further noted by persons of ordinary skill in the art that valves as described in the description above are termed as 'bypass' or 'two-way' depending upon their use. Thus, valves are termed 'bypass valves' when they bypass a component, such as the dialyzer. Otherwise they are termed 'two-way valves' and simply direct the flow in at least two directions. However, the bypass and two-way valves may be identical in construction.

In one embodiment, the two-way valves used in the present invention are fabricated as elastomeric membranes that are pressed against an orifice by a mechanism contained inside the dialysis machine to stop flow having fluid contact with the rest of the fluidic circuit, as further discussed below.

Two-way valves 6945 and 6946 can be used for changing the mode of operation for the blood processing system. Referring to FIG. 69C, fluid flow in blood and dialysate circuits 6920 and 6925 is depicted. Since the system is operating in hemofiltration mode, the spent dialysate tube 6903 is connected to a drain while the fresh, dialysate tube 6904 is connected to fresh ultrapure and injectable grade dialysate reservoirs 6952. Fresh dialysate through a ball-valve drip chamber 6953 passes through a heater bag 6954 to flow into the fresh dialysate tube 6904. The rest of the elements and fluidic paths of the blood and dialysate circuits 6920, 6925 are similar to those of FIG. 69B, except that in hemofiltration fresh dialysate or replacement fluid is introduced into the dialysate circuit 6925 as the spent dialysate is drained and not reused. Also, in the infusate subsystem, components 6942, 6950, 6941 and 6951 are unused.

The blood circuit 6920 comprises a peristaltic blood pump 6921 that draws a patient's arterial impure blood along tube 6901 and pumps the blood through dialyzer 6905. An optional pump 6907 injects an anticoagulant, such as heparin, into the drawn impure blood stream. Pressure sensor 6908 is placed at the inlet of the blood pump 6921 while pressure sensors 6909 and 6911 are placed upstream and downstream of the dialyzer 6905. Purified blood from the dialyzer 6905 is pumped through tube 6902 past a blood temperature sensor 6912, air eliminator 6913 and air (bubble) sensors 6914 and back to a vein of the patient. A pinch valve 6916 is also placed to completely stop blood flow if air is sensed by the bubble sensor 6914 in the line upstream of the pinch valve 6916, thereby preventing the air from reaching the patient.

The dialysate circuit 6925 comprises two dual-channel dialysate pumps 6926, 6927. Dialysate pumps 6926, 6927 draw spent dialysate solution from the dialyzer 6905 and the fresh dialysate solution from reservoirs 6952 respectively. Spent dialysate from the outlet of the dialyzer 6905 is drawn through blood leak sensor 6928 and bypass valve 6929 to reach two-way valve 6930. Pressure sensor 6931 is placed between the valves 6929 and 6930. An ultrafiltrate pump 6932 is operated periodically to draw ultrafiltrate waste from the spent dialysate and store it in an ultrafiltrate bag 6933 (that is emptied periodically). Fresh dialysate from the reservoirs 6952 passes through flow restrictor 6935 and pressure sensor 6936 to reach two-way valve 6937. Persons of ordinary skill in the art would realize that in this protocol infusate and concentrate is not needed and elements 6941, 6942, 6950, 6951 associated with those functions may not be used.

The heater bag 6954 raises the temperature of the fresh dialysate sufficiently so that the temperature of the ultrafiltered blood going back to the patient from the dialyzer 6905 or the overall temperature of the mixture of ultrafiltered blood from dialyzer 6905 and the fresh dialysate infused directly into the purified blood by actuating the valves 6945, 6946 is equivalent to the body temperature of the patient, thereby preventing any thermal shock.

Figure 70:
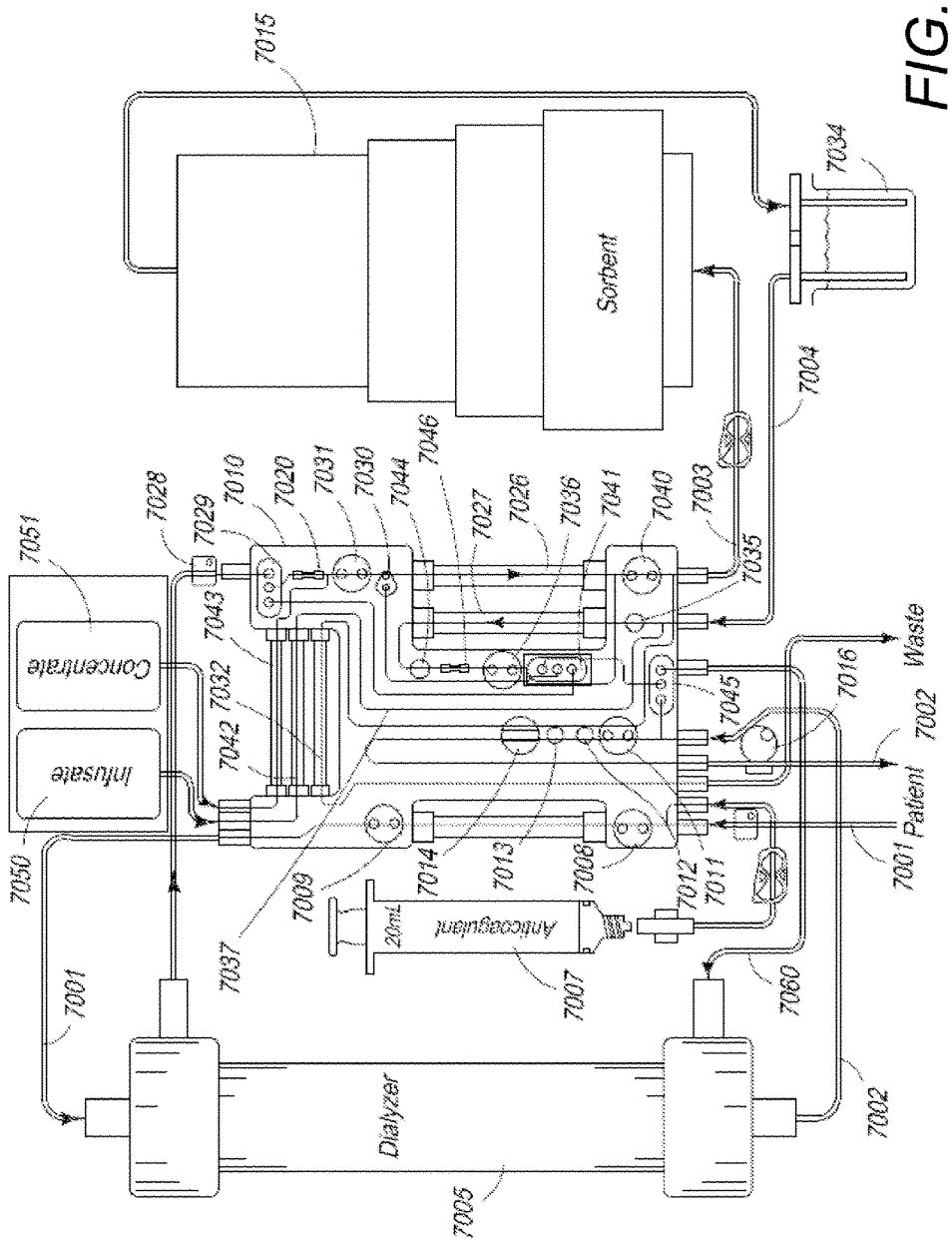
FIG. 70 is a thirteenth exemplary fluid circuit diagram.

FIG. 70 shows an alternative embodiment of the fluidic circuits where the backup two-way valve 6946 is not used. The blood circuit comprises a peristaltic blood pump that draws a patient's arterial impure blood along tube 7001 and pumps the blood through dialyzer 7005. A syringe or pump 7007 injects an anticoagulant, such as heparin, into the drawn impure blood stream. Pressure sensor 7008 is placed at the inlet of the blood pump while pressure sensors 7009 and 7011 are placed upstream and downstream of a manifold segment. Purified blood from the dialyzer 7005 is pumped through tube 7002 past a blood temperature sensor 7012, air eliminator 7013 and air (bubble) sensor 7014 and back to a vein of the patient. A pinch valve 7016 is also placed before circuit connection to the patient to completely stop blood flow if air is sensed by the air (bubble) sensor 7014 in the line upstream of the pinch valve 7016, thereby preventing the air from reaching the patient.

The dialysate circuit 7010 comprises two dialysate pump segments 7026, 7027 in pressure communication with pumps. Dialysate pump segments 7026, 7027 draw spent dialysate solution from the dialyzer 7005 and the regenerated dialysate solution from reservoir 7034 respectively. Spent dialysate from the outlet of the dialyzer 7005 is drawn through blood leak sensor 7028 to reach bypass valve 7029. Flow sensor 7020 is one of two flow sensors (the other being flow sensor 7046) which determine the volume of dialysate flowing through the circuit. Valve 7030 is similar in construction to a two-way valve and is used to bypass dialysate pump 7026. Valve 7030 is normally closed in the direction of the bypass. In the event the dialysate pump 7026 is stopped, valve 7030 is opened to direct flow around pump 7026. Pressure sensor 7031 is placed between the flow sensor 7020 and the valve 7030. During normal flow, the spent dialysate is pumped through pressure sensor 7040, tube 7003, and sorbent cartridges 7015 where the spent dialysate is cleansed and filtered. The cleansed/filtered dialysate then enters reservoir 7034. An ultrafiltrate pump 7032 is operated periodically to draw ultrafiltrate waste from the spent dialysate and store in an ultrafiltrate bag (not shown) that is emptied periodically.

Regenerated dialysate from the reservoir 7034 passes through tube 7004, flow restrictor 7035, dialysate temperature sensor 7044, flow sensor 7046 and pressure sensor 7036 to reach two-way valve 7045 through bypass valve 7041. When the respective flow paths of bypass valves 7029, 7045 and 7041 are activated they direct regenerated dialysate to bypass the dialyzer 7005. Infusate and concentrate streams from infusate and concentrate reservoirs 7050, 7051 are directed by infusate and concentrate pump segments 7042, 7043 into the cleansed dialysate emanating from the reservoir 7034 via tube 7037 and the spent dialysate downstream of flow sensor 7020, respectively.

The two-way valve 7045 determines what mode the system is operating in. Thus, in one mode of operation the two-way valve 7045 allows the regenerated dialysate to enter dialyzer via tube 7060 to enable normal hemodialysis of the patient's blood. In another mode of operation, the two-way valve 7045 is actuated to direct fluid flow of ultra pure infusate grade dialysis fluid into the venous blood line and directly to patient. Accordingly, the versatile valves enable the mode of operation to switch between hemofiltration and hemodialysis. For example, in hemofiltration shown in FIG. 69C, infusible grade fluid is routed through the three valves directly into the blood stream where valve 6946 connects to the post dialyzer. In this mode valve 6945 prevents the dialysate fluid from entering the lower port of the dialyzer. In hemodialysis, shown in FIG. 69B, valve 6946 is closed and valves 6947 and 6945 route dialysate fluid to the dialyzer. It should be noted that the embodiment of FIG. 69B uses pump swapping and a plurality of valves to control fluid volume while the embodiment of FIG. 70 uses flow sensors 7020 and 7046 to control fluid volume.

As discussed above, valves are preferably implemented in a manifold using elastic membranes at flow control points which are selectively occluded, as required, by protrusions, pins, or other members extending from the manifold machine. In one embodiment, fluid occlusion is enabled using a safe, low-energy magnetic valve.

The valve system comprises a magnetic displacement system that is lightweight and consumes minimum power, making it ideal even when the portable kidney dialysis system uses a disposable manifold for fluidic circuits. The system can be used in conjunction with an orifice in any structure. In particular, an orifice is any hole, opening, void, or partition in any type of material. This includes pathways in tubing, manifolds, disposable manifolds, channels, and other pathways. One of ordinary skill in the art would appreciate that the presently disclosed valve system would be implemented with a disposable manifold by positioning the displacement member and magnets, as further discussed below, external to the manifold at the desired valve location. The actuator is also separate and distinct from the disposable manifold and generally part of the non-disposable portion of the kidney dialysis system.

Functionally, the valve of the present invention has two stable states: open and closed. It operates by using magnetic forces to move a displacement member against a diaphragm and thereby create sufficient force to press the diaphragm against a valve seat and cause the diaphragm to close the orifice. Closing of the orifice shuts off fluid flow. The reverse process, namely the use of magnetic forces to move a displacement member away from the diaphragm and thereby release the diaphragm from compression against the valve seat, opens the orifice and permits fluid to flow.

Figure 71A:
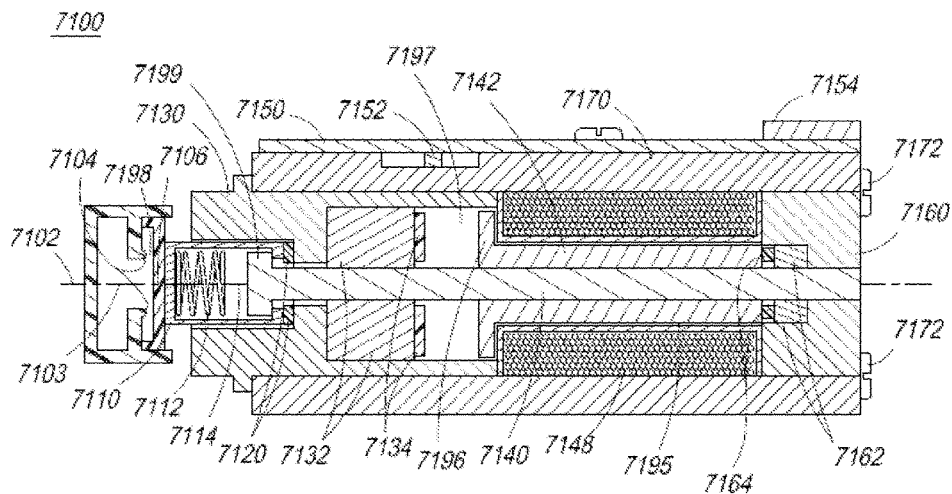
FIG. 71A is a first schematic view of an exemplary magnetic valve system.
Figure 71B:
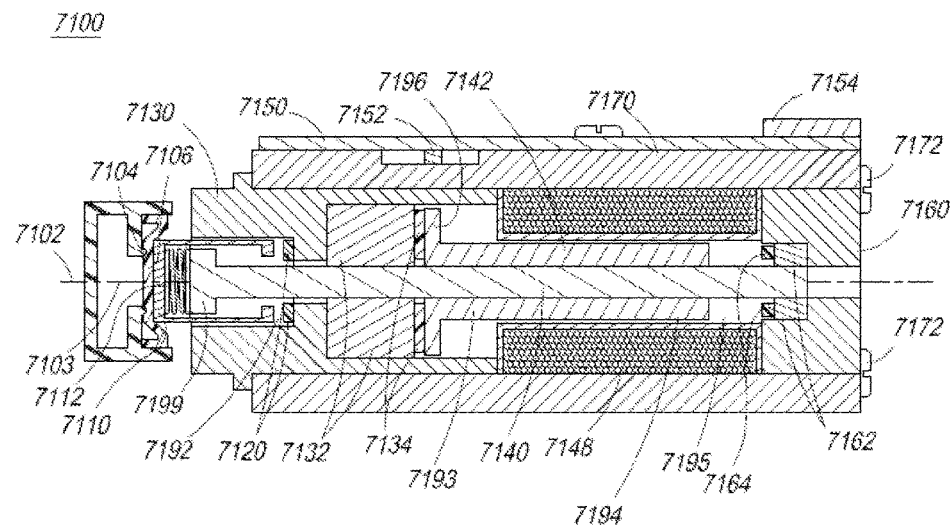
FIG. 71B is a second schematic view of an exemplary magnetic valve system.
Figure 73:
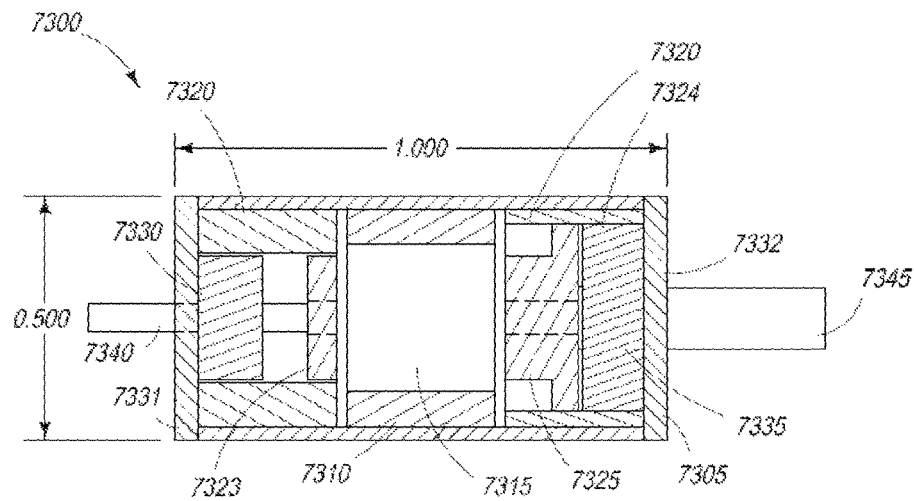
FIG. 73 is a schematic view of another exemplary magnetic valve system.

It should be appreciated that while the present invention shall be discussed in terms of a preferred embodiment, depicted in FIGS. 71A and 71B, and a non-preferred embodiment, depicted in FIG. 73, the present invention is generally directed to any use of a valve in a kidney dialysis system having the following attributes: a) two stable states, open and closed, b) changing states requires energy input, c) maintaining a state does not require energy input, d) a state is changed by the use of magnetic forces to modify the position of a displacement member which, when modified, causes a valve to either open or close.

In one embodiment, referring to FIGS. 71A and 71B, the valve system of the present invention 7100 is used to control fluid flow through a fluidic flow channel 7102, which is bounded by valve seats 7104 to thereby create a valve annular orifice 7103. Orifice 7103 is any hole, opening, void, or partition in any type of material, in particular, manifolds, disposable manifolds, channels, and other pathways 7110. The valve 7100 is shown in an open state. The components of the valve system include an orifice closing member, a displacement member, a mechanism for moving the displacement member, an optional optical sensor, a coil driver circuit, and an actuator having a coil.

In one embodiment, the orifice closing member comprises a diaphragm 7106 which, when compressed by the displacement member, as discussed below, presses against the valve seats 7104, thereby causing the valve annular orifice 7103 to close. In an open state, the main body of the diaphragm 7106 is separated from the valve seats 7104 by a gap 7198. In one embodiment, the diaphragm 7106 is made from a soft material such as silicone rubber. The diaphragm 7106 must maintain its shape over time, temperature, and actuations. The valve 7100 relies upon the diaphragm material 7106 to return to its uncompressed shape when the displacement member (compressing force) is removed in the open state.

One of ordinary skill in the art should appreciate that the orifice closing member can comprise any combination of spring, compressible, or non-compressible structures which, when pushed by the displacement member, closes the orifice. In one embodiment, the valve seats 7104 can be molded into a manifold. Suitable materials for the valve seat are polycarbonate, ABS and similar plastics. The valve orifice 7103 in the preferred embodiment ranges from 0.1 to 0.3 inches in diameter (and more particularly 0.190 inches). Orifice dimensions can be increased to increase flow for alternate applications of the invention or, alternatively, decreased to decrease flow for alternate applications.

In one embodiment, the displacement member comprises a plunger cap, or housing, 7110, which, when the valve is in an open state, is aligned against the diaphragm 7106, but not substantially compressing the diaphragm 7106. Positioned inside the plunger cap 7110 is a compliant component, such as a spring 7112 and the head of plunger 7199, which are separated by an air gap 7114. The plunger cap 7110 is encompassed on the outside by a fluid seal 7120, which, in one embodiment, is a thin, soft silicone rubber washer. In one embodiment, the plunger cap 7110 is forced against the silicone rubber washer and compresses the washer to form the fluid seal 7120. When in a closed position, the plunger cap 7110 is not forced against the washer, which is therefore not compressed and positioned loose to the end cap 7130. The spring 7112 is any elastic or compliant material and, in one embodiment, comprises a wave spring.

The plunger cap 7110, internal spring 7112, air gap 7198, plunger head 7199, plunger body 7140, and core 7142 are the components of the preferred displacement member of the present invention. In one embodiment, the plunger body 7140 has an outer diameter in the range of 0.1 to 0.2 inches (more particularly 0.122 inches) and is approximately 0.5 to 2.5 inches long. It should be appreciated that the plunger body 7140 is any rod structure of any length, depending on the application. The plunger body 7140 is positioned within an annular core 7142, which has one larger end and one smaller end, and is attached to the core via any method known to ordinary skill in the art, including epoxy, screw attachment, pinned, or welded. The outer diameter of the larger end of the core 7142 is in the range of 0.3 inches to 0.5 inches (and more particularly 0.395 inches), the thickness is in the range of 0.03 to 0.15 inches (and more particularly 0.05 to 0.10 inches), and the length is in the range of 0.50 to 1.75 inches long (and more particularly 1.05 inches). The small end of the core 7142 has a diameter of 0.1 to 0.4 inches, and more particularly 0.25 inches.

At least partially encompassing the small end of the core is a coil bobbin 7195 which keeps the coil 7148 in place and provides dimensional stability to the coil 7148. A gap preferably exists between the coil bobbin 7195 and core 7142. The size of the gap is approximately 0.01 to 0.03 inches (and more particularly 0.02 inches). The coil bobbin 7195 is, in one embodiment, a glass filled nylon structure, which should be nonmetallic and non-ferromagnetic. The coil bobbin 7195 is an annular structure with an outer diameter of a size sufficient to provide a tight fit into the housing bore and an inner diameter sufficient to enclose the core such that it has room to move and undergo some degree of thermal expansion. The two end caps 7130, 7160 wedge the bobbin 7195 into place and keep it from moving or slipping, particularly when exposed to electromagnetic forces.

The plunger body is made of metal or non-metal material, such as brass or fiberglass, and the core is also made of metal, particularly steel. Preferably, the plunger body is non-magnetic and the core body is ferrous-magnetic. As discussed further below, the plunger body 7140 and core 7142 are moved by the mechanism for moving the displacement member.

The mechanism for moving the displacement member comprises a large magnet component, a small magnet component and a housing within which the magnets and a portion of the displacement member, namely the plunger body 7140 and core 7142, are contained. More particularly, referring to FIGS. 71A and 71B, the mechanism to moving the displacement member comprises a large magnet end cap 7130, to hold and align the large magnet, a large magnet 7132, an elastic material 7134, a gap 7197, a coil 7148, a small magnet component 7162, a small magnet mount and end cap 7160, and an elastic material 7164.

The large magnet end cap 7130 holds and aligns the large magnet component 7132 and coil bobbin 7195 in place within a housing 7170, referred to as the actuator body which has a borehole through which the components described herein are placed. The large magnet component 7132 needs to be properly aligned with the core 7142, plunger body 7140, and small magnetic component 7162 to ensure the proper movement of the displacement member. Both end caps 7130 and 7160 secure the coil bobbin 7195 and coil 7148 in position.

Additionally, a mounting plate can be used to capture and hold end cap 7130. In one embodiment, the mounting plate is positioned vertically and flush against the side of the end cap and between the end cap and bore. The mounting plate has a hole in it, roughly the same size as the smaller diameter of the end cap. A clamping mechanism holds the body against the plate; alternatively the plate can be permanently fixed, using any bonding technique known to persons of ordinary skill in the art. Unlike the prior art, such as U.S. Pat. No. 6,836,201, in a preferred embodiment, the magnets are located inside, not outside, the bore and provide bearings for the plunger, as discussed below.

The large magnet component 7132 is separated from the core 7142 by a gap 7197 and elastic material 7134, such as a silicone washer, which, in one embodiment, has an outer diameter of 0.3 to 0.5 inches (and more particularly 0.37 inches), an inner diameter of 0.1 to 0.3 inches (and more particularly 0.188 inches), a thickness of 0.005 to 0.015 inches (and more particularly 0.01 inches), and a durometer of 35 to 45 (and more particularly 40). The small magnet component 7162 is separated from the core by an elastic material 7164, such as a silicone washer, which, in one embodiment, has an outer diameter of 0.1 to 0.4 inches (and more particularly 0.24 inches), an inner diameter of 0.1 to 0.3 inches (and more particularly 0.188 inches), a thickness of 0.005 to 0.015 inches (and more particularly 0.01 inches), and a durometer of 35 to 45 (and more particularly 40). The small magnetic component 7162 is held and kept properly aligned within the housing 7170 by a small magnet mount and end cap 7160. The small magnet end cap screws 7172 also serve to capture and hold in place the small magnet end caps 7160.

Referring to FIG. 71A, the valve system of the present invention further comprises a coil driver circuit board 7150, which drives the actuator, comprising coil 7148, and is preferably mounted to the actuator body 7170 via small screws, a coil driver connector 7154, and an optical sensor 7152, which senses the position of the large end of the core 7196. Coil 7148 serves to effectuate changes in magnetic fields in order to cause movement of the core 7142 and plunger body 7140. In one embodiment, the coil is approximately 0.05 to 1.5 inches long (and more particularly 1 inch long), has an outer diameter of 0.35 to 0.55 inches (and more particularly 0.46 inches), and an inner diameter of 0.15 to 0.35 inches (and more particularly 0.26 inches), with six layers of wire 29 AWG wire.

The various elastic materials used in the displacement member and mechanism for moving the displacement member provide a "soft" stop to the movement of the rod 7140 when the valve opens or closes. In particular, it serves to ensure the movement of the core does not damage the magnets.

The large magnet component 7132 can be one unitary magnet or, in a preferred embodiment, comprised of a plurality of magnets, such as three. The small magnet component 7162 can also be unitary or comprised of a plurality of magnets. In one embodiment, the magnets are made of preferably Alnico, Samarium Cobalt, Neodymium, Rare Earth, or Ceramic magnets. In one embodiment, the large magnet 7132 is a Neodymium ring magnet with an outer diameter of 0.2 to 0.5 inches (and more particularly 0.375 inches), an inner diameter of 0.05 to 0.3 inches (and more particularly 0.125 inches), and a length of 0.2 to 0.5 inches (and more particularly 0.375 inches). In one embodiment, the small magnet 7162 is made of a Neodymium ring magnet, with an outer diameter of 0.15 to 0.4 inches (and more particularly 0.25 inches), an inner diameter of 0.05 to 0.3 inches (and more particularly 0.125 inches), and a length of 0.15 to 0.4 inches (and more particularly 0.25 inches). The larger magnet 7132 is used closer to the orifice closing member because the size is necessary to generate sufficient opposition force to the valve seat. Further, the actuation force caused by the actuation coil is substantially equal even though the magnets are of a different size, thereby enabling a simple coil driver circuit.

In one embodiment, the rod, plunger or other elongated member 7140 uses the magnets' center holes as a linear bearing. Accordingly, the magnets' center holes should preferably have a bearing surface, such as chrome or any smooth hard surface with minimal friction. A gap is placed between the coil bobbin 7195 and the core 7142 because of thermal expansion of the bobbin, bobbin creepage over time, and bobbin, core, and magnet tolerances. However, under all operating conditions, the gap should be sufficient such that the plunger body 7140 can move freely and not bind in the openings of the magnets and coil. In a preferred embodiment, the gap is approximately 0.01 to 0.06 inches (and more particularly 0.02 inches) at room temperature.

When the valve is closed, referring to FIG. 71B, the valve system of the present invention 7100 controls fluid flow through a fluidic flow channel 7102, which is bounded by valve seats 7104, by compressing the orifice closing member, e.g. diaphragm 7106, and thereby obstructing valve annular orifice 7103. In a closed state, the main body of the diaphragm 7106 is pressed against the valve seats 7104 and, accordingly, substantially eliminates gap 7198 (seen in FIG. 71A).

Once just adjacent to the diaphragm 7106, the displacement member now compresses the diaphragm 7106. In particular, plunger cap 7110 has moved to compress the diaphragm 7106. The plunger cap 7110 has moved because a change in magnetic fields causes the core body 7142 to move toward the large magnet component 7132. The core body 7142 stops moving when the core head 7196 passes through the gap 7197 (in FIG. 71A) and stops at the elastic material 7134 positioned adjacent to the large magnet component 7132. Movement of the core 7142 causes the plunger body 7140, to which the core 7142 is bonded, to move as well. Movement of the plunger body 7140 causes the plunger head 7199 to move within the plunger cap 7110, pass through the gap 7114 (in FIG. 71A), and compress the spring 7112. After a certain amount of compression, the plunger cap 7110 moves and compresses the diaphragm 7106. Movement of the plunger cap 7110 creates a new gap 7192 between the cap body 7110 and the elastic material 7120 that is positioned adjacent to the large magnet end cap 7130.

As shown in FIG. 71B, the other components of the valve remain the same, including the actuator body 7170, coil driver circuit 7150, coil connector 7154, coil 7148, coil bobbin 7193, small end cap screws 7172, optical sensor 7152, and small magnet end cap 7160. It should be appreciated however, that, by virtue of the core 7142 movement, a gap 7195 is created between the smaller end of the core 7194 and the elastic material 7164, which is positioned adjacent to the small magnetic component 7162.

It should be appreciated that, to close the valve, the displacement member applies a force to the orifice closing member, e.g. diaphragm 7106. The force required, from the displacement member, to deform the diaphragm to the point where the diaphragm touches the valve seat is substantially linear and can be modeled as a linear spring. However, the force requirements increase exponentially as the diaphragm is compressed into the valve seat. Thus, the force profile for the displacement member becomes nonlinear and far more complex. Accordingly, there are several unique challenges associated with the design of the valve and the tolerances between the various components of the displacement member, the orifice closing member, and the hard stop of the displacement mechanism. The displacement mechanism must be able to deliver the nonlinear force profile without permanently deforming the diaphragm. This means that the mechanism must deliver just the right amount of force.

As discussed above, the displacement member comprises a rod, plunger or other elongated member that is bonded to another structure, referred to as a core, which has a larger diameter and can function as a stopper when forced up against another structure, such as a magnet face. One of ordinary skill in the art should appreciate that the displacement member or moveable member is not limited to a rod and cylinder configuration. On the contrary, it can include non-cylindrical structures, unitary pieces, or multiple pieces that are welded or, in any other manner, bonded together. In sum, the displacement member can comprise many different structures, provided the movement of the member can exert the requisite force on the orifice compressing member in a manner that is reliable and consistent.

For example, referring to FIG. 73, an alternate, less preferred embodiment is shown. For kidney dialysis applications, this embodiment does not typically reliably maintain the valve in a closed state. The displacement member 7300 comprises a housing 7305 that includes an electromagnet 7310 with a substantially cylindrical structure and a borehole 7315 running through it. The electromagnet 7310 is securely positioned centrally within the housing 7305 by non-magnetic spacers 7320 which, in one embodiment are the end caps. The end caps have two purposes—hold the magnets in place and sandwich the coil in place. In one embodiment, elements 7331 and 7320 comprise a first unitary piece and 7305 and 7320 comprise a second unitary piece. A cylindrically shaped ferromagnetic core 7325, having a first face 7323 and a second face 7324, is positioned to allow a portion of the core 7325, between the first face 7323 and the second face 7324, to have a linearly slide-able fit with the bore 7315. The second face 7324 is sufficiently larger than the bore 7315 thereby restricting the linear motion of the core 7325. In one embodiment, the second face is differently sized relative to the first face to generate sufficient magnetic force to keep the valve in a closed position. The core 7325 is capable of left and right linear sliding motion within the bore 7315.

Two differently sized magnets 7330, 7335 are also affixed within and at the two end caps 7331, 7332 of the housing 7305. The first face 7323 of the core 7325 contacts with the first magnet 7330 to form a first stable state of the displacement system 7300 and the second face 7324 of the core 7325 contacts with the larger magnet 7335 to form a second stable state of the displacement system 7300. The placement of the permanent magnets 7330, 7335 is designed to be within the diameter of housing 7305, as it reduces the size of the displacement system 7300. A first rod 7340 connected to the first face 7323 of the core 7325 passes through the first magnet 7330 thereby protruding from the housing 7305 at one end and a second rod 7345 connected to the second face 7324 of the core 7325 passes through the second magnet 7335 thereby protruding from the housing 7305 at the other end. The rods 7340, 7345 can be made of non-corrosive, non magnetic material known in the art, such as but not limited to, brass. While one embodiment has two rods connected to two faces of the core, in an alternate embodiment there is only one rod connected to one of the faces of the shuttle.

Persons of ordinary skill in the art would appreciate that the magnetic force exerted by the electromagnet 7310 on the core 7325 is sufficiently high to overcome the retention force of the permanent magnets 7330, 7335 so that the displacement system 7300 can be changed from the first stable state to the second. Moreover, one of ordinary skill in the art would appreciate that the rod/plunger 7345 moves with the core 7325, thereby creating the motive force to compress or decompress the orifice closing member. However, this embodiment has been determined to be inferior to the first embodiment because it fails to sufficiently hold the closed state.

Several design features of the orifice closing member operating in conjunction with the displacement member and mechanism should be appreciated. First, referring to FIG. 74, and as discussed above in relation to FIGS. 71A and 71B, a gap 7408 exists between the plunger cap 7404 and the orifice closing member 7405, in particular the first diaphragm face 7405. The gap 7408 is in the range of 0.040 to 0.070 inches and more particularly approximately 0.055 inches. The diaphragm comprises silicone, preferably of a thickness of 0.040 inches, and can be modeled as a spring ($K_{V2}$) having a spring constant of 270 lbf/in. The second diaphragm face 7406 is separated from the valve seat 7407 and acted upon by magnetic forces modeled as a spring, $K_{V1}$ having a spring constant of approximately 22.5 lbf/in and a thickness of approximately 0.047 inches.

The rod 7404 translates the force generated by the magnetic attraction of the core 7401 to the magnet 7403 modeled by spring $K_P$, which is separated from the core head 7401 by a washer, e.g. 0.010 inches of silicone in a closed state and is separated from core head 7401 by approximately 0.110 inches in an open state. This silicone washer provides forces which are modeled as a spring, $K_{SL}$. The core 7401 is bonded to the rod 7404. When the valve is actuated, the rod 7404 moves in the direction of the valve seat 7407 because the core, to which the rod is bonded, moves in the direction of the large magnet 7403.

Figure 74:
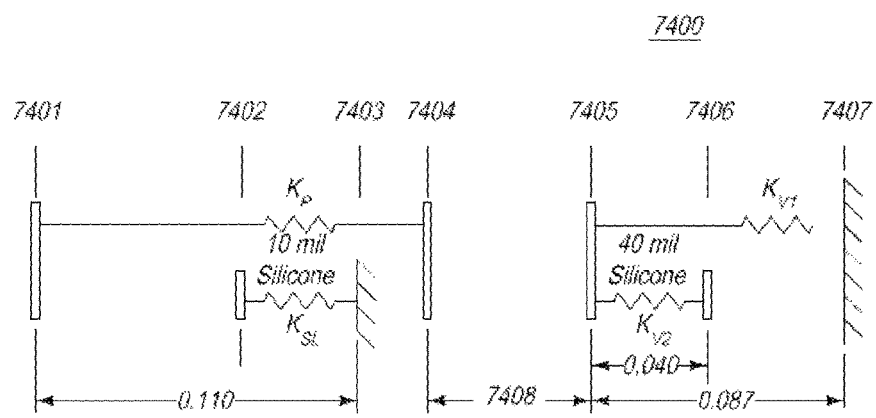
FIG. 74 is a diagram depicting the operation of an exemplary magnetic valve system.

Referring to FIG. 74, $K_{v2}$ and $K_{SL}$ correspond to elastic material, such as silicone, which are modeled as rigid springs. It should be appreciated that, when a valve is in a closed state, there are two positions of importance. First is the position of the rod against the diaphragm and second is the position of the core face against the large magnet. When the valve is closed, the rod is pressing on the valve diaphragm with enough force to resist at least 600 mm Hg back pressure generated within the fluid passage of the kidney dialysis system. In this embodiment, fluid pressures can reach 2600 mm Hg and this system 7400 is designed to maintain the diaphragm firmly pressed against the valve seat to seal the orifice up to and including 2600 mm Hg.

Additionally, when the valve is closed, the core's large face is pulled close to, or directly against, the large magnet. The magnetic attraction of the core to the large magnet generates the force that the rod applies to the orifice closing member, e.g. diaphragm. To generate a consistent and reliable force, the spacing between the core face and the face of the large magnet must be consistent. Therefore, it is preferred to place an elastic material 7402 between the core face 7401 and the magnet face 7404. The elastic material has a nonlinear spring constant and will compress until the resultant forces for the elastic material equals the magnetic forces. When the rod applies force to the diaphragm via the core, the core will experience the resultant force. For a static condition to occur, the sum of these forces on the core must equal zero. Furthermore, the elastic material serves to protect the magnet face from chipping or breakage during actuation.

Figure 76:
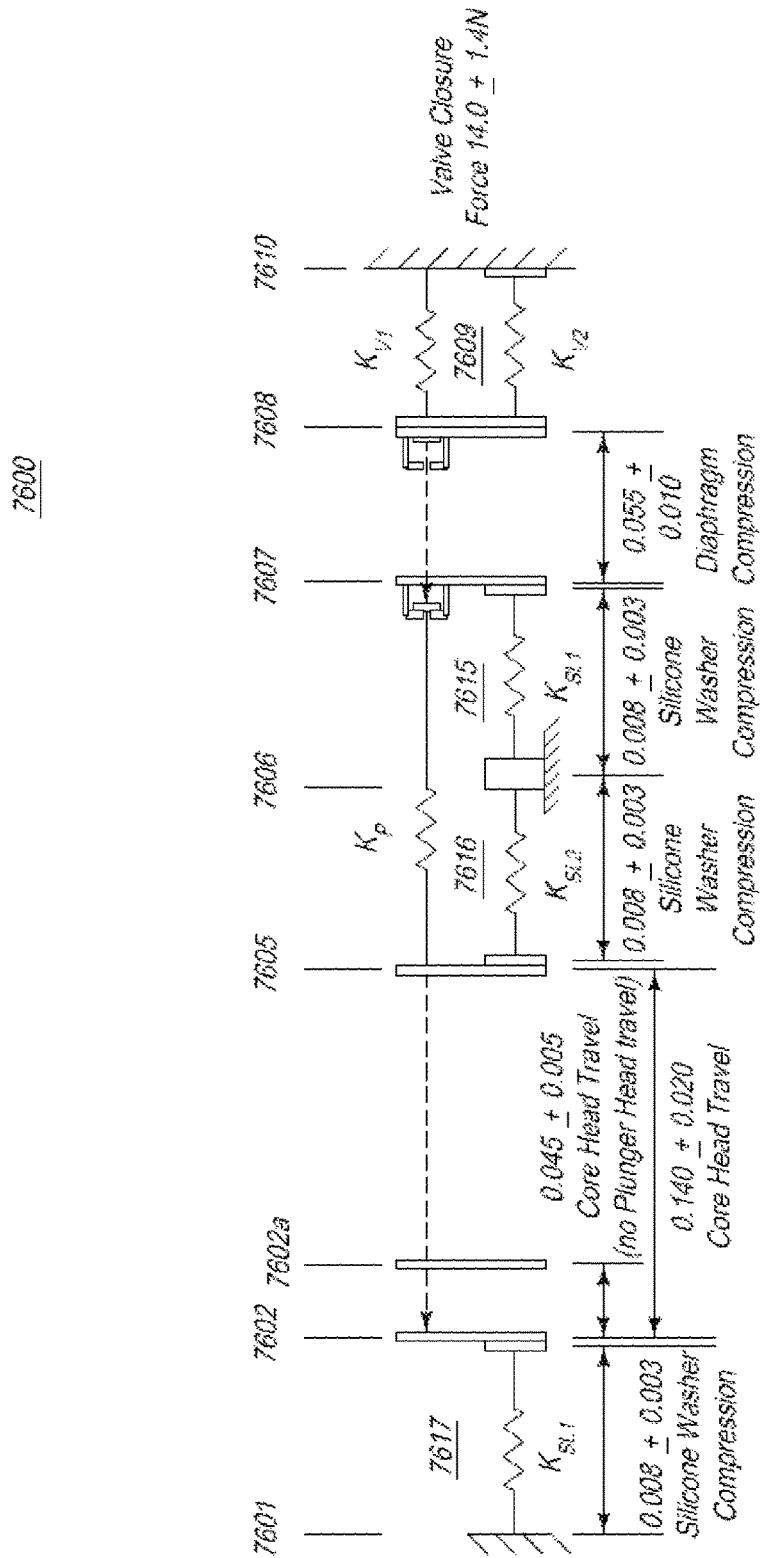
FIG. 76 is a diagram depicting the operation of an exemplary magnetic valve system.

Referring to FIG. 76, when the valve 7600 is in a closed state, the core head 7605, 7602 has moved away from the small magnet face 7601 (from position 7602 a to position 7602 ). When in position 7602, the core head is separated from the small magnet 7601 by an elastic material 7617, such as a silicone washer having a thickness of approximately 0.015 inches. When in position 7605, the core head will have moved approximately 0.140+/−0.20 inches, including a distance of 0.45+/−0.005 inches during which the rod 7608 does not move, and is stopped against an elastic material 7616 (e.g. a silicone washer having a thickness of approximately 0.015 inches), which separates the core head 7605 from the large magnet face 7606. The large magnet 7606 is, in turn, separated from the rod head 7607.

When the valve is in an open state, the large magnet 7606 is separated from the rod head 7607 by an elastic material 7615, such as a silicone washer having a thickness of approximately 0.015 inches. When the valve is in a closed state, the large magnet 7606 is separated from the rod head 7607 by an elastic material 7615, such as a silicone washer having a thickness of approximately 0.015 inches and a distance of approximately 0.055+/−0.10 inches. When the valve is closed, the rod head 7607 has moved from being proximate to the large magnet 7606 and elastic material 7615 to being proximate to the valve seat 7610. Specifically, the rod head 7607 moves to compress the diaphragm 7608 and thereby press against an elastic material 7609 (e.g. silicone having a thickness of approximately 0.040 inches) which, in turn, presses against the valve seat 7610. This causes the valve to close with an approximate force of 14 N.

Figure 75:
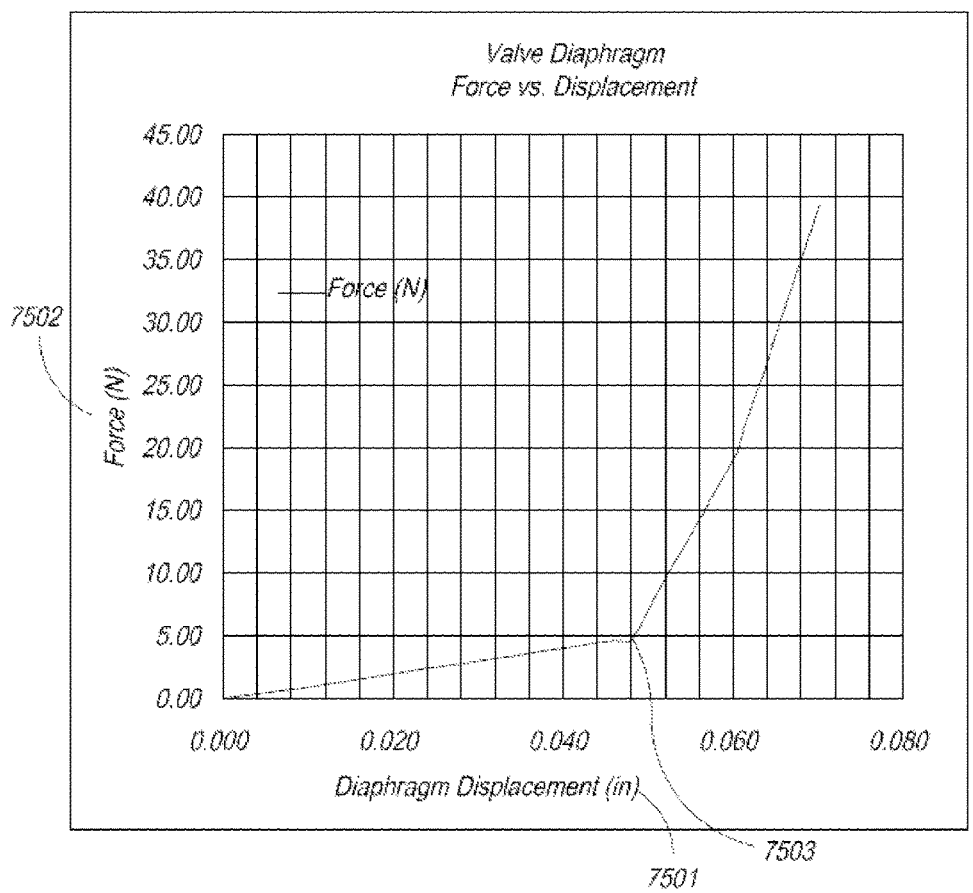
FIG. 75 is a chart relating diaphragm displacement to force for an exemplary magnetic valve system.

It should be appreciated that the configuration of the displacement member and mechanism relative to the orifice closing member and the tolerances described herein provide for a diaphragm displacement profile 7500, as shown in FIG. 75, which is suitable for applications that need to resist at least 600 mm Hg back pressure, such as kidney dialysis systems. Referring to FIG. 75, an exemplary diaphragm displacement profile 7501 is provided, where the force 7502 exerted by the displacement member is provided on the y-axis and the corresponding diaphragm displacement is provided on the x-axis. The inflection point on this curve 7503 indicates when the diaphragm starts being compressed against the valve seat. To the left of the inflection 7503, the diaphragm is being forced to flex toward the valve seat, but there is no substantial compression against the valve seat. To the right of the inflection point 7503, the diaphragm is flexed against the valve seat, deforming the diaphragm material and affecting a good seal against the fluid pressure.

Figure 72:
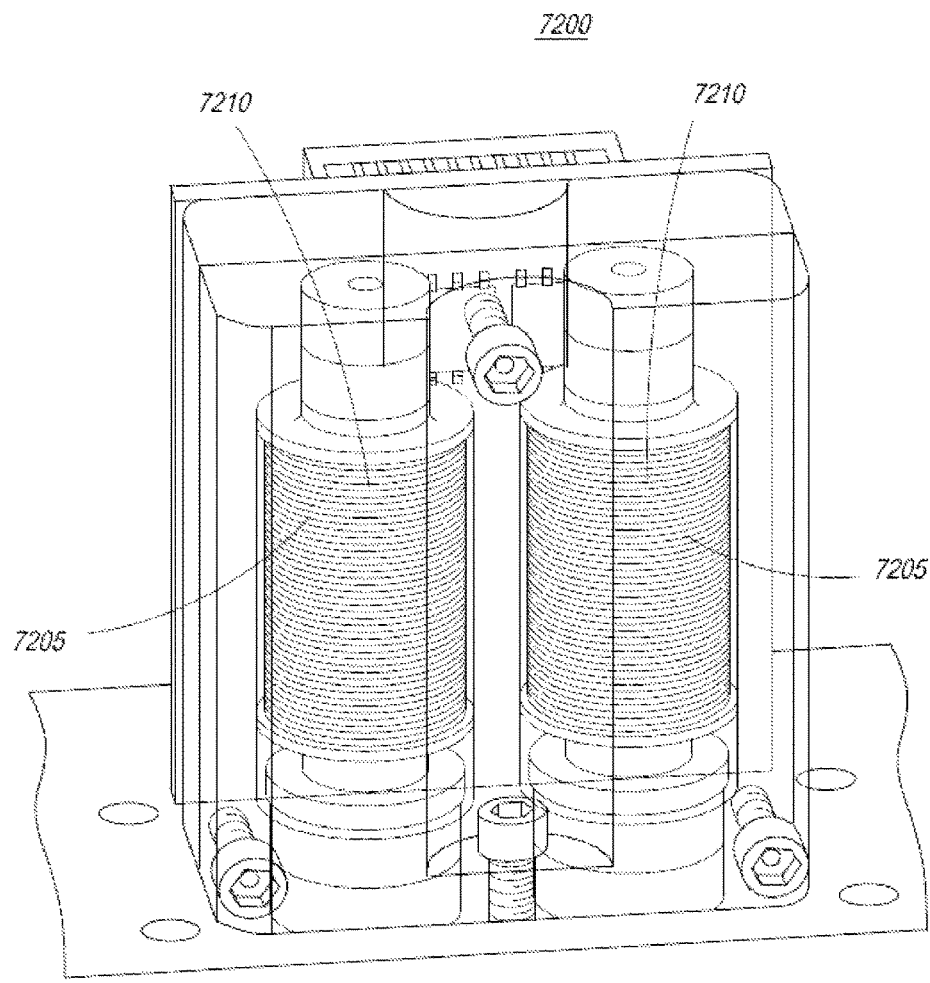
FIG. 72 is a schematic view of a component of an exemplary magnetic valve system.

Another important component of the displacement mechanism system is an actuator system 7200 depicted in FIG. 72. During the actuation process, coils 7205 are energized and the magnetic field builds, thus creating magnetic force opposing the small magnet attraction force. As the force builds, the core, discussed above, starts to move to the closed position (large magnet). Once the core moves past a point of no return, the attraction forces on the core of the large magnet have overcome the attraction forces of the small magnet. To ensure that the opposing forces caused by the valve diaphragm do not overcome the attraction forces of the large magnet, a gap is provided as discussed above.

The coil design is made of coil form and magnet wire 7210. The size of the coil form size is preferably based upon commercially available coil forms, the pulsed current capability of the power supply, and, in particular, the required actuation force and the power supply voltage. The actuation force is proportional to the amp-turn rating of the coil. In one embodiment, it is preferred to limit the coil current to 6 amperes or less.

Factors important in the coil design include the number of layers, packing factor, wire diameter, and coil resistance. In one embodiment, the present invention uses a bobbin with 6 layers of wire and approximately 0.010 inches space between the bobbin flange diameter and the last layer. With an insulation requirement of heavy poly nylon and a coil resistance of 3.5+/−0.5 Ohms, the wire size is approximately 29 AWG. Any size coil form can be used.

The circuit used to drive the coil is an H-bridge circuit which enables current to be reversed for open and closed operations. The H-Bridge circuit is driven via a unique pulse width modulated (PWM) signal. The PWM signal is used to generate a cosine current pulse through the coil. The period of the cosine pulse is related to the mass of the core and the opposing force. The preferred embodiment does not use a bipolar DC power switch or sense switch; rather, the optical sensor operates to determine the position of the core, conclude the valve state, and generate an electronic drive cosine waveform to move the plunger in the desired direction, thereby changing the state of the valve.

Optionally, as shown in FIGS. 71A and 71B as element 7152, the valve system 7100 uses a sensor, preferably an optical sensor 7152, to determine the state of the valve (open or closed). This can be achieved by positioning the optical sensor 7152 in a location that has a sufficient difference in reflectivity, or other optical properties, between a valve open state and a valve closed state. For example, when the valve is closed, in one embodiment, the large end of the core 7196 is positioned against an elastic material 7134 and the large magnet component 7132. The large end of the core 7196 has a width wide enough to be sensed by a reflective optical sensor 7152, but not too wide so the optical sensor 7152 has position resolution. The optical sensor 7152 will be placed on the outside of the displacement member/mechanism and look through its body, which is preferably made of transparent polycarbonate. The optical sensor's 7152 wavelength will be in the near infrared range (NIR) so as to have good transmission through the polycarbonate body. One of ordinary skill in the art would appreciate that the sensor can be chosen to suit any material structure, provided it includes the appropriate filters. Here, the optical sensor 7152 preferably has built into it a long pass optical filter for NIR responsivity.

Functionally, when the core is in the open position, as shown in FIG. 71A, the large end of the core 7196 moves out of the field of view of the optical sensor 7152, thus very little reflection will be seen by the optical sensor. When the large end of the core 7196 is in the field of view, as shown in FIG. 71B, there will be a reflection that the sensor 7152 will see, thus indicating the core is in the closed position. One of ordinary skill in the art would appreciate that the sensor 7152 can be positioned such that it senses a great deal of reflectivity from the core when the valve 7100 is in the open position and much less reflectivity (because the core is moved out of the field of view) when the valve 7100 is in the closed position. Further, one of ordinary skill in the art would appreciate that the sensor 7152 could be positioned proximate to the gap to sense when the gap is present and when the gap is absent, thereby indicating the state of the valve 7100.

While the substantially planar surface of the manifold diaphragm in the above embodiments results in functional system, the responsivity of such a system is delayed. Specifically, the gap, or dead space, between the sensor, or pin, which is in the dialysis machine, and the diaphragm surface generates the responsivity curve seen in FIG. 75. A response is not seen until inflection point 7503, when the diaphragm starts being compressed against the valve seat. However, in certain embodiments, a more immediate responsiveness may be desired. Therefore, in other embodiments, the manifold includes one or more diaphragms with raised portions or protrusions on its exterior surface configured to come into sufficiently close contact with the dialysis machine pins or sensors that the gap, which exists in the above described embodiments, is eliminated. Eliminating the gap, or dead space, results in improved linearity of the system's response to the movement of pins into the diaphragm.

Figure 71C:
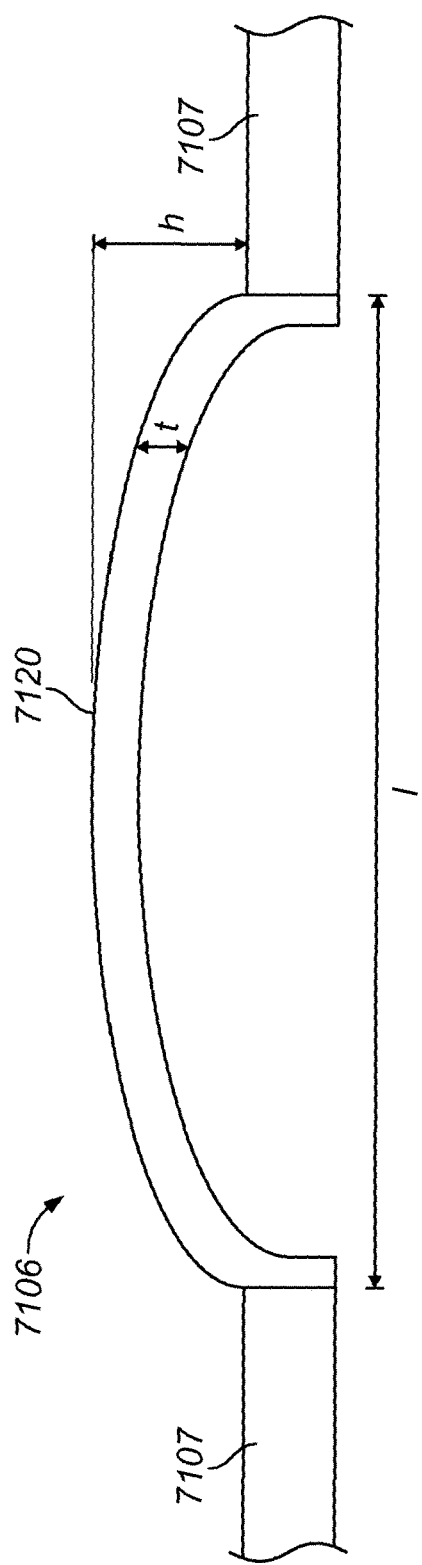
FIG. 71C is a cross-sectional view illustration of one embodiment of a manifold diaphragm with a raised convex surface.

FIG. 71C is a cross-sectional view illustration of one embodiment of a manifold diaphragm 7106 with a raised convex surface 7120. The surface 7120 of the diaphragm 7106 begins at the same level of the manifold 7107, increasing and then decreasing in height h over its length l, relative to the height of the manifold 7107. In one embodiment, the length l of the diaphragm measures approximately 0.625 inches to 0.675 inches. In one embodiment, the total increase in height h at the middle, relative to the manifold 7107 exterior surface, is between 0.03 and 0.04 inches. In one embodiment, the thickness t of the diaphragm is relatively constant throughout its length l and measures between 0.03 and 0.04 inches. A convex diaphragm would be desired to squeeze bubbles out when the transducer touches the surface of the diaphragm. However, creating and maintaining a convex diaphragm structure is challenging to manufacture due to the heat generated.

Figure 71D:
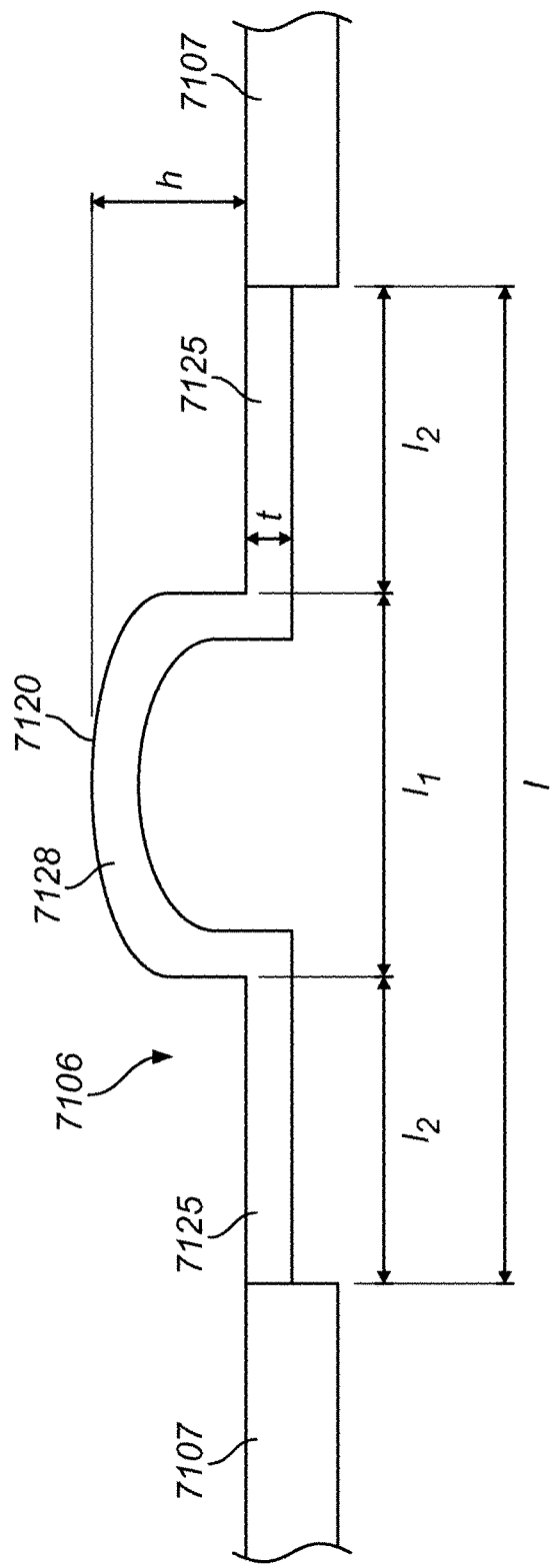
FIG. 71D is a cross-sectional view illustration of one embodiment of a manifold diaphragm with a centrally located raised convex protrusion within a substantially planar periphery.

A small dome or protrusion within a substantially flat diaphragm surface is more resistant to heat and easier to manufacture. FIG. 71D is a cross-sectional view illustration of one embodiment of a manifold diaphragm 7106 with a centrally located raised convex protrusion 7128 within a substantially planar periphery 7125. The periphery 7125 of the diaphragm 7106 has a surface height that is substantially level with that of the surrounding manifold 7107 exterior surface. In or around the center of the diaphragm 7106 is a raised protrusion 7128 with a distinct step increase in height relative to the substantially flat periphery 7125. The protrusion 7128 has a convex surface 7120 designed to contact the pin or sensor. In one embodiment, the total length l of the diaphragm measures approximately 0.625 inches to 0.675 inches. The length $l_1$ of the protrusion measures between 0.125 and 0.15 inches, within the sensing diameter of the pressure transducer which is, in one embodiment, 0.185 inches. The length of the periphery $l_2$ on each side of the protrusion measures between 0.25 and 0.2625 inches. In one embodiment, the total height h of the protrusion measures between 0.03 and 0.04 inches. The increase in height is capped by the curved surface of the protrusion. In one embodiment, the thickness t of the diaphragm is relatively constant throughout its total length l and measures between 0.03 and 0.04 inches. In one embodiment, the raised protrusion 7128 represents 10% to 40%, preferably 19% to 23%, of the total diaphragm surface.

Figure 71E:
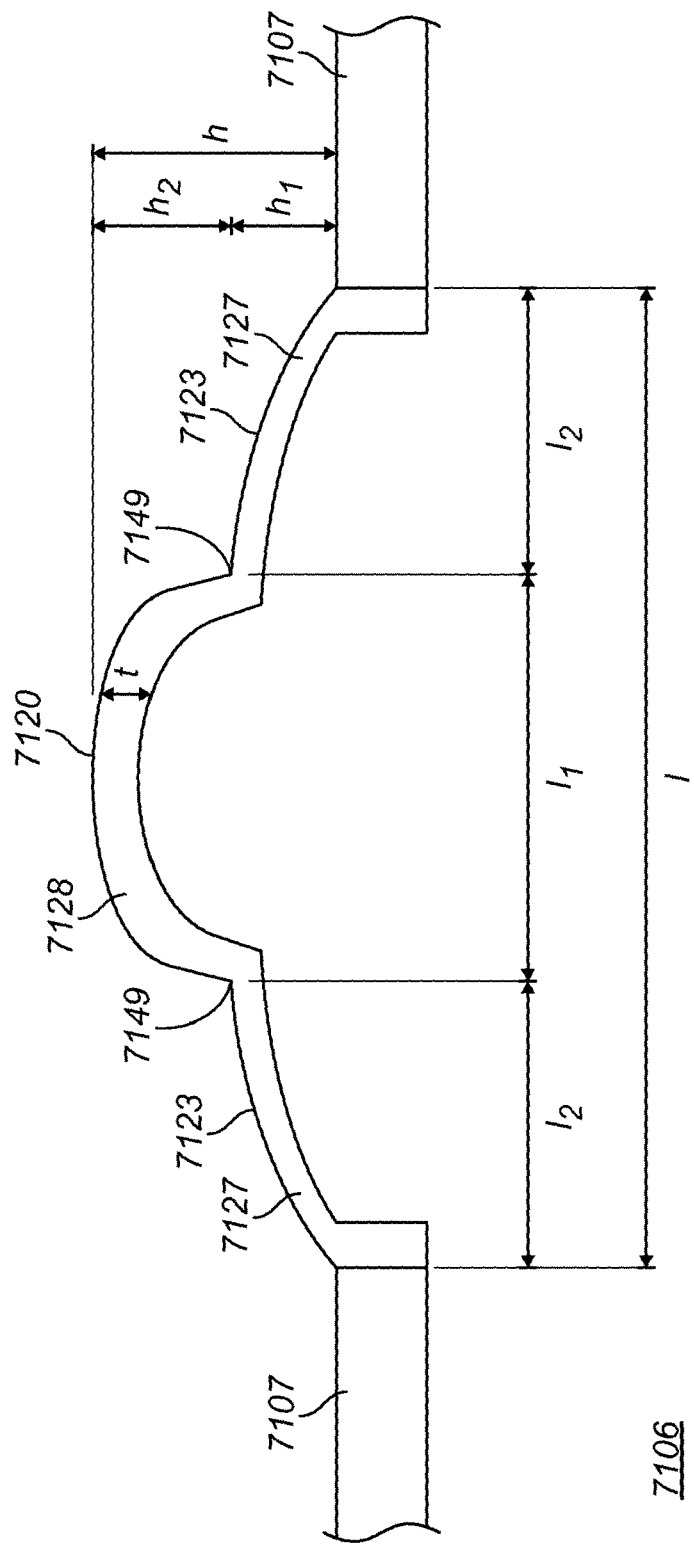
FIG. 71E is a cross-sectional view illustration of one embodiment of a manifold diaphragm with a centrally located raised convex protrusion within a raised convex periphery.

In another embodiment, both the periphery of the diaphragm and the raised protrusion have convex surfaces, but with different total heights relative to the manifold external surface. FIG. 71E is a cross-sectional view illustration of one embodiment of a manifold diaphragm 7106 with a centrally located raised convex protrusion 7128 within a raised convex periphery 7127. The periphery 7127 of the diaphragm 7106 has a surface height that increases with respect to the substantially level external surface of the surrounding manifold 7107. The periphery 7127 includes a convex surface 7123. In the center of the diaphragm 7106 is a raised protrusion 7128 with a distinct step increase in height relative to the convex periphery 7127. The protrusion 7128 has a convex surface 7120 configured to contact the pin or sensor. In one embodiment, the total length l of the diaphragm measures approximately 0.625 inches to 0.675 inches. The length $l_1$ of the protrusion measures between 0.125 and 0.15 inches, within the sensing diameter of the pressure transducer which is, in one embodiment, 0.185 inches. The length of the periphery $l_2$ on each side of the protrusion measures between 0.25 and 0.2625 inches. In one embodiment, the total height h of the protrusion measures between 0.03 and 0.04 inches. In one embodiment, the height $h_2$ of the protrusion measures between 0.10 and 0.02 inches above the inflection points on each side of the periphery which define the end of the periphery and start of the protrusion. The height $h_1$ of the periphery measures approximately 0.02 inches above the manifold external surface. The increase in height is capped by the curved surface of the protrusion. In one embodiment, the thickness t of the diaphragm is relatively constant throughout its total length l and measures between 0.03 and 0.04 inches. It should be appreciated that, in each of the above embodiments, the diaphragm could have a thickness which is not constant throughout its total length l, although that is not preferred.

By constructing the entirety of the diaphragm surface (which may include a periphery and protrusion) to have a relatively constant thickness and to include a central area with an increased high relative to the rest of the diaphragm, the linearity of the pressure response is improved. It should be appreciated that additional variations of the disclosed embodiments are covered by this specification, including diaphragms where there is a substantially flat periphery, a first protrusion that extends upwards in a curved manner within the boundaries of the periphery, and a second protrusion centered within the first protrusion that also extends upwards in a curved manner within the boundaries of the first protrusion. In this manner, protrusions can be layered within each other to create a multiple step-wise increase in height from the periphery toward the center of the diaphragm. As many such protrusions and steps are possible and only limited by the quality of the pressure response and the manufacturability of the design.

Figure 77:
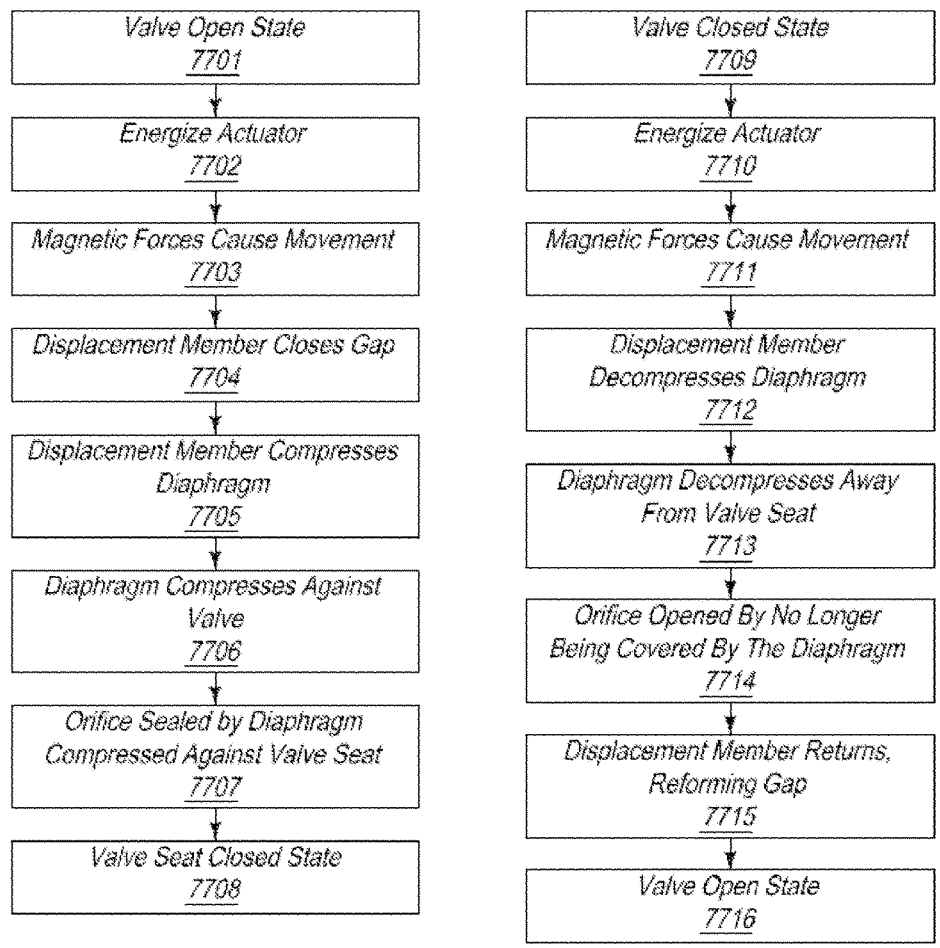
FIG. 77 is a flowchart depicting the operation of an exemplary magnetic valve system.

Operationally, as referred to in FIG. 77, a valve is in initially one of two states, open or closed. Assuming the valve is in an open state 7701, the first step in closing the valve is to energize the coil driver circuit 7702 and thereby cause the magnetic field generated by the coil to pass through the core, create an opposing magnetic force between the core and small magnet, and create a weak attraction force between the large magnet and the large end of the core. As the displacement member starts to move 7703, the small magnet attraction forces diminish as the large magnet attraction forces increase. The displacement member moves 7703 until a point of no return, after which the displacement member 7704 closes a gap 7704 and compresses the orifice closing member, namely the diaphragm 7705, against the valve seat 7706. The compression of the diaphragm 7706 causes the diaphragm to close the orifice 7707 and close the valve 7708.

Assuming the valve is in a closed state 7709, the first step in opening the valve is to energize the coil driver circuit 7710 and thereby cause the magnetic field generated by the coil to pass through the core, create an opposing magnetic force between the core and large magnet, and create a weak attraction force between the small magnet and the small end of the core. As the displacement member starts to move 7711, the large magnet attraction forces diminish as the small magnet attraction forces increase. The displacement member moves 7711 until a point of no return, after which the displacement member decompresses the diaphragm 7712 away from the valve seat 7713. The orifice opens by virtue of no longer being covered by the diaphragm 7714. The displacement member returns to its original position and recreates the gap 7715, thereby returning to an open state 7716.

Since the first and second stable states of the core are maintained even when power to the electromagnet is switched off, the displacement system is able to have low power consumption and low heat generation relative to prior art actuators where continuous power supply is needed to maintain states, additionally resulting in high heat generation.

Saline Rinse Back

Referring to FIG. 86, a method and system for safely and efficiently performing a saline rinse back is shown. Conventionally, a saline rinse back, which serves to flush the system with saline, is performed by detaching a tubular segment 8658 that connects the dialysis blood circuit to the patient at connection 8651 and attaching the tubular segment 8658 to a saline source 8602 via connection points 8652 and 8653. This conventional approach has disadvantages, however, including the breaching of a sterile connection. It should be appreciated that the connection points can be any form of connection, including luer connections, snap fits, needleless inserts, valves, or any other form of fluidic connection.

Another approach to a saline rinse back includes connecting the saline source 8602 via connection point 8652 to connection point 8653, while maintaining the connection to the patient. While it avoids breaching the sterile connection, it exposes a patient to a saline fluid flow that may contain air bubbles. Because no air bubble detector is typically present in the tubular segment 8658 between the point of saline connection 8653 and the point of connection to the patient 8651, there is a danger that an excessively large air bubble would form and, because there is no mechanism to detect such an air bubble and inform the patient, enter the patient's blood stream, causing substantial injury.

Alternatively, a preferred approach to performing a saline rinse back is to maintain the blood circuit connection between the patient and the dialysis system via tubular segment 8658, which connects to the manifold 8600 at port C 8605 and the patient at connection point 8651 and fluidically connect the saline source 8602 to the manifold 8600 at port D 8606. With the patient still fluidically connected to the dialysis system, saline is permitted to flow, by gravity or applied pressure, into the manifold 8600 via port D 8606, which is adjacent to port C 8605. The saline flow serves to flush the manifold 8600 with saline and, in particular, to flow out of the manifold 8600 via port C 8605, through tubular segment 8658, and into the patient via connection 8651. Because an air bubble detector is present in region 8654, proximate to port C 8605, when the manifold 8600 is installed in the controller unit and therefore adapted to detect air bubbles in fluid flow exiting port C 8605, saline exiting the manifold 8600 and toward the patient will be monitored for air bubbles, via the air bubble detector in region 8654. If an air bubble is detected, an alarm will sound, thereby signaling to a patient that he or she should either disconnect from the system or extract the air bubble, using a syringe, from access point 8610. Accordingly, this method and system for conducting a saline rinse back maintains a sterile connection while still monitoring and alarming for the presence of air bubbles.

Improved Hardware Architecture

Embodiments of the dialysis system disclosed herein may further comprise a hardware architecture that provides for a more rapid method of terminating system operations. Conventionally, when an alarm state is encountered during dialysis operations or if a user wishes to terminate operations, an instruction issued at a higher application layer must progress through multiple lower layers in order to actively terminate hardware operations. This architecture subjects users to the unnecessary risk of a delayed shutdown which, in critical applications, may be unacceptable.

Figure 78:
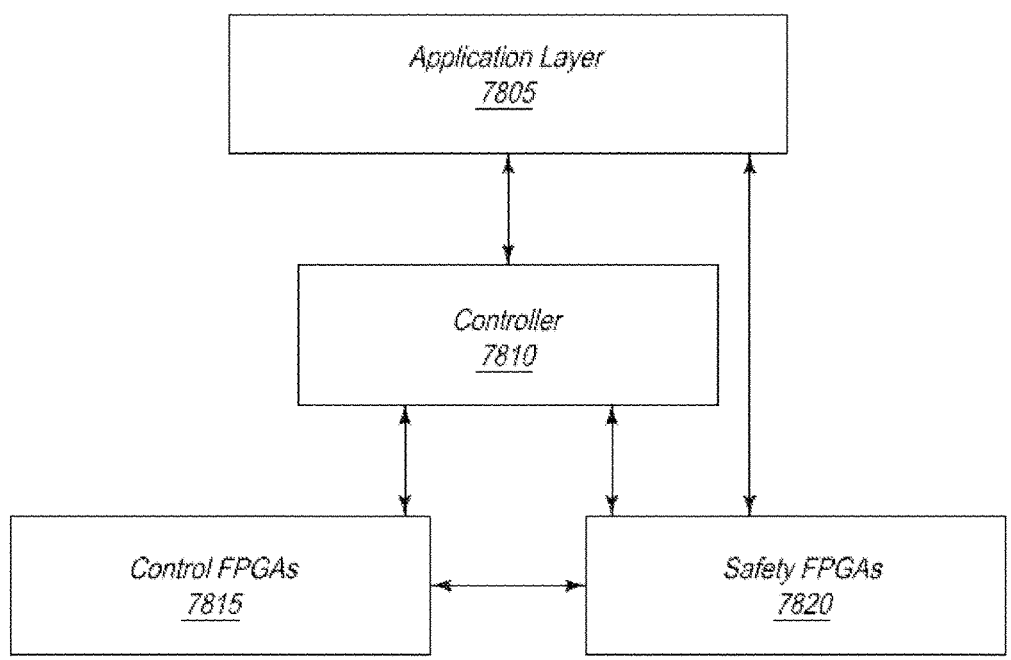
FIG. 78 is a diagram of an exemplary hardware architecture for one embodiment of the dialysis system.

Referring to FIG. 78, the dialysis system comprises at least one processor and a memory for storing programmatic instructions which, when executed, communicates with a software application layer 7805. The software application layer 7805 interfaces with a master controller 7810 that is in data communication with a plurality of field programmable gate arrays responsible for controlling various pumps, sensors, and valves (Control FPGAs) 7815 and in data communication with a plurality of field programmable gate arrays responsible for monitoring the operation of various pumps, sensors, and valves for failure states or states which exceed accepted operational parameters 7820 (Safety FPGAs).

Control FPGAs 7815 execute hardware instructions for controlling the operation of all system components, including pumps, sensors, and valves, and transmitting state information of the components to both the controller 7810, which, in turn, processes the information and passes certain data for further processing and/or display to the application layer 7805, and the Safety FPGAs 7820, which monitor the state information for an alarm condition, such as an operational parameter exceeding or not meeting one or more predefined threshold values.

Where the Control FPGAs 7815 generate data indicative of an alarm condition or generally indicative of a need to terminate or suspend operations, the controller 7810 or application layer 7805 may issue one or more commands to terminate operations. Independently, however, the Safety FPGAs 7820 receive the data and may directly issue commands, or otherwise cause, the operation of one or more valves, pumps, or sensors to terminate, suspend, or otherwise change state. The Safety FPGAs 7820 may do so after receiving data directly from the Control FPGAs 7815 or independently if directly instructed by the controller 7810 or directly instructed by the application layer 7805. By having the Safety FPGAs directly receive data from the Control FPGAs 7815 and instructions from the application layer 7805 and controller 7810, with no mediating layer in between, the system can effectuate a shutdown, suspension, or other modification in state in response to an alarm condition or user instructions more rapidly and reliably.

Graphical User Interfaces

Embodiments of the dialysis system further comprise interfaces through which users interact with the system. As previously discussed, the controller unit comprises a display for presenting a graphical user interface to a user. The interface enables a user to accurately measure and verify prescription additives and provides functionality to check the integrity and authenticity of the disposables employed in the system as well as that of the prescription additives.

As previously discussed, the dialysis system comprises a scale, which can be integrated on the shelf atop the controller unit, inside the reservoir unit of the portable dialysis system, to the side of the bottom unit proximate holders for the sorbent cartridge or infusate, or in any other location. Measurement readings taken by the digital scale are displayed via graphical user interfaces (GUIs) shown on the display integrated into the top controller unit.

In one embodiment, the controller unit is programmed in accordance with the user's prescription. This can be done by means of an initial setup in which the user places all the packets of prescription additives one by one on the scale tray. The measurements made by the digital scale are recorded and stored in an internal memory. The controller thus has access to the data regarding names and prescribed weights of the additives. Therefore, when a packet of any prescription additive is placed on the scale for measurement prior to starting the dialysis process, the controller compares the measured weight with the prescribed weight stored in an internal memory. In case of any discrepancy between the measured weight and the correct or prescribed weight, the controller directs the GUI to display an alarm or directs an audio generation unit to generate an auditory alarm. Therefore, such an alarm may be visual, such as a flashing error message on the GUI screen, and may also be accompanied by an audible alarm. Alternatively, a user is not permitted to continue the dialysis set up process.

FIG. 79 illustrates an exemplary table of data for prescription additives that may be stored as a file, flat file, or table in the internal memory of the portable dialysis system. Column 7901 describes the packet contents and column 7902 shows the corresponding weight. As can be seen from column 7902, the weight difference between the different packages is several grams, which can be read by a digital scale. In one embodiment, the digital scale of the present invention is designed with a weight resolution of the order of 0.1 gm, which, given the weight of additives, provides a greater than 5 times resolution advantage and, more preferably, 10 times resolution advantage. This resolution is sufficient to differentiate between the typically used additives.

Optionally, the structure of the digital scale is designed such that the weighing process is not affected by the manner in which a user places the packets of prescription additives on the scale. This is because the structure of the scale in the present invention comprises multiple weight-sensitive members at multiple suspension points. In one embodiment for example, the scale comprises three sensors on a three point suspension. The total weight is computed by the scale system as the SUM of that measured by all the sensors. The advantage of using this computing scheme is that the packet weight need not be evenly distributed on the scale platform. Thus, even if the packets are placed on the scale tray slightly off to one side, flat or scrunched, it would not affect the accuracy of weight measurement made by the scale. That is, a user is not constrained in the manner in which he places the packets on the scale.

It should further be appreciated that the sensor weight can be determined using any calculation method known in the art. In one embodiment, a processor in data communication with the scale receives data readings from the scale and determines a weight as follows:

Sensor_Weight(i)=K1(i)*ADC(reading)+K0(i)

Bag_Weight=(Sensor_Weight(0)+Sensor_Weight(1)+Sensor_Weight(2)+Sensor Weight(3))/4

As previously discussed with respect to FIG. 16, the portable dialysis system has an exposed reader 1605, such as a bar code reader or RFID tag reader, which can be used to read codes or tags on the packets of prescribed additives. For initial setup, a user would preferably swipe all of the codes/tags on the packets of prescription additives by the reader 1605. The user can be assisted through an initial GUI message which prompts the user to swipe each packet of prescription additive pass the reader 1605. Upon doing so, the reader obtains identifying information about the additive and transmits that identifying information to an internal table stored in memory. After this initial setup, whenever a prescription additive is to be added to the dialysate prior to starting dialysis, the identifying information of the concerned packet (read by the reader 1605 ) is compared to the identifying information for that additive already stored in the internal table during initial setup. This helps to verify that the correct additives have been selected for use with the dialysate and helps rule out any spurious additives. The contents of the internal table can be generated either by manual input of data regarding the identity and weight of the additives or by remote access to a prescription that details the identity and amount of the additives.

In one embodiment, the GUI of the present invention is generated by a plurality of programmatic instructions stored and executed by a processor resident in the controller unit. One set of programmatic instructions is designed to walk a user through a process for verifying the identity and amount of additives to be used. A first GUI screen prompts a user to expose a bar code on an additive bag to the bar code reader. One of ordinary skill in the art would appreciate that this identifying mechanism can be a bar code, RFID tag, or other electronic tag, and the reader can be a bar code reader, RFID tag reader, or other electronic tag reader. The reader reads the coded information, processes it using a processor, and transmits the processed information to a memory. The memory has a programmatic routine that translates the processed information into an identity of an additive. In one embodiment, the translation is facilitated by a table that matches various identifiers to specific additive names. This table can be manually inputted prior to the procedure or downloaded from a server via a wired or wireless connection to the controller.

Once the additive identity is obtained, the GUI communicates the identity of the additive to the user and instructs the user to place the additive on the scale. The digital scale weighs the additive and communicates the measured weight to a second table. The second table maps the additive identity with the expected weight. This second table may be manually inputted prior to the procedure or downloaded from a server via a wired or wireless connection to the controller. If the additive identity and measured weight match, the user is instructed to open the packet and pour the contents into the appropriate location. This process is repeated for all the additives. In one embodiment, a user is not permitted to continue the process if there is a discrepancy between the identity of the packet and its weight or if the coded identity of the packet cannot be read or is unknown. Thus, the system provides a one step or two-step verification mechanism: a) using the digital scale by itself or b) using the digital scale in combination with the bar code or tag reader, which ensures that the user has, in his or her possession, all of the required additives and that the correct additives are being used and not counterfeit or unsuitable.

Figure 80:
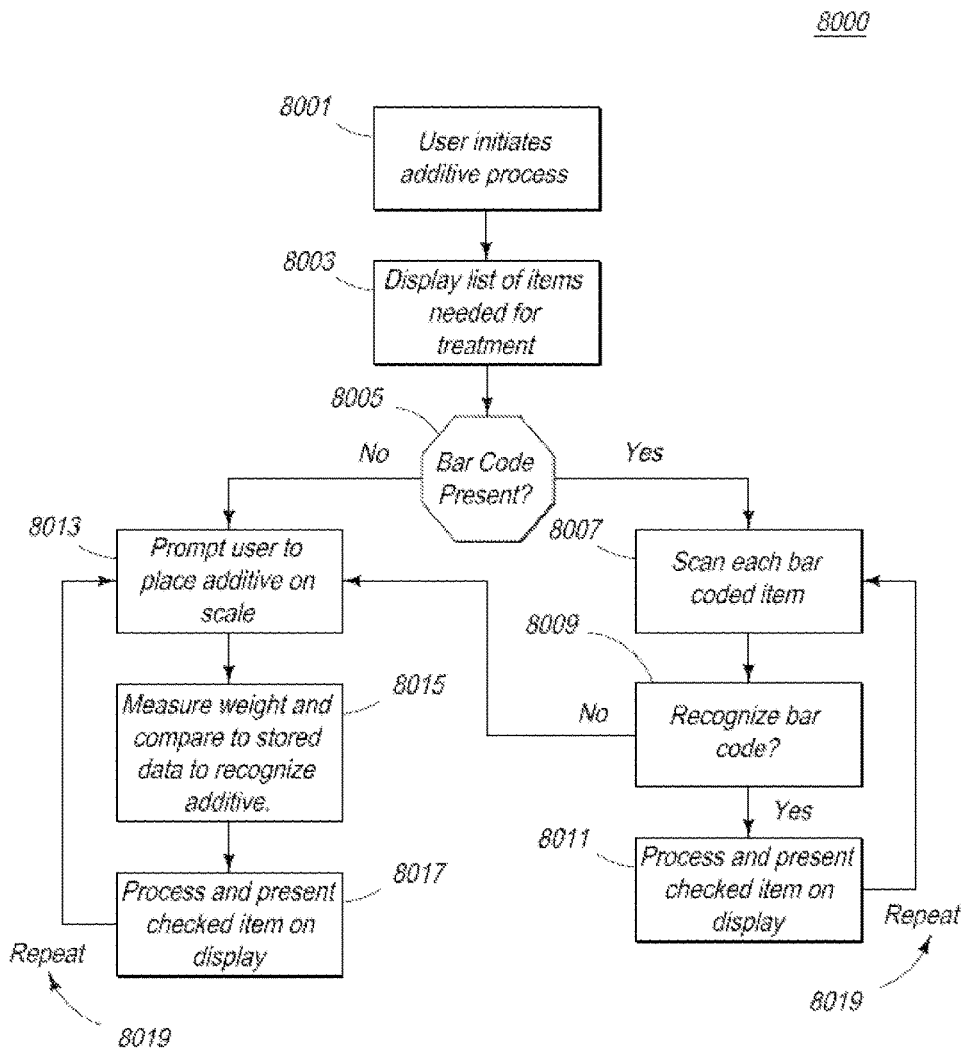
FIG. 80 is a flowchart depicting one embodiment of a process for enabling users to accurately add additives.

Referring to FIG. 80, a flowchart showing another process 8000 for initiating a dialysis treatment is shown. In one embodiment, the controller unit 8001 comprises at least one processor and memory storing a plurality of programmatic instructions. When executed by the processor, the programmatic instructions generate a plurality of graphical user interfaces, displayed on the controller display, which directs a user through a series of actions designed to reliably acquire and measure the additives required for use in a dialysis treatment. A first graphical user interface is generated through which a user can prompt the system to initiate the additive accounting process 8001. The initial prompt can be through a specific icon for initiating the process or can occur as part of a larger system setup.

A second graphical user interface is then generated 8003 which displays in text or graphical form the additives required, preferably including a visual image of the actual additive package to permit a user to visually compare the additive required with the product the user has on-hand. The user is then prompted 8005 to indicate whether he wishes to verify the additive using a bar code scan or by weight. If the user indicates he wishes to use the bar code scan, through, for example, pressing an icon, a third graphical user interface is generated 8007 prompting the user to pass the first additive past the bar code scanner. The user then passes an additive, preferably in any order, past the bar code scanner, registering a read. It should be appreciated that the bar code scanner can comprise a light, such as a red light, which changes color, such as to green, upon a successful reading.

If the system successfully reads the bar code it processes 8009 the code by checking the code against a table stored in memory. The table stored in memory associates bar codes with specific additives. Once a specific additive is identified, the second graphical user interface, as described above, is updated 8011 with a check mark or highlight to indicate which additive has been successfully scanned and the user is instructed to set the additive aside. This process is repeated 8019 for all additives. In one embodiment, once all additives are highlighted or checked, the system automatically proceeds to the next step in the dialysis set up or initialization process. In another embodiment, once all additives are highlighted or checked, the system presents a graphical user interface informing the user that all additives have been registered, after which a user causes the system to manually proceed to the next step in the dialysis set up or initialization process. It should be appreciated that, while the term bar code is used, any electronic tagging or labeling system can be used.

If, for any scanning step 8009 the bar code is not recognized, the additives do not have bar codes, or the user prefers to verify additives using weighing, as opposed to scanning, a graphical user interface is presented to the user prompting 8013 the user to place a first additive on the scale. The scale measures the additive package weight 8015 and compares the measured weight to a table of weight values associated with specific additives in order to recognize the additive. Once recognized, the second graphical user interface, as described above, is updated 8017 with a check mark or highlight to indicate which additive has been successfully scanned and the user is instructed to set the additive aside. This process is repeated 8019 for all additives. In one embodiment, once all additives are highlighted or checked, the system automatically proceeds to the next step in the dialysis set up or initialization process. In another embodiment, once all additives are highlighted or checked, the system presents a graphical user interface informing the user that all additives have been registered, after which a user causes the system to manually proceed to the next step in the dialysis set up or initialization process. It should be appreciated that, while the term bar code is used, any electronic tagging or labeling system can be used.

If the additive is not recognized, the user is informed that the additive is not part of the treatment process and is prompted to weigh a proper additive. In another embodiment, if the user fails to scan or weigh a recognized additive, the user is not permitted to continue the initialization or set up process.

One of ordinary skill in the art would appreciate that although the aforementioned verification procedure has been described for prescription additives, the same procedure may also be extended to the disposable components used with the dialysis system, such as sorbent cartridges and other disposables.

It should further be appreciated that the process of scanning and weighing the additives can be integrated and automated. As discussed above, a user can be prompted to initiate the additive weighing process and a display of items needed for treatment may be displayed. A user places an additive on a scale which has a bar code reader proximate to or integrated therein. In one embodiment, the user is prompted to place the additive in a specific position or configuration to ensure the bar code can be properly read. Upon placing the additive on the scale having an integrated or combined bar code reader, the bar code reader scans the additive, attempts to recognize the bar code, and, if recognized, processes the item by checking or highlighting the identified additive on the display. If the bar code reader fails to identify the additive, if the system requires an additional, supplemental check, or if the system wishes to obtain or otherwise record weight information, the scale measures the weight and attempts to recognize the additive against stored values. If identified, the system processes the item by checking or highlighting the identified additive on the display. The scale measurement and bar code reader can therefore occur without having to move the additive from one location or position to another.

It should further be appreciated that the additives can be inserted into a holding container, chute, cylinder, box, bucket, or staging area that will automatically drop, place, or otherwise position each additive into the appropriate position on a scale/bar code reader. Accordingly, the user can place all additives into a single container, activate the system, and have each additive sequentially positioned on the scale and identified automatically. A user may be prompted to remove each additive after each additive is recognized or may be prompted to allow all additives to be processed first.

It should further be appreciated that the additive can be added to the system automatically after identification, manually after identification, and either before or after the hemofilter and/or sorbent cartridge is installed. In one embodiment, the top or bottom unit of the portable dialysis system also preferably has electronic interfaces, such as Ethernet connections or USB ports, to enable a direct connection to a network, thereby facilitating remote prescription verification, compliance vigilance, and other remote servicing operations. The USB ports also permit direct connection to accessory products such as blood pressure monitors or hematocrit/saturation monitors. The interfaces are electronically isolated, thereby ensuring patient safety regardless of the quality of the interfacing device.

In another embodiment, the dialysis machine comprises an interface, in the form of a graphical user interface with touch screen buttons, physical keypad, or mouse, which can be manipulated to cause a dialysis machine loaded with a manifold to start operation in either a treatment mode or priming mode. When instructed to operate in treatment mode, the controller generates a signal (in response to that treatment mode command) to cause the manifold valve to switch from an open, priming state to a closed, treatment state. When instructed to operate in priming mode, the controller generates a signal (in response to that priming mode command) to cause the manifold valve to switch from a closed, treatment state to an open, priming state. One of ordinary skill in the art would appreciate that all of the aforementioned control and user command functions are effectuated by incorporating one or more processors executing programming embodying the aforementioned instructions, which are stored in local memory.

Figure 84:
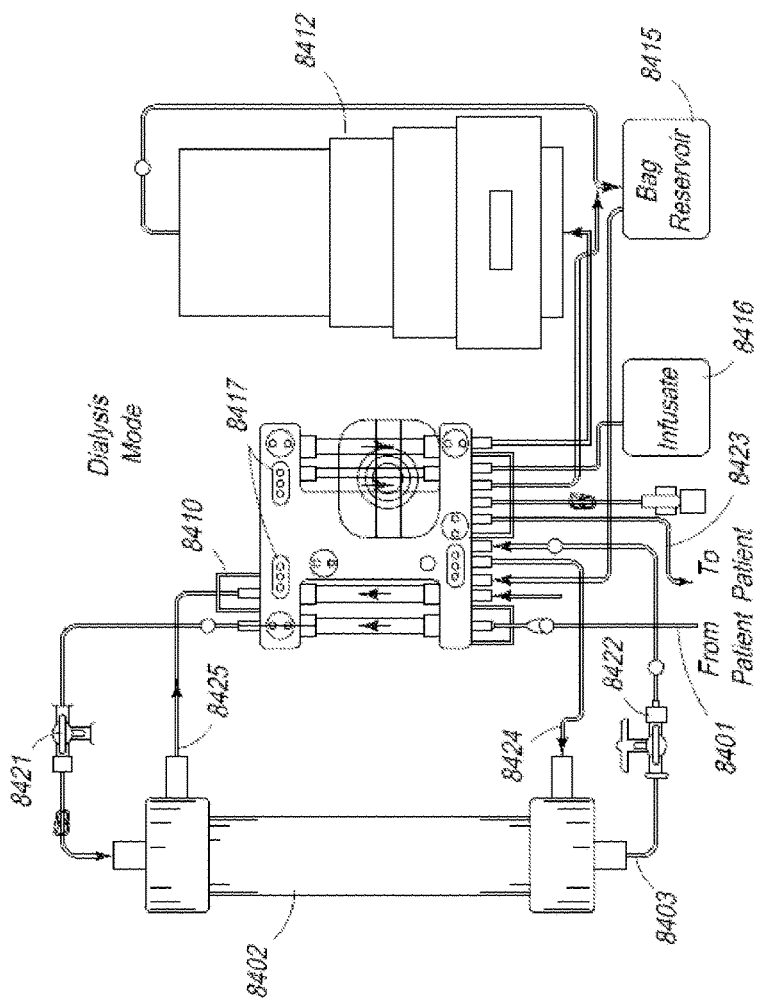
FIG. 84 is a fourteenth exemplary fluid circuit diagram.

When properly actuated, the system can operate in at least a priming mode and a treatment mode, which can comprise other modes of operation (such as hemodialysis, hemofiltration, or, simply, a non-priming mode). With respect to an exemplary treatment mode and referring to FIG. 84, the dialysis system 8400 operating in dialysis mode comprises a dialyzer 8402, sorbent regeneration system (e.g. cartridge) 8412, manifold 8410, infusate source 8416 entering into the manifold 8410 through a port, and reservoir 8415 from which fresh dialysate is input back into the manifold 8410 via a port. In operation, blood enters the blood line 8401, into the manifold 8410 through a port, through a two-way valve 8421 which is in a first position, and into the dialyzer 8402. The purified blood exits the dialyzer 8402 through outlet 8403, through a two-way valve 8422 which is in a first position, and into the manifold 8410 through a port. The blood passes through the manifold, passing through a plurality of valves 8417, as described above in relation to manifold 8410, and out of a port and into a blood line 8423 entering the patient.

Concurrently, infusate passing from a source 8416 passes into the manifold 8410 through a port, through the manifold 8410, out through another port, and into reservoir 8415, from which dialysate is delivered via a dialysate in-line 8424 and into dialyzer 8402. After passing through the dialyzer 8402, the dialysate passes through an out-line 8425 and back into the manifold 8410 through a port where it is routed to the sorbent-based dialysate regeneration system 8412 via a port. Regenerated dialysate passes back through the manifold 8410 via a port and is re-circulated through the dialyzer 8402 with new dialysate, if and when required. To manage dialysate fluid flow, a reservoir 8415 is used to store regenerated dialysate, if and when needed. In one embodiment, the reservoir holds 5 liters of dialysate and has the capacity to hold up to 10 liters of dialysate and effluent from the patient.

Figure 85:
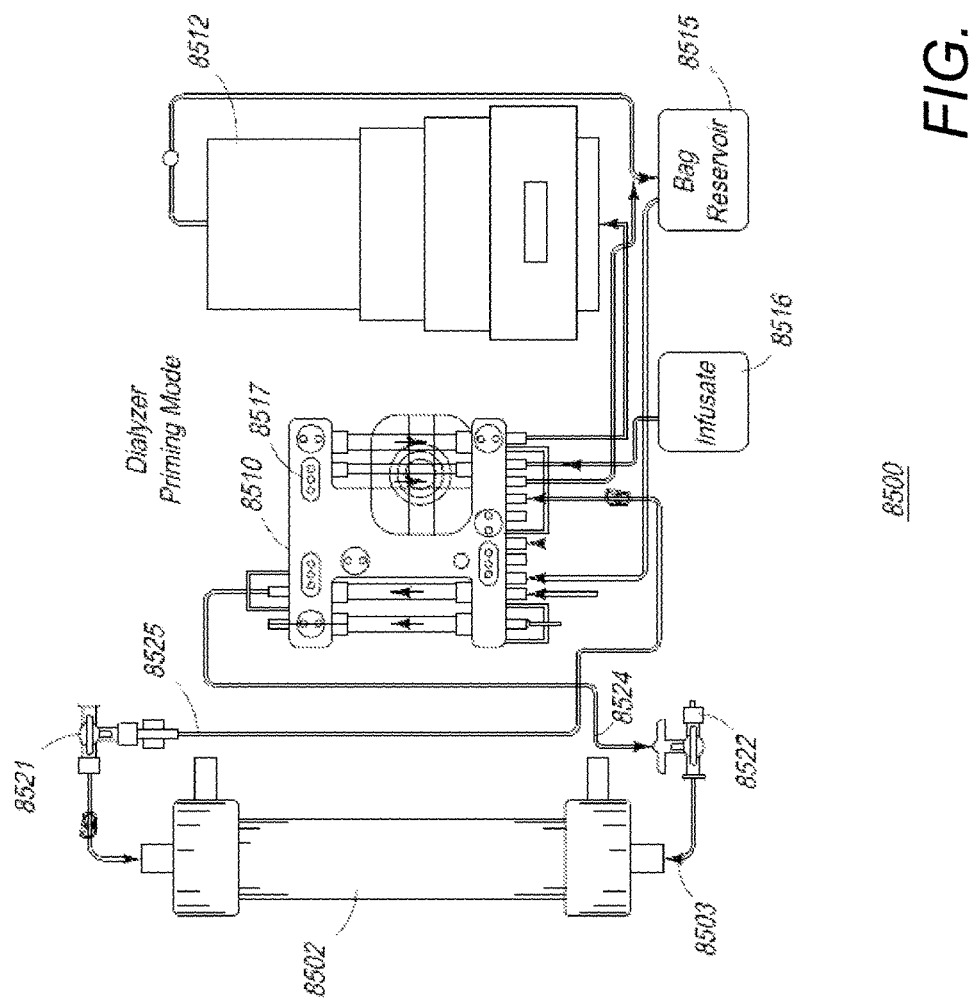
FIG. 85 is a fifteenth exemplary fluid circuit diagram showing a priming mode of operation.

With respect to an exemplary priming mode and referring to FIG. 85, a dialysis system 8500 operating in priming mode comprises a dialyzer 8502, sorbent regeneration system (e.g. cartridge) 8512, manifold 8510, infusate source 8516, and reservoir 8515. In operation, the bloodline from the patient (e.g. 8401 in FIG. 84) into the manifold 8510 is not connected and therefore, no blood is flowing, or capable of flowing, into the manifold 8510. Rather, dialysate passing from a source 8515 passes into the manifold 8510 through a plurality of ports and through a dialysate in-line 8524, which is connected to the two-way valve port 8522.

In a preferred embodiment, a single two-way valve 8517 is incorporated into the physical body of the manifold 8510 and manipulated to switch between a treatment mode of operation and a priming mode of operation, as discussed above. In this embodiment, a manifold 8510 comprises a two-way valve 8517 which, if activated or switched from a first positioned (e.g. closed) to a second position (e.g. open), causes a change to the internal flow path of liquid within the manifold. As a result of this flow path change, the blood and dialysate circuits, which, when the valve is closed, are fluidically isolated from each other, are now placed in fluid communication with each other. Preferably, no additional valves or switches need to be manipulated in order to achieve this state change, namely, to cause separate blood and dialysate circuits to become fluidly connected.

The valve switch may be effectuated by any means known in the art, including by physically manipulating a mechanical control on the surface of the manifold or electronically through the operation of a dialysis machine causing a change to the valve state through an interface between the dialysis machine, which has a controller to control the state of the valve in accordance with a user selected operational mode, and a valve interface integrated into the surface of the manifold.

In priming mode, the valve 8517 would be opened, thereby causing dialysate fluid flowing through a pump to pass through the manifold 8510, into the dialyzer 8502 via tubes 8524, 8503 and two-way valve port 8522, out of the dialyzer, back into the manifold 8510 via two-way valve port 8521 and tube 8525, and out of manifold 8510. Accordingly, in the priming mode, the valve 8517 ensures that the dialysate circulates through the blood circuit, thereby placing the blood and dialysate circuits in fluid communication. Functionally, the manifold 8510 is placed in priming mode by manipulating the state of the two-way valve 8517.

After a specified volume of dialysate is pumped into and through the blood circuit, the two-way valve is closed. Pumping of dialysate may or may not continue. If continued, the fresh dialysate circulates through the dialysate circuit only. In the blood circuit, residual dialysate remains. To purge the dialysate from the blood circuit, a patient is connected to the "From Patient Line" 8401, shown in FIG. 84 and typically referred to as the arterial access line. The "To Patient Line" 8423, typically referred to as the venous return line is either held over a waste container or connected to a patient.

By placing the system in treatment mode, blood from the patient is drawn into the blood circuit, passing into the manifold, through pumps, out of the manifold, through the dialyzer, back into the manifold, and back out of the manifold. The blood thereby causes the residual priming fluid to be 'chased' through the blood circuit, removing any remaining air pockets in the process, and into either a waste container or the patient, depending on the connected state of the venous return line. After blood has completely filled the blood circuit, the system stops the blood pump or the user stops the pump manually. If not already connected, the venous return line is then connected to the patient and the treatment continues.

In another embodiment, a filter, such as a 0.22µ filter, can be used to help remove any remaining undesirable substances if the sorbent-canister is inadequate to produce essentially sterile dialysate. In one embodiment, the filter is positioned in-line with the reservoir input line, proximate to Port E of the manifold, and is used both during priming and operation.

By using this priming system, one avoids having to use an additional and separate set of disposables to just prime the blood side of the circuit. In particular, this approach eliminates the need for a separate saline source, such as a 1 liter bag of saline, and, accordingly, also eliminates the need for connectors and tubing to the separate saline source, including dual-lumen spikes or single lumen spikes used to connect blood lines to the saline.

Disposable Kits

Figure 81:
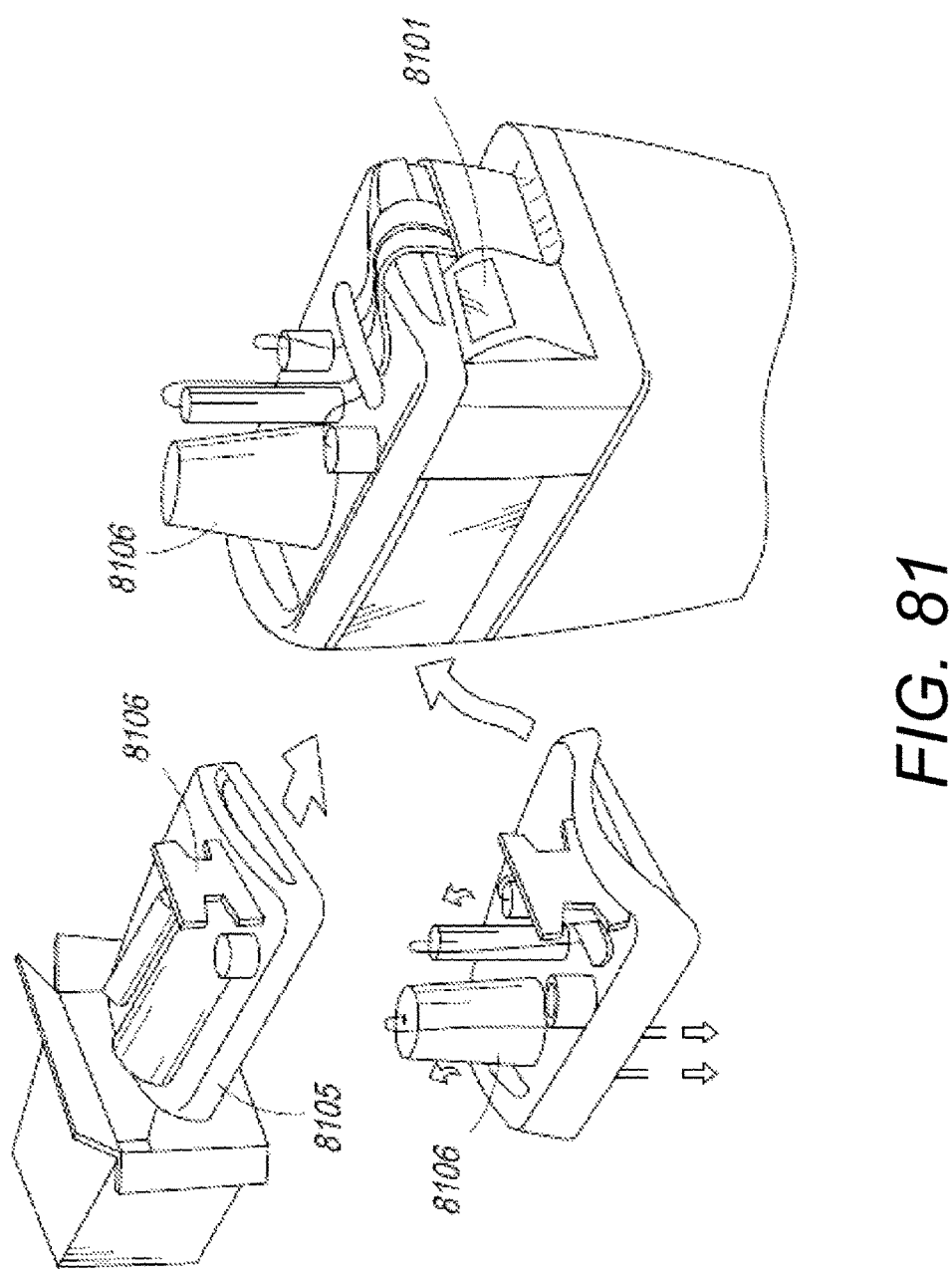
FIG. 81 is a schematic showing a packaged disposable kit.

Embodiments of the dialysis system disclosed herein are designed to use a plurality of disposable components. Referring to FIG. 81, in one embodiment, disposables 8106 for use in the system are shipped in packaging preassembled on a tray 8105. The tray 8105 is placed on top of the controller unit 8101 workspace, thereby permitting easy access to, and management of, the required disposables, which is of particular importance for home users. The controller unit 8101 is waterproof rated so that in case of a liquid spill, it should not seep into and damage the top controller unit 8101.

Figure 82:
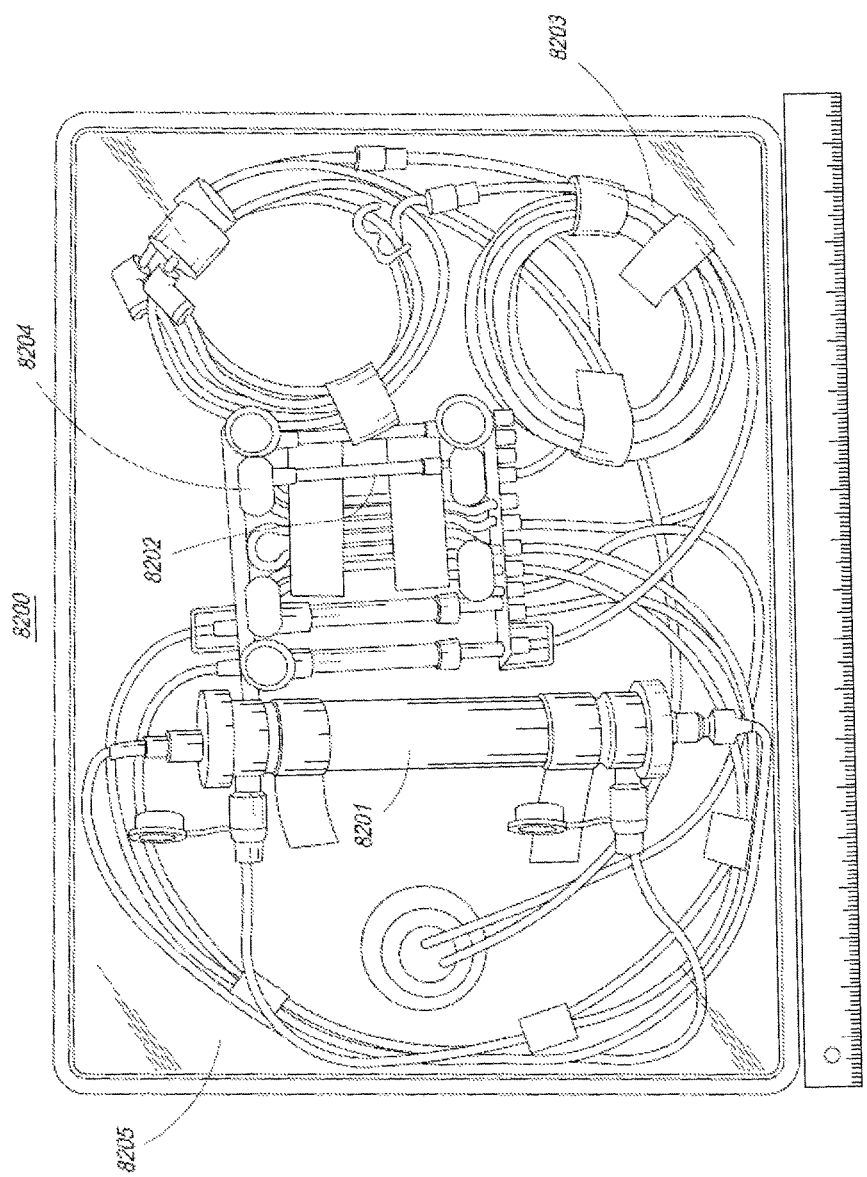
FIG. 82 is a schematic showing one embodiment of a disposable kit comprising a manifold and dialyzer attached to a plurality of tubes.

In one embodiment, the kit 8200 contains a manifold 8202, dialyzer 8201, and tubing 8203 which are all preattached. Referring to FIG. 82, the disposable kit 8200 comprises a dialyzer 8201, manifold 8202, tubing 8203, valves 8204 (as part of the manifold), reservoir bag 8205, which are all preattached and configured for direct installation into the dialysis machine by a user.

More specifically, the disposable components, particularly the fully disposable blood and dialysate circuits, are prepackaged in a kit (which includes dialyzer, manifold, tubing, reservoir bag, ammonia sensor, and other components) and then installed by a user by opening the front door of the top unit (as discussed above), installing the dialyzer and installing the manifold in a manner that ensures alignment against non-disposable components such as pressure sensors and other components. A plurality of pump shoes integrated into the internal surface of the front door makes loading of disposable components easy. The manifold only needs to be inserted and no pump tubing needs to be threaded between the rollers and shoes. This packaged, simple approach enables easy disposables loading and cleaning of the system. It also ensures that the flow circuitry is properly configured and ready for use. In operation, the top unit is attached to the bottom unit with reservoir.

Figure 83:
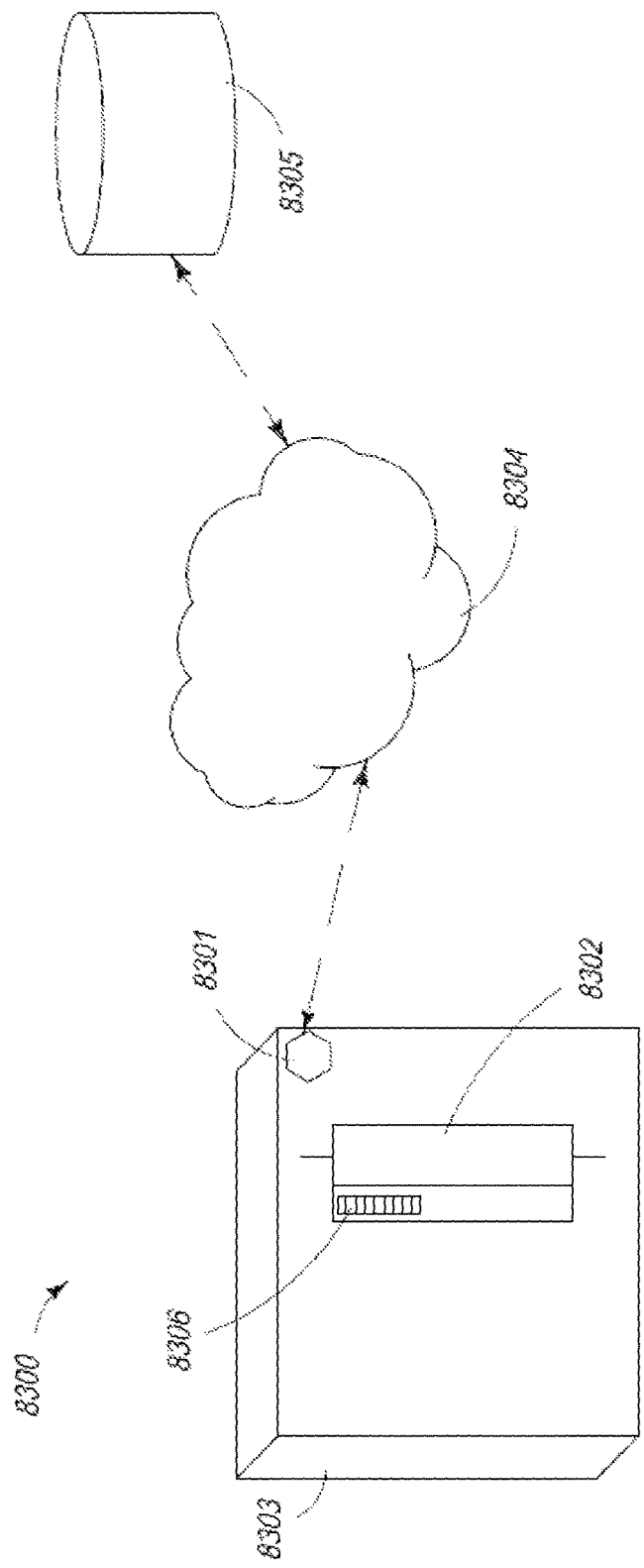
FIG. 83 is a schematic showing one embodiment of an electronic lock-out system integrated into disposables.

Optionally, the disposable components, and particularly the manifold, comprise an electronic-based lockout ("e-lockout") system. FIG. 83 is a functional block diagram showing one embodiment of the e-lockout system of the present invention. In one embodiment, e-lockout system 8300 comprises a reader 8301 that detects and reads identification data 8306 embedded in disposable items 8302, such as disposable manifolds, disposable sorbents used in dialysate regeneration and/or dialyzers. The identification data 8306 may be stored on disposable items 8302 via barcode, RFID tags, EEPROM, microchip or any other identification means that uniquely identifies the disposable items 8302 to be used in the dialysis system 8303. The reader 8301 is correspondingly a barcode reader, RFID reader, microchip reader, or any other reader that corresponds to the identification technology employed as is known to persons of ordinary skill in the art. In one embodiment, the reader 8301 is connected with a transceiver for wirelessly connecting to a remote database 8305 through a network 8304 such as the Internet or any other public or private network known to persons of ordinary skill in the art. In another embodiment, the reader 8301 is directly aligned with the identification data 8306.

The database 8305, located remote from the dialysis system, stores a plurality of information about the disposable items 8302 that can be used in the system 8303. The information comprises unique identification data 8306 along with information for the corresponding disposable item such as authenticity, usability in terms of whether or not the item is likely to be in working condition, or if the item has been recalled by the manufacturer owing to a defect, its expiry date, if any, and/or any other such value-added information that would advantageously be evident to persons of ordinary skill in the art.

In operation, when a disposable item 8302, such as a dialyzer, manifold, or a hemofilter cartridge, is loaded into the system 8303 the reader 8301 detects the disposable item 8302 through identification data 8306 embedded onto item 8302. This identification data 8306 is read by reader 8301, which, in turn, communicates, either wired or wirelessly, with database 8305 to request more information on the item 8302 stored therein, based on identification data 8306, or confirm the validity or integrity of the item 8302 based on identification data 8306.

For example, in one embodiment, dialyzer cartridge 8302 identified by the reader 8301 may have been called back by the manufacturer on account of some defect. This call-back information is stored on the database 8305 and is returned back to the reader 8301 as a result of the request signal sent by the reader 8301 to the database 8305 through the network 8304. As a result of the call-back information received from the database 8305, the microprocessor controlling the blood purification system supported by the system 8303 does not allow the user to proceed with treatment. This is achieved, in one embodiment, by suspending functioning of the pumps that propel fluids through the fluid circuits of the blood purification system 8303. Additionally, an audio/visual alarm may also be displayed to this effect.

In another example, dialyzer cartridge 8302 identified by the reader 8301 may not be authentic. As a result of which, the microprocessor would not allow functioning of the blood purification system of the system 8303. Thus, the e-lockout system 8300 of the present invention prevents usage of the system 8303 in case the disposable items 8302 attached to the manifold 8303 are in a compromised state.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A dialysis system comprising:
a dialysis machine having a controller, sensor component, a reservoir and a dialyzer;
a disposable monolithic manifold in fluid communication with the reservoir and dialyzer, wherein the disposable monolithic manifold has a diaphragm integrated therein and is adapted for installation in the dialysis machine, wherein the diaphragm is adapted to be compressed by the sensor component located within the dialysis machine and external to the disposable manifold, and wherein the diaphragm comprises: a convex exterior surface protruding outward from the manifold and fixedly attached to the manifold at a first end and at a second end, wherein a distance between the first end and second end defines a length and height of the diaphragm, wherein the diaphragm at the first end and second end has the same height as the manifold, wherein the height of the convex exterior surface increases from the first end to a first height relative to the manifold, and wherein the height of the convex exterior surface decreases from the first height to the second end.

2. The dialysis system of claim 1, wherein the first height of the diaphragm is between 0.03 and 0.04 inches relative to the manifold.

3. The dialysis system of claim 1, wherein the diaphragm has a thickness along the length from the first end to the second end and wherein the thickness is substantially constant along the length.

4. The dialysis system of claim 1, wherein the thickness of the diaphragm is between 0.03 and 0.04 inches.

5. The dialysis system of claim 1, wherein a total length of the diaphragm is between 0.625 and 0.675 inches.

6. A dialysis system comprising:
a dialysis machine having a controller, a sensor component, a reservoir and a dialyzer;
a disposable monolithic manifold having a diaphragm integrated therein and adapted for installation in the dialysis machine, wherein the diaphragm has a substantially planar periphery and a raised convex protrusion, wherein the convex protrusion is centrally located within the substantially planar periphery, wherein the periphery has a height equal to a height of an external surface of the manifold, wherein the convex protrusion has a height greater than the height of the planar periphery, wherein the convex protrusion represents a surface area ranging from 10% to 40% of a total surface area of the diaphragm and wherein the convex protrusion is adapted to be compressed by the sensor components located within the dialysis machine and external to the manifold.

7. The dialysis system of claim 6 wherein the diaphragm has a length ranging from 0.625 inches to 0.675 inches.

8. The dialysis system of claim 6 wherein the convex protrusion has a height ranging from 0.03 inches to 0.04 inches.

9. The dialysis system of claim 6 wherein the raised convex protrusion represents a surface area ranging from 19% to 23% of a total surface area of the diaphragm.

10. A dialysis system comprising:
a dialysis machine having a controller, a sensor component, a reservoir and a dialyzer;
a disposable monolithic manifold having a diaphragm integrated therein and adapted for installation in the dialysis machine, wherein the diaphragm comprises a convex periphery having a first height which is greater than a height of an external surface of the manifold and a raised convex protrusion located in a center of the diaphragm adapted to contact, and be compressed by, the sensor component, wherein the convex protrusion is located within the convex periphery, wherein the convex protrusion has a second height greater than the first height.

11. The dialysis system of claim 10 wherein the diaphragm has a length ranging from 0.625 inches to 0.675 inches.

12. The dialysis system of claim 10 wherein the convex protrusion has a height ranging from 0.03 inches to 0.04 inches.

13. The dialysis system of claim 10 wherein the convex protrusion has a height ranging from 0.1 inches to 0.02 inches above a plurality inflection points on each side of the periphery, the inflection points defining an end of the periphery and a beginning of the protrusion.

14. The dialysis system of claim 10 wherein the periphery has a height of 0.02 inches with respect to the manifold external surface.

15. The dialysis system of claim 10 wherein a thickness of the diaphragm is constant throughout a surface area of the diaphragm, wherein the thickness ranges from 0.03 inches to 0.04 inches.

* * * * *